United States Patent
Shemi et al.

(10) Patent No.: US 9,687,500 B2
(45) Date of Patent: Jun. 27, 2017

(54) METHODS AND COMPOSITIONS FOR TREATING CANCER

(71) Applicant: SILENSEED LTD., Jerusalem (IL)

(72) Inventors: Amotz Shemi, Herzliya (IL); Elina Zorde Khvalevsky, Jerusalem (IL); Rachel Malka Gabai, Mata (IL)

(73) Assignee: SILENSEED LTD., Jerusalem (IL)

( * ) Notice: Subject to any disclaimer, the term of this patent is extended or adjusted under 35 U.S.C. 154(b) by 0 days.

(21) Appl. No.: 14/711,800

(22) Filed: May 14, 2015

(65) Prior Publication Data

US 2015/0238517 A1    Aug. 27, 2015

Related U.S. Application Data

(63) Continuation of application No. PCT/IL2013/050944, filed on Nov. 14, 2013.

(60) Provisional application No. 61/726,029, filed on Nov. 14, 2012.

(51) Int. Cl.
| | | |
|---|---|---|
| *A61K 31/713* | (2006.01) | |
| *A61M 1/12* | (2006.01) | |
| *A61P 35/00* | (2006.01) | |
| *A61K 31/712* | (2006.01) | |
| *A61K 45/06* | (2006.01) | |
| *A61K 31/7105* | (2006.01) | |
| *A61K 31/7115* | (2006.01) | |
| *C12N 15/113* | (2010.01) | |
| *A61K 9/00* | (2006.01) | |
| *A61K 9/70* | (2006.01) | |
| *A61K 9/14* | (2006.01) | |
| *A61K 9/50* | (2006.01) | |
| *A61K 47/34* | (2017.01) | |
| *A61K 47/48* | (2006.01) | |

(52) U.S. Cl.
CPC .......... *A61K 31/713* (2013.01); *A61K 9/0024* (2013.01); *A61K 9/14* (2013.01); *A61K 9/5031* (2013.01); *A61K 9/7007* (2013.01); *A61K 31/712* (2013.01); *A61K 31/7105* (2013.01); *A61K 31/7115* (2013.01); *A61K 45/06* (2013.01); *A61K 47/34* (2013.01); *A61K 47/48007* (2013.01); *C12N 15/1135* (2013.01); *C12N 15/1136* (2013.01); *C12N 15/1137* (2013.01); *C12N 15/1138* (2013.01); *C12Y 207/07049* (2013.01); *C12N 2310/14* (2013.01); *C12N 2310/351* (2013.01); *C12N 2310/3515* (2013.01); *C12N 2320/30* (2013.01)

(58) Field of Classification Search
USPC ....... 435/6.1, 91.1, 91.31, 455, 458; 514/44, 514/19.3; 536/23.1, 24.5; 424/489, 497
See application file for complete search history.

(56) References Cited

U.S. PATENT DOCUMENTS

| | | | |
|---|---|---|---|
| 2005/0255487 A1* | 11/2005 | Khvorova | A61K 31/713 435/6.11 |
| 2007/0167384 A1* | 7/2007 | Leake | C12N 15/111 514/44 A |
| 2009/0170837 A1* | 7/2009 | Gourdeau | A61K 31/551 514/220 |
| 2011/0195123 A1 | 8/2011 | Shemi | |
| 2012/0022137 A1* | 1/2012 | Rivers | A61K 9/0051 514/44 A |
| 2012/0164207 A1 | 6/2012 | Gooberman | |
| 2012/0171240 A1* | 7/2012 | Shirwan | C07K 14/70532 424/196.11 |
| 2013/0142875 A1 | 6/2013 | Shemi et al. | |

FOREIGN PATENT DOCUMENTS

| | | | |
|---|---|---|---|
| WO | WO 2008/015232 | | 2/2008 |
| WO | WO 2008/084643 | * | 7/2008 |
| WO | WO 2010/086849 | | 8/2010 |

OTHER PUBLICATIONS

Dietrich et al, Chapter: Solid Pancreatic Tumors from the book Ultrasonography of the Pancreas (Springer-Verlag Italia) (2012).*
Song et al, Cancer Science, vol. 101, No. 7, pp. 1754-1760 (2010).*
Liu L. et al. "Loss of the human polycomb group protein BMI1 promotes cancer-specific cell death." Oncogene, 25(31): 4370-4375 (2006).
Wu Z. et al. "Overexpression of BMI-1 promotes cell growth and resistance to cisplatin treatment in osteosarcoma." PLoS One. 6(2)e14648 (2011).
Wu XM. et al. "RNAi-mediated silencing of the Bmi-1 gene causes growth inhibition and enhances doxorubicin-induced apoptosis in MCF-7 cells." Genet Mol Biol. 32(4): 697-703 (2009).
Lu ZX et al. "Development of small interfering RNA delivery system using PEI-PEG-APRPG polymer for antiangiogenic vascular endothelial growth factor tumor-targeted therapy." Int J Nanomedicine. 6: 1661-73 (2011).
Comandeur S. et al. "Polymers, drug release, and drug eluting stents" of (J. Interv Cardiol. 19(6): 500-6; 2006).

* cited by examiner

*Primary Examiner* — Jane Zara
(74) *Attorney, Agent, or Firm* — JMB Davis Ben-David

(57) ABSTRACT

Treatment of cancer by regional and prolonged release of one or more nucleotide-based agents is provided.

18 Claims, 10 Drawing Sheets

METHODS AND COMPOSITIONS FOR TREATING CANCER

CROSS REFERENCE TO RELATED APPLICATIONS

This is a Continuation of International Patent Application No. PCT/IL2013/050944, filed Nov. 14, 2013, which claims the benefit of U.S. Provisional Patent Application No. 61/726,029, filed Nov. 14, 2012. The contents of these patent applications are incorporated by reference herein in their entirety.

FIELD

Treatment of cancer by regional and prolonged release of one or more nucleotide-based agents is provided.

BACKGROUND

RNA Interference

Non-coding RNAi molecules regulate genes post-transcriptionally and can lead to gene silencing. Endogenous dsRNA initiates RNAi by activating the ribonuclease protein Dicer, which binds and cleaves double-stranded RNAs (dsRNAs) to produce double-stranded fragments of 20-25 base pairs with a 2-nucleotide overhang at the 3' end, known as siRNAs. These interfering RNAs (siRNAs) are integrated into an active RNA-induced silencing complex (RISC), while being separated into single "sense" and "antisense" strands. Within the RISC, the antisense strand then base-pairs to its target mRNA and induces cleavage of the mRNA, thereby preventing it from being used as a translation template. Synthetic RNAi molecules can vary significantly in their design, including the specific sequence along the mRNA, accessibility to Dicer and RISC, the length of each strand, optional symmetrical, asymmetrical, blunt, and loop structures, and chemical modifications of many types.

The delivery of RNAi to target tissue is a major challenge. Systemic injection of siRNA into the vascular system needs to overcome renal filtration and phagocytosis and degradation in the bloodstream, and needs to achieve targeting to the diseased site, transport across the vascular endothelial barrier, diffusion through the extracellular matrix, uptake into the cell, escape from the endosome, and unpackaging and releasing the siRNA to the cell RNAi machinery. Systemic delivery today is limited to a small number of target tissues, in particular to the liver.

Even direct injection of naked siRNA to topical targets (for example the eye, skin, mucus membranes, and localized tumors) and intranasal/intratracheal instillation of aerosolized siRNA into the lung is subject to rapid dose decline by diffusion and degradation and increased pressure (in some cases of injection). Repeated injections at a frequency of about one per week are often required.

Alshamsan et al. (*STAT3 Silencing in Dendritic Cells by siRNA Polyplexes Encapsulated in PLGA Nanoparticles for the Modulation of Anticancer Immune Response, Molecular Pharmaceutics* 7(5): 1643-1654, 2010) reported nanoparticles containing siRNA complexed with polyethylenimine (PEI). However, these devices exhibit fast drug release, typically on the order of one week, and are ineffective to carry high drug loads to a wide tissue area, for a sufficient treatment period.

US Patent Publication No. US2008/0124370 (Marx) describes reagents, methods and systems to treat inflammation and pain in a subject using small interfering RNA (siRNA) molecules targeted to either TNF-alpha, IL1, IL6 and other pro-inflammatory cytokines.

US Patent Publication No. US 2011/0195123 (Shemi) describes an implantable medical device eluting drug locally and for a prolonged period, treatment methods, and implantation methods. The device comprises a polymeric substrate and a drug, for example gene silencing drugs based on RNA interference (RNAi), including siRNA, against targets such as K-ras. The human ras family consists of three closely related proto-oncogenes: c-Harvey (H)-ras, c-Kirsten (K)-ras, and N-ras, which share 90% of their peptide sequence. Ras proteins are localized in the inner cell membrane, bind GDP and GTP, and possess an intrinsic GTPase activity, implicated in the regulation of their activity. Ras proteins influence proliferation, differentiation, transformation, and apoptosis by relaying mitogenic and growth signals into the cytoplasm and the nucleolus. In a normal cell, most of the ras molecules are present in an inactive GDP-bound conformation.

A continuing need exists for improved RNAi-containing compositions to effectively treat solid tumors, including the identification of targets that work particularly well with this technology.

SUMMARY

Provided herein are systems and methods for treatment of solid tumors and the identification of targets that work particularly well with this technology. The described systems and methods may include manufacturing and implanting polymeric implant(s) loaded with a nucleotide-based agent. Additionally included, in some embodiments, are particular release parameters enabling treatment periods of various lengths, exploiting the RNAi machinery for specific silencing and RNAi for non-specific immune triggering, the shielding of the agent against degradation until it is released from the implant, the selected targets, and the release of naked, modified, complexed or conjugated types of siRNA. Such modifications can enable improved treatment efficiency by enhancing cellular uptake and/or spatial distribution, and can reduce toxicity levels.

BRIEF DESCRIPTION OF THE FIGURES

FIG. 2A: short release periods (~1.5 month). NC=uncoated drug delivery device (DDD); C=coated DDD; Additive I=Mannitol ("Add1", 5% and 10%); Additive II=Trehalose ("Add2", 1%, 5% and 10%); "Conjugated"=cholesterol-conjugated (with Mannitol 10%). All samples were non-coated, except for the one indicated as coated. FIG. 2B: longer release periods ~(3-6 months).

BRIEF DESCRIPTION OF THE DESCRIBED SEQUENCES

Figure 1:
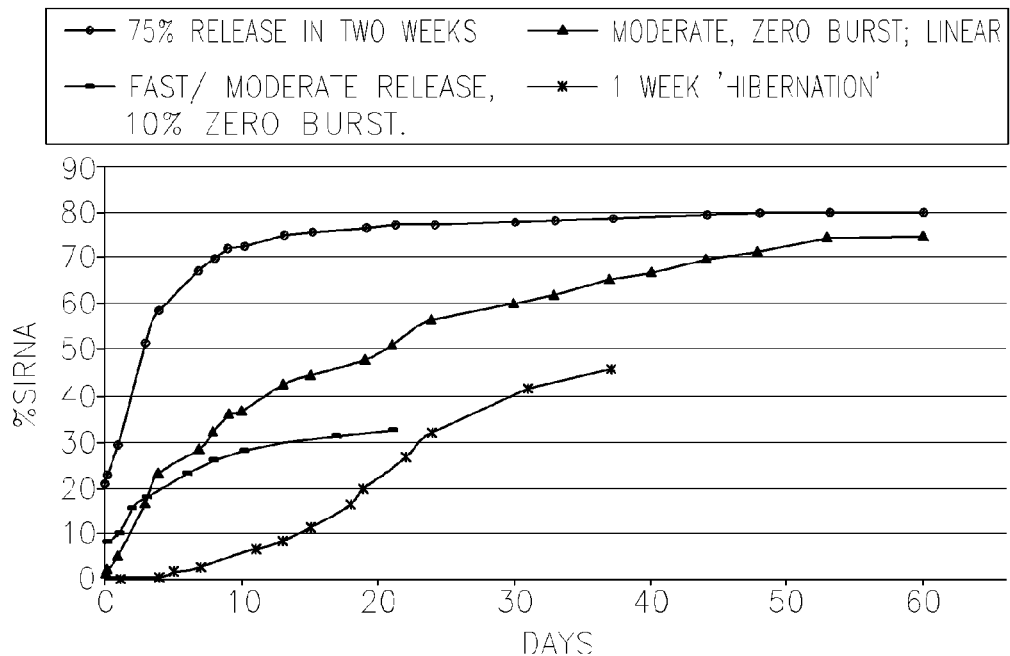
FIG. 1 shows exemplary time-release curves of siRNA, as measured in PBS, pH~7.

The nucleic and/or amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named 2142_7_3_seq.txt, created May 14, 2015, about 400 KB, which is incorporated by reference herein.

DETAILED DESCRIPTION

Described herein is a DDD, comprising: (a) biocompatible polymeric composition; and (b) a nucleotide-based agent that targets a gene, where the nucleotide-based agent is within the composition, and where the gene is selected from the targets described herein, for treating a cancer other than prostate carcinoma. Typically, the polymeric composition is a biodegradable polymeric matrix, comprising a biodegradable polymer. In some embodiments, the RNAi agent is incorporated within the biodegradable matrix. In other embodiments, the RNAi agent is dispersed within the biodegradable matrix. Alternatively or in addition, the nucleotide-based agent is an RNAi agent.

In some embodiments, the target gene is selected from the group consisting of BMI1 polycomb ring finger oncogene (BMI-1), TERT telomerase reverse transcriptase (hTERT), IL6ST interleukin 6 signal transducer/gp130, and CD44.

In more particular embodiments, the gene is BMI-1. Recently, Song et al (Cancer Sci 2010; 101:1754-1760) found that BMI-1 plays an important role in the late progression of pancreatic cancer and may represent a novel therapeutic target for the treatment of pancreatic cancer.

In other embodiments, the gene is hTERT (human telomerase reverse transcriptase). hTERT is a ribonucleoprotein polymerase that maintains telomere ends by addition of the telomere repeat TTAGGG. The enzyme consists of a protein component with reverse transcriptase activity, encoded by hTERT, and an RNA component which serves as a template for the telomere repeat. hTERT expression plays a role in cellular senescence, as it is normally repressed in postnatal somatic cells, resulting in progressive shortening of telomeres. Deregulation of hTERT expression in somatic cells may be involved in oncogenesis. Studies in mouse models suggest that TERT also participates in chromosomal repair, since de novo synthesis of telomere repeats may occur at double-stranded breaks. Alternatively spliced variants encoding different isoforms of hTERT have been identified.

In other embodiments, the gene is gp130. The protein encoded by this gene is a signal transducer shared by many cytokines, including interleukin 6 (IL6), ciliary neurotrophic factor (CNTF), leukemia inhibitory factor (LIF), and oncostatin M (OSM). This protein functions as a part of the cytokine receptor complex. The activation of this protein is dependent upon the binding of cytokines to their receptors. vIL6, a protein related to IL6 and encoded by the Kaposi sarcoma-associated herpesvirus, can bypass the interleukin 6 receptor (IL6R) and directly activate this protein. Alternatively spliced transcript variants encoding distinct isoforms have been described.

In other embodiments, the gene is CD44. CD44 is a multifunctional protein involved in cell adhesion and signaling. Studies have shown both tumor-promoting and tumor-inhibiting effects of CD44 in cancer development and progression (Patrawala et al).

In yet other embodiments, a DDD described herein comprises nucleotide-based agents, in some embodiments RNAi agents, in more specific embodiments siRNA agents, targeting at least 2 genes selected from the group consisting of: BMI-1, hTERT, gp130, and CD44.

In other embodiments, the target is selected from PAPPA pregnancy-associated plasma protein A (Pappalysin), Neurophilin and tolloid-like 2 (NETO2), Protein tyrosine phosphatase receptor a (PTPRA), BRD4 bromodomain containing 4 (BRD4), ErbB3/HER3, PSCA prostate stem cell antigen (PSCA), Enhancer of zeste homolog 2 (EZH2), TMPRSS2/ERG, CA12 Carbonic anhydrase XII (CA12), MEK4/MAP2K4, p63/KET, Transmembrane and coiled-coil protein 1 (TMCC1), TMCC2, TMCC3, Neurotrimin, CD70, Tmem50b, Claudin-11, and Neuroplastin NPTN. Each target represents a separate embodiment.

In certain, more specific embodiments, the target is associated with cancer stem cells. Non-limiting examples of cancer stem cell targets are CA12, p63, Pappalysin, NETO2, Protein tyrosine phosphatase receptor a, TMCC1, TMCC2, TMCC3, Neurotrimin, CD70, Tmem50b, Claudin-11, and Neuroplastin NPTN. In other embodiments, the target is another cancer stem cell-specific target.

TABLE 1

Exemplary RNAi Targets:

| Name | Synonyms/GenBank Gene ID No./representative SEQ ID No(s): | Exemplary GenBank Accession #'s | Remarks |
|---|---|---|---|
| Androgen Receptor | KD; AIS; TFM; DHTR; SBMA; HYSP1; NR3C4; SMAX1; HUMARA Gene ID #: 367. SEQ ID No: 37 | NM_000044.3 NM_001011645.2 NM_000044.2 M20132.1 FJ235918 NM_001011645.1 | |
| Pappalysin | PAPPA pregnancy-associated plasma protein A Gene ID #: 5069. SEQ ID No: 38 | NM_002581.3 | |
| NETO2 | Neurophilin (NRP) and tolloid (TLL)-like 2; BTCL2; NEOT2. Gene ID #: 81831. SEQ ID No: 39 | NM_001081324.1 NM_001201477.1 (variant 2) NM_018092.4 (variant 1) | Transcript variants 1 and/or 2 can be targeted |
| Protein tyrosine phosphatase receptor α (PTPRA) | LRP; HLPR; PTPA; HEPTP; HPTPA; RPTPA; PTPRL2; HPTPalpha; R-PTP-alpha. Gene ID #: 5786. SEQ ID No: 40 | NM_080840.2 NM_001163688.1 | |
| BMI-1 | BMI1 polycomb ring finger oncogene, Gene ID # 648. SEQ ID No: 41 | NM_005180 | |
| gp130 | IL6ST interleukin 6 signal transducer; CD130; CDW130; IL-6RB. Gene ID # 3572. SEQ ID No: 42-44 | NM_001190981.1 NM_175767.2 NM_002184.3 | |
| hTERT | TERT telomerase reverse transcriptase Gene ID #7015. SEQ ID No: 45-46 | NM_001193376 NM_198253.2 | |
| BRD4 | BRD4 bromodomain containing 4; CAP; MCAP; HUNK1; HUNKI. Gene ID # 23476. SEQ ID No: 47 | NM_014299.2 NM_058243.2 | |
| ErbB3 | HER3; LCCS2; ErbB-3; c-erbB3; erbB3-S; MDA-BF-1 Gene ID # 2065. SEQ ID No: 48 | NM_001005915.1 NM_001982.3 NP_001973 | |
| PSCA | PSCA prostate stem cell antigen; PRO232 Gene ID # 8000. SEQ ID No: 49 | NM_005672.4 NP_005663 | |
| EZH2 | Enhancer of zeste homolog 2; ENX1; EZH1; KMT6; WVS2; ENX-1; KMT6A. Gene ID # 2146. SEQ ID No: 50 | NM_004456.4 NM_152998.2 NM_001203247.1 NM_001203248.1 NM_001203249.1 | |
| CD44 | Gene ID# 960. SEQ ID No: 51-58 | NM_001202557.1 NM_001202556.1 NM_001202555.1 NM_001001392.1 NM_001001391.1 NM_001001390.1 NM_001001389.1 NM_000610.3 | |

TMPRSS2/ERG fusion gene is a fusion of ERG (v-ets erythroblastosis virus E26 oncogene homolog; also known as erg-3; Gene ID#: 2078) to TMPRSS2 transmembrane protease, serine 2 (also known as PP9284 or PRSS10; Gene ID#: 7113). It is expressed in 15-80% of prostate cancer lesions. Representative GenBank sequences: NM_001136154.1 (ERG) and NM_001135099.1 (TMPRSS2).

CA12 Carbonic anhydrase XII (also known as CAXII or HsT18816; Gene ID #: 771) is a transmembrane and extracellular enzyme involved in the regulation of microenvironment acidity and tumor malignancy. CA XII has a central role in hypoxia and tumor acidosis, invasion and metastasis. Representative GenBank sequence: NM_001218.3.

MEK4 (also known as MAP2K4; JNKK; MEK4; MKK4; SEK1; JNKK1; SERK1; MAPKK4; PRKMK4; SAPKK1; and SAPKK-1; Gene ID #: 6416) regulates prostate cancer cell invasion/metastasis. See US 2009/0124569. Representative GenBank sequence: NM_003010.2.

p63 (also known as KET, p51A/B, CUSP, p40, and p73L; Gene ID #: 8626) is a transcription factor and homologue of p53. Representative GenBank sequences: NM_001114978.1, NM_001114979.1, NM_001114980.1, NM_001114981.1, NM_001114982.1, and NM_003722.4.

Transmembrane and coiled-coil proteins (TMCCs) are a group of putative proteins that contain a coiled-coil domain and two transmembrane domains. Both transmembrane domains are located in the C-terminal region (571-653a.a.). There are three family members in humans, which share high sequence homology, namely TMCC1, TMCC2, and TMCC3 (GenBank Gene ID #'s 23023, 9911, and 57458, respectively). Representative GenBank sequence: NM_001017395.3, NM_001242925.1, and NM_020698.2, respectively.

Neurotrimin is a glycosylphosphatidylinositol (GPI)-anchored cell adhesion molecule expressed on neuronal populations (GenBank Gene ID #50863). Representative GenBank sequences: NM_001048209.1, NM_001144058.1, NM_001144059.1, and NM_016522.2.

CD70, a member of the tumour necrosis factor (TNF) superfamily, is a type II integral membrane protein and the ligand for CD27 (GenBank Gene ID #970). Representative GenBank sequence: NM_001252.3.

Tmem50B (GenBank Gene ID #757) is one of two genes in the transmembrane 50 group. Representative GenBank sequence: NM_006134.6.

Claudin-11, also known as oligodendrocyte-specific protein, was first identified to be specifically expressed in the tight junction (TJ) strands of oligodendrocytes in brain and in sertoli cells of rats and mice (GenBank Gene ID #5010). Representative GenBank sequences: NM_001185056.1 and NM_005602.5.

Neuroplastin NPTN (previously known as stromal cell derived factor receptor I) is a cell adhesion molecule of the immunoglobulin (Ig) superfamily (GenBank Gene ID #27020). Representative GenBank sequences: NM_001161363.1, NM_001161364.1, NM_012428.3, and NM_017455.3.

PSCA: Marra et al (BMC Cancer. 2010 Apr. 7; 10:129) showed that PSCA is a glycosylphosphatidylinositol (GPI)-anchored protein expressed not only in prostate, but also in pancreas and bladder cancer. Delay of growth of human bladder cancer cells by PSCA downregulation was associated with activation of immune signaling pathways.

Androgen Receptor (AR): Wu et al (Urology, volume 75, Issue 4, Pages 820-827, April 2010) found that Androgen Receptor (AR) is a potential therapeutic target for bladder cancer. AR expression knockdown produced increased apoptosis, decreased proliferation, and migration of bladder cancer cells.

All isoforms of the proteins mentioned herein may be included. The mention of particular representative sequences is not intended to exclude isoforms not exemplified herein.

In other embodiments, a DDD of methods and compositions described herein comprises two or more separate nucleotide-based agents, in some embodiments RNAi agents, in more specific embodiments siRNA agents. In other embodiments, 2 of the above-listed genes are targeted.

In still other embodiments, a DDD described herein further comprises a nucleotide-based agent, in some embodiments an RNAi agent, in more specific embodiments an siRNA agent, targeting Kirsten rat sarcoma 2 viral oncogene homolog (K-ras). K-ras mutations appear inter alia in lung cancer, CRC, and pancreatic cancer. Representative GenBank sequences: BC013572, BC010502, BC029545.1, BT007153, JX512447, and EU332849 (SEQ ID Nos 59-64).

In certain embodiments, the DDD comprises at least one nucleotide-based agent, in some embodiments an RNAi agent, in more specific embodiments an siRNA agent, that targets a gene selected from BMI-1, hTERT, gp130, and CD44, and another nucleotide-based agent, in some embodiments an RNAi agent, in more specific embodiments an siRNA agent, that targets K-ras.

In certain embodiments, the DDD comprises at least one nucleotide-based agent, in some embodiments an RNAi agent, in more specific embodiments an siRNA agent, that targets a gene selected from Pappalysin, NETO2, PTPRA, BRD4, ErbB3/HER3, PSCA, EZH2, TMPRSS2/ERG, CA12, MEK4/MAP2K4, p63/KET, TMCC1, TMCC2, TMCC3, Neurotrimin, CD70, Tmem50b, Claudin-11, and Neuroplastin NPTN; and another agent that targets K-ras.

In certain embodiments, the target K-ras is a G12D-mutated K-ras. In some embodiments, the nucleotide sequence of the duplex region of the sense strand of the nucleotide-based agent consists of:
  a sequence selected from SEQ ID No: 1-7, namely GUUGGAGCUGAUGGCG (SEQ ID No: 1), GUUGGAGCUGUUGGCG (SEQ ID No: 2), GUUGGAGCUGCUGGCG (SEQ ID No: 3), GUUGGAGCUAGUGGCG (SEQ ID No: 4), GUUGGAGCUUGUGGCG (SEQ ID No: 5), GUUGGAGCUGGUGACG (SEQ ID No: 6), and GUUGGAGCUGGUUGCG (SEQ ID No: 7), either alone or followed by:
  a sequence selected from: (i) UAGGCAAGAGUGCC (SEQ ID No: 8) and (b) a 5'-fragment of 1-13 nucleotides inclusive of SEQ ID No: 8. "Followed by" in this regard means that the 3'-terminus of the sequence selected from SEQ ID No: 1-7 is connected to the 5'-terminus of SEQ ID No: 8 or a fragment thereof.

For purposes of illustration, the following sense strands contain SEQ ID No: 1 and all or a portion of SEQ ID No: 8: GUUGGAGCUGAUGGCGU (SEQ ID No: 16), GUUGGAGCUGAUGGCGUA (SEQ ID No: 17), GUUGGAGCUGAUGGCGUAG (SEQ ID No: 18), GUUGGAGCUGAUGGCGUAGG (SEQ ID No: 19), GUUGGAGCUGAUGGCGUAGGC (SEQ ID No: 20), GUUGGAGCUGAUGGCGUAGGCA (SEQ ID No: 21), GUUGGAGCUGAUGGCGUAGGCAA (SEQ ID No: 22), GUUGGAGCUGAUGGCGUAGGCAAG (SEQ ID No: 23), GUUGGAGCUGAUGGCGUAGGCAAGA (SEQ ID No: 24), GUUGGAGCUGAUGGCGUAGGCAAGAG (SEQ ID No: 25), GUUGGAGCUGAUGGCGUAG-GCAAGAGU (SEQ ID No: 26), GUUGGAGCUGAUG-GCGUAGGCAAGAGUG (SEQ ID No: 27), GUUG-GAGCUGAUGGCGUAGGCAAGAGUGC (SEQ ID No: 28), and GUUGGAGCUGAUGGCGUAG-GCAAGAGUGCC (SEQ ID No: 29) Similar sense strains may be readily derived from each of SEQ ID No: 2-7 together with all or a portion of SEQ ID No: 8.

In certain embodiments, the aforementioned 5' fragment of SEQ ID No: 8 is at least 3 nucleotides in length; thus, the duplex region of the antisense nucleotide is at least 19 nucleotides in length.

In other embodiments, the duplex region is 19 nucleotides in length (thus comprising both one of SEQ ID No: 1-7 with a 3-nucleotide fragment of SEQ ID No: 8). More specific embodiments of such sequences are those selected from GUUGGAGCUGAUGGCGUAG (SEQ ID No: 9), GUUG-GAGCUGUUGGCGUAG (SEQ ID No: 10), GUUG-GAGCUGCUGGCGUAG (SEQ ID No: 11), GUUG-GAGCUAGUGGCGUAG (SEQ ID No: 12), GUUGGAGCUUGUGGCGUAG (SEQ ID No: 13), and GUUGGAGCUGGUGACGUAG (SEQ ID No: 14), and GUUGGAGCUGGUUGCGUAG (SEQ ID No: 15).

In other embodiments, the duplex region is 16 nucleotides in length (thus consisting of one of SEQ ID No: 1-7 alone). In other embodiments, the duplex region is 17, 18, 20, 21, 22, 23, 24, 25, 26, 27, 28, or 29 nucleotides in length (thus comprising one of SEQ ID No: 1-7, together with a fragment of SEQ ID No: 8 that is 1, 2, 4, 5, 6, 7, 8, 9, 10, 11, 12, or 13 nucleotides, respectively). In other embodiments, the duplex region is 30 nucleotides in length (thus comprising one of SEQ ID No: 1-7, together with SEQ ID No: 8 in its entirety).

Reference herein to the "duplex region of the sense strand" indicates the portion of the sense strand that exists in a duplex structure after hybridization to the antisense strand. Similarly, reference to the "duplex region of the antisense strand" indicates the portion of the antisense strand that exists in a duplex structure after hybridization to the sense strand. In various embodiments, the duplex region of the sense strand may be either the entire sense strand or a fragment thereof. Similarly, the duplex region of the antisense strand may be either the entire antisense strand or a fragment thereof.

In certain preferred embodiments, the duplex region is perfectly complementary. Thus, the duplex region of the antisense strand is complementary to the duplex region of the sense strand. For purposes of illustration, the following antisense strands have a sequence perfectly complementary to SEQ ID No: 1-7, respectively: CGCCAUCAGCUC-CAAC (SEQ ID No: 30), CGCCAACAGCUCCAAC (SEQ ID No: 31), CGCCAGCAGCUCCAAC (SEQ ID No: 32), CGCCACUAGCUCCAAC (SEQ ID No: 33), CGCCA-CAAGCUCCAAC (SEQ ID No: 34), CGUCACCAGCUC-CAAC (SEQ ID No: 35), and CGCAACCAGCUCCAAC (SEQ ID No: 36).

In other embodiments, the nucleotide sequence of the sense strand of the anti-mutated K-ras agent is GUUG-GAGCUGAUGGCGUAGdTdT (SEQ ID No: 65), and the sequence of the antisense strand is CUACGCCAUCAG-CUCCAACdTdT (SEQ ID No: 66).

In other embodiments, the mutated K-ras is a G12V-mutated K-ras. siRNA's that specifically recognize G12V-mutated K-ras, for example the siRNA having sense and antisense sequences such as GUUGGAGCUGUUG-GCGUAG (SEQ ID No: 10), and CUACGCCAACAG-CUCCAAC (SEQ ID No: 67), respectively, can in another embodiment be utilized. siRNA G12V is relevant to treatment of a number of malignancies, among them lung cancer and colon cancer.

In other embodiments, the DDD further comprises a nucleotide-based agent, in some embodiments an RNAi agent, in more specific embodiments an siRNA agent, that targets a gene involved in vasculogenesis, angiogenesis and endothelial growth, and/or epidermal growth. In a more specific embodiment, the target is selected from VEGF (Vascular endothelial growth factor), Aurora B kinase (AURKB), and EGFR (epidermal growth factor receptor).

VEGF is also known as vascular endothelial growth factor A. Its NCBI Gene ID No. is 7422. Representative nucleotides sequences are NM_001025366, NM_001025367, NM_001025368, NM_001025369, NM_001025370, NM_001033756, NM_001171622, NM_001171623, NM_001171624, NM_001171625, NM_001171626, NM_001171627, NM_001171628, NM_001171629, NM_001171630, NM_001204384, NM_001204385, and NM_003376 (SEQ ID Nos: 185-202).

AURKB's NCBI Gene ID No. is 9212. Representative nucleotides sequences are NM_001256834, NM_001284526, and NM_004217.3 (SEQ ID Nos: 203-205).

EGFR NCBI Gene ID No. is 1956. Representative nucleotides sequences are NM_005228, NM_201282, NM_201283, and NM_201284 (SEQ ID Nos: 206-209).

In other embodiments, the angiogenesis target is targeted together with gene from Table 1. For example, a DDD may comprise (a) a first agent that targets a gene selected from BMI-1, hTERT, gp130, and CD44; and (b) a second agent that targets a gene selected from VEGF, AURKB, and EGFR. In other embodiments, the first agent targets a gene selected from Pappalysin, NETO2, PTPRA, BMI1, IL6ST/gp130, hTERT, BRD4, ErbB3/HER3, PSCA, EZH2, TMPRSS2/ERG, CA12, MEK4/MAP2K4, p63/KET, TMCC1, TMCC2, TMCC3, Neurotrimin, CD70, Tmem50b, Claudin-11, Neuroplastin NPTN, and CD44; and the second agent targets a gene selected from VEGF, AURKB, and EGFR. In other embodiments, the DDD comprises a first agent that targets a gene selected from Pappalysin, NETO2, PTPRA, BMI-1, IL6ST/gp130, hTERT, BRD4, ErbB3/HER3, PSCA, and EZH2; and a second agent that targets a gene selected from VEGF, AURKB, and EGFR. In still other embodiments, the DDD comprises a first agent that targets a gene selected from Pappalysin, NETO2, PTPRA, BMI-1, IL6ST/gp130, BRD4, and EZH2; and a second agent that targets a gene selected from VEGF, AURKB, and EGFR.

In other embodiments, the angiogenesis target is targeted together with a cancer stem cell target. In other embodiments, the DDD comprises a first nucleotide-based agent, in some embodiments an RNAi agent, in more specific embodiments an siRNA agent, that targets a gene selected from CA12, p63, Pappalysin, NETO2, Protein tyrosine phosphatase receptor a, TMCC1, TMCC2, TMCC3, Neurotrimin, CD70, Tmem50b, Claudin-11, and Neuroplastin NPTN; and a second nucleotide-based agent, in some embodiments an RNAi agent, in more specific embodiments an siRNA agent, that targets a gene selected from VEGF, AURKB, and EGFR.

In other embodiments, the angiogenesis gene is targeted together with two targets listed in Table 1.

In other embodiments, the target of an siRNA present in a DDD of the methods and compositions described herein is one of the target sequences set forth in Table 2.

In other embodiments, the sense sequence of an siRNA present in a DDD of the described methods and compositions is one of the sense siRNA sequences set forth in Table 2. In other embodiments, the antisense sequence of an siRNA present in a DDD of the described methods and compositions is one of the antisense siRNA sequences set forth in Table 2:

TABLE 2

Exemplary target sequences and siRNA sequences.

| Sequence name/ siRNA number* | Target sequence/siRNA sense sequence/siRNA antisense sequence, 5'-3' SEQ ID No follows sequences in parenthesis | Position and GenBank Accession No. of targets |
|---|---|---|
| siAR-1 201 | UGCCAGGGACCAUGUUUG (68)<br>UGCCAGGGACCAUGUUUGdTdT (69)<br>CAAAACAUGGUCCCUGGCAdTdT (70) | NM_000044.3;<br>NM_001011645.2 |
| siAR-2 202 | CGGAAAUGUUAUGAAGCAG (71)<br>CGGAAAUGUUAUGAAGCAGdTdT (72)<br>CUGCUUCAUAACAUUUCCGdTdT (73) | NM_000044.3<br>NM_001011645.2 |
| siAR-3 203 | GCUGAAGAAACUUGGUAAU (74)<br>GCUGAAGAAACUUGGUAAUdTdT (75)<br>AUUACCAAGUUUCUUCAGCdTdT (76) | NM_000044.3<br>NM_001011645.2 |
| siAR-4 204 | UGAUUUAUACUUCUCUGUU (77)<br>UGAUUUAUACUUCUCUGUUdTdT (78)<br>AACAGAGAAGUAUAAAUCAdTdT (79) | NM_000044.3<br>NM_001011645.2 |
| siBMI1-1 205 | UGAUUUAUACUUCUCUGUU (80)<br>UGAUUUAUACUUCUCUGUUdTdT (81)<br>AACAGAGAAGUAUAAAUCAdTdT (82) | NM_005180 |
| siBMI1-2 206 | AUGAAUGGAACCAGCAACA (83)<br>AUGAAUGGAACCAGCAACAdTdT (84)<br>UGUUGCUGGUUCCAUUCAUdTdT (85) | See above |
| siCDC44-1 207 | CUGAGCAUCGGAUUUGAGACUG (86)<br>CUGAGCAUCGGAUUUGAGAdTdT (87)<br>UCUCAAAUCCGAUGCUCAGdTdT (88) | NM_001202557.1;<br>NM_001202556.1;<br>NM_001202555.1;<br>NM_001001392.1;<br>NM_001001391.1;<br>NM_001001390.1;<br>NM_001001389.1;<br>NM_000610.3 |
| siCDC44-2 208 | GGCGCAGAUCGAUUUGAAU (89)<br>GGCGCAGAUCGAUUUGAAUdTdT (90)<br>UGAGACGCUCGGCCCUCUUdTdT (91) | See above |
| si-hTERT-1 209 | AAGAGGGCCGAGCGUCUCA (92)<br>AAGAGGGCCGAGCGUCUCAdTdT (93)<br>AUUCAAAUCGAUCUGCGCCdTdT (94) | NM_198253.2<br>NM_001193376.1 |
| si-hTERT-2 210 | GAACGUUCCGCAGAGAAAA (95)<br>GAACGUUCCGCAGAGAAAAdTdT (96)<br>UUUUCUCUGCGGAACGUUCdTdT (97) | See above |
| si-hTERT-3 211 | GCACUUCCUCUACUCCUCA (98)<br>GCACUUCCUCUACUCCUCAdTdT (99)<br>UGAGGAGUAGAGGAAGUGCdTdT (100) | See above |
| si-hTERT-4 212 | CACCAAGAAGUUCAUCUCC (101)<br>CACCAAGAAGUUCAUCUCCdTdT (102)<br>GGAGAUGAACUUCUUGGUGdTdT (103) | See above |
| si-hTERT-5 213 | CAUCGCCAGCAUCAUCAAA (104)<br>CAUCGCCAGCAUCAUCAAAdTdT (105)<br>UUUGAUGAUGCUGGCGAUGdTdT (106) | See above |
| siNETO2-1 214 | GACUCAUAUCCACCAAACA (107)<br>GACUCAUAUCCACCAAACAdTdT (108)<br>UGUUUGGUGGAUAUGAGUCdTdT (109) | NM_001201477.1<br>NM_018092.4 |
| siNETO2-2 215 | CAGGGAGAUUCAUGUGGAU (110)<br>CAGGGAGAUUCAUGUGGAUdTdT (111)<br>AUCCACAUGAAUCUCCCUGdTdT (112) | See above |
| siNETO2-3 216 | GUCUUGGUCCUUCUCAUUA (113)<br>GUCUUGGUCCUUCUCAUUAdTdT (114)<br>UAAUGAGAAGGACCAAGACdTdT (115) | See above |

TABLE 2-continued

Exemplary target sequences and siRNA sequences.

| Sequence name/ siRNA number* | Target sequence/siRNA sense sequence/siRNA antisense sequence, 5'-3' SEQ ID No follows sequences in parenthesis | Position and GenBank Accession No. of targets |
|---|---|---|
| siAR-3-O-Me 217 | GCUGAAGAAACUUGGUAAU (116)<br>GCoUGAAGAAACUoUGGoUAAU (117)<br>AUoUACoCAAGUUUCUUoCAGC (118) | See above (siAR-1) |
| siNETO2-1-O-Me 218 | GACUCAUAUCCACCAAACA (119)<br>GACUoCAoUAUCoCACoCAAAoCA (120)<br>oUGUUoUGGoUGGAUAoUGAGUC (121) | See above (siNETO2-1) |
| gp130 219 | GGCAUACCUUAAACAAGCU (122)<br>GGCAUACCUUAAACAAGCUdTdT (123)<br>AGCUUGUUUAAGGUAUGCCdTdT (124) | NM_001190981.1<br>NM_175767.2<br>NM_002184.3 |
| PTPRA-1 220 | GACGACAAUAAGCUCUUCA (125)<br>GACGACAAUAAGCUCUUCAdTdT (126)<br>UGAAGAGCUUAUUGUCGUCdTdT (127) | NM_080840.2 |
| PTPRA-2 221 | CCUUAUGACCACUCUAGAG (128)<br>CCUUAUGACCACUCUAGAGdTdT (129)<br>CUCUAGAGUGGUCAUAAGGdTdT (130) | See above |
| PTPRA-3 222 | GAUGAGACACCAAUUAUUG (131)<br>GAUGAGACACCAAUUAUUGdTdT (132)<br>CAAUAAUUGGUGUCUCAUCdTdT (133) | See above |
| PTPRA-4 223 | GCCAAAACUUCAAAUCCAA (134)<br>GCCAAAACUUCAAAUCCAAdTdT (135)<br>UUGGAUUUGAAGUUUUGGCdTdT (136) | See above |
| PTPRA-5 224 | CCACAAGAACAGCAAGCAC (137)<br>CCACAAGAACAGCAAGCACdTdT (138)<br>GUGCUUGCUGUUCUUGTGGdTdT (139) | See above |
| PAPPA-1 225 | CGACGACAUGAAUAAGAUC (140)<br>CGACGACAUGAAUAAGAUCdTdT (141)<br>GAUCUUAUUCAUGUCGUCGdTdT (142) | NM_002581.3 |
| PAPPA-2 226 | CCAUCAGCUACCCAUAUUC (143)<br>CCAUCAGCUACCCAUAUUCdTdT (144)<br>GAAUAUGGGUAGCUGAUGGdTdT (145) | See above |
| PAPPA-3 227 | GGAAGGCAACCAGCUGUUA (146)<br>GGAAGGCAACCAGCUGUUAdTdT (147)<br>UAACAGCUGGUUGCCUUCCdTdT (148) | See above |
| siErbB3-1 228 | GCUGAGAACCAAUACCAGA (149)<br>GCUGAGAACCAAUACCAGAdTdT (150)<br>UCUGGUAUUGGUUCUCAGCdTdT (151) | NM_001982.3<br>NM_001005915.1 |
| siErbB3-2 229 | CAACUCUCAGGCAGUGUGU (152)<br>CAACUCUCAGGCAGUGUGUdTdT (153)<br>ACACACUGCCUGAGAGUUGdTdT (154) | See above |
| siPSCA-1 230 | CACGAAGGCUGUGCUGCUU (155)<br>CACGAAGGCUGUGCUGCUUdTdT (156)<br>AAGCAGCACAGCCUUCGUGdTdT (157) | NM_005672.4 |
| siPSCA-2 231 | CGUGCUGUGACACCGACUU (158)<br>CGUGCUGUGACACCGACUUdTdT (159)<br>AAGUCGGUGUCACAGCACGdTdT (160) | See above |
| siBrd4-1 232 | CCAACGCAGCCAGCACCAA (161)<br>CCAACGCAGCCAGCACCAAdTdT (162)<br>UUGGUGCUGGCUGCGUUGGdTdT (163) | NM_014299.2<br>NM_058243.2 |
| siBrd4-2 233 | CUGGAAUGCUCAGGAAUGU (164)<br>CUGGAAUGCUCAGGAAUGUdTdT (165)<br>ACAUUCCUGAGCAUUCCAGdTdT (166) | See above |

TABLE 2-continued

Exemplary target sequences and siRNA sequences.

| Sequence name/ siRNA number* | Target sequence/siRNA sense sequence/siRNA antisense sequence, 5'-3' SEQ ID No follows sequences in parenthesis | Position and GenBank Accession No. of targets |
|---|---|---|
| siEZH2-1 234 | CCUGACCUCUGUCUUACUU (167) CCUGACCUCUGUCUUACUUdTdT (168) AAGUAAGACAGAGGUCAGGdTdT (169) | NM_004456.4, NM_152998.2, NM_001203247.1, NM_001203248.1, NM_001203249.1 |
| siEZH2-2 235 | CUGGGAAGAAAUCUGAGAA (170) CUGGGAAGAAAUCUGAGAAdTdT (171) UUCUCAGAUUUCUUCCCAGdTdT (172) | See above |

Figure 4A:
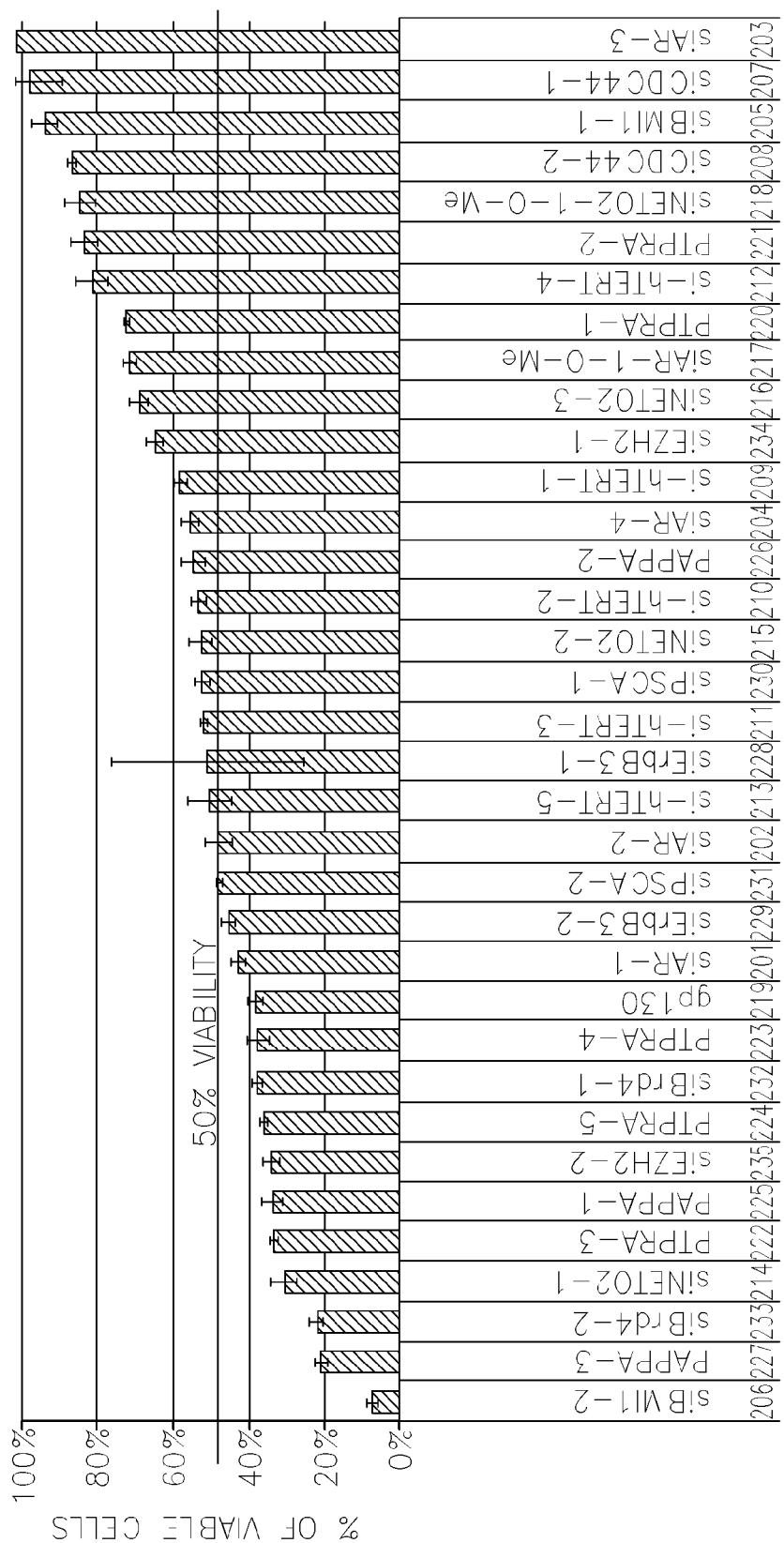
FIGS. 4A-4D show the effect of treatment by various siRNA on viability of PC3 cells, ordered by efficacy (FIG. 4A), and on mRNA levels (FIGS. 4B, 4C, and 4D). PC3 were seeded in E-well plates one day before transfection. Transfection was performed using Lipofectamine 2000 transfection reagent. The indicated siRNAs were used at a 150 nM concentration, which is 6-µg/well. Scrambled (non-targeting) siRNA was used as a transfection control. For the viability test, cells were grown for 72 hrs, fixed in 4% PFA and stained as by Methylene blue (MB). Percentage viability was normalized to the viability of the scrambled-transfected cells. In each case, the difference between the siRNA-treated cells the scrambled-transfected cells was significant when compared to the difference between the quadruplicate samples. For RNA quantization, 24-hrs post-transfection, total RNA was purified using Trizol® reagent (Invitrogen™). cDNA was prepared using gScript™ cDNA Synthesis kit (Quanta Biosciences). Relative mRNA level was assessed compared to HPRT endogenous control using the Image Gauge computer program.

*"siRNA number" refers to the internal reference number used in FIG. 4A.

RNAi Agents

The term "nucleotide-based agent", as used herein, refers to a single-stranded or double-stranded nucleotide molecule containing DNA, RNA, or a mixture thereof, including modified bases. In certain embodiments, when modified bases are used, only modified bases that retain the qualities of the unmodified bases (such as, for example, hybridization to a complementary sequence or ability to program a ribosome) are utilized.

The term "RNAi agent", as used herein, refers to a nucleotide molecule that decreases or "downregulates" the level of an RNA target in a cell in a sequence-specific manner. In other embodiments, the RNA target is a messenger RNA.

In particular embodiments, RNAi nucleotides are short (or small) interfering RNA (siRNA), short hairpin RNA (shRNA), and microRNA. Other embodiments include longer polynucleotide molecules that are processed intracellularly to yield siRNA. Such molecules include DsiRNA, which are cleaved by the RNase III class endoribonuclease dicer into 21-23 base duplexes having a 2-base 3'-overhang; UsiRNAs, which are duplex siRNAs that are modified with non-nucleotide acyclic monomers, termed unlocked nucleobase analogs (UNA), in which the bond between two adjacent carbon atoms of ribose is removed—these may be designed to enter the RNAi (RNA inhibitory) pathway via Dicer enzyme or directly into RISC; self-delivering RNA (sdRNA) such as rxRNA® of RXi Therapeutics, which has a single-stranded phosphorothioate region, a short duplex region, and contains a variety of nuclease-stabilizing and lipophilic chemical modifications; aptamers, triple-helix antisense nucleotides, DNAzymes; and agents inhibiting the pre-mRNA maturation step of polyA tail addition such as the U1 adaptor (Integrated DNA Technologies (IDT) Inc). The U1 adaptor consists of two parts, a target-gene binding domain and a U'1 domain that attracts and inhibits the cellular splicing apparatus. By combining both capabilities in the same molecule, the U1 adaptor can inhibit the pre-mRNA maturation step of polyA tail addition.

Modifications of Specific Sequences

The above sequences are, in some embodiments, one or both strands of an siRNA described herein is modified by 2'-OMe, 2'-F, or other modifications. In some embodiments, the positions identified below with an "o" may be modified with 2'-OMe:

AR siRNA (internal ref. no. 217):
Sense:
(SEQ ID No: 117)
5' GCoUGAAGAAACUoUGGoUAAU Anti sense:
(SEQ ID No: 118)
3' AUoUACoCAAGUUUCUUoCAGC siNETO2 (internal ref. no. 218):
Sense:
(SEQ ID No: 120)
5' GACUoCAoUAUCoCACoCAAAoCA Antisense:
(SEQ ID No: 121)
5' oUGUUoUGGoUGGAUAoUGAGUC.

2'-OMe-modified oligonucleotides may be used with or, in other embodiments without, overhangs at the 3' end of each of the strands. In certain embodiments, the overhangs each consist of two unpaired nucleotides. In more specific embodiments, as exemplified herein, the overhangs are each dTdT (2 deoxythymidine residues). Specific, non-limiting examples of siRNA molecules with 2'-OMe-modifications and dTdT tails are shown further below.

In other embodiments, the following 4 sequence criteria are used to design additional siRNA molecules:
(1) AU richness in the 5'-terminal, 7-bp-long region of the antisense strand;
(2) G/C at the 5' end of the sense strand; and
(3) the absence of any long GC stretch of >9 bp in length.
(4) a G/C content ranging from 36% to 52%.

In certain embodiments, an RNAi agent that is used is between 25-30 nt, inclusive, in length. More specifically, the length may be 25-27 nt. In other embodiments, the length is 19-25-nt. In other embodiments, the length is 19 nt. In other embodiments, the sense strand and/or the antisense strand further comprises a 1-6-nt 3'-overhang. In other embodiments, a two-base 3' overhang is present. In more specific embodiments, the sense strand and the antisense strand each further comprises a 2-nt 3'-overhang.

siRNA structure determinants: In one embodiment, the A-form helix of the guide strand-mRNA duplex is preferred. A 25-30-nt asymmetric dsRNAs with a 5' blunt end and a 2-nt 3' overhang on the other end is also preferred. In certain embodiments, a blunt structure at the 3' end is present, followed by a 5' overhang.

Loops, if present, may be preferably on the 3' end of the sense strand, or also may be on the 5' end of the sense strand. The loop may contain nucleotides optionally in combination with non-nucleotide residues.

In other embodiments, an siRNA used in the described methods and compositions has a 19+2 overhang design, namely sense and anti-sense of 19 base-paired nucleotides and two unpaired nucleotides at the 3' end of each of the strands. In certain embodiments, as exemplified herein, the overhangs are each dTdT (2 deoxythymidine residues). Non-limiting examples of siRNA molecules with dTdT tails are shown in Table 2. Additional examples are GUUG-GAGCUGUUGGCGUAGdTdT (SEQ ID No: 173), CUACGCCAACAGCUCCAACdTdT (SEQ ID No: 174), and the AR and siNETO sequences below.

```
AR siRNA + tail:
Sense:
                                      (SEQ ID No: 175)
5' GCoUGAAGAAACUoUGGoUAAUdTdT Antisense:
                                      (SEQ ID No: 176)
3' AUoUACoCAAGUUUCUUoCAGCdTdT siNETO2 + tail:
Sense:
                                      (SEQ ID No: 177)
5' GACUoCAoUAUCoCACoCAAAoCAdTdT Antisense:
                                      (SEQ ID No: 178)
5' oUGUUoUGGoUGGAUAoUGAGUCdTdT.
```

Chemical Modifications

In other embodiments, an RNAi agent, for example an siRNA agent, used in the described methods and compositions may be chemically modified. In another embodiment, the modification is a backbone or linkage modification. In another embodiment, the modification is a nucleoside base modification. In another embodiment, the modification is a sugar modification. In more specific embodiments, the modification is selected from the modifications appearing in Table 2 hereinbelow. In more specific embodiments, the modification is selected from a 2'-O-methyl (2'-OMe), 2'-O-(2-methoxyethyl) (MOE) and 2'-fluorine modification. In still more specific embodiments, the modification is a 2'-O-methyl (2'-OMe) modification. In other embodiments, the modification is selected from a locked nucleic acid (LNA) and/or peptide nucleic acid (PNA) backbone.

Figure 7A:
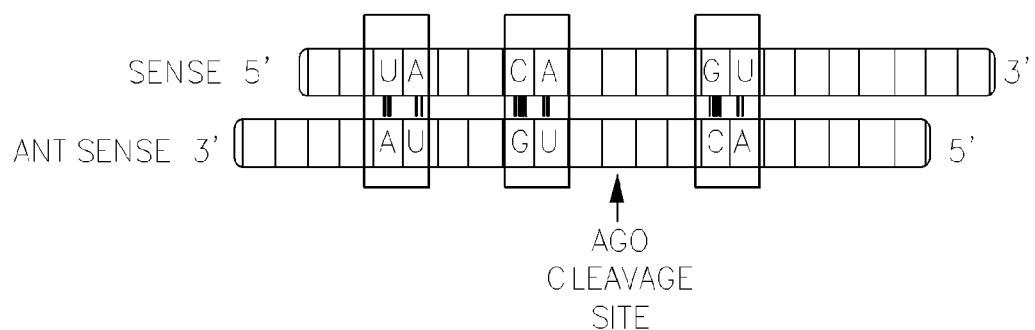
FIG. 7A shows the Argonaut (Ago) cleavage site on an siRNA with overhangs and exemplary sites for modifications.
Figure 7B:
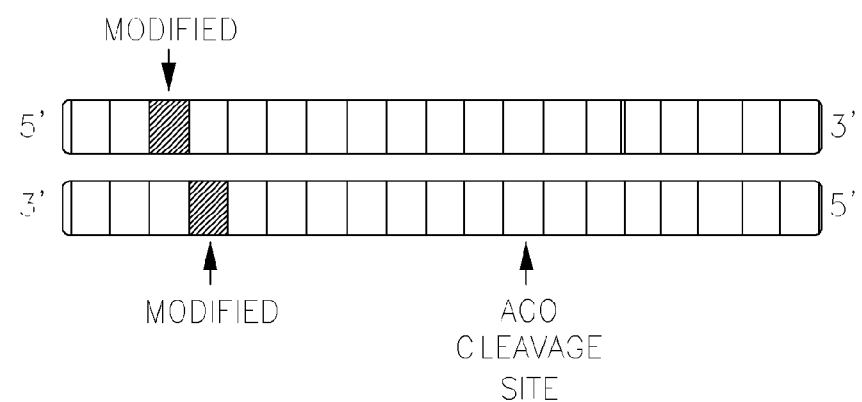
FIG. 7B. shows the Ago cleavage site on a blunt-ended siRNA, and exemplary sites for modifications.

In some embodiments, siRNA modifications are designed based on the following guidelines:

1. Cluster modifications around endonuclease cleavage sites: 5'-UA, 5'-CA, 5'-UG
2. When choosing modification sites use the following guiding rules:
   a. Fewer modifications on the antisense strand compared to the sense strand.
   b. Avoid modifications on the Argonaut (Ago) cleavage site (the 10nth nucleotide on antisense strand; FIGS. 7A-B).
   c. As modification increases duplex stability, therefore make fewer modifications on the 3' end of the sense strand or the 5' end of antisense strand.
3. Order modifications in diagonal 5' to 5'.
4. Use of blunt ends instead of overhangs lower exonuclease activity.

TABLE 3

Selected chemical modifications.

| Modification | Position of the substitution |
|---|---|
| Sugar modifications | |
| dNTPs-dTdT | 3'-overhangs of sense and anti-sense strands |
| dNTPs-dNPs | Any number of residues in the sense strand; 0-4 residues at the 5' end of the antisense strand |
| 2'-O-methyl (2'OMe) rNPs | Any number of residues in the sense and antisense strands |
| 2'-fluoro (2'-F) rNPs | Any number of pyrimidine residues in the sense and antisense strands |
| combined use of 2'OMe and 2'-F | Any number of pyrimidine residues in the sense and antisense strands to 2'-F; and any number of purine residues in the sense and antisense strands to 2'-OMe. |
| 2'-O-(2-methoxyethyl) (MOE) rNPs | Any number of pyrimidine residues in the sense and antisense strands |
| 2'-fluoro-β-D (FANA) rNPs | Any number of pyrimidine residues in the sense strand |
| Locked nucleic acids (LNA) | from none till 4 last ribonucleotides at the 3' end of the sense strand; and 3' overhangs of the antisense strand |
| combined use of DNA and 2'-F | substitution of any number of pyrimidine (T and C) ribonucleotides to 2'-F ribonucleotides and any number of purines (A and G) to deoxyribonucleotides in sense and antisense strands |
| phosphate linkage modifications - phosphorotioate (PS) | |
| phosphodiester | substitution of any number of ribonucleotides in sense and antisense strands |
| phosphothioate (PS) | substitution of any number of ribonucleotides in sense and antisense strands |
| boranophosphate DNA or RNA | substitution of any number of ribonucleotides in sense and antisense strands |
| amide-linked | substitution of any number of ribonucleotides in sense and antisense strands |
| phosphoramidate | substitution of any number of ribonucleotides in sense and antisense strands |
| methylphosphonate | substitution of any number of ribonucleotides in sense and antisense strands |
| 2',5'-linked DNA or RNA | substitution of any number of ribonucleotides in sense strand |
| Base modifications | |
| 5-bromouracil (5-Br-Ura) | substitution of any number of ribouraciles in sense and antisense strands |
| 5-iodouracil (5-I-Ura) | substitution of any number of ribouraciles in sense and antisense strands |
| dihydrouracil | substitution of any number of ribouraciles in sense and antisense strands |
| 2-thiouracil | substitution of any number of ribouraciles in sense and antisense strands |
| 4-thiouracil | substitution of any number of ribouraciles in sense and antisense strands |
| pseudouracil | substitution of any number of ribouraciles in sense and antisense strands |
| diaminopurine | substitution of any number of adenines in both sense and antisense |
| difluorotoruene | substitution of any number of adenines in both sense and antisense |
| peptide nucleic acids (PNAs) (2-aminoethylglycine) | substitution of any number of ribonucleotides in sense and antisense strands |
| modifications to the overhangs and termini | |
| 2-nt-3'-DNA overhang | 3' end of sense and antisense strands |
| 2-nt-3'-RNA overhang | 3' end of sense and antisense strands |
| blunt-ended duplexes | 3' end of sense and antisense strands |
| chemical conjugation | |
| cholesterol | covalently attached to sense strand |
| vitamin-E (α-tocopherol) | covalently attached to sense strand |

In other embodiments, the chemical modification is a modification described in paragraphs 0040-0050 of US Patent Application Pub. No. 2011/0195123, the contents of which are incorporated herein by reference.

In other embodiments, the chemical modification is a modification to the overhang(s) and/or termini, or to the duplex architecture, as described in paragraphs 0061 and 0062, respectively, of US Patent Application Pub. No. 2011/0195123.

In other embodiments, an RNAi agent, for example an siRNA agent, used in the described methods and compositions may be conjugated to a molecule. In more specific embodiments, a non-nucleotide molecule is used. In more specific embodiments, the molecule may be cholesterol, a cell penetrating peptide, or alpha-tocopherol-vitamin E. In certain embodiments, the cholesterol may be conjugated to the 3' end of the sense strand. In other embodiments, the cholesterol may be conjugated to the 5' end of the sense strand. In certain embodiments, in the case of a hairpin-shaped molecule, the cholesterol may be conjugated to the loop. In other embodiments, the non-nucleotide molecule is a molecule described in paragraphs 0051-0060 of US Patent Application Pub. No. 2011/0195123.

In certain embodiments, the RNAi agent, for example an siRNA agent, is associated, either via covalent attachment or via non-covalent complexation, with a cell-penetrating peptide (CPP), also referred to as protein transduction domains (PTDs). A CPP is a peptide that has the ability to traverse the plasma membrane and facilitate the delivery of a molecular cargo to the cytoplasm. CPP's include HIV-1 Tat (NCBI Gene ID: 155871) or a fragment thereof comprising the sequence YGRKKRRQRRR (SEQ ID No: 179); pAntp (penetratin) and pIsl, which originate from the third helix of homeodomain proteins (Antennapedia (NCBI Gene ID: 40835; Terrone et al) and Is1-1 (NCBI Gene ID: 3670 and Magzoub et al), respectively); Transportan, a synthetic chimera of galanin and mastoparan (GWTLNSAGYLLGKIN-LKALAALAKKIL-amide; Pooga et al; SEQ ID No: 180), MPG (GALFLGFLGAAGSTMGA; SEQ ID No: 181); Pep-1 (KETWWETWWTEW; SEQ ID No: 182); and secondary amphipathic peptides based on aromatic tryptophan and arginine residues linked with lysine as spacer ("CADY"; SEQ ID No: 183), which contain a short peptide sequence of 20 amino acids, with the sequence "Ac-GLWRALWRLL-RSLWRLLWRA-cysteamide" (SEC) ID No: 184). CPP's are known to those skilled in the art and are described inter alia in Deshayes et al.

In other embodiments, an RNAi agent used in the described methods and compositions is a hairpin-shaped siRNA molecule. In another embodiment, an RNAi agent used in the described methods and compositions is a double-stranded molecule containing 2 separate strands. In another embodiment, the RNAi agent is selected from the group consisting of a small interfering RNA (siRNA), a short hairpin RNA (shRNA), a Dicer-substrate siRNAs (DsiR-NAs), a microRNA, and a non-coding RNA.

Millimeter-Scale Implant/Drug Delivery Technology

The drug delivery device of the described methods and compositions may be a cylinder, a sphere, or any other shape suitable for an implant (i.e. that can be implanted in a subject). In certain embodiments, the device is a cylinder.

"Millimeter-scale", as used herein, refers to a device whose smallest diameter is a least 0.3 mm. In certain embodiments, each of the dimensions (diameter, in the case of a sphere or cylinder; and height and/or width or length, in the case of a cylinder, box-like structure, cube, or other shape with flat walls) is between 0.3-20 mm, inclusive. In other embodiments, each dimension is between 0.5-15 mm, inclusive. In still other embodiments, each dimension is between 0.6-5.2 mm, inclusive, between 0.7-4 mm, inclusive, or between 0.78-3 mm, inclusive.

Table 3 presents the range of needle gauge and internal diameters that may be used in some embodiments. In some embodiments, the internal diameter of the needle dictates the diameter of the DDD, that is typically designed to be reduced by 1%-15% percent.

TABLE 3

(Source: Hamilton Company, Reno USA)

| Needle gauge | Internal Diameter (ID) in millimeters |
|---|---|
| 25 | 0.26 |
| 24 | 0.311 |
| 23s | 0.116 |
| 23 | 0.337 |
| 22s | 0.168 |
| 22 | 0.413 |
| 21 | 0.514 |
| 20 | 0.603 |
| 19 | 0.686 |
| 18 | 0.838 |
| 17 | 1.067 |

In yet other embodiments, the device is a cylinder, having a diameter in the range of 0.4-0.84 mm. In other preferred embodiments, the cylinder has a length of 5 mm. In other embodiments, the cylinder has a diameter of 0.8 mm and a length of 5 mm. In other embodiments, a DDD of the described methods and compositions has the diameter of an 18-gauge needle.

In yet other embodiments, the device is cylindrical, with an 0.83-mm diameter (~0.033") and a length of 5 mm.

In other embodiments, the volume of the device is between 0.1 mm$^3$ and 1000 mm$^3$, between 0.2 mm$^3$ and 500 mm$^3$, between 0.5 mm$^3$ and 300 mm$^3$, between 0.8 mm$^3$ and 250 mm$^3$, between 1 mm$^3$ and 200 mm$^3$, between 2 mm$^3$ and 150 mm$^3$, between 3 mm$^3$ and 100 mm$^3$, or between 5 mm$^3$ and 50 mm$^3$.

An exemplary embodiment of a DDD has a diameter of 0.8 mm and a length of 5 mm, containing 25% w/w siRNA, namely about 650 µg of siRNA. In other embodiments, the DDD's contain siRNA; PLGA 85:15; D-Mannitol, and sodium bicarbonate. In other experiments, the DDD's contain siRNA, PLGA, trehalose, and sodium bicarbonate. In more particular embodiments, the molecular weight of the PLGA is between 5-15 kDa, inclusive.

In other embodiments, the w/w agent:polymer load ratio is above 1:100. In more preferred embodiments, the load is above 1:20. In more preferred embodiments, the load is above 1:9. In more preferred embodiments, the load is above 1:3

In other embodiments, the device is DDD that is described in US Patent Application Pub. No. 2011/0195123.

The DDD is designed in some embodiments to preferably employ degradable polymers, wherein the release mechanism includes both bulk erosion and diffusion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). The term "constant" refers to a diffusion rate that is preferably maintained above the lower threshold of therapeutic effectiveness, but which may still optionally feature an initial burst and/or fluctuate, for example increasing and decreasing to a certain degree. In other embodiments, there is an initial burst of less than 10% of the total amount of drug, which may be considered negligible. In other embodiments, there is an initial burst of about 20% of the total amount of drug. In other embodiments, the design enables initial a strong burst of 30% or more of the total amount of drug. The diffusion rate is preferably so maintained for a prolonged period, and it can be considered constant to a certain level to optimize the therapeutically effective period, for example the effective silencing period. These embodiments are described in US Patent Application Pub. No. 2011/0195123.

In other embodiments, the described DDD comprises small particles incorporated into a polymeric matrix, wherein the small particles themselves contain, in some embodiments, a polymeric material, and the compositions can contain the drug within the matrix in addition to the drug encapsulated in the particles. In certain embodiments, the diameter (or longest dimension, in the case of a non-spherical device) of the DDD is at least 100-fold greater than the mean particle diameter by a factor of 100, and the volume of the DDD is at least 1,000,000-fold greater than the mean particle volume.

In certain embodiments, the small particles also comprise a polymeric material. In these embodiments, the polymeric material in the particles is referred to below as the "first polymeric material", while the polymeric material in the matrix is referred to as the "second polymeric material". In various embodiments, the polymeric material in the particles may be entirely different from, similar to, or identical to that in the matrix. "Entirely different from" refers to a polymer made from different building blocks from that in the matrix, for example PCL (poly-caprolactone) as opposed to poly (lactic-co-glycolic acid) (PLGA). "Similar to" refers to a polymer sharing at least one building block with the polymer in the matrix, for example poly(lactic acid) (PLA) as opposed to PLGA. Another example of similar polymers are polymers containing a particular enantiomer as opposed to a racemic mixture of a given building block (L-PLA vs. DL-PLA), polymers containing the same building blocks in a different ratio (having either the same or different molecular weight (MW), or containing the same building blocks but having a different MW (having either the same or different ratio. "Identical to" refers to polymers with the same building blocks, in the same ratio, and with the same MW. "Identical to" in this context does not preclude polymers that contain different materials other than the polymer building blocks). In certain embodiments, the polymer in the particles is non-identical to the polymer in the matrix.

In certain embodiments, all the RNAi agent in the composition is contained within the small particles. In other embodiments, there is also RNAi agent present within the matrix.

In other embodiments, the presence of drug both within and outside the particles enables biphasic drug release. The presence of drug outside the particles can achieve a higher drug load, for example as high as ~30% of the mass of the device. On the other hand, the presence of drugs within the particles enables a larger effective volume of drug penetration (FIG. 1). The combination of these two phases thus simultaneously optimizes drug load and effective radius for certain applications.

In other embodiments, less than 50% by weight of the RNAi agent in the composition, for example less than 45%, 40%, 35%, 30%, or 25% of the RNAi agent is contained within the small particles. In still other embodiments, less than 20% by weight of the RNAi agent in the composition is contained within the small particles. In yet other embodiments, less than 18%, 16%, 14%, 12%, 10%, 8%, 7%, 6%, 5%, or 4% by weight of the RNAi agent in the composition is contained within the small particles.

In other embodiments the volume ratio [total volume of particles/volume of DDD] is less than 70%, less than 60%, less than 50%, less than 40%, less than 30%, or less than 20%, and the extra-particle volume contains additional drug.

DDD's containing nanoparticles are described inter alia in US Patn. Appl. Publ. No. 2013/0122096 to Shemi Amotz et al, the contents of which are incorporated herein by reference.

Suitable Release Profiles

In preferred embodiments, a device of the described methods and compositions is designed to release the nucleotide-based agent, in some embodiments the RNAi agent, in more specific embodiments the siRNA agent, in a controlled fashion. It will be apparent to those of skill in the art, in light of the knowledge in the art taken together with the information provided herein, that the PLA:PGA ratio, composition and additives, and/or the molecular weight (MW) of the polymer, and controlling the surface-to-volume ratio of the implant may be adjusted to achieve a particular release profile. For example, deviating the PLA:PGA ratio from 50:50, or increasing the MW, or reducing surface-to-volume ratio can increase the release time.

In other embodiments, the DDD of the described methods and compositions is designed with a particular release profile. One relevant parameter is the time point at which 95% of the active agent has been released. In some embodiments, the DDD releases 95% of the active agent in vivo, for example in a human pancreas, at a time point between 3-24 months inclusive, for example, in various embodiments, 3, 4, 5, 6, 8, 10, 12, 14, 16, 18, 20, 22, or 24 months. In other embodiments, the time point of release of 95% of the active agent is between 3-12 months inclusive, between 2-24 months inclusive, between 2-15 months inclusive, between 3-15 months inclusive, between 3-12 months inclusive, between 3-10 months inclusive, between 4-24 months inclusive. Another relevant parameter is the time point at which 90% of the active agent has been released; this may be any of the aforementioned time frames.

Another relevant parameter is the percent of active agent released at a given time point. For example, in some embodiments, 80-99% inclusive of the active agent is released at the 3-month timepoint. In other embodiments, 80-99% inclusive of the active agent is released at the 2-month timepoint or the 4-month, 6-month, 9-month, 12-month, or 24-month timepoint, each of which is considered a separate embodiment.

Alternatively or in addition, in some embodiments no more than 30-50% of the active agent of a DDD of the described methods and compositions is released during the first 3 weeks.

In other embodiments, a delayed-release DDD is utilized. "Delayed-release", as used herein, refers to DDD's that do not release more than 10% of their drug load within the first 2 months (discounting an initial burst of up to 20%, which sometimes occurs). In other embodiments, the DDD does not release more than 10% of its drug load within the first 3 months. The inventors have discovered that, in some embodiments, DDD's containing 1% trehalose exhibit delayed release. Trehalose has the additional advantage that, in some embodiments, it is effective at a concentration of only 1% (as opposed to 5-10% for mannitol, for example), thus allowing an increased drug load.

In other embodiments, the DDD is coated (by dipping, spraying, or any other method known to those skilled in the art) with a slowly-degraded polymer that contains no drug. Various embodiments of slowly-degraded polymers are described herein, each of which can be utilized to create a delayed-release DDD. In some embodiments, the coating comprises a linear-chain monosaccharide; a disaccharide; a cyclic monosaccharide, a cyclic disaccharide. In other embodiments, the coating comprising an additive selected from lactose, sucrose, dextran, and hydroxyethyl starch. In yet other embodiments, the coating comprises mannitol. Alternatively, the coating may comprise trehalose. In still other embodiments, the coating does not comprise a sugar.

In certain embodiments, less than 5% of the RNAi agent is released from the DDD during the first 1 month starting from implantation. In other embodiments, less than 10% of the RNAi agent is released from the DDD during the first 1 month starting from implantation. In other embodiments, less than 10% of the RNAi agent is released during the first three months starting from implantation.

In other embodiments, a delayed-release DDD is provided, comprising an siRNA against a target that is not a prostate-cancer-related target gene. In some embodiments, the target is an oncogene that is not overexpressed in prostate cancer.

In other embodiments, a therapeutic package is provided, comprising both (a) one or more delayed-release DDD and (b) one or more DDD that is not delayed-release. In some embodiments, the DDD comprise an siRNA against a prostate-cancer-related target gene. In other embodiments, siRNA is against a target that is not a prostate-cancer-related target gene, which in some embodiments is an oncogene.

In other embodiments, a DDD described herein is a delayed-release DDD. In other embodiments, a therapeutic package is provided, comprising both (a) one or more delayed-release DDD and (b) one or more DDD that is not delayed-release.

Other exemplary release profiles are depicted in FIG. 1.

In some embodiments the DDD is design as a polymeric uniform matrix. In some additional embodiments the DDD is designed as a reservoir. Drug is released approximately as per the following power lows $t^{1/2}$ and t as follows:

Matrix $$Q=(DpCp(2A-Cp))^{1/2} \times t^{1/2}$$

Reservoir $$Q=(DpCp)/h \times t$$

Where:
Q: cumulative amount of drug released per unit area (mg/mm$^2$),
t: time (days),
A: initial amount of drug loading per unit volume in a matrix system (mg/mm$^3$),
Dp: diffusion coefficient of the drug in the polymer (mm$^2$/sec),
Cp: solubility of the drug in the polymer (mg/mm$^3$), and
h: thickness of the sheet layer in the reservoir-type system (mm).

Suitable Biodegradable Matrices

In certain embodiments, the biodegradable matrix present in the drug delivery device comprises poly(lactic acid) (PLA). In other embodiments, the biodegradable matrix comprises poly(glycolic acid) (PGA). In other embodiments, the biodegradable matrix comprises both PLA and PGA (known as poly(lactic-co-glycolic acid) or PLGA).

Methods for making PLGA matrices that incorporate RNAi agents are well known in the art. Exemplary methods are described in described in US Patent Application Pub. No. 2011/0195123—for example in Examples 1.1 and 1.2 thereof.

In other embodiments, the PLA/PGA ratio of PLGA used in the methods and compositions is between 25:75 and 75:25. In other embodiments, the ratio is between 50:50 and 75:25, meaning that there is between 50-75% PLA and between 25-50% PGA in the biodegradable matrix (discounting substances other than polymer building blocks). In other embodiments, the PLA/PGA ratio is between 25:75 and 50:50, between 35:65 and 75:25, between 45:55 and 75:25, between 55:45 and 75:25, between 65:35 and 75:25, between 75:25 and 35:65, between 75:25 and 45:55, between 75:25 and 55:45, or between 75:25 and 65:25. In other embodiments, the PLA/PGA ratio is between 80:20 and 90:10, inclusive.

In other embodiments, the PLA/PGA ratio is larger than 75:25, between 75:25 and 85:15, or between 75:25 and 95:5. Alternatively, the ratio is smaller than 25:75, between 25:75 and 15:85, or between 25:75 and 5:95.

In other embodiments, the polymer comprises a polymer selected from the group consisting of poly(glycolide-co-lactide) (PLGA), polylactic acid (PLA) and polyglycolic acid (PGA) and polyethylene glycol (PEG). In other embodiments, the polymer comprises both PLA and PEG (poly(ethylene glycol)). In other embodiments, the polymer comprises PLA, PGA, PEG, PLGA, poly-caprolactone (PCL), dihydrolipoic acid (DHLA), and combinations thereof. In still other embodiments, the polymer is selected from PLA, PGA, PEG, PLGA, PCL, DHLA, and combinations thereof.

In other embodiments, tri-block PLA-PCL-PLA is used.

In other embodiments, Poly(D,L-lactide) (DL-PLA), poly (D,L-glycolide), or poly(D,L-lactide-co-glycolide) is used, each of which is considered a separate embodiment.

Design of biodegradable controlled drug-delivery carriers containing PLA, PGA, PEG, and/or PCL to have a specified release profile is well-within the ability of those skilled in the art, and is described inter alia in Makadia and Siegel, *Poly Lactic-co-Glycolic Acid (PLGA) as Biodegradable Controlled Drug Delivery Carrier*, Polymers 2011, 3:1377-1397.

In another embodiment, the polymer is a polymer described in paragraphs 0076-0078 of US Patent Application Pub. No. 2011/0195123.

In some embodiments, a polymer used in the methods and compositions described herein has a molecular weight (MW) of greater than 5 kilodaltons (kDa). In other embodiments, the MW is greater than 50 kDa. In other embodiments, the MW is greater than 7 kDa, greater than 10 kDa, greater than 15 kDa, greater than 20 kDa, greater than 30 Da, greater than 70 kDa, greater than 100 kDa, greater than 150 kDa, or greater than 200 kDa. In other embodiments, the MW is between 5-100 kDa, inclusive, between 7-80 kDa, inclusive, between 10-60 kDa, inclusive, between 20-50 kDa, inclusive, or between 25-50 kDa, inclusive. As provided herein (Example 2), very slow release (approximately 6 months) can be achieved, PLGA of high PLA:PGA ratio, such as 90:10, and MW (molecular weight) higher than 50 KDa. A similar effect can be achieved by use of PLA.

In some embodiments, the polymer is L-PLA that has a molecular weight of greater than 5 kilodaltons (kDa). In other embodiments, the MW of the L-PLA is greater than 50 kDa. In other embodiments, the MW is greater than 7 kDa, greater than 10 kDa, greater than 15 kDa, greater than 20 kDa, greater than 30 Da, greater than 70 kDa, greater than 100 kDa, greater than 150 kDa, or greater than 200 kDa. In other embodiments, the MW of the L-PLA is between 5-100 kDa, inclusive, between 7-80 kDa, inclusive, between 10-60 kDa, inclusive, between 20-50 kDa, inclusive, or between 25-50 kDa, inclusive.

In some embodiments, the polymer is PLGA that has a molecular weight of greater than 5 kilodaltons (kDa). In other embodiments, the MW of the PLGA is greater than 50 kDa. In other embodiments, the MW is greater than 7 kDa, greater than 10 kDa, greater than 15 kDa, greater than 20 kDa, greater than 30 Da, greater than 70 kDa, greater than 100 kDa, greater than 150 kDa, or greater than 200 kDa. In other embodiments, the MW of the PLGA is between 5-100 kDa, inclusive, between 7-80 kDa, inclusive, between 10-60 kDa, inclusive, between 20-50 kDa, inclusive, or between 25-50 kDa, inclusive.

In some embodiments, the polymer has a PLA:PGA ratio of between 80:20 and 90:10, inclusive, for example 80:20, 82:18, 84:16, 86:14, 88:12, or 90:10, and a MW of greater than 50 KDa, for example greater than 50 Da, greater than 70 kDa, greater than 100 kDa, greater than 150 kDa, or greater than 200 kDa. In other embodiments, the polymer has a PLA:PGA ratio larger than 75:25, for example 76:24, 78:22, 80:20, 82:18, 84:16, 86:14, 88:12, 90:10, 92:8, 94:6, 96:4, or 98:2, and a MW of greater than 50 KDa. In yet other embodiments, the polymer has a PLA:PGA ratio smaller than 25:75, inclusive, for example 24:76, 22:78, 20:80, 18:82, 16:84, or 14:86, 12:88, 10:90, 8:92, 6:94, 4:96, or 2:98, and a MW of greater than 50 KDa. Each of the aforementioned PLA:PGA ratio may be freely combined with each MW value.

Additives

In other embodiments, the biodegradable matrix further comprises an additive for modulating hydrophilic-hydrophobic interactions; in other embodiments for enabling dispersion of the drug and eliminating aggregation; in other embodiments for preserving the drug in hot-temperature or cold-temperature storage conditions, for example 55° C. and −20° C., respectively, or significantly colder, in the case of lyophilization with liquid nitrogen; in other embodiments for facilitating creation of cavities in the implant that affect to drug diffusion from the matrix. Hydrophilic-hydrophobic interactions may cause aggregation of the active substance in cases of hydrophilic active substances, such as siRNA, incorporated within a hydrophobic polymer, resulting in aggregation during production or subsequently when the device is implanted into the body of a subject and it is subjected for example to hydrolysis. Non-limiting examples of such additives are open monosaccharides, for example mannitol; disaccharides such as trehalose; sorbitol; and other cyclic monosaccharides such as glucose, fructose, galactose and disaccharides such as sucrose. The above additives, when chiral, may be in the form of the D-enantiomer, the L-enantiomer, or a racemic mixture. Additional, non-limiting examples of such additives are lactose, sucrose, dextran, and hydroxyethyl starch.

In other embodiments, more than one additive is present.

In other embodiments, the biodegradable matrix further comprises an additive for protecting the drug against low pH after implantation. The microenvironment in the implant interior tends to be acidic. Unlike chemotherapy, pH should preferably be maintained above a threshold. While doxorubicin is stable in an acidic environment, with minimal hydrolytic degradation within a pH range of 3 to 6.5, RNAi drugs might degrade at pH<3. In more specific embodiments, this additive may be selected from bicarbonates and carbonates, for example sodium bicarbonate, sodium carbonate, and magnesium hydroxide.

In other embodiments, the biodegradable matrix further comprises a small-molecule therapeutic agent against the cancer that is being treated.

In other embodiments, the DDD comprises an immunotherapy agent (Guo et al and references therein; Clinical Immunotherapy Trials Network www.CITNinfo.com). Non-limiting examples of immunotherapy agents are ipilimumab (Yervoy; Bristol-Myers Squibb), sipuleucel-T (Dendreon Corp, Seattle, Wash.), IL-7, CP-870,893 (Pfizer), Allovectin-7 (Vical), BiovaxID (Biovest International), IMA901 (Immatics Biotechnologies GmbH), MAGE-A3 (GlaxoSmithKline), Multikine (CEL-SCI Corporation), NeuVax (Galena Biopharma), PROSTVAC (Bavarian Nordic A/S), Rindopepimut (CDX-110) (Celldex Therapeutics), Stimuvax (Oncothyreon and Merck KGaA), Talimogene laherparepvec (Amgen), and TG4010 (Transgene and Novartis). In certain embodiments, the immunotherapy agent does not comprise live cells.

Numerous types of immunotherapeutic agents have been developed, and a number of intratumoral immunotherapies are currently being examined in clinical trials (Cancer Immunotherapy Trial Network www.CITNinfo.org). Agents include T-cell and NK-cell growth factors like IL-15, others that stimulate T cells or activate dendritic cells, so-called immune checkpoint inhibitors like ipilimumab, and others that inhibit or neutralize factors secreted by tumors that suppress the immune system. Recently, two agents have been selected to be tested in CITN-led trials, selected from the 20 identified in the CITN 2007 workshop, IL-15 and a dendritic cell-activating monoclonal antibody called CP-870,893.

Immunotherapy agent interleukin-15 (IL-15) is a recombinant agent that is chemically identical or similar to the endogenous cytokine interleukin-15 (IL-15) with immunomodulating activity. IL-15, secreted by mononuclear phagocytes (and some other cell types) following viral infection, regulates T and natural killer cell activation and proliferation. This cytokine induces activation of transcription activators STAT3, STATS, and STATE via JAK kinase signal transduction pathways in mast cells, T cells, and dendritic epidermal T cells.

CP-870,893 is a fully human monoclonal antibody (mAb) agonist of the cell surface receptor CD40 with potential immunostimulatory and antineoplastic activities. Similar to the CD40 ligand (CD40L or CD154), CD40 agonist monoclonal antibody CP-870,893 binds to CD40 on a variety of immune cell types, triggering the cellular proliferation and activation of antigen-presenting cells (APCs), activating B cells and T cells, and enhancing the immune response; in addition, this agent can activate CD40 present on the surfaces of some solid tumor cells, resulting in apoptosis and decreased tumor growth.

Dosage and Drug Percentage

A DDD of the described methods and compositions may, in certain embodiments, contain at least 10 µg siRNA. In other embodiments, the amount is between 10-2000 µg (inclusive) siRNA per device. In more specific embodiments, the amount is between 300-1700 (inclusive) µg siRNA per device. In still other embodiments, the amount is between 300-1100 (inclusive), in other embodiments, between 400-1000 (inclusive) µg siRNA per device.

In yet other embodiments, the amount of the nucleotide-based agent, in some embodiments the RNAi agent, in more specific embodiments the siRNA agent, in all the DDD's administered as a batch (a single dose) is at least 4 µg, for example, in various embodiments, at least 5 µg, at least 6 µg, at least 7 µg, at least 8 µg, at least 10 µg, at least 12 µg, or at least 15 µg. In still other embodiments, the amount of RNAi agent present per dose is between 2-10 µg, inclusive, for example 2, 3, 4, 5, 6, 7, 8, 9, or 10 µg.

In yet other embodiments, all the DDD's administered as a batch deliver a dose of 0.008-0.065 mg/kg/month, inclusive, for example 0.008 mg/kg/month, 0.01 mg/kg/month, 0.015 mg/kg/month, 0.02 mg/kg/month, 0.03 mg/kg/month, 0.05 mg/kg/month, or 0.065 mg/kg/month.

In certain embodiments, the drug percentage of a device of the described methods and compositions is at least 20%. In another embodiment, the drug percentage is at least 30%, for example 30%, 35%, 40%, 45%, 50%, 55%, or 60%. In another embodiment, the drug percentage is between 8-30%, inclusive, for example 8%, 9%, 10%, 11%, 12%, 13%, 14%, 15%, 16%, 17%, 18%, 19%, 20%, 22%, 24%, 26%, 28%, or 30%. Some exemplary formulations are as follows:

64-76% PLGA; 16-27% drug; 5-12% mannitol; an exemplary specific formulation is 70% PLGA; 20% drug; 10% mannitol.

In other embodiments, a trehalose-containing DDD is provided, comprising an siRNA against a target described herein. In still other embodiments, a DDD of the methods and compositions described herein comprises trehalose and does not comprise mannitol. In still other embodiments, the DDD comprises both trehalose and mannitol. In more specific embodiments, the DDD may contain 70-91.2% PLGA; 8-30% siRNA; 0.6-1.5% trehalose; and 0.1-0.4% sodium bicarbonate. In other embodiments, the DDD may contain 75-91.2% PLGA; 8-25% siRNA; 0.6-1.5% trehalose; and 0.1-0.4% sodium bicarbonate. In still other embodiments, the DDD may contain 80-91.2% PLGA; 8-20% siRNA; 0.6-1.5% trehalose; and 0.1-0.4% sodium bicarbonate. In yet other embodiments, the DDD may contain 85-91.2% PLGA; 8-15% siRNA; 0.6-1.5% trehalose; and 0.1-0.4% sodium bicarbonate. In additional embodiments, the DDD may contain 88-91.2% PLGA; 8-12% siRNA; 0.6-1.5% trehalose; and 0.1-0.4% sodium bicarbonate. In yet other embodiments, the DDD may contain 89-91% PLGA; 8-10% siRNA; 0.6-1.5% trehalose; and 0.1-0.4% sodium bicarbonate. In still other embodiments, the DDD may contain about 90% PLGA 85:15, about 9% siG12D, about 1% Trehalose, and about 0.2% $NaHCO_3$.

In other embodiments, the DDD has less than 5% trehalose, for example in different embodiments 0.5%, 1%, 1.5%, 2%, 2.5%, 3%, 3.5%, 4%, or 4.5%. Those skilled in the art will appreciate that the release profiles and efficacies of DDD's having varying percentages of trehalose can readily be tested in light of the information provided herein.

Sodium bicarbonate is an excipient that in some embodiments facilitates cavity formation. In other embodiments, sodium bicarbonate facilitates modulation of or decrease in pH. An exemplary specific formulation is 70% PLGA; 28% drug; 1% trehalose; 1% sodium bicarbonate and/or >1% of an excipient that facilitates modulation of decrease in pH.

Additional Features

In other embodiments, a DDD of the described methods and compositions is coated. A coating can be designed for a number of characteristics, including modulating the release rate or preventing protein stickiness during long-term storage. The coating in some embodiments comprises the same material used to form the matrix, for example a PLGA matrix, only without the drug. In other embodiments, the coating comprises a material similar to that used to form the matrix (for example containing the same building blocks in a different ratio, or containing the same polymer but with a different MW), only without the drug. In other embodiments, the polymer of the coating comprises the same building blocks as the polymer used to form the matrix, together with at least one other building block such as PEG. In other embodiments, the coating is selected from polylactic acid (PLA) and PLA:PGA (polyglycolic acid) in a ratio of at least 80:20, inclusive for example 80:20, 82:18, 84:16, 85:15, 86:14, 88:12, 90:10, 92:8, 94:6, 96:4, 98:2, and 99:1, and a MW greater than 50 KDa, for example 60 KDa, 70 KDa, 80 KDa, 100 KDa, 120 KDa, 1500 KDa, or 200 KDa). In more particular embodiments, the coating comprises PLGA in a ratio of at least 80:20, inclusive, having a MW of 50,000-100,000, inclusive.

In certain embodiments, DDD's of dimensions larger than ~0.8 mm can be identified by standard ultrasound (US). In other embodiments, materials to visualization in a medical or surgical procedure, for example CT, MRI or US visualization are included. Non-limiting examples of contrast agents are barium, diatrizoate, ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride.

Activating Device:

Some embodiments include activation via an external device, such as a radiation source or an ultrasound probe, to affect drug release, and/or penetration into cells. Activation can be performed along the time span of the DDD, at a single or several defined time points. The protocol defining such time points can be based on a pre-defined treatment plan and/or changes in patient read-outs.

Other embodiments provide methods of making DDDs described herein. Methods of making various DDD's similar to those presented herein are described in US Patent Application Pub. No. 2011/0195123.

Therapeutic Methods

Also provided is a method of treating a cancer other than prostate carcinoma, comprising the step of implanting the DDD described herein into the vicinity of said tumor. In certain embodiments, the cancer is a carcinoma. In other embodiments, the cancer is selected from the group consisting of cancer of the pancreas, colon, lung, neuroblastoma, glioblastoma, and kidney; hepato-cellular carcinoma, and ovarian cancer. In other embodiments, the cancer is selected from a pancreatic tumor, a colon tumor, a lung tumor, brain cancer, liver cancer, kidney cancer, melanoma, endometrial carcinoma, gastric carcinoma, renal carcinoma, biliary carcinoma, cervical carcinoma, thyroid cancer, cancer of the salivary glands, bladder carcinoma, and esophageal cancer. In more specific embodiments, the cancer is selected from pancreatic carcinoma, pancreatic ductal adenocarcinoma, small-cell lung carcinoma, and colorectal cancer.

In some preferred embodiments, a device is implanted intratumorally. In still other embodiments, the device is implanted into the vicinity of the tumor. In more specific embodiments, in the case of a well-defined solid tumor, several devices are spaced within the tumor volume. In yet other embodiments, several devices are implanted along a needle cavity within the tumor. In still other embodiments, the device or devices are implanted such that they are not in a direct contact with the perimeter of the tumor. Alternatively, in the case of a poorly defined solid tumor, the device is inserted into an area believed to contain tumor cells. In other embodiments, the DDD is implanted into the subject using a biopsy needle.

In other embodiments, the DDD is implanted into the subject using a delivery device as described in WO 2010/086849 to Silenseed Ltd.

Also provided herein is a device described herein, for treating a cancer other than prostate carcinoma. In certain embodiments the subject is a human patient. In other embodiments, the subject is a veterinary patient.

In certain, more specific embodiments, the DDD is designed for implantation into a subject using a biopsy needle via an ultrasound probe. In certain, still more specific embodiments, the needle is a needle in the range of 22-18 gauge, and the number of DDDs implanted is between 2-22, inclusive, for example 2, 4, 6, 8, 9, 10, 11, or 12, 14, 16, 18, 20, 22

In other embodiments, the DDD is designed for implantation into a subject using a delivery device as described in International Patent Publication No. WO 2010/086849 to Silenseed LTD, the contents of which are incorporated herein by reference.

In another embodiments the drug load in DDD is between 150-300 µg, in another embodiment about 200 µg, per mm length of the DDD.

In yet other embodiments, all the DDD's, administered as a batch, deliver a dose of 0.008-0.065 mg/kg/month, inclusive, for example 0.008 mg/kg/month, 0.01 mg/kg/month, 0.015 mg/kg/month, 0.02 mg/kg/month, 0.03 mg/kg/month, 0.05 mg/kg/month, or 0.065 mg/kg/month.

In still more specific embodiments, 8-32 DDD per patient are implanted, for example 8, 9, 10, 12, 14, 16, 18, 20, 22, 24, 26, 28, 30, or 32 DDD. In yet more specific embodiments, 12 DDD per patient are implanted.

In other embodiments, at least one DDD described herein that is a delayed-release DDD and at least one DDD described herein that is a non-delayed-release DDD are implanted together. "Together" in this embodiment, refers to implantation during the same procedure. Alternatively, the delayed-release DDD and non-delayed-release DDD are implanted on the same day. Provision of a combination of delayed-release and non-delayed-release DDD's in some embodiments enables a longer time course of significant siRNA release, without the need for repeated therapeutic intervention.

In other embodiments, a trehalose-containing DDD as described herein is administered to treat a solid tumor other than prostate cancer. In some embodiments, the cancer is selected from a pancreatic tumor, a colon tumor, a lung tumor, brain cancer, liver cancer, kidney cancer, melanoma, endometrial carcinoma, gastric carcinoma, renal carcinoma, biliary carcinoma, cervical carcinoma, and bladder carcinoma. In more specific embodiments, the cancer is selected from pancreatic carcinoma, pancreatic ductal adenocarcinoma, small-cell lung carcinoma, and colorectal cancer.

In still other embodiments, the described method further comprises the step of administering an anti-cancer agent to the patient. In more specific embodiments, the anti-cancer agent comprises a pyrimidine analogue, non-limiting examples of which are 5-azacytidine, 5-aza-2'-deoxycytidine, 5-fluoro-uracil, 5-fluoro-deoxyuridine (floxuridine), and 5-fluorodeoxyuridine monophosphate. In more specific embodiments, the anti-cancer agent is an inhibitor of ribonucleoside-diphosphate reductase large subunit (EC 1.17.4.1), non-limiting examples of which are motexafin gadolinium (CHEBI: 50161); hydroxyurea; gemcitabine (2',2'-difluorodeoxycytidine); elacytarabine (CP-4055; an ara-C-5'elaidic-acid-ester) and CP-4126, (CO 1.01; a gemcitabine-5'elaidic-acid-ester; Adema A D et al, *Metabolism and accumulation of the lipophilic deoxynucleoside analogs elacytarabine and CP*-4126. Invest New Drugs. 2011 Oct. 15. [Epub ahead of print]), and those described in WO2011/062503, the contents of which are incorporated herein by reference. In even more specific embodiments, the anti-cancer agent comprises gemcitabine. In alternative embodiments, the anti-cancer agent is gemcitabine. In yet other embodiments, the anti-cancer agent is an EGFR tyrosine kinase inhibitor. In yet other embodiments, the anti-cancer agent comprises a thymidylate synthase inhibitor. In more specific embodiments, the anti-cancer agent comprises leucovorin (Folinic acid; 2-[[4-[(2-amino-5-formyl-4-oxo-1,6,7,8-tetrahydropteridin-6-yl)methylamino]benzoyl]amino] pentanedioic acid). In yet other embodiments, the anti-cancer agent comprises irinotecan. In yet other embodiments, the anti-cancer agent comprises oxaliplatin. In still other embodiments, the anti-cancer agent comprises FOLFIRIN (5-fluorouracil, leucovorin, and irinotecan in combination). In still other embodiments, the anti-cancer agent is FOLFIRINOX (5-fluorouracil, leucovorin, irinotecan, and oxaliplatin in combination), or any combination of a subset of the four agents in FOLFIRINOX. In yet other embodiments, the anti-cancer agent comprises an EGFR tyrosine kinase inhibitor. In more specific embodiments, the anti-cancer agent is Erlotinib.

In some embodiments, the anti-cancer agent is administered to the patient after administration of the DDD. In more specific embodiments, the anti-cancer agent may be administered to the patient up to 10 days after administration of the DDD. Alternatively, the anti-cancer agent is administered to the patient simultaneously with administration of the DDD. In still other embodiments, the anti-cancer agent is administered to the patient before administration of the DDD. In yet other embodiments, the DDD is administered during ongoing administration of the anti-cancer agent. In still other embodiments, the anti-cancer agent is administered to the patient intratumorally, by a method such as injection and controlled release, or including in other embodiments administration from the same DDD.

In still other embodiments, the described method further comprises the step of administering radiation therapy to the patient. In some embodiments, the radiation is administered to the patient after administration of the DDD. In more specific embodiments, the radiation may be administered to the patient up to 10 days after administration of the DDD. Alternatively, the radiation is administered to the patient simultaneously with administration of the DDD. In still other embodiments, the radiation is administered to the patient before administration of the DDD. In yet other embodiments, the DDD is administered during ongoing administration of the radiation.

Animal and Human Testing

In animal models, tumor progress may be monitored by any method known in the art. One method is by removing and weighing the tumor. This may be done, for example, by weighing slices after histology slice preparation.

The presence and amount of therapeutic siRNA in tissue samples may be determined by any method known in the art, for example by a method described herein. RNA quantity may be assessed, for example, by Nanodrop, and RNA quality by gel electrophoresis. RNA quantity may also be assessed by PCR, e.g. real-time PCR, Northern blot, HPLC, MSLC (Membrane surface liquid culture), or in situ hybridization.

Excised tumor tissue from human or animal studies may be preserved by any method known in the art, for example by freezing in liquid nitrogen (for subsequent studies requiring live cells), or may be fixed, for example in paraformaldehyde solution.

Characterization of tissue samples may include various methods known in the art, including but not limited to hematoxylin and eosin staining, immunohistochemistry staining, and measuring levels of gene products, such as the genes targeted by the therapeutic siRNA, in some cases in the presence of an internal control.

In other cases, the effects of devices described herein on the excised tissue sample may be studied, for example in an experimental animal or in culture.

EXPERIMENTAL DETAILS SECTION

Example 1: Production of DDD's Containing RNAi Molecules Against Various Targets DDD's containing various RNAi molecules were produced in a biological-class hood in a clean room, as follows:
Step 1: Preparation of siRNA/D-Mannitol/Sodium Bicarbonate Mixture:
 siRNA was added to the pre-weighed D-Mannitol and Sodium Bicarbonate, and they were dissolved in RNase-free sterile water.
Step 2: Freezing:
 The liquid was placed into glass vials, frozen in dry ice, and lyophilized for 48 hours.
Step 3: PLGA Preparation:
 PLGA was dissolved in Ethyl Acetate.
Step 4: Combining PLGA with D-Mannitol/Sodium Bicarbonate/siRNA:
 The PLGA solution was poured into the glass vial containing the lyophilized D-Mannitol/Sodium Bicarbonate/siRNA in fractions and stirred until homogenization
Step 5: Solvent Evaporation.
 The solution was poured into a Teflon-covered dedicated glass dish and left to evaporate inside a dedicated container for 3-5 days.
Step 6: Release of Film:
 The film was released from the glass dish using tweezers and a scalpel.
Step 7: Excision of Individual DDDs:
 Individual DDDs were excised using a dedicated puncher. Each DDD was of a cylindrical shape, with a length and diameter of ~1.3 mm and ~0.6 mm, respectively.

Example 2: In Vitro Testing of Release Characteristics of DDDs

Figure 2A:
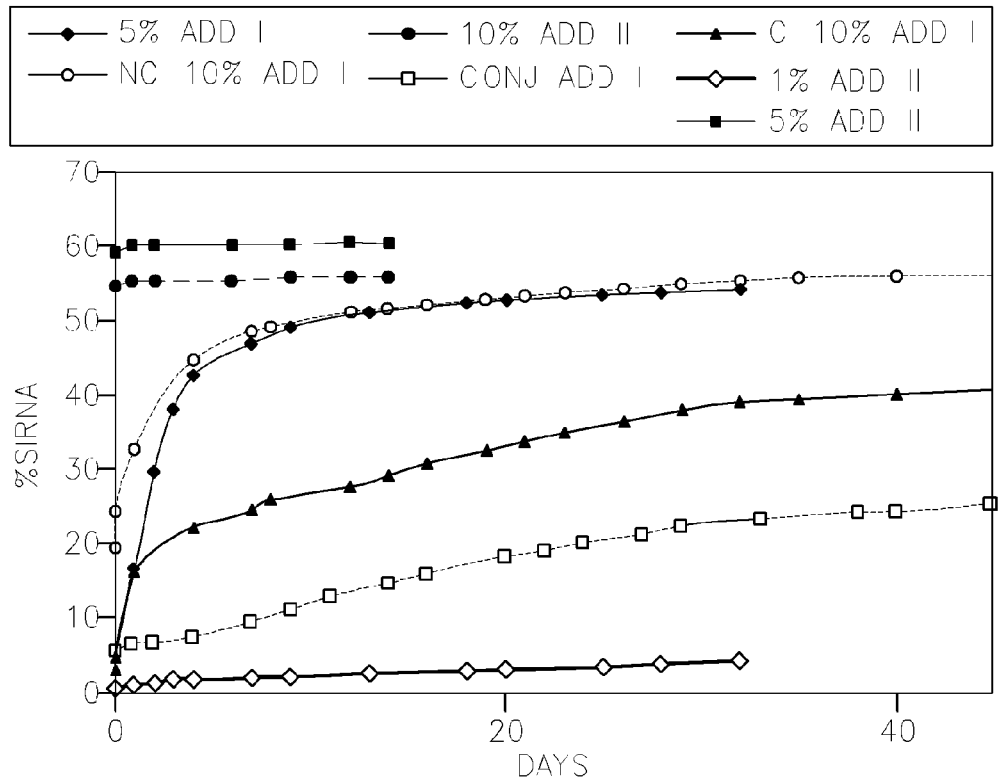
FIGS. 2A and 2B show working examples of siRNA release in PBS and its dependence on coating, additives, percent of additives, and conjugation.
Figure 2B:
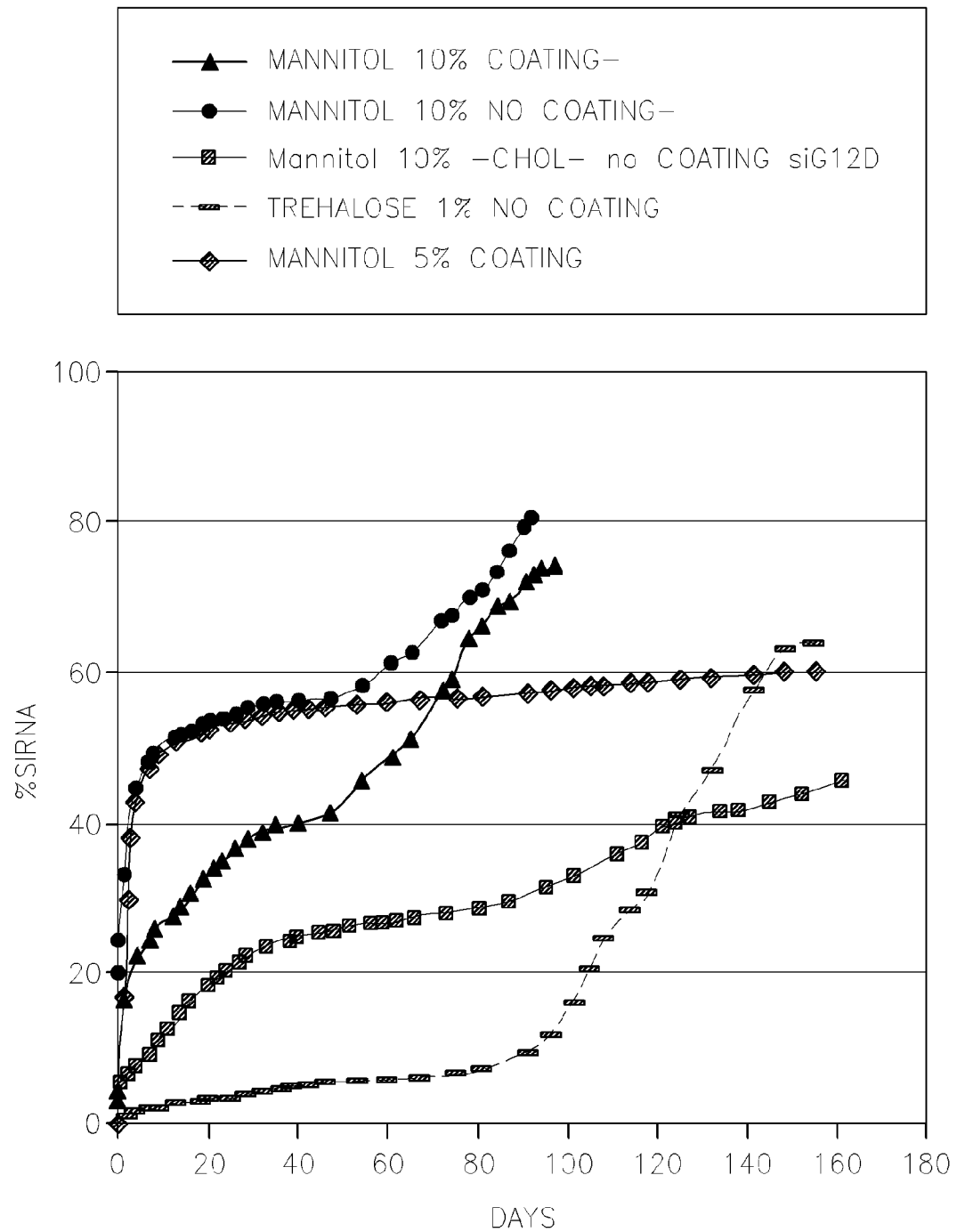

FIG. 2 describes variations in release characteristics that were achieved by varying the composition of DDDs. The curve "1% add II" provides a working demonstration of very slow release that can last 6 months, for example using PLGA of high PLA:PGA ratio, such as 90:10, and MW (molecular weight) higher than 50 KDa.

The following protocol was used to make the DDD, covering all cases in FIG. 2:
1. Mix siRNA 40 mg (naked, 5'-chol) RNAse free water solution with 1% $NaHCO_3$ (Sigma) and with Mannitol (10% or 5%) or Trehalose (10%, 5% or 1%) and lyophilize overnight.
2. Weight 450 mg PLGA 85:15 (Boehringer-Ingelheim), add to the lyophilized powder and mix. The viscosity of the PLGA was 0.63-0.67 dl/gr, and its estimated MW was 60,000-80,000.
3. Add Ethyl acetate (~1.5 ml) (Sigma) and mix to get clear white solution.
4. Pour onto Teflon covered glass dish (D=2 cm).
5. Dry (5-7 days) to get a film.
6. Punch the film with 19 G puncher to get 19 G DDDs.
PLGA Coating:
 1. Dissolve PLGA 85:15 30% in Ethyl acetate and drip onto each DDD.
 2. Push the DDDs out of the drop after 2 sec.
 3. Dry.

Measurements of release were done by Nanodrop at a specific wavelength of 260 nm and/or 230 nm. Measurements were taken at time points of 0 h, 4 h, 12 h, 24 h, 3 d, 7 d, 2 w, 4 w, 6 w, and 8 w, and, in some experiments, at additional time points after and between these times. Each measurement utilized 1.5 microliters (μL) of siRNA solution (PBS or water) and results are given in nanogram/microliter. Prior to each measurement, a null measurement of solution only (PBS) was performed for subtraction. Each time point contained five parallel measurements (from five different DDDs). Presented in FIGS. 1-2 are the averages of such five points.

Example 3: Testing of Targets in Cell Culture

Methods
Viability Test
 PC3 cells were seeded on 96-well plates one day before transfection. Transfection was performed using Lipofectamine 2000 transfection reagent, according to the manufacturer's protocol. siRNAs were used at the indicated concentration. Scrambled non-targeting siRNA was used as transfection control. 72 hrs post transfection, viable cells were fixed and stained by Methylene Blue (MB). Relative cell amounts were assessed using a microplate absorbance reader. The results are presented relative to cells transfected with scrambled siRNA.
Methylene Blue (MB) Assay
 The protocol was adapted from Oliver et al. Cells were seeded in a 96-well plate, then treated as follows:
1. Remove medium from plate.
2. Wash cells twice with PBS (250-400 ul)
3. Fix cells: Add 100-μl 4% formaldehyde. Keep at room temperature for 20 min or for up to several weeks at +4° C. (cold room, wrapped so the liquid will not evaporate).
4. Wash twice with PBS (250-400 μl).
3. Wash cells twice with 200 μl 0.2M borate buffer, pH 8.5.
4. Stain cells with 50 μl 1% Methylene blue in borate buffer. Incubate for 20 min at room temperature.
5. Wash with tap water until control well (without cells) is white.
6. Color elution: add 100 μl 0.1M HCl. Incubate at room temperature for at least 2 hrs, up to overnight (wrapped so the liquid will not evaporate)
7. Measure OD at 585 nM.
0.2M Borate Buffer pH 8.5:
 Add 7.628 gr/100 ml of borate (sodium tetraborate) ($Na_2B_4O_7 \cdot 10H_2O$; MW 381.3) and 1.2378 gr/100 ml boric acid ($H_3BO_3$; MW 61.83). Titrate with NaOH if needed.
0.1M HCl:
 50 ml DDW+0.5 ml 37% HCl (=10.1 M)

PBS Solution:

0.26 g $KH_2PO_4$, 2.17 g $Na_2HPO_4$-$7H_2O$, and 8.71 g NaCl in 800 mL $dH_2O$. Adjust pH to 7.4 and bring volume to 1 L with $dH_2O$.

Results

PC3 cells (ATCC #CRL-1435) were grown and tested for *mycoplasma* contamination, and were found to be *mycoplasma* free.

Figure 3:
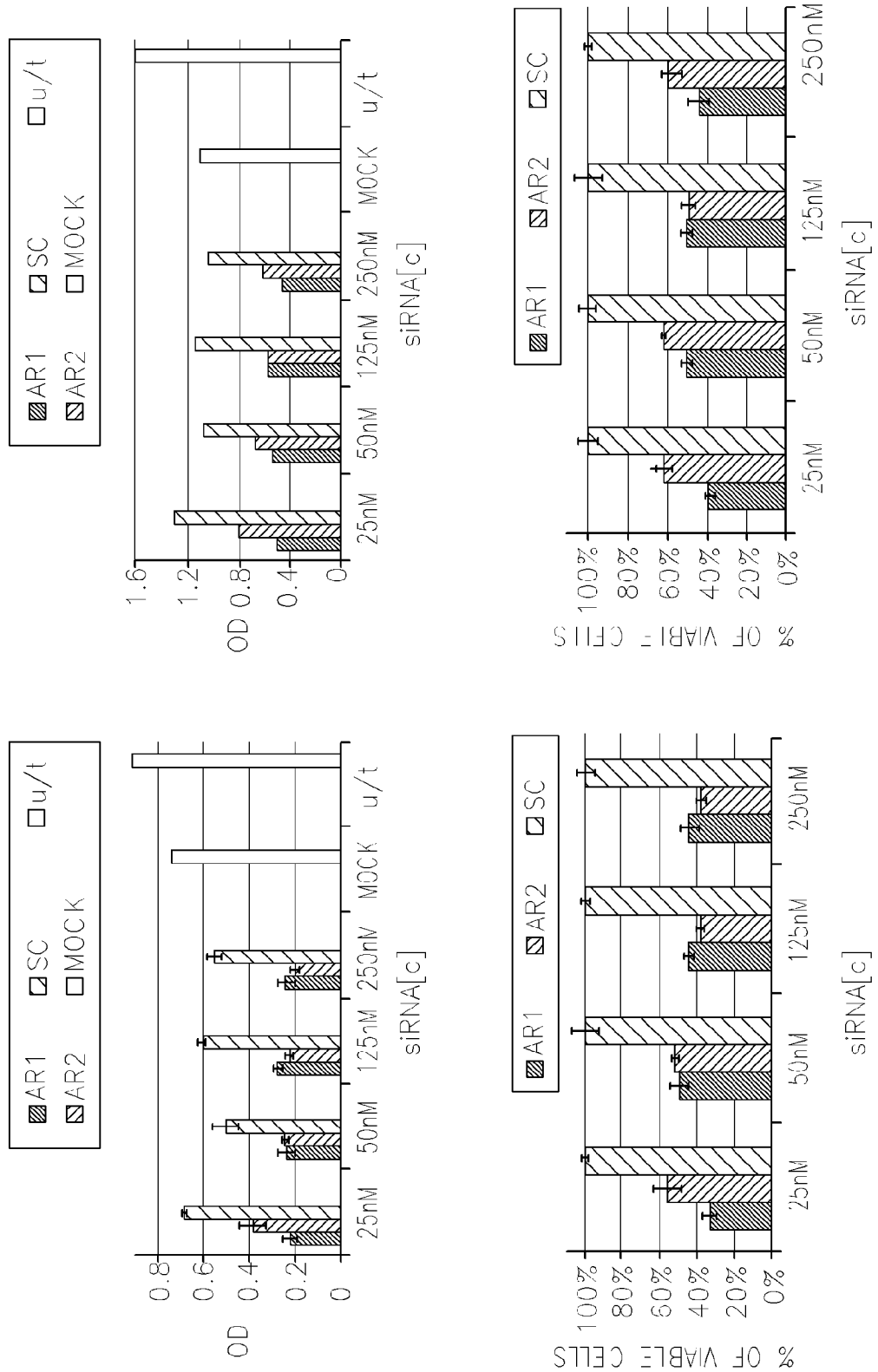
FIG. 3 shows the effect of down-regulation of Androgen Receptor (AR), by two different siRNA sequences, on cell viability of PC3 prostate cancer cells. Also shown are the calibration and selection of siRNA doses. AR1 & AR2 refer to siAR-1 and siAR-2, respectively. Mock=mock-transfected; u/t=untransfected; SC=scrambled (non-targeting) siRNA. Testing was done at $0.5 \times 10^4$ (left panels) and $0.75 \times 10^4$ (right panels) cells/well. Vertical axis: upper panel—OD; lower panel—percentage of viable cells (calculated relative to mock transfected cells). Horizontal axis: siRNA concentration. All changes were significant, with a p value of less than 0.001.

Viability testing was done by the MB assay. Based on growth calibration, two cell concentrations of 0.5 and 0.75× $10^4$ cells/well were tested with two AR siRNAs. For transfection calibration, cells were seeded at the indicated concentration and transfected at the indicated siRNA concentrations. The optimum concentration was found to be 125 nM, which corresponds to 0.375 μg siRNA/well (FIG. 3).

Figure 4B:
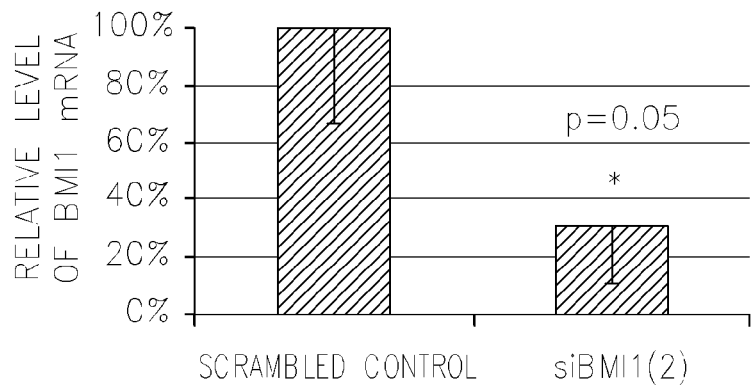
Figure 4C:
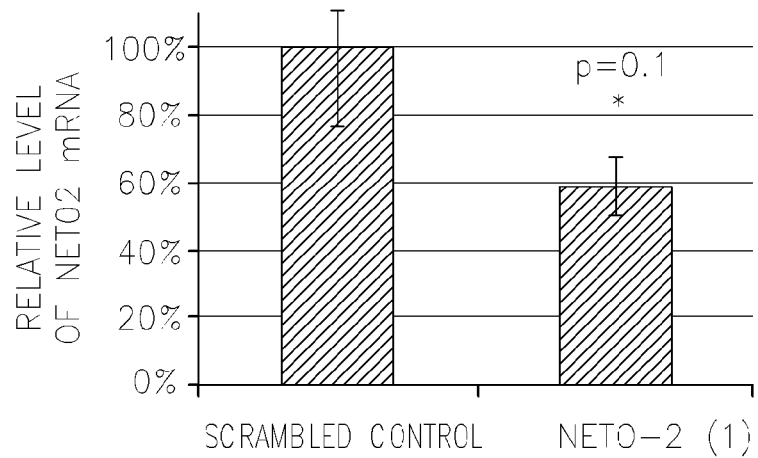
Figure 4D:
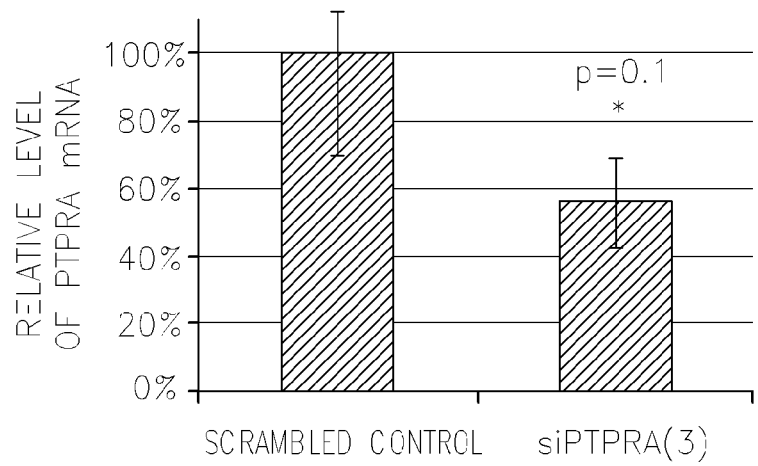

Next, viability testing was performed with siRNA molecules targeting various genes. As shown in Table 4 and FIG. 4, many of the constructs exhibited growth inhibition. Notably, the 2-O-Me-modified constructs retained a significant amount of activity. Their relative activity compared to non-modified constructs is expected to be greater in vivo, where their resistance to nucleases will confer an advantage of durability. Furthermore, the effects of anti-BMI-1-2, anti-NETO2-1, and anti-PTPRA-3 on the levels of their target genes were assessed. Each tested siRNA caused a significant decrease in the level of the target (FIGS. 4B-D).

TABLE 4

Viability testing of PC3 cells treated with indicated siRNA's.

| target | no. | siRNA-name | Average percentage of viable cells | SEM % |
|---|---|---|---|---|
| Androgen receptor | 201 | siAR-1 | 43% | 2% |
| | 202 | siAR-2 | 48% | 4% |
| | 204 | siAR-4 | 55% | 2% |
| | 203 | siAR-3 | 111% | 1% |
| | 217 | siAR-1-O—Me | 71% | 2% |
| BMI1 | 205 | siBMI1-1 | 94% | 4% |
| | 206 | siBMI1-2 | 7% | 1% |
| Brd4 | 233 | siBrd4-2 | 22.2% | 1.7% |
| | 232 | siBrd4-1 | 37.6% | 1.5% |
| CDC44 | 207 | siCDC44-1 | 98% | 8% |
| | 208 | siCDC44-2 | 87% | 1% |
| EtbB3 | 229 | siErbB3-2 | 45.2% | 1.8% |
| | 228 | siErbB3-1 | 50.9% | 25.5% |
| EZH2 | 235 | siEZH2-2 | 34.0% | 2.0% |
| | 234 | siEZH2-1 | 64.8% | 2.1% |
| gp130 | 219 | gp130 | 38% | 2% |
| hTERT | 213 | si-hTERT-5 | 50% | 6% |
| | 211 | si-hTERT-3 | 52% | 1% |
| | 210 | si-hTERT-2 | 53% | 2% |
| | 209 | si-hTERT-1 | 58% | 2% |
| | 212 | si-hTERT-4 | 81% | 4% |
| NETO2 | 214 | siNETO2-1 | 31% | 3% |
| | 215 | siNETO2-2 | 53% | 3% |
| | 216 | siNETO2-3 | 69% | 3% |
| | 218 | siNETO2-1-O—Me | 84% | 4% |
| PAPPA | 227 | PAPPA-3 | 21% | 2% |
| | 225 | PAPPA-1 | 34% | 3% |
| | 226 | PAPPA-2 | 54% | 3% |
| PSCA | 231 | siPSCA-2 | 47.6% | 1.0% |
| | 230 | siPSCA-1 | 52.3% | 1.8% |
| PTPRA | 222 | PTPRA-3 | 33% | 1% |
| | 224 | PTPRA-5 | 36% | 1% |
| | 223 | PTPRA-4 | 38% | 3% |
| | 220 | PTPRA-1 | 72% | 1% |
| | 221 | PTPRA-2 | 84% | 4% |

Example 4: Manufacturing and Testing of Trehalose-Containing DDD's

1% Trehalose-containing DDD's were produced as follows:
1. Dissolve 40 mg siG12D (BioSpring GmbH) in 2 ml DNAse/RNAse free water.
   The sequences of the sense and antisense strands of siG12D were GUUGGAGCUGAUGGCGUAGdTdT (SEQ ID No: 65) and CUACGCCAUCAGCUCCAACdTdT (SEQ ID No: 66), respectively.
2. Add siRNA solution to pre-weighed Trehalose (4 mg.) and $NaHCO_3$ (1 mg) and vortex for several min.
3. Freeze solution of siG12D, Trehalose and $NaHCO_3$ in liquid nitrogen and lyophilize for 48 h.
4. Combine 400 mg of lyophilized PLGA with the lyophilized siG12D, Trehalose and $NaHCO_3$ powder and mixed.
5. Dissolve the mixed powder in 1.5 ml Ethyl acetate to obtain a milky solution. Mix and pour into a Teflon-covered glass dish, diameter 2 cm.
6. Dry for 3 days to obtain a film.
7. Punch the film to obtain DDD's.

The final composition was 89.89% PLGA 85:15 (supplier: Boehringer Ingelheim Pharma GmbH), 9% siG12D, 1% Trehalose, and 0.22% $NaHCO_3$. DDD dimensions were 2-3 mm×1 mm.

The release profiles of DDD's were measured in vitro at 37° C. in PBS and in vivo. For in vivo testing, C57b1/6 mice were anesthetized using ketamine and xylazine (for a 25-gram mouse, a 50 ill intra-peritoneal injection of 0.9 ml ketamine+0.1 ml xylazine). The DDD's were inserted subcutaneously into a minimal incision made in the skin.

Release in vitro was quantified using a Nanodrop® apparatus. For validation, release from in vivo trials was also quantified by electrophoresis in a 10% urea-acrylamide gel. Gels were visualized using Pharmacia Biotech ImageMaster™ VDS (cat #80-6246-82) and quantified using Image-Gauge software.

Figure 5:
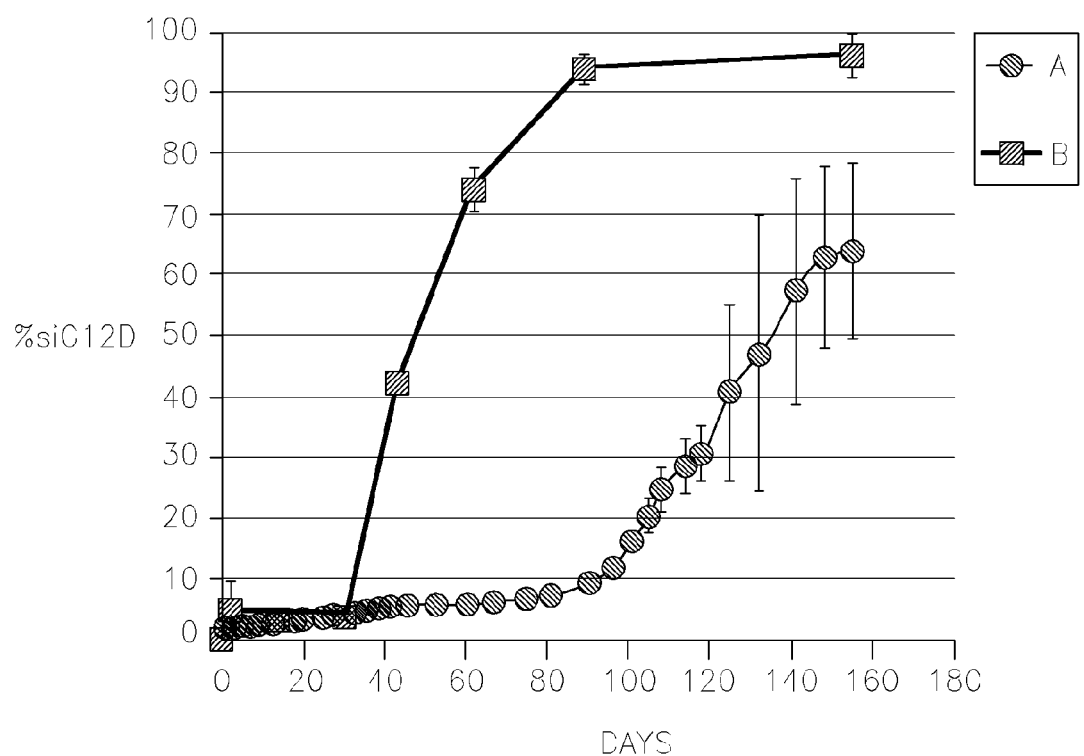
FIG. 5 shows release profiles of DDDs that "hibernate" (i.e. do not release a significant amount of drug) during an initial period. In the depicted examples, the cumulative drug released during the first three months is less than ~10% (in vitro at 37° C. in PBS; data set A) and/or the release during the first month is less than ~5% (in vivo, inside a mouse; data set B). The DDDs contain trehalose.
Figure 6:
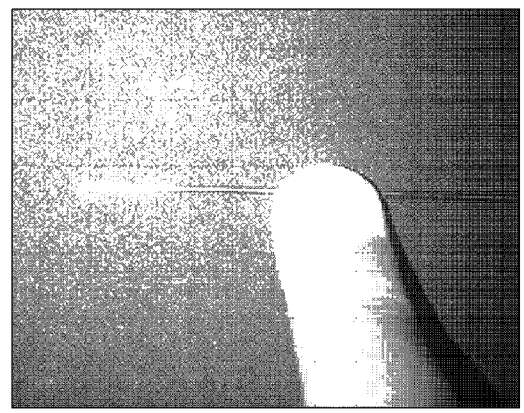
FIG. 6 shows a picture of the distal end of an 18-gauge biopsy needle and DDDs of dimensions 0.8 mm×1.7 mm.

In vitro, the trehalose-containing DDD's exhibited delayed release, with less than 10% of the siRNA released after 90 days, followed by a steady release of the next 55% of the siRNA over the next 70%. In vivo, these DDD's steadily released about 90% of the siRNA over the first 90 days, followed by a slower release of most of the remaining siRNA over the next 70 days (FIG. 5).

Example 5: Effect of Anti-BMI-1 and Anti-hTERT siRNA on Various Cancer Cell Lines Anti BMI-1 (si-BMI1) and anti-hTERT-5 siRNAs were administered to several cancer cell lines, and the effect on cell viability was tested. The cell lines used included prostate, pancreas, colon (two lines), lung (two lines), neuroblastoma, embryonic kidney, and hepato-cellular carcinoma lines, as follows:
PC3 Human prostate adenocarcinoma.
Panel Human pancreatic ductal carcinoma.
HT29 Human colorectal adenocarcinoma.
H460 Human large cell lung carcinoma.
SHY86 Human neuroblastoma.
HEK293T Human embryonic kidney.
Huh7 Human hepatocellular carcinoma.
H1299 Human non-small cell lung carcinoma.
RKO Human colon carcinoma.

Figure 8:
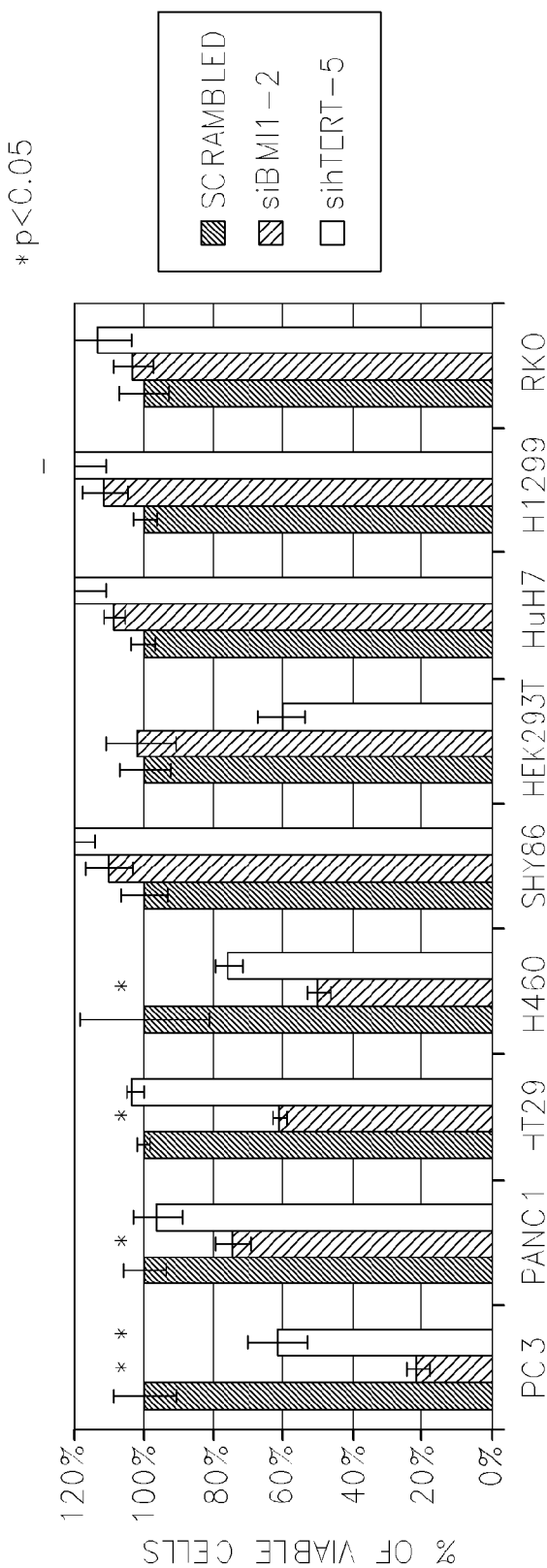
FIG. 8: Effect of DDDs containing anti BMI-1 (si-BMI1) and anti-hTERT siRNA on cell viability in several cancer cell lines, namely prostate, pancreas, colon (two lines), lung (two lines), neuroblastoma, embryonic kidney, and hepatocellular carcinoma.

Experimental Description:

The indicated cell lines were seeded in a 96-well plate one day before transfection. Transfection was performed using Lipofectamine 2000 transfection reagent. The indicated siRNAs were used at a 125 nM concentration, which is 0.375-µg/well. Scrambled non-targeting siRNA was used as transfection control. 72 hrs post-transfection, the reaction was stopped, and viable cells were fixed and stained by Methylene blue. Relative cell amounts were assessed using a microplate absorbance reader) (Tecan Group Ltd, model Infinite F50), and data was processed using the Magellan™ program (Tecan). The siRNA's were each effective in a number of cancer cell lines (FIG. 8). The results are presented relative to scrambled siRNA-transfected cells.

Example 6: Expression of BMI-1 (A), hTERT (B), Gp130 (C) and K-RAS in Various Cell Lines Methods GeneNote, BioGPS Normal, and BioGPS Cancer Expression array images were utilized.

Tissue Types:

Duplicate measurements were obtained for 12 normal human tissues (out of 28 tissues shown) hybridized against Affymetrix GeneChips HG-U95A-E (GeneNote data) and for 22 normal human tissues hybridized against HG-U133A (BioGPS data). The intensity values (shown on the y-axis) were first averaged between duplicates, then probeset values were averaged per gene, global median-normalized and scaled to have the same median of about 70 (half-way between the GeneNote and BioGPS medians). HG-U133A expression data for 18 NCI60 cancer cell lines, available at BioGPS, was processed and added to the display (a single measurement was taken and normalized according to the BioGPS normal data).

Figure 9A:
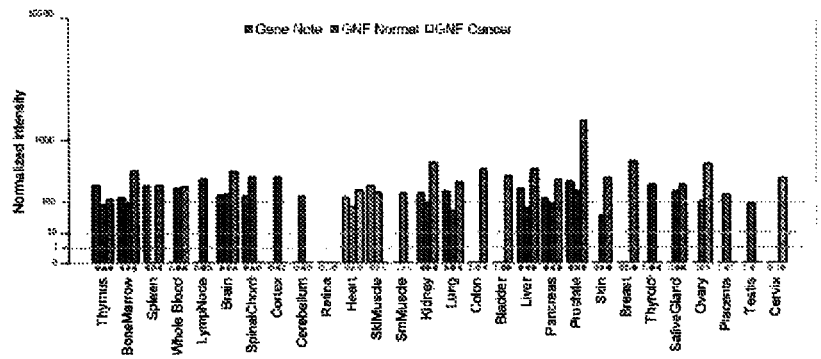
FIGS. 9A-9D: Expression of BMI-1 (FIG. 9A), hTERT (FIG. 9B), gp130 (FIG. 9C) and K-Ras (including mutated forms of K-Ras) (FIG. 9D), showing the high expression of these targets in cancers other than prostate cancer, including pancreatic, cervical cancer, breast, colon, thyroid and lung cancers.
Figure 9B:
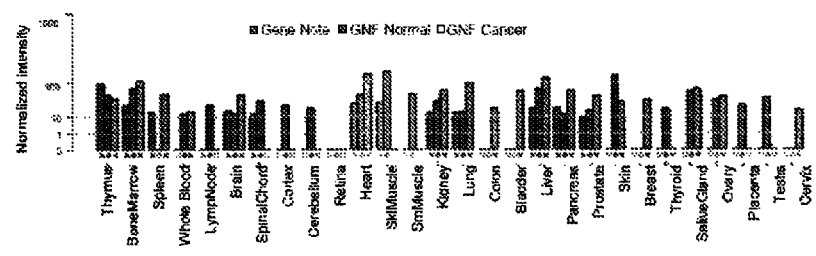
Figure 9C:
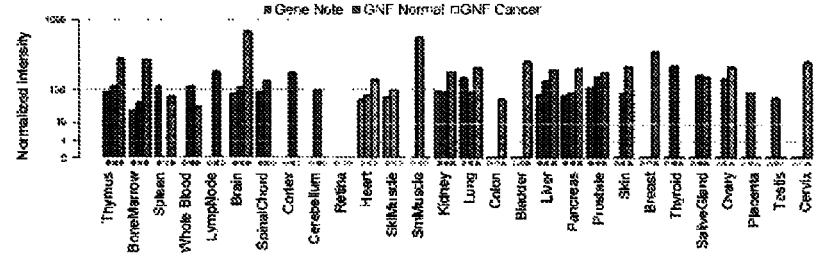
Figure 9D:
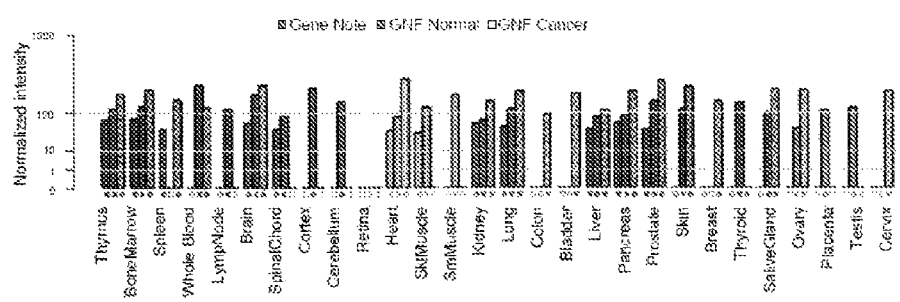

Each gene was found to be highly expressed in a significant fraction of the cell lines, as shown for BMI-1 (FIG. 9A), hTERT (B), gp130 (C) and K-ras (D).

Example 7: Further In Vitro Testing of Targets

Following transfection with siRNA, siRNA functionality is measured by proliferation assay, colony-forming assay, and in other experiments by scratch assay, for example in one or more of the cells lines mentioned herein. In some experiments, kinetic studies are performed.

In other experiments, target mRNA inhibition is measured, for example using semi-quantitative PCR or quantitative PCR.

In other experiments, the effect on target protein level is measured, for example by Western blotting.

In other experiments, the stability of siRNAs in a RNase-rich environment is studied by incubation in a RNase-rich environment, followed by analysis of siRNA content, for example by gel electrophoresis.

In other experiments, siRNAs are modified to improve their stability and functionality, and their efficacy and stability are tested.

In other experiments, the release rate of siRNA is determined, for example using the methods described herein.

In other experiments, the effect of the siRNA's is tested in cancer stem cells, for example by colony-forming ability, proliferation assay, or apoptosis assay.

Example 8: In Vivo Testing of Anti-Cancer Activity of DDDs

Figure 10:
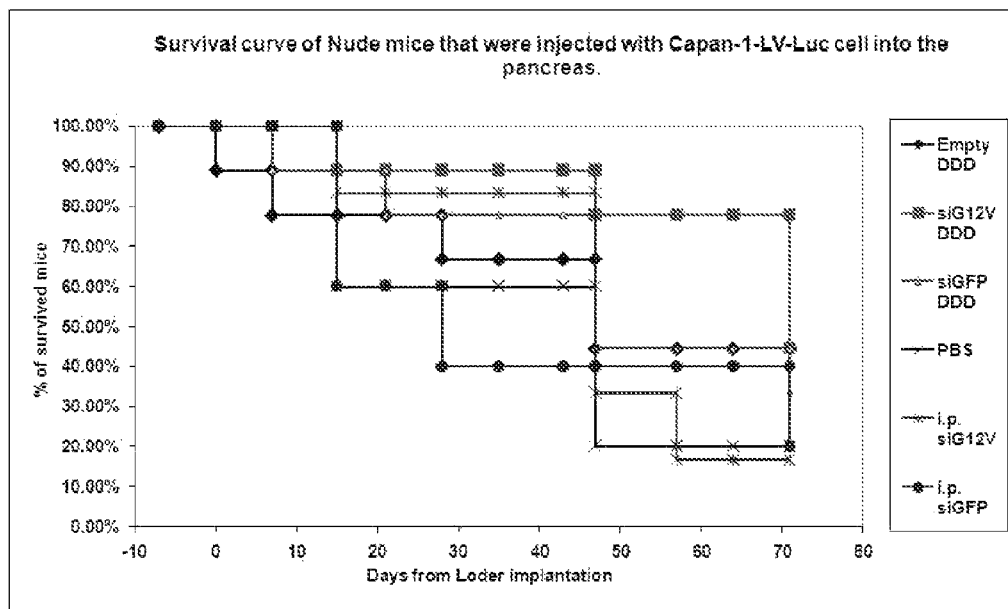
FIG. 10: In-vivo study of down-regulation of K-Ras G12V: Nude mice were injected with Capan-1-LV-Luc (dominant mutation: K-Ras G12V mutation) cell into the pancreas. One month later, DDDs were implanted. Depicted is survival curve of Nude mice treated as follows: (1. DDD without drug ("empty"); 2. DDDs with siRNA against G12V-mutated K-Ras ("siG12V DDD"); 3 non-targeting siRNA (siGFP DDD); 4. mock-treatment ("PBS"); 5. direct intraperitoneal (I.P.) injection of siRNA without DDD ("IP siG12V"); and 6. I.P. injection of non-targeting siRNA ("IP siGFP"). 72 days after implantation, all surviving mice were sacrificed. 80% of the siG12V DDD-treated mice survived, vs. 10-40% of the other groups.

FIG. 10 shows an in-vivo study of down-regulation of K-Ras G12V: Nude mice were injected with Capan-1-LV-Luc (dominant mutation: K-Ras G12V mutation) cells into the pancreas. One month later, DDDs were implanted. Depicted is survival curve of Nude mice treated as follows: (1. DDD without drug ("empty"); 2. DDDs with siRNA against G12V-mutated K-Ras ("siG12V DDD"); 3 non-targeting siRNA (siGFP DDD); 4. mock-treatment ("PBS"); 5. direct intraperitoneal (I.P.) injection of siRNA without DDD ("IP siG12V"); and 6. I.P. injection of non-targeting siRNA ("IP siGFP"). 72 days after implantation, all surviving mice were sacrificed. 80% of the siG12V DDD-treated mice survived, vs. 10-40% of the other groups. The sequences of the sense and antisense strands of siG12V were GUUGGAGCUGUUGGCGUAG (SEQ ID No: 10), and CUACGCCAACAGCUCCAAC (SEQ ID No: 67), respectively.

Example 9: In Vivo Testing of Additional DDDs

One or more DDDs are implanted in a mouse xenograft tumor model or other suitable cancer model, for example utilizing injection of Capan-1 cells into the pancreas. When tumors reach a suitable size, DDD's containing no-siRNA or anti-BMI1, anti-hTERT, anti-IL6ST/gp130, and/or anti-CD44 siRNA are implanted into the tumors. Tumor growth and/or the amount of therapeutic siRNA is assessed by imagining and/or by histopathology over the next several weeks. In some experiments, measurement of tumor volume is used to follow tumor growth. In other experiments, the survival of mice bearing the tumor is followed. Impaired tumor growth and/or tumor shrinkage is indicative of enhanced therapeutic efficacy.

In other experiments, an orthotopic model is utilized to follow tumor growth during and after treatment with siRNA's.

Example 10: Testing of Anti-Cancer Activity of DDDs in Humans

Humans with solid tumors are implanted with DDD's described herein and the anti-tumor activity is tested.

Example 11: Testing of Trehalose-Containing DDDs

Trehalose-containing DDD's are tested in an animal model, or in other experiments in human subjects, using an appropriate experimental setup, relative to mannitol-containing DDD's. Impaired tumor growth is indicative of enhanced therapeutic efficacy.

Example 12: Testing of Delayed-Release DDDs

Delayed-release DDDs (e.g. trehalose-containing DDD's) are tested in an animal model, or in other experiments in human subjects, using an appropriate experimental setup, relative to non-delayed-release DDDs. In some experiments, delayed-release DDDs are implanted together with non-delayed-release DDDs, and are compared to non-delayed-release DDDs alone. siRNA release and tumor progression are monitored. A longer time course of significant siRNA release and/or impaired tumor growth are indicative of enhanced therapeutic efficacy.

It will be apparent that the precise details of the methods and compositions described herein may be varied or modified without departing from the spirit of the described invention. We claim all such modifications and variations that fall within the scope and spirit of the claims below, including all equivalents thereof.

REFERENCES

1. Patrawala et al, Highly purified CD44+ prostate cancer cells from xenograft human tumors are enriched in tumorigenic and metastatic progenitor cells. Oncogene (2006) 25:1696-1708).
2. M. H. Oliver et al, "A rapid convenient assay for counting cells cultures in microwell plates: application for assessment of growth factors." Journal of Cell Science 92, 513-519 (1989).
3. Guo et al., In situ vaccination with CD204 gene-silenced dendritic cell, not unmodified dendritic cell, enhances radiation therapy of prostate cancer." *Molecular Cancer Therapeutics*, Mol Cancer Ther. 2012 Nov. 6. [Epub ahead of print].
4. Terrone et al, Penetratin and related cell-penetrating cationic peptides can translocate across lipid bilayers in the presence of a transbilayer potential. *Biochemistry*. 2003 Dec. 2; 42(47):13787-99.
5. Magzoub et al, Interaction and structure induction of cell-penetrating peptides in the presence of phospholipid vesicles. *Biochim Biophys Acta*. 2001 May 2; 1512(1): 77-89.
6. Pooga et al, Cell penetration by transportan. FASEB J. 1998 January; 12(1):67-77.

We claim:

1. A method for treating a solid tumor other than prostate carcinoma, comprising:
   administering to a subject having a non-prostate solid tumor selected from the group consisting of a pancreatic cancer, colon cancer, and lung cancer, a millimeter-scale drug delivery device (DDD) comprising
   a biocompatible polymeric composition comprising a mixture of polylactic acid (PLA) and polyglycolic acid, wherein the PLA:PGA ratio is 50:50, or between 65:35 and 95:5, inclusive;
   and at least one RNAi (RNA interference) agent incorporated within the biodegradable polymeric matrix, wherein the RNAi agent comprises a sense strand and an antisense strand, wherein the sequences of the sense strand and the antisense strand target BMI1 polycomb ring finger oncogene (BMI-1), and wherein the sequence of the sense strand consists essentially of the sequence set forth as SEQ ID NO: 83,
   wherein the DDD is administered to the subject by implantation into at least one of within the solid tumor and into the vicinity of the solid tumor, thereby treating the solid tumor.

2. The method of claim 1, wherein the DDD comprises between 0.15-1.1, inclusive, milligrams of the RNAi agent per DDD.

3. The method of claim 1, wherein the polymeric composition has a molecular weight of greater than 50 KDa.

4. The method of claim 1, wherein the DDD further comprises at least one additive selected from the group consisting of a pH-modulating additive and trehalose.

5. The method of claim 1, wherein the DDD is coated with a coating comprising a biodegradable polymer.

6. The method of claim 5, wherein the DDD is a delayed-release DDD.

7. The method of claim 1, wherein at least two DDDs are implanted together, and wherein one of the implanted DDDs is a delayed release DDD, and one of the implanted DDDs is a non-delayed release DDD.

8. The method of claim 1, wherein 95% of said nucleotide-based agent is released from said DDD at a time point between 1-24 months, inclusive, after implantation.

9. The method of claim 1, wherein less than 5% of the RNAi agent is released from the DDD over a time period of one month starting from implantation.

10. The method of claim 1, wherein less than 10% of the RNAi agent is released from the DDD over a time period of three months starting from implantation.

11. The method of claim 1, wherein the number of DDDs per treatment is determined to achieve a dose of 0.008-0.065 mg/kg/month.

12. The method of claim 1, wherein the at least one RNAi agent includes an additional RNAi agent that targets a gene selected from the group consisting of Kirsten rat sarcoma 2 viral oncogene homolog (K-ras), EGFR, VEGF, and AURKB.

13. The method of claim 12, wherein said K-ras is a G12D-mutated K-ras.

14. The method of claim 1, wherein the at least one RNAi agent includes an additional RNAi agent that targets at least one gene selected from the group consisting of: hTERT, gp130, interleukin 6 signal transducer (IL6ST), and CD44.

15. The method of claim 1, wherein the at least one RNAi agent is chemically modified with a modification selected from the group consisting of 2'-O-methyl (2'-OMe), 2'-O-(2-methoxyethyl) (MOE), and 2'-fluorine.

16. The method of claim 1, wherein the at least one RNAi agent is conjugated to a moiety selected from the group consisting of a cholesterol moiety, spermine, hydrophobized hyaluronic acid-spermine conjugates (HHSCs), alpha-tocopherol-vitamin E; and a cell penetrating peptide; or is complexed with a cationic molecule.

17. The method of claim 1, wherein the sense and/or the antisense strand of the at least one RNAi agent each have a dTdT overhang at the 3'-end.

18. The method of claim 4, wherein the DDD comprises at least one pH-modulating additive selected from the group consisting of sodium bicarbonate, sodium carbonate, and magnesium hydroxide.

* * * * *

SEQUENCE LISTING

```
<160> NUMBER OF SEQ ID NOS: 209

<210> SEQ ID NO 1
<211> LENGTH: 16
<212> TYPE: RNA
<213> ORGANISM: Artificial Sequence
<220> FEATURE:
<223> OTHER INFORMATION: siRNA sequence

<400> SEQUENCE: 1
guuggagcug auggcg                                                     16

<210> SEQ ID NO 2
<211> LENGTH: 16
<212> TYPE: RNA
<213> ORGANISM: Artificial Sequence
<220> FEATURE:
<223> OTHER INFORMATION: siRNA sequence

<400> SEQUENCE: 2
guuggagcug uuggcg                                                     16

<210> SEQ ID NO 3
<211> LENGTH: 16
<212> TYPE: RNA
<213> ORGANISM: Artificial Sequence
<220> FEATURE:
<223> OTHER INFORMATION: siRNA sequence

<400> SEQUENCE: 3
guuggagcug cuggcg                                                     16

<210> SEQ ID NO 4
<211> LENGTH: 16
<212> TYPE: RNA
<213> ORGANISM: Artificial Sequence
<220> FEATURE:
<223> OTHER INFORMATION: siRNA sequence

<400> SEQUENCE: 4
guuggagcua guggcg                                                     16

<210> SEQ ID NO 5
<211> LENGTH: 16
<212> TYPE: RNA
<213> ORGANISM: Artificial Sequence
<220> FEATURE:
<223> OTHER INFORMATION: siRNA sequence

<400> SEQUENCE: 5
```
guuggagcuu guggcg                                                        16

<210> SEQ ID NO 6
<211> LENGTH: 16
<212> TYPE: RNA
<213> ORGANISM: Artificial Sequence
<220> FEATURE:
<223> OTHER INFORMATION: siRNA sequence

<400> SEQUENCE: 6
guuggagcug gugacg                                                        16

<210> SEQ ID NO 7
<211> LENGTH: 16
<212> TYPE: RNA
<213> ORGANISM: Artificial Sequence
<220> FEATURE:
<223> OTHER INFORMATION: siRNA sequence

<400> SEQUENCE: 7
guuggagcug guugcg                                                        16

<210> SEQ ID NO 8
<211> LENGTH: 14
<212> TYPE: RNA
<213> ORGANISM: Artificial Sequence
<220> FEATURE:
<223> OTHER INFORMATION: siRNA sequence

<400> SEQUENCE: 8
uaggcaagag ugcc                                                          14

<210> SEQ ID NO 9
<211> LENGTH: 19
<212> TYPE: RNA
<213> ORGANISM: Artificial Sequence
<220> FEATURE:
<223> OTHER INFORMATION: siRNA sequence

<400> SEQUENCE: 9
guuggagcug auggcguag                                                     19

<210> SEQ ID NO 10
<211> LENGTH: 19
<212> TYPE: RNA
<213> ORGANISM: Artificial Sequence
<220> FEATURE:
<223> OTHER INFORMATION: siRNA sequence

<400> SEQUENCE: 10
guuggagcug uuggcguag                                                     19

<210> SEQ ID NO 11
<211> LENGTH: 19
<212> TYPE: RNA
<213> ORGANISM: Artificial Sequence
<220> FEATURE:
<223> OTHER INFORMATION: siRNA sequence

<400> SEQUENCE: 11
guuggagcug cuggcguag                                                     19

<210> SEQ ID NO 12
<211> LENGTH: 19
<212> TYPE: RNA
<213> ORGANISM: Artificial Sequence

```
<220> FEATURE:
<223> OTHER INFORMATION: siRNA sequence

<400> SEQUENCE: 12
guuggagcua guggcguag                                                19

<210> SEQ ID NO 13
<211> LENGTH: 19
<212> TYPE: RNA
<213> ORGANISM: Artificial Sequence
<220> FEATURE:
<223> OTHER INFORMATION: siRNA sequence

<400> SEQUENCE: 13
guuggagcuu guggcguag                                                19

<210> SEQ ID NO 14
<211> LENGTH: 19
<212> TYPE: RNA
<213> ORGANISM: Artificial Sequence
<220> FEATURE:
<223> OTHER INFORMATION: siRNA sequence

<400> SEQUENCE: 14
guuggagcug gugacguag                                                19

<210> SEQ ID NO 15
<211> LENGTH: 19
<212> TYPE: RNA
<213> ORGANISM: Artificial Sequence
<220> FEATURE:
<223> OTHER INFORMATION: siRNA sequence

<400> SEQUENCE: 15
guuggagcug guugcguag                                                19

<210> SEQ ID NO 16
<211> LENGTH: 17
<212> TYPE: RNA
<213> ORGANISM: Artificial Sequence
<220> FEATURE:
<223> OTHER INFORMATION: siRNA sequence

<400> SEQUENCE: 16
guuggagcug auggcgu                                                  17

<210> SEQ ID NO 17
<211> LENGTH: 18
<212> TYPE: RNA
<213> ORGANISM: Artificial Sequence
<220> FEATURE:
<223> OTHER INFORMATION: siRNA sequence

<400> SEQUENCE: 17
guuggagcug auggcgua                                                 18

<210> SEQ ID NO 18
<211> LENGTH: 19
<212> TYPE: RNA
<213> ORGANISM: Artificial Sequence
<220> FEATURE:
<223> OTHER INFORMATION: siRNA sequence

<400> SEQUENCE: 18
guuggagcug auggcguag                                                19
```

```
<210> SEQ ID NO 19
<211> LENGTH: 20
<212> TYPE: RNA
<213> ORGANISM: Artificial Sequence
<220> FEATURE:
<223> OTHER INFORMATION: siRNA sequence

<400> SEQUENCE: 19
guuggagcug auggcguagg                                                   20

<210> SEQ ID NO 20
<211> LENGTH: 21
<212> TYPE: RNA
<213> ORGANISM: Artificial Sequence
<220> FEATURE:
<223> OTHER INFORMATION: siRNA sequence

<400> SEQUENCE: 20
guuggagcug auggcguagg c                                                 21

<210> SEQ ID NO 21
<211> LENGTH: 22
<212> TYPE: RNA
<213> ORGANISM: Artificial Sequence
<220> FEATURE:
<223> OTHER INFORMATION: siRNA sequence

<400> SEQUENCE: 21
guuggagcug auggcguagg ca                                                22

<210> SEQ ID NO 22
<211> LENGTH: 23
<212> TYPE: RNA
<213> ORGANISM: Artificial Sequence
<220> FEATURE:
<223> OTHER INFORMATION: siRNA sequence

<400> SEQUENCE: 22
guuggagcug auggcguagg caa                                               23

<210> SEQ ID NO 23
<211> LENGTH: 24
<212> TYPE: RNA
<213> ORGANISM: Artificial Sequence
<220> FEATURE:
<223> OTHER INFORMATION: siRNA sequence

<400> SEQUENCE: 23
guuggagcug auggcguagg caag                                              24

<210> SEQ ID NO 24
<211> LENGTH: 25
<212> TYPE: RNA
<213> ORGANISM: Artificial Sequence
<220> FEATURE:
<223> OTHER INFORMATION: siRNA sequence

<400> SEQUENCE: 24
guuggagcug auggcguagg caaga                                             25

<210> SEQ ID NO 25
<211> LENGTH: 26
<212> TYPE: RNA
<213> ORGANISM: Artificial Sequence
<220> FEATURE:
<223> OTHER INFORMATION: siRNA sequence
```

```
<400> SEQUENCE: 25
guuggagcug auggcguagg caagag                                                    26

<210> SEQ ID NO 26
<211> LENGTH: 27
<212> TYPE: RNA
<213> ORGANISM: Artificial Sequence
<220> FEATURE:
<223> OTHER INFORMATION: siRNA sequence

<400> SEQUENCE: 26
guuggagcug auggcguagg caagagu                                                   27

<210> SEQ ID NO 27
<211> LENGTH: 28
<212> TYPE: RNA
<213> ORGANISM: Artificial Sequence
<220> FEATURE:
<223> OTHER INFORMATION: siRNA sequence

<400> SEQUENCE: 27
guuggagcug auggcguagg caagagug                                                  28

<210> SEQ ID NO 28
<211> LENGTH: 29
<212> TYPE: RNA
<213> ORGANISM: Artificial Sequence
<220> FEATURE:
<223> OTHER INFORMATION: siRNA sequence

<400> SEQUENCE: 28
guuggagcug auggcguagg caagagugc                                                 29

<210> SEQ ID NO 29
<211> LENGTH: 30
<212> TYPE: RNA
<213> ORGANISM: Artificial Sequence
<220> FEATURE:
<223> OTHER INFORMATION: siRNA sequence

<400> SEQUENCE: 29
guuggagcug auggcguagg caagagugcc                                                30

<210> SEQ ID NO 30
<211> LENGTH: 16
<212> TYPE: RNA
<213> ORGANISM: Artificial Sequence
<220> FEATURE:
<223> OTHER INFORMATION: siRNA sequence

<400> SEQUENCE: 30
cgccaucagc uccaac                                                               16

<210> SEQ ID NO 31
<211> LENGTH: 16
<212> TYPE: RNA
<213> ORGANISM: Artificial Sequence
<220> FEATURE:
<223> OTHER INFORMATION: siRNA sequence

<400> SEQUENCE: 31
cgccaacagc uccaac                                                               16

<210> SEQ ID NO 32
```

```
<210> SEQ ID NO 32
<211> LENGTH: 16
<212> TYPE: RNA
<213> ORGANISM: Artificial Sequence
<220> FEATURE:
<223> OTHER INFORMATION: siRNA sequence

<400> SEQUENCE: 32
cgccagcagc uccaac                                                      16

<210> SEQ ID NO 33
<211> LENGTH: 16
<212> TYPE: RNA
<213> ORGANISM: Artificial Sequence
<220> FEATURE:
<223> OTHER INFORMATION: siRNA sequence

<400> SEQUENCE: 33
cgccacuagc uccaac                                                      16

<210> SEQ ID NO 34
<211> LENGTH: 16
<212> TYPE: RNA
<213> ORGANISM: Artificial Sequence
<220> FEATURE:
<223> OTHER INFORMATION: siRNA sequence

<400> SEQUENCE: 34
cgccacaagc uccaac                                                      16

<210> SEQ ID NO 35
<211> LENGTH: 16
<212> TYPE: RNA
<213> ORGANISM: Artificial Sequence
<220> FEATURE:
<223> OTHER INFORMATION: siRNA sequence

<400> SEQUENCE: 35
cgucaccagc uccaac                                                      16

<210> SEQ ID NO 36
<211> LENGTH: 16
<212> TYPE: RNA
<213> ORGANISM: Artificial Sequence
<220> FEATURE:
<223> OTHER INFORMATION: siRNA sequence

<400> SEQUENCE: 36
cgcaaccagc uccaac                                                      16

<210> SEQ ID NO 37
<211> LENGTH: 10661
<212> TYPE: DNA
<213> ORGANISM: Homo sapiens

<400> SEQUENCE: 37
cgagatcccg gggagccagc ttgctgggag agcgggacgg tccggagcaa gcccagaggc       60
agaggaggcg acagagggaa aaagggccga gctagccgct ccagtgctgt acaggagccg      120
aagggacgca ccacgccagc cccagcccgg ctccagcgac agccaacgcc tcttgcagcg      180
cggcggcttc gaagccgccg cccggagctg ccctttcctc ttcggtgaag tttttaaaag      240
ctgctaaaga ctcggaggaa gcaaggaaag tgcctggtag gactgacggc tgcctttgtc      300
ctcctcctct ccacccgcc tccccccacc ctgccttccc ccctccccc gtcttctctc       360 ccgcagctgc ctcagtcggc tactctcagc caaccccct caccacccctt ctccccaccc      420
```

```
gcccccccgc ccccgtcggc cagcgctgc cagcccgagt ttgcagagag gtaactccct      480
ttggctgcga gcgggcgagc tagctgcaca ttgcaaagaa ggctcttagg agccaggcga      540
ctggggagcg gcttcagcac tgcagccacg acccgctgg ttaggctgca cgcggagaga      600
accctctgtt ttcccccact ctctctccac tcctcctgc cttccccacc ccgagtgcgg      660
agccagagat caaaagatga aaaggcagtc aggtcttcag tagccaaaaa acaaaacaaa      720 caaaacaaa aaagccgaaa taaagaaaa agataataac tcagttctta tttgcaccta      780
cttcagtgga cactgaattt ggaaggtgga ggattttgtt tttttctttt aagatctggg      840
catcttttga atctacccatt caagtattaa gagacagact gtgagcctag cagggcagat      900
cttgtccacc gtgtgtcttc ttctgcacga gactttgagg ctgtcagagc gcttttttgcg      960 tggttgctcc cgcaagtttc cttctctgga gcttcccgca ggtgggcagc tagctgcagc     1020
gactaccgca tcatcacagc ctgttgaact cttctgagca agagaagggg aggcggggta     1080
agggaagtag gtgaagatt cagccaagct caaggatgga agtgcagtta gggctgggaa     1140
gggtctaccc tcggccgccg tccaagacct accgaggagc tttccagaat ctgttccaga     1200
gcgtgcgcga agtgatccag aaccgggcc ccaggcaccc agaggccgcg agcgcagcac     1260
ctcccggcgc cagtttgctg ctgctgcagc agcagcagca gcagcagcag cagcagcagc     1320
agcagcagca gcagcagcag cagcagcagc agcaagagac tagccccagg cagcagcagc     1380
agcagcaggg tgaggatggt tctccccaag cccatcgtag aggccccaca ggctacctgg     1440
tcctggatga ggaacagcaa ccttcacagc cgcagtcggc cctggagtgc caccccgaga     1500
gaggttgcgt cccagagcct ggagccgccg tggccgccag caaggggctg ccgcagcagc     1560
tgccagcacc tccggacgag gatgactcag ctgccccatc cacgttgtcc ctgctgggcc     1620
ccactttccc cggcttaagc agctgctccg ctgaccttaa agacatcctg agcgaggcca     1680
gcaccatgca actccttcag caacagcagc aggaagcagt atccgaaggc agcagcagcg     1740
ggagagcgag ggaggcctcg ggggctccca cttcctccaa ggacaattac ttaggggca     1800 cttcgaccat ttctgacaac gccaaggagt tgtgtaaggc agtgtcggtg tccatgggcc     1860
tgggtgtgga ggcgttggag catctgagtc caggggaaca gcttcggggg gattgcatgt     1920
acgccccact tttgggagtt ccacccgctg tgcgtcccac tccttgtgcc ccattggccg     1980
aatgcaaagg ttctctgcta gacgacacgc caggcaagag cactgaagat actgctgagt     2040 attcccctt caagggaggt tacaccaaag gctagaagg cgagagccta ggctgctctg     2100
gcagcgctgc agcagggagc tccgggacac ttgaactgcc gtctaccctg tctctctaca     2160
agtccggagc actggacgag gcagctgcgt accagagtcg cgactactac aactttccac     2220
tggctctggc cggaccgccg ccccctccgc cgcctcccca tccccacgct cgcatcaagc     2280
tggagaaccc gctggactac ggcagcgcct gggcggctgc ggcggcgcag tgccgctatg     2340
gggacctggc gagcctgcat ggcgcgggtg cagcgggacc cggttctggg tcaccctcag     2400
ccgccgcttc ctcatcctgg cacactctct tcacagccga agaaggccag ttgtatggac     2460
cgtgtggtgg tggtgggggt ggtggcggcg gcggcggcgg cggcggcggc ggcggcggcg     2520
gcggcggcgc cggcgaggcg ggagctgtag ccccctacgg ctacactcgg cccccctcagg    2580 ggctggcggg ccaggaaagc gacttcaccg cacctgatgt gtggtaccct gcggcatgg     2640 tgagcagagt gccctatccc agtcccactt gtgtcaaaag cgaaatgggc ccctggatgg     2700
atagctactc cggaccttac ggggacatgc gtttggagac tgccagggac catgttttgc     2760
```

-continued

```
ccattgacta ttactttcca ccccagaaga cctgcctgat ctgtggagat gaagcttctg      2820
ggtgtcacta tggagctctc acatgtggaa gctgcaaggt cttcttcaaa agagccgctg      2880
aagggaaaca gaagtacctg tgcgccagca gaaatgattg cactattgat aaattccgaa      2940
ggaaaaattg tccatcttgt cgtcttcgga aatgttatga agcagggatg actctgggag      3000
cccggaagct gaagaaactt ggtaatctga aactacagga ggaaggagag gcttccagca      3060
ccaccagccc cactgaggag acaacccaga agctgacagt gtcacacatt gaaggctatg      3120
aatgtcagcc catcttttctg aatgtcctgg aagccattga gccaggtgta gtgtgtgctg      3180
gacacgacaa caaccagccc gactcctttg cagccttgct ctctagcctc aatgaactgg      3240
gagagagaca gcttgtacac gtggtcaagt gggccaaggc cttgcctggc ttccgcaact      3300
tacacgtgga cgaccagatg gctgtcattc agtactcctg gatggggctc atggtgtttg      3360
ccatgggctg gcgatccttc accaatgtca actccaggat gctctacttc gccctgatc      3420 tggttttcaa tgagtaccgc atgcacaagt cccggatgta cagccagtgt gtccgaatga      3480
ggcacctctc tcaagagttt ggatggctcc aaatcacccc ccaggaattc ctgtgcatga      3540
aagcactgct actcttcagc attattccag tggatgggct gaaaaatcaa aaattctttg      3600
atgaacttcg aatgaactac atcaaggaac tcgatcgtat cattgcatgc aaaagaaaaa      3660
atcccacatc ctgctcaaga cgcttctacc agctcaccaa gctcctggac tccgtgcagc      3720
ctattgcgag agagctgcat cagttcactt ttgacctgct aatcaagtca cacatggtga      3780
gcgtggactt tccggaaatg atggcagaga tcatctctgt gcaagtgccc aagatccttt      3840
ctgggaaagt caagcccatc tatttccaca cccagtgaag cattggaaac cctatttccc      3900
caccccagct catgcccct ttcagatgtc ttctgcctgt tataactctg cactactcct      3960
ctgcagtgcc ttggggaatt tcctctattg atgtacagtc tgtcatgaac atgttcctga      4020
attctatttg ctgggctttt ttttttctctt tctctcctttt ctttttcttc ttccctccct      4080
atctaaccct cccatggcac cttcagactt tgcttcccat tgtggctcct atctgtgttt      4140
tgaatggtgt tgtatgcctt taaatctgtg atgatcctca tatggcccag tgtcaagttg      4200
tgcttgttta cagcactact ctgtgccagc cacacaaacg tttacttatc ttatgccacg      4260
ggaagtttag agagctaaga ttatctgggg aaatcaaaac aaaacaagc aaacaaaaaa      4320 aaaaagcaaa aacaaacaa aaaataagcc aaaaaacctt gctagtgttt tttcctcaaa      4380
aataaataaa taaataaata aatacgtaca tacatacaca catacataca aacatataga      4440
aatccccaaa gaggccaata gtgacgaaa ggtgaaaatt gcaggcccat ggggagttac      4500
tgattttttc atctcctccc tccacgggag actttatttt ctgccaatgg ctattgccat      4560
tagagggcag agtgacccca gagctgagtt gggcagggg gtggacagag aggagaggac      4620
aaggagggca atggagcatc agtacctgcc cacagccttg gtccctgggg gctagactgc      4680
tcaactgtgg agcaattcat tatactgaaa atgtgcttgt tgttgaaaat ttgtctgcat      4740
gttaatgcct cacccccaaa cccttttctc tctcactctc tgcctccaac ttcagattga      4800 cttttcaatag ttttttctaag acctttgaac tgaatgttct cttcagccaa aacttggcga      4860
cttccacaga aaagtctgac cactgagaag aaggagagca gagatttaac cctttgtaag      4920 gccccattg gatccaggtc tgctttctca tgtgtgagtc agggaggagc tggagccaga      4980
ggagaagaaa atgatagctt ggctgttctc ctgcttagga cactgactga atagttaaac      5040
tctcactgcc actaccttttt ccccacctttt aaaagacctg aatgaagttt ctgccaaac      5100 tccgtgaagc cacaagcacc ttatgtcctc ccttcagtgt tttgtgggcc tgaatttcat      5160
```

```
cacactgcat tcagccatg gtcatcaagc ctgtttgctt cttttgggca tgttcacaga     5220
ttctctgtta agagccccca ccaccaagaa ggttagcagg ccaacagctc tgacatctat    5280
ctgtagatgc cagtagtcac aaagatttct taccaactct cagatcgctg gagcccttag   5340
acaaactgga agaaggcat caaagggatc aggcaagctg ggcgtcttgc ccttgtcccc    5400
cagagatgat accctcccag caagtggaga agttctcact tccttcttta gagcagctaa  5460
aggggctacc cagatcaggg ttgaagagaa aactcaatta ccagggtggg aagaatgaag   5520
gcactagaac cagaaaccct gcaaatgctc ttcttgtcac ccagcatatc cacctgcaga   5580
agtcatgaga agagagaagg aacaaagagg agactctgac tactgaatta aaatcttcag   5640
cggcaaagcc taaagccaga tggacaccat ctggtgagtt tactcatcat cctcctctgc   5700
tgctgattct gggctctgac attgcccata ctcactcaga ttccccacct tgttgctgc    5760 ctcttagtca gagggaggcc aaaccattga gactttctac agaaccatgg cttctttcgg   5820
aaaggtctgg ttggtgtggc tccaatactt tgccacccat gaactcaggg tgtgccctgg   5880
gacactggtt ttatatagtc ttttggcaca cctgtgttct gttgacttcg ttcttcaagc  5940
ccaagtgcaa gggaaaatgt ccacctactt tctcatcttg gcctctgcct ccttacttag  6000
ctcttaatct catctgttga actcaagaaa tcaagggcca gtcatcaagc tgcccatttt   6060
aattgattca ctctgtttgt tgagaggata gtttctgagt gacatgatat gatccacaag  6120
ggtttccttc cctgatttct gcattgatat taatagccaa acgaacttca aaacagcttt   6180
aaataacaag ggagagggga acctaagatg agtaatatgc caatccaaga ctgctggaga   6240
aaactaaagc tgacaggttc cctttttggg gtgggataga catgttctgg ttttctttat   6300
tattacacaa tctggctcat gtacaggatc acttttagct gttttaaaca gaaaaaaata  6360
tccaccactc ttttcagtta cactaggtta cattttaata ggtcctttac atctgttttg   6420
gaatgatttt catcttttgt gatacacaga ttgaattata tcattttcat atctctcctt   6480
gtaaatacta gaagctctcc tttacatttc tctatcaaat ttttcatctt tatgggtttc   6540
ccaattgtga ctcttgtctt catgaatata tgttttttcat ttgcaaaagc caaaaatcag  6600
tgaaacagca gtgtaattaa aagcaacaac tggattactc caaatttcca aatgacaaaa   6660
ctagggaaaa atagcctaca caagccttta ggcctactct ttctgtgctt gggtttgagt   6720
gaacaaagga gattttagct tggctctgtt ctcccatgga tgaaaggagg aggatttttt  6780
ttttcttttg gccattgatg ttctagccaa tgtaattgac agaagtctca ttttgcatgc   6840
gctctgctct acaaacagag ttggtatggt tggtatactg tactcacctg tgagggactg   6900
gccactcaga cccacttagc tggtgagcta aagatgagg atcactcact ggaaaagtca    6960
caaggaccat ctccaaacaa gttggcagtg ctcgatgtgg acgaagagtg aggaagagaa   7020
aaagaaggag caccagggag aaggctccgt ctgtgctggg cagcagacag ctgccaggat   7080
cacgaactct gtagtcaaag aaaagagtcg tgtggcagtt tcagctctcg ttcattgggc   7140
agctcgccta ggcccagcct ctgagctgac atgggagttg ttggattctt tgtttcatag   7200 cttttctat gccataggca atattgttgt tcttggaaag tttattattt tttaactcc    7260 cttactctga gaaagggata ttttgaagga ctgtcatata tctttgaaaa aagaaaatct   7320
gtaatacata tattttatg tatgttcact ggcactaaaa aatatagaga gcttcattct    7380
gtcctttggg tagttgctga ggtaattgtc caggttgaaa aataatgtgc tgatgctaga   7440
gtccctctct gtccatactc tacttctaaa tacatatagg catacatagc aagttttatt   7500
```

```
tgacttgtac tttaagagaa aatatgtcca ccatccacat gatgcacaaa tgagctaaca    7560
ttgagcttca agtagcttct aagtgtttgt ttcattaggc acagcacaga tgtggccttt    7620 cccccttct ctcccttgat atctggcagg gcataaaggc ccaggccact tcctctgccc     7680
cttcccagcc ctgcaccaaa gctgcatttc aggagactct ctccagacag cccagtaact    7740
acccgagcat ggcccctgca tagccctgga aaaataagag gctgactgtc tacgaattat    7800
cttgtgccag ttgcccaggt gagagggcac tgggccaagg gagtggtttt catgtttgac    7860
ccactacaag gggtcatggg aatcaggaat gccaaagcac cagatcaaat ccaaaactta    7920
aagtcaaaat aagccattca gcatgttcag tttcttggaa aaggaagttt ctaccccctga   7980 tgcctttgta ggcagatctg ttctcaccat taatcttttt gaaaatcttt taaagcagtt    8040
tttaaaaaga gagatgaaag catcacatta tataaccaaa gattacattg tacctgctaa    8100
gataccaaaa ttcataaggg caggggggga gcaagcatta gtgcctcttt gataagctgt    8160
ccaaagacag actaaaggac tctgctggtg actgacttat aagagctttg tgggtttttt    8220
tttccctaat aatatacatg tttagaagaa ttgaaaataa tttcgggaaa atgggattat    8280
gggtccttca ctaagtgatt ttataagcag aactggcttt cctttctct agtagttgct      8340 gagcaaattg ttgaagctcc atcattgcat ggttggaaat ggagctgttc ttagccactg     8400
tgtttgctag tgcccatgtt agcttatctg aagatgtgaa accttgctg ataagggagc      8460 atttaaagta ctagattttg cactagaggg acagcaggca gaaatcctta tttctgccca    8520
ctttggatgg cacaaaaagt tatctgcagt tgaaggcaga agttgaaat acattgtaaa     8580 tgaatatttg tatccatgtt tcaaaattga aatatatata tatatatata tatatatata    8640
tatatatata tagtgtgtgt gtgtgttctg atagctttaa ctttctctgc atctttatat    8700
ttggttccag atcacacctg atgccatgta cttgtgagag aggatgcagt tttgttttgg    8760
aagctctctc agaacaaaca agacacctgg attgatcagt taactaaaag ttttctcccc    8820
tattgggttt gacccacagg tcctgtgaag gagcagaggg ataaaaagag tagaggacat    8880
gatacattgt actttactag ttcaagacag atgaatgtgg aaagcataaa aactcaatgg    8940
aactgactga gatttaccac agggaaggcc caaacttggg gccaaaagcc tacccaagtg    9000
attgaccagt ggcccctaa tgggacctga gctgttggaa gaagagaact gttccttggt      9060
cttcaccatc cttgtgagag aagggcagtt cctgcattg gaacctggag caagcgctct      9120
atctttcaca caaattccct cacctgagat tgaggtgctc ttgttactgg gtgtctgtgt    9180
gctgtaattc tggttttgga tatgttctgt aaagattttg acaaatgaaa atgtgttttt    9240
ctctgttaaa acttgtcaga gtactagaag ttgtatctct gtaggtgcag gtccatttct    9300
gcccacaggg agggtgtttt tctttgatta agagattgac acttctgttg cctaggacct    9360
cccaactcaa ccatttctag gtgaaggcag aaaaatccac attagttact cctcttcaga    9420
catttcagct gagataacaa atcttttgga attttttcac ccatagaaag agtggtagat    9480
atttgaattt agcaggtgga gtttcatagt aaaaacagct tttgactcag ctttgattta    9540
tcctcatttg atttggccag aaagtaggta atatgcattg attggcttct gattccaatt    9600
cagtatagca aggtgctagg ttttttcctt tccccacctg tctcttagcc tggggaatta    9660
aatgagaagc cttagaatgg gtggcccttg tgacctgaaa cacttcccac ataagctact    9720
taacaagatt gtcatggagc tgcagattcc attgcccacc aaagactaga acacacacat    9780
atccatacac caaaggaaag acaattctga aatgctgttt ctctggtggt tccctctctg    9840
gctgctgcct cacagtatgg gaacctgtac tctgcagagg tgacaggcca gatttgcatt    9900
```

| | |
|---|---|
| atctcacaac cttagccctt ggtgctaact gtcctacagt gaagtgcctg gggggttgtc | 9960 |
| ctatcccata agccacttgg atgctgacag cagccaccat cagaatgacc cacgcaaaaa | 10020 |
| aaagaaaaaa aaaattaaaa agtcccctca caacccagtg acacctttct gctttcctct | 10080 |
| agactggaac attgattagg gagtgcctca gacatgacat tcttgtgctg tccttggaat | 10140 |
| taatctggca gcaggaggga gcagactatg taaacagaga taaaaattaa ttttcaatat | 10200 |
| tgaaggaaaa aagaaataag aagagagaga gaaagaaagc atcacacaaa gattttctta | 10260 |
| aaagaaacaa ttttgcttga aatctcttta gatgggctc atttctcacg gtggcacttg | 10320 |
| gcctccactg ggcagcagga ccagctccaa gcgctagtgt tctgttctct ttttgtaatc | 10380 |
| ttggaatctt ttgttgctct aaatacaatt aaaaatggca gaaacttgtt tgttggacta | 10440 |
| catgtgtgac tttgggtctg tctctgcctc tgctttcaga aatgtcatcc attgtgtaaa | 10500 |
| atattggctt actggtctgc cagctaaaac ttggccacat cccctgttat ggctgcagga | 10560 |
| tcgagttatt gttaacaaag agacccaaga aaagctgcta atgtcctctt atcattgttg | 10620 |
| ttaatttgtt aaaacataaa gaaatctaaa atttcaaaaa a | 10661 |

<210> SEQ ID NO 38
<211> LENGTH: 11025
<212> TYPE: DNA
<213> ORGANISM: Homo sapiens

<400> SEQUENCE: 38

| | |
|---|---|
| gagcatcttt tggggggagg gaattcagcg gatcagtctt aagaggagct ttttttttgga | 60 |
| gcgagaaatc atataaaata aaatgaaata aaacaaggag gaaggcaacc agctgttagg | 120 |
| ggaaaaataa ggcagataaa ggagcgggga gagaaattaa ttgccaacca ggaggagttg | 180 |
| ggctgtattt ttcaaaggtg gggagagtgg agcacacacc ttgaggagga aagcgagaaa | 240 |
| gaaaagaaaa aagcaagtgg aaagggggc tcgcccaaga agggtgaaga agcgaagaaa | 300 |
| gtcgaggcgc cgaggctccc aaagctggca gctccgggtg gcggtgcagg ggcgaagggg | 360 |
| gggcggggg aaccgtcgga catgcggctc tggagttggg tgctgcacct ggggctgctg | 420 |
| agcgccgcgc tgggctgcgg gctggccgag cgtccccgcc gggcccggag agacccgcgg | 480 |
| gccggccgac ccccgcgccc cgccgccggc ccggccacct gcgccacccg ggcggcccgc | 540 |
| ggccgccgcg cctcgccgcc gccgccgccg cgccggggcg gtgcctggga agccgtcgcc | 600 |
| gtccccggc ggcggcagca gcgggaggcg aggggcgcca ccgaggagcc gagcccgccg | 660 |
| agccgggcgc tctatttcag cgggcgaggc gagcagctgc gcctccgggc cgacctcgag | 720 |
| ctgccccggg acgcgttcac gctgcaagtg tggctgcgag cggagggggg ccagaggtct | 780 |
| ccggcagtga tcacagggct gtatgacaaa tgttcttata tctcacgtga ccgaggatgg | 840 |
| gtcgtgggca ttcacaccat cagtgaccaa gacaacaaag acccacgcta cttttttctcc | 900 |
| ttgaagacag accgagcccg gcaagtgacc accatcaatg cccaccgcag ctacctccca | 960 |
| ggccagtggg tatacctagc tgccacctat gatgggcagt tcatgaagct ctatgtgaat | 1020 |
| ggtgcccagg tggccacctc tggggaacaa gtgggtggca tattcagccc actgacccag | 1080 |
| aagtgcaaag tgctcatgtt aggggcagt gccctgaatc acaactaccg gggctacatc | 1140 |
| gagcacttca gtctgtggaa ggtggccagg actcagcggg agatactgtc tgacatggaa | 1200 |
| acccatggcg cccacactgc tctacctcag ctcctcctcc aggagaactg ggacaatgtg | 1260 |
| aagcatgcct ggtcccccat gaaggatggc agcagcccca aagtggaatt cagcaatgcc | 1320 |

```
cacggctttc tgctggacac gagtctggag cctcctctgt gcggacagac attgtgtgac    1380
aacacagagg tcattgccag ctacaatcag ctctcaagtt ccgccagcc caaggtggtg     1440 cgctaccgcg tggtcaacct ctatgaagat gatcataaga acccgacggt gacgcgcgag    1500
caggtggact ccagcacca tcagctggct gaggccttca agcaatacaa catctcctgg     1560
gagctggacg tgctggaggt gagcaactcc tcccttcgcc gccgcctcat cctggccaac    1620
tgtgacatca gcaagattgg ggatgagaac tgtgaccccg agtgcaacca cacgctgacg    1680
ggccacgacg gcggggattg ccgccacctg cgccaccctg ccttcgtgaa gaagcagcac    1740
aacggggtgt gtgacatgga ctgcaactat gaacggttca actttgatgg tggagagtgc    1800
tgtgaccctg aaatcaccaa tgtcactcag acttgctttg accccgactc tccacacaga    1860
gcctacttgg atgttaatga gctgaagaac attcttaaat tggatggatc aacacatctc    1920
aatattttct ttgcaaaatc ctcagaggag gagttggcag gagtagcaac ttggccatgg    1980
gacaaggagg ccctgatgca cttaggtggc attgtcttga acccatcttt ctatggcatg    2040
cctgggcaca cccacaccat gatccatgag attggtcaca gcctgggcct ctatcacgtc    2100
ttccgaggca tctcagaaat ccagtcctgc agtgacccct gcatggagac agagccctcc    2160
ttcgagactg agacctctg caatgatacc aacccagccc ctaaacacaa gtcctgtggt     2220
gacccagggc caggaaatga cacctgtggc tttcatagct tcttcaacac tccttacaac    2280
aacttcatga gctatgcaga tgacgactgt acggactcct tcacgcccaa tcaagtcgcc    2340
agaatgcact gttacctgga cctggtctac cagggctggc agccctccag gaaaccagcg    2400
cctgttgccc tcgcccccca gttctgggc cacacaacgg actctgtgac actggagtgg    2460
ttcccaccta tagatggcca tttctttgaa agagaattgg gatcagcatg tcatctttgc    2520
ctggaaggga gaatcctggt gcagtatgct tccaacgctt cctccccaat gccctgcagc    2580
ccatcaggac actggagccc tcgtgaagca gaaggtcatc ctgatgttga acagccctgt    2640
aagtccagtg tccgcacctg gagcccaaat tcagctgtca acccacacac ggttcctcca    2700
gcctgccctg agcctcaagg ctgctacctc gagctggagt tcctctaccc cttggtccct    2760
gagtctctga ccatttgggt gacctttgtc tccactgact gggactctag tggagctgtc    2820
aatgacatca aactgttggc tgtcagtggg aagaacatct ccctgggtcc tcagaatgtc    2880
ttctgtgatg tcccactgac catcagactc tgggacgtgg gcgaggaggt gtatggcatc    2940
caaatctaca cgctggatga gcacctggag atcgatgctg ccatgttgac ctccactgca    3000
gacaccccac tctgtctaca gtgtaagccc ctgaagtata aggtggtccg ggaccctcct    3060
ctccagatgg atgtggcctc catcctacat ctcaatagga aattcgtaga catggatcta    3120
aatcttggca gtgtgtacca gtattgggtc ataactattt caggaactga agagagtgag    3180
ccatcacctg ctgtcacata catccatgga agtgggtact gtggcgatgg cattatacaa    3240
aaagaccaag gtgaacaatg cgacgacatg aataagatca atggtgatgg ctgctccctt    3300
ttctgccgac aagaagtctc cttcaattgt attgatgaac ccagccggtg ctatttccat    3360
gatggtgatg gggtatgtga ggagtttgaa caaaaaacca gcattaagga ctgtggtgtc    3420
tacacgcccc agggattcct ggatcagtgg gcatccaatg cttcagtatc tcatcaagac    3480
cagcaatgcc aggctgggt catcatcgga cagccagcag catcccaggt gtgtcgaacc    3540
aaggtgatag atctcagtga aggcatttcc cagcatgcct ggtacccttg caccatcagc    3600
tacccatatt cccagctggc tcagaccact ttttggctcc gggcgtattt ttctcaacca    3660
atggttgccg cagctgtcat tgtccacctg gtgacggatg ggacatatta tgggggaccaa    3720
```

```
aagcaggaga ccatcagcgt gcagctgctt gataccaaag atcagagcca cgatctaggc    3780
ctccatgtcc tgagctgcag gaacaatccc ctgattatcc ctgtggtcca tgacctcagc    3840
cagcccttct accacagcca ggcggtacgt gtgagcttca gttcgcccct ggtcgccatc    3900 tcggggggtgg ccctccgttc cttcgacaac tttgaccccg tcaccctgag cagctgccag    3960
agagggagaa cctacagccc tgccgagcag agctgcgtgc acttcgcatg tgagaaaact    4020
gactgtccag agctggctgt ggagaatgct tctctcaatt gctccagcag cgaccgctac    4080
cacggtgccc agtgtactgt gagctgccgg acaggctacg tgctccagat acggcgggat    4140
gatgagctga tcaagagcca gacgggaccc agcgtcacag tgacctgtac agagggcaag    4200
tggaataagc aggtggcctg tgagccagtc gactgcagca tcccagatca ccatcaagtc    4260
tatgctgcct ccttctcctg ccctgagggc accacctttg gcagtcaatg ttccttccag    4320
tgccgtcacc ctgcacaatt gaaaggcaac aacagcctcc tgacctgcat ggaggatggg    4380
ctgtggtcct tcccagaggc cctgtgtgag ctcatgtgcc tcgctccacc ccctgtgccc    4440
aatgcagacc tccagaccgc ccggtgccga gagaataagc acaaggtggg ctccttctgc    4500
aaatacaaat gcaagcctgg ataccatgtg cctggatcct ctcggaagtc aaagaaacgg    4560
gccttcaaga ctcagtgtac ccaggatggc agctggcagg agggagcttg tgttcctgtg    4620
acctgtgacc cacctccacc aaaattccat gggctctacc agtgtactaa tggcttccag    4680
ttcaacagtg agtgtaggat caagtgtgaa gacagtgatg cctcccaggg acttgggagc    4740
aatgtcattc attgccggaa agatggcacc tggaacggct ccttccatgt ctgccaggag    4800
atgcaaggcc agtgctcggt tccaaacgag ctcaacagca acctcaaact gcagtgccct    4860
gatggctatg ccatagggtc ggagtgtgcc acctcgtgcc tggaccacaa cagcgagtcc    4920
atcatcctgc caatgaacgt gaccgtgcgt gacatccccc actggctgaa ccccacacgg    4980
gtagagagag ttgtctgcac tgctggtctc aagtggtatc ctcaccctgc tctgattcac    5040
tgtgtcaaag gctgtgagcc cttcatggga gacaattatt gtgatgccat caacaaccga    5100
gcctttgtca actatgacgg tgggggattgc tgcacctcca cagtgaagac caaaaaggtc    5160
accccattcc ctatgtcctg tgatctacaa ggtgactgtg cttgtcggga cccccaggcc    5220
caagaacaca gccggaaaga cctccgggga tacagccatg gctaaggaag gacaagaagt    5280
tgtcaaagaa ttcccaacgc caggacccac atcccttttgg tattgatttc acagtcagct    5340
gctcaacgga atggcctctc cacaccaggg atccttagca cccaaccggt ctgccttta    5400 ttttacccag gaaggactca cattgggcg aatgaaccaa gtttcgccat gctggatgat    5460
gaaatggatt cccatcccaa agtctgagat ggattgcata tacagtgtgc agtcccagag    5520
cctcctaaaa ttctagccat tgtcacaca accacagcaa gaaacgtgtt ctatatctag    5580
agtgtgccca tctgtgttta gtacacatgc atgcatacac acccatacaa acatctgtgt    5640
gagggcagtt ctggagatga gcagagagag accggaataa actcaatctt ttctttccca    5700
agctcctagc caacactatc cttgggagaa agaaatttgc agaaactgct aagaccaagt    5760
gtggagatgt caagctagtt cacactctga ggctcagaat atgtaggaca tgcacaattg    5820
tgcagtcctt tgggattgga agtgaaacag tctgtgatcc cctaccttct agggaactag    5880
gacctaggaa gaggtaaaga ttatcaggta tgcaaagcgc cccaattctt ctgctgccat    5940
gggggatttt accccaactc cagggttcga ggccaatctg agaatggctt aggattgcaa    6000
tgtcaaggta ttatatcagc cccttgcttg aggcttgagg tcataatatc cctctaggac    6060
```

```
ttacctgttc ccccagatct tgccttggga ccacatttgc tgctactttt cctgctgctc    6120
tatcctatac attgaataat ccaagatggt agaactaggt taggaaaaat tccacacaac    6180
caaacagtct gccttaaaag tgacccacat ttttccatag ctcctcactt tttagccctt    6240
ctgcaagaga aaaaccctca tgggtccaca tggtgagaag ttaagtttcc tgtaagtggg    6300
cctctcaccc tggaaaggag ttgagggaca tcagatgctg gaaccctcac tgaaagtcca    6360
gaatgtctaa gccagtgtta gattttgtaa acaagtggaa cagtgttaaa tttctatgat    6420
gttggagcca tccagagact actggaattg tcgagacttt tggattatta tccttatcct    6480
tatcctaatc ttcctagccc ttcaggctag agtaggcttc gatcctgaga accttgctgt    6540
tgctctgagg agatataatt ctgggagaaa gaatctttta taagaacagt acagattgtt    6600
ctcaagaggg ccatcagaag gaagccaaag agttcacagc ctcagcacca acaactcaac    6660
atggtcatca tgttttctat atggttttc cagctagcag tactcccttc catacctgtg    6720
actgggcagt gcttttctct ctcccatgtc tagcctccaa aagttaagtg aaaattagtc    6780
aactgcacgt ggaagccccc accactttgg ggatctcttt atttcttttc agccagggac    6840
ctgtccactc cctttgaatt aatatgggaa gaaattaata caggatgaac tggagagaag    6900
ggttgagtgt ggcatacttt ctgaaacctg gagctgggaa ttgcggagaa gggaaggtct    6960
agactagtta catcacatag ggattactgt aaatcaagtc atctcaagtc tagtgaagac    7020
agccaacaga aacaaaacct agcatatggga tagaaaatac catgcacgtg tgcagcccca    7080
cctaattcct gcatccaagg caggtgttgt taatctatca tagcacttaa aaaaaaaaa     7140
aaaaagagac caaaaataac tttaggaacc accatattat atcactccca atagcactga    7200
cctggtgatc aaaaacactt gagaagacat ctattggcca tctctggcca attacactaa    7260
gaaacatatc aaggtgcttt tggcacaggt gcccacaaat acggatgcag tgctgagata    7320
gtttatgaga cttgtaccat ttcacaaact ctgaaattgg gttccatatt ggcaaggctg    7380
ccacagttgt taagaataat cctctatgtt tcttcctcac aaaaccatat ctcatttata    7440
tccagaccat tacttcacta taattacaag gacaaattat tagcaagaaa taagaatagt    7500
attagaagaa ttgatcctat tttgaacccc tctccagtat cttcacactc ttgtcaactc    7560
tccaggcctc tctcttgccc tgagttatca gcctgtgtgg tgttaactac cttagaaggt    7620
acaagctaag aaatgtaaca gtatcaaccc tcccagttgc ttaattatac ccataggtaa    7680
tacaaaaagc tctgaagacc caaagatgac attactaatg atgtgatttc aggagccaca    7740
gaagaacctt accagcttcc ctcaaatcag tccttatcct cttctatct tcactcccat     7800
catcatctat tttcacacta tccagctaag caaagattcc tggaggctga cttgtatctt    7860
cagactcaca gagtgaattc agctcttctg aatcaagacc cacccagtct ctttcattca    7920
gacctgttgc taacaaattt atatttgcca aggatattag gcaaagagg ctacttgatt      7980
ggtggccaac ctcgtgccca catggaaggt atctttaata gggtcttttc aaaccttagt    8040
ggaggagggt cagctcaatt tggcaatgc atttgttccc agtttcattt tcttcctggg     8100
aattaactcg tcatttcatt ccttcagtca tcttctgtgt aggtgaccgg agcactgaga    8160
ggcagctctg atgcactatt gtgtgtcagc agctcaaagg ccctaaaaca ctgaaggttc    8220
tgcatctgaa gtattagatt gttagcagca aaatatgaaa gatgaggtgg acagtcctct    8280
aagccctatt tagggaagct tttccaagcc acaatcttaa ctacctaccc aaaggatttg    8340
cattacccccc agattctgtg ccaacaacct tttaaggaaa tacagtcctt gggaaatgag   8400
ttttgatggt gaattggggt gttaaggaag ggaaagattg tcatagatgg tagggctttg    8460
```

```
aaaatgcagg gtatcagctg ccactcctgg cttcaacaca ttgagtcact gcctagacgg   8520
ttctcttggt cttattccca tcctggccaa tgcttaaata ctatttgttg aaaataattc   8580
tttgagacag atttcagcta cctcccttcc aggttcgatt taacttggtt gtaattgtca   8640
atttgttgtt ataggtctta cctgtgtgaa agaaagaaaa agaaagaaag aaagaaagag   8700
aaaggaaatt ataaggtcaa gttaacagtt ttgaggtttt gtgttttttt ctggaactac   8760
ttcaagtgag aaaataaaaa aaaatggtga caaagctgta cagatagaga taatagaaga   8820
caaagagatt aaaaggaaat aaaaatgcat gattaaaaac taagaataaa aaacctattt   8880
ttatgtttcc taaaggaaat tgtttattct acagcctcag taggtagaca caaacataaa   8940
gatttcccta gaagacatag agtgggattt gataacactg tctgttattt tctgtacatt   9000
gtggtaggtc caggaaatat gacatttttcc cccttgatgt gttattgttg ttgttgggtg   9060
gggtgggcat tttgtttatt tgtttggtgg caatcagtgg tagtagggag tgggagggct   9120
tatattggtt tttccagcta ttaaggggac atattgtgtc gttgtgcttt tcacgttata   9180
aaatgtttat atttaccagt acagcactgg gctttataaa gactgcactc agaaccacac   9240
tgcacagtcc agtttttttaa aaagctgcta catgacagac aggtaatccc actgagtgag   9300
ttttgagaaa caaatcaaac gaagtaaaca agaaacataa aaaccaaata gcaaatgaat   9360
aaaagcctgt tcttgtaact tattcaactt ttgccaaatt cctaccaatc acttgctttt   9420
taaaagaaat gtataatagc caaaagagaa attatgtccc tgttgtacag aagttagaat   9480
ttttgactcc aggcagcagt ttgctcagtg atcttgaaca agttatccaa ttgcctctac   9540
atttgcatca gtttctctag ctgcaaaatg gggataatac tatataccta cctcacagtg   9600
ggagggcagg agattttgag gccctgaggt tttaggtggg ctgtgagggc aacgcttga    9660 cacaaagtcc atgggttatt attcaagaat gcacaggccc atcggccttt tagaaagaca   9720
agacagggag tgcttgtttg atatttcaag gaataaagcc ggagctcctg aattgtagtc   9780
caccttaaaa gagagacctg tattggagaa tattttattt ttttggcaaa tttgatctta   9840 cccttaccagttctataat ttggttaaaa gctgattatg tcctacaatg tcaaagtcag   9900
ctaactgtcg tctacttaag acttctggtc atttccaact tatagaggaa gggagtctct   9960
aaaatctctt cttcagaagg cacctcactt ctcagactta aaattccaca tcaagtgttc  10020
cattaaaaga agataaggca ttctgagtgc aaacaaatgg gggcttctta aactacacac  10080
cagcagtcag tgaggaaaac tttgaacaat tattgagttg ctttcttggg tctctataat  10140
caataacctg tctgcagata tctatctata taaagatatt atatataaat ataaatttac  10200
atatatatgc acatgtatat atagttgtac atatatgtgt gtatatatat acttaaatgt  10260
aatatttaca aaataaaact gtgatctcgt ctagagaaaa tgtattcata ttacaaactg  10320
ctcttccata tttatgtacc atattatacc tttttattat tgttataatt attatgggta  10380
tttctaatta atatgatgtt gaaacctgtt tggcaccttc tggaagctac caaaaaaatg  10440
acactccatt gaagtgctta aaagctgttc tcataagaat tctactggcc tattgtaaaa  10500
aagaaaaaaa aaaagaaaaa gaagaaagac acaaagaaaa taatctaaac accaaaaact  10560
aaacacaatt ccaatccttt ttctgtacct cacgcgcata aatttgctgc tcctattttt  10620
ttttctgttt atgtgttttt atggatctaa gttaaatctt ttggcaatat ataaaaatgt  10680
aaatagtaaa cttatttat taagaatgtc atcttttttta atttatattt acacaattgt  10740
tcatctaatt tattttttct atacagttttt aaatactcag acatattttg ctgttcatga  10800
```

```
tattttttatc ctgttctcat ggatttgttt tcccatactg ttttctctga tctcaattac    10860
aggttggatc tcacaaataa taatgtcaga gacagaaata ttttgccact gttgattact    10920
atactttaaa gttctatatt atgaaaatat ataatagctt gtacgcttca aaaaaaaaaa    10980
aaaaaaaaaa aaaaaaaaaa aaaaaaaaaa aaaaaaaaaa aaaaa                    11025

<210> SEQ ID NO 39
<211> LENGTH: 5646
<212> TYPE: DNA
<213> ORGANISM: Homo sapiens

<400> SEQUENCE: 39
cataactgtc atctgagaag cttcatccag caactgatgg gaacaaatgc agtgacccac       60
agccaaacat taggcagagc ttggggaatc ctgtggaaga taaggatgg aatgagccag       120 aatgatcaag gacaccataa gaaaacatac agaattaact tacctggacc catagtgttg       180
ctgataacag tacttgtcgt ggaagggatt gctgtggccc aaaaaaccca agatggacaa       240
aatattggaa tcaagcacat tcctgcaacc cagtgtggta tttgggttcg aaccagcaat       300
ggaggtcatt ttgcttcacc aaattatcct gactcatatc caccaaacaa ggagtgtatc       360
tatattttgg aagctgctcc tcgtcaacga atagagctga cctttgatga acgctattat       420
atagagccat cattcgaatg tcggtttgat cacttggaaa ttcgagacgg gccatttggt       480
ttttctcctc ttatagatcg ttactgtggc atgaaaagcc ctgcattaat taggtcaacg       540
ggaagattca tgtggattaa atttagttct gatgaagaac ttgaaggact aggatttcga       600
gcaaaatact cattcatccc agatccagac tttacttacc ttggagattg ccagtttgag       660
ctctctggag ctgatggaat agtacggtct agccaagtag agcaagaaga gaaaacaaag       720
cctggccaag cagttgattg catatggaca attaaagcta ctccaaaagc taagatttat       780
ttgaggttcc tagattacca aatggaacac tcaaatgaat gcaaaagaaa ttttgtggca       840
gtctatgatg gaagcagtgc tatcgaaaat ctgaaggcca agttctgcag cactgtggct       900
aatgatgtca tgttgaaaac aggagtcgga gtgatccgga tgtgggcaga cgaaggcagt       960
cggcttagca ggtttaggat gctcttcact tcctttgtgg aacctccctg tacaagcagc      1020 actttcttt gccatagcaa catgtgcatc aacaattctt tagtctgtaa tggtgttcaa      1080
aactgtgcat accccttggga tgagaatcac tgtaaagaaa agaaaaaagc tggactattt      1140
gaacaaatca ctaaaactca tgggacaatt attggcatta catcaggaat tgtcttggtc      1200
cttctcatta tttctatttt agtacaagtg aaacagcccc ggaaaaaggt tatggcttgc      1260
aaaactgcat ttaataaaac tgggttccag gaagtatttg atcctcctca ttatgaacta      1320
ttttcactaa gagagaaaga gatttctgca gatctggcag atttgtcaga gaacttgac      1380 aactaccaga agttgcggcg ctcctccacg gcctcccggt gcattcacga ccaccactgt      1440
ggatcacaag catccagtgt gaaacaaagc aggaccaacc tcagttccat ggaacttccc      1500
ttccgaaatg attttgcaca accacagcca atgaaaacat taatagcac cttcaaaaaa      1560 agcagctaca ctttcaaaca agctcatgag tgccctgaac aggctctaga ggacagagtg      1620
atggaggaga ttccctgtga aatttatgtc agagggcgag acgattctgc acaagcatcc      1680
atatccatcg acttttaatt gctgactaaa ggcattattg ttaagtgtgt atgcagccta      1740
caccaacact cattctatct ccgcatccaa tcttgttcta tcaaatttag aaagcccttc      1800
ataacttatc ataatgctga tgattttatt atctcaggca atctatatat gtgaaaccaa      1860
ctaagaaact taaatgtatt cagtggaaag aaggcatcat ctgttgctgg tatcttaacc      1920
```

```
tgtaaaacac caccagtgca atagcagctg aggagcaggt catgcatgtt aagtcaggca    1980
gagcagcccg gtgctgtgaa caccaggcac tgtgcgtgtc tgcacagccc catcaacttg    2040
atctcacagt aaatttaaaa gttttttctt tatattcctt ttgtccttct tttttctgtt    2100
atgttttctt tgcctgtggt tttaccattt cagtttcctg cagacgggga taatatgtca    2160
ctcaattcag catggccatg catttgctcc taaatgagtg taatacggct agtactgtaa    2220
taagtggcag tttaagatgc agtcatattt catttcttcc tgactgattt ctacactgtt    2280
gtctttaata actgcatctt tagttctgct tttctatggg aagtaggact tatcaccttt    2340
aatcatgttt catcttagtt atactaaaaa agtaagaatc ctagggtata ttattaccag    2400
atacacatga acagaatttt gagaaagatt aaaaacttgt agcaacctct gaagttttcc    2460
ccactgggtc tcaattcagt gacagtaatc agggtcctag aactcacctg tgagcagacc    2520
tttaattatg gctccatgca gagcttctca gatcttattc cctatcatct ttcaaaacga    2580
tttctttgtt ctcttggtat tggtttgtct tggacatggc catggttggt ggaagcttaa    2640
agaaattctc agagaaactg tgttagccct tacatagctt ctgcttgaaa cagtgcattt    2700
ttctacccat tatcgagaag agcaatttca actttttttt taagctgcac ttttaacctt    2760
atgtttttta agtatataa aacaataatt tataaacacg gtatcaaaac tcattgtgtt    2820
ttttagact tttgatatta tttgatattg tataaacttt attagatcaa gatttaagac    2880
atacaagaca atttctttaa gtcttcacag tagtgacttt atatagaaga atactgtgat    2940
gggactgtac tgtaatttat tataaagacc ttgctcatgg tgatatgtac atacattttt    3000
cttctttg ctgctgtgtt agttggtaat aagttttca ctgtgtggta tttattgttc       3060
taaatcacaa cagaaatctt atattagagt atacattaat tcatgatcct tcaattatat    3120
tatttatagc aggaatcctt tgaataagat atagatgagg aagaattcat atatttaatg    3180
ataaccaata gagataatgc cattttaaag aagtaaattc tcattttcta tattgaacta    3240
aatttccaat gaatgaaaag ttgaggtttc actagatttc atttattttt ttaagtacta    3300
cataaatctg atttctcaga ttactaaaaa ctttgacctt tagtgtgatg tactttctga    3360
ccaaagtgtg ttttctgtat gacattttt ttattttttaa aaaggaaatt atatcaagaa     3420
tattgggaaa acttacccct ggcataagca tgacttaatt ttttaagtca gtagatgttc    3480
ctgctttgta aaatagaact tggaaaagta aaaggaatct caaaacatag taatcactga    3540
actatccaga gaaaaattaa atgttctttc agtaactata agcattttat tatgtgactt    3600
agaccagcca ccactccaac accatagtaa atacttaaat tgatagctat gataccatag    3660
tgaaataaaa attaacaatt ttataaatta tatccactat aaaaatagtt gtcatattca    3720
tcattaattt taagattata gtttatagta tgccttcata catcatgatc acttgtaggt    3780
gtattttat ttttaacact attctatttt aaaggaattt gaagggattt acaaaacagt     3840
tgtttgtaca aaatactgaa cattccaacc atgtaaattt gcatgatctc atgcatcagc    3900
aagagaaact cgggtgatca tttggttcta aattctctaa ctagaaagtt gatccttttc    3960
acagtagaaa acacttatat tcagaggcta aagtgaaagc cataaactta agcagtaaca    4020
aatatgaagt taagctgtct tatgtgagtt attataccct acaaagtacc tgtgttaaac    4080
acacccttca gtgaaaaatg caaagccaga ggatagtaaa aatctccagt gcaagaaagt    4140
actaagtaca aactatatga taccaacaca ttgctgtcgt tcatcccaag ttcactacaa    4200
gctgtcagct cccaagtagc cacagactgc aacctacaca tcccactgtc tcaaagacat    4260
```

```
gggaataaac tgttatttgt ttgcagaaga gagttatcaa tataaatatt gaacaaaaac    4320
caaaggatgt ttacatttca catcatggat ctgaaaggct cccttagctt tgctttagga    4380
gagtctttgt cactctccta catgcgtttt gtatcattgc taagcattaa ggaactgcag    4440
tctgcactga acatttctat actttggata ctacctaatg atggtacttg cttgggtcag    4500
gaacatatca gctaagatga gaaaaggctg cttgtagttc caggaataat taacattcag    4560
agattacact ttgttgcaaa atgatgtctg ccatatgccc acttttattt actacaagtg    4620
ttaagagaaa tgtgcctgaa tcacattgat tgtggacaga aggaacttta ttttgttctg    4680
tttaaagatc caagagagat gatctagtct agttttgtca atgagaagac aaaaccctga    4740
tggtgaagta gctccccatg gctccatcct cctagcccag taaccttcct tggcttcttc    4800
tctccctgct tagcttttaa aagtcacata attccaaaca tcagcctaga tgttccatgc    4860
aaaacttgtt agttatgctt acttaaaatg taatgctgta attttgtata caagggggt     4920 ttcaccctcc cttttaatt tatataacac tgttatccca tcagttttgt taccagactt    4980
ccttggcacc tgcagaatat gtaattactg tgaattctta gtaaacagtg ctggttagca    5040
gcacataggc tgatgccaga agaaagctc tgtgctttca cgtttgtaat ttttttagtt    5100
aaaattaaca atgtacatta tagaaattaa atattgggta ctgtatcttg agttttgaga    5160
attatttgag tctgaaccac tgtaagagaa caagctgacc tgggatatcc ttttagcttc    5220
ctacaccatc tgttacctgt tatgtatctt tcctagtagt atgttcttct tcactcggct    5280
ttttaagata cttttgacta tatttctgag attggtttac tggctcaaaa agcctccaag    5340
ctaatgatga gggtgcacgt atagtgagta ctacctaaac ttgttttttt aaggagtaga    5400
tttctattag agacaaactt ccagatcatg taagaattct cattgcttaa tccagatttg    5460
gcactttaaa gtacttaacc cttgaaatgc aaataaaaat tcctcttttg attttcttcc    5520
ttgcctcaat tctgaagcgt gtaaaagtag aacatttagc tactttggac atttataggc    5580
ccttcctaaa acagtacgaa ttcctatttg ctgcattcca aataaaatag tcagggttta    5640
tttgtt                                                              5646

<210> SEQ ID NO 40
<211> LENGTH: 3328
<212> TYPE: DNA
<213> ORGANISM: Homo sapiens

<400> SEQUENCE: 40
ctgcggcgag tgcggcgctg acagagacgc gcgcgcgcgc gatcgcgctc ggaccccggc      60
cgctgccgcc atcactgtcg cccgcccagt cgcccctcag ccgcttcccc tcgccatgga     120
ggcgaggccg ccgccgccgc cgcggggctc ggagccgcgg gccgggcggc ggccctgagg     180
gctagtggcg gcccgaaacg ccgccgcgga gccgaggcgg agccgctgtc ctcgtcccca     240
gcggtcccgc ccaacgcccg actctgtgac acaactaaaa aaaacaaag gtatttatgg      300 aattccactg agtggtaatg gatgatgcag ttcaaataac taaggacaca tgttcaaaga     360
gcataattaa cttttaaaa gaagctaata agcatggatt cctggttcat tcttgttctg     420
ctcggcagtg gtctgatatg tgtcagtgcc aacaatgcta ccacagttgc accttctgta     480
ggaattacaa gattaattaa ctcatcaacg gcagaaccag ttaaagaaga ggccaaaact     540
tcaaatccaa cttcttcact aacttctctt tctgtggcac caacattcag cccaaatata     600
actctgggac ccacctattt aaccactgtc aattcttcag actctgacaa tgggaccaca     660
agaacagcaa gcaccaattc tataggcatt acaatttcac caaatggaac gtggcttcca     720
```

```
gataaccagt tcacggatgc cagaacagaa ccctgggagg ggaattccag caccgcagca    780
accactccag aaactttccc tccttcagat gagacaccaa ttattgcggt gatggtggcc    840
ctgtcctctc tgctagtgat cgtgtttatt atcatagttt tgtacatgtt aaggtttaag    900
aaatacaagc aagctgggag ccattccaat tctttccgct tatccaacgg ccgcactgag    960
gatgtggagc cccagagtgt gccacttctg gccagatccc caagcaccaa caggaaatac   1020
ccacccctgc ccgtggacaa gctggaagag gaaattaacc ggagaatggc agacgacaat   1080
aagctcttca gggaggaatt caacgctctc cctgcatgtc ctatccaggc cacctgtgag   1140
gctgcttcca aggaggaaaa caaggaaaaa atcgatatg taaacatctt gccttatgac   1200
cactctagag tccacctgac accggttgaa ggggttccag attctgatta catcaatgct   1260
tcattcatca acggctacca agaaaagaac aaattcattg ctgcacaagg accaaaagaa   1320
gaaacggtga atgatttctg gcggatgatc tgggaacaaa acacagccac catcgtcatg   1380
gttaccaacc tgaaggagag aaaggagtgc aagtgcgccc agtactggcc agaccaaggc   1440
tgctggacct atgggaatat tcgggtgtct gtagaggatg tgactgtcct ggtggactac   1500
acagtacgga agttctgcat ccagcaggtg ggcgacatga ccaacagaaa gccacagcgc   1560
ctcatcactc agttccactt taccagctgg ccagactttg gggtgccttt taccccgatc   1620
ggcatgctca agttcctcaa gaaggtgaag gcctgtaacc ctcagtatgc aggggccatc   1680
gtggtccact gcagtgcagg tgtagggcgt acaggtacct ttgtcgtcat tgatgccatg   1740
ctggacatga tgcatacaga acggaaggtg acgtgtatg gctttgtgag ccggatccgg   1800
gcacagcgct gccagatggt gcaaaccgat atgcagtatg tcttcatata ccaagccctt   1860
ctggagcatt atctctatgg agatacagaa ctggaagtga cctctctaga aacccacctg   1920
cagaaaattt acaacaaaat cccagggacc agcaacaatg gattagagga ggagtttaag   1980
aagttaacat caatcaaaat ccagaatgac aagatgcgga ctggaaacct tccagccaac   2040
atgaagaaga accgtgtttt acagatcatt ccatatgaat tcaacagagt gatcattcca   2100
gttaagcggg gcgaagagaa tacagactat gtgaacgcat cctttattga tggctaccgg   2160
cagaaggact cctatatcgc cagccagggc cctcttctcc acacaattga ggacttctgg   2220
cgaatgatct gggagtggaa atcctgctct atcgtgatgc taacagaact ggaggagaga   2280
ggccaggaga agtgtgccca gtactggcca tctgatggac tggtgtccta tggagatatt   2340
acagtggaac tgaagaagga ggaggaatgt gagagctaca ccgtccgaga cctcctggtc   2400
accaacacca gggagaataa gagccggcag atccggcagt tccacttcca tggctggcct   2460
gaagtgggca tccccagtga cggaaagggc atgatcagca tcatcgccgc cgtgcagaag   2520
cagcagcagc agtcagggaa ccaccccatc accgtgcact gcagcgccgg ggcaggaagg   2580
acggggacct tctgtgccct gagcaccgtc ctggagcgtg tgaaagcaga ggggattttg   2640
gatgtcttcc agactgtcaa gagcctgcgc tacagaggc cacacatggt ccagacactg   2700
gaacagtatg agttctgcta caaggtggtg caggagtata ttgatgcatt ctcagattat   2760
gccaacttca gtaagcggc aacaagggtc cgtggaccag gaggattgcc tttaatattt   2820
tgtaatattc tgttttgtta atataccca aattgtgtat atatcttata actgttttag   2880
aaattggtac ataggcttct attacctatt aggtggaaat tttatatgta aatgtgttag   2940
cactgatagt ccttttttcca atgttttatt ggggaattaa atagtgtgat gtttggattt   3000
atatcgtgaa atcctcagcc gagaaattgg gctggattgt gctttggtta atacatcttt   3060
```

```
ccctaaagaa gataaacaca aaatccattc caggtagctc ggcaccaact aagaaaaaaa    3120
gcacaaagtt ctcagagctc tcgaggaaag tggttgtccc cgtaccacca tgcactgtaa    3180
atatccctcc cctctctccc tggtcccctc ccccatcccc accactgata tcatggggag    3240
taataggacc agagcggtat ctctggcacc acactaggga ctatcaggta ataaaagctt    3300
tgactccctg aaaaaaaaaa aaaaaaaa                                       3328

<210> SEQ ID NO 41
<211> LENGTH: 3435
<212> TYPE: DNA
<213> ORGANISM: Homo sapiens

<400> SEQUENCE: 41
acagcaacta tgaaataatc gtagtatgag aggcagagat cggggcgaga caatggggat      60
gtgggcgcgg gagccccgtt ccggcttagc agcacctccc agccccgcag aataaaaccg     120
atcgcgcccc ctccgcgcgc gccctccccc gagtgcggag cgggaggagg cggcggcggc     180
cgaggaggag gaggaggagg ccccggagga ggaggcgttg gaggtcgagg cggaggcgga     240
ggaggaggag gccgaggcgc cggaggaggc cgaggcgccg gagcaggagg aggccggccg     300
gaggcggcat gagacgagcg tggcggccgc ggctgctcgg ggccgcgctg gttgcccatt     360
gacagcggcg tctgcagctc gcttcaagat ggccgcttgg ctcgcattca ttttctgctg     420
aacgactttt aactttcatt gtcttttccg cccgcttcga tcgcctcgcg ccggctgctc     480
tttccgggat ttttttatcaa gcagaaatgc atcgaacaac gagaatcaag atcactgagc     540
taaatcccca cctgatgtgt gtgctttgtg gagggtactt cattgatgcc acaaccataa     600
tagaatgtct acattccttc tgtaaaacgt gtattgttcg ttacctggag accagcaagt     660
attgtcctat ttgtgatgtc caagttcaca agaccagacc actactgaat ataaggtcag     720
ataaaactct ccaagatatt gtatacaaat tagttccagg gcttttcaaa aatgaaatga     780
agagaagaag ggattttat gcagctcatc cttctgctga tgctgccaat ggctctaatg     840
aagatagagg agaggttgca gatgaagata agagaattat aactgatgat gagataataa     900
gcttatccat tgaattcttt gaccagaaca gattggatcg gaaagtaaac aaagacaaag     960
agaaatctaa ggaggaggtg aatgataaaa gatacttacg atgcccagca gcaatgactg    1020
tgatgcactt aagaaagttt ctcagaagta aaatggacat acctaatact ttccagattg    1080
atgtcatgta tgaggaggaa ccttttaaagg attattatac actaatggat attgcctaca    1140
tttatacctg gagaaggaat ggtccacttc cattgaaata cagagttcga cctacttgta    1200
aaagaatgaa gatcagtcac cagagagatg gactgacaaa tgctggagaa ctggaaagtg    1260
actctgggag tgacaaggcc aacagcccag caggaggtat tccctccacc tcttcttgtt    1320
tgcctagccc cagtactcca gtgcagtctc ctcatccaca gtttcctcac atttccagta    1380
ctatgaatgg aaccagcaac agccccagcg gtaaccacca atcttctttt gccaatagac    1440
ctcgaaaatc atcagtaaat gggtcatcag caacttcttc tggttgatac ctgagactgt    1500
taaggaaaaa aattttaaac ccctgattta tatagatatc ttcatgccat tacagctttc    1560
tagatgctaa tacatgtgac tatcgtccaa tttgctttct tttgtagtga cattaaattt    1620
ggctataaaa gatggactac atgtgatact cctatggacg ttaattgaaa agaaagattg    1680
ttgttataaa gaattggttt cttggaaagc aggcaagact ttttctctgt gttaggaaag    1740
atgggaaatg gtttctgtaa ccattgtttg gatttggaag tactctgcag tggacataag    1800
cattgggcca tagtttgtta atctcaacta acgcctacat tacattctcc ttgatcgttc    1860
```

```
ttgttattac gctgttttgt gaacctgtag aaaacaagtg cttttttatct tgaaattcaa    1920
ccaacggaaa gaatatgcat agaataatgc attctatgta gccatgtcac tgtgaataac    1980
gatttcttgc atatttagcc attttgattc ctgtttgatt tatacttctc tgttgctacg    2040
caaaaccgat caaagaaaag tgaacttcag ttttacaatc tgtatgccta aaagcgggta    2100
ctaccgttta ttttactgac ttgtttaaat gattcgcttt tgtaagaatc agatggcatt    2160
atgcttgttg tacaatgcca tattggtata tgacataaca ggaaacagta ttgtatgata    2220
tatttataaa tgctataaag aaatattgtg tttcatgcat tcagaaatga ttgttaaaat    2280
tctcccaact ggttcgacct tgcagatac ccataaccta tgttgagcct tgcttaccag     2340
caaagaatat ttttaatgtg gatatctaat tctaaagtct gttccattag aagcaattgg    2400
cacatctttc tatactttat atactttct ccagtaatac atgttactt taaagattgt      2460
tgcagtgaag aaaaaccttt aactgagaaa tatggaaacc gtcttaattt tccattggct    2520
atgatggaat taatattgta ttttaaaaat gcatattgat cactataatt ctaaaacaat    2580
tttttaaata aaccagcagg ttgctaaaag aaggcatttt atctaaagtt attttaatag    2640
gtggtatagc agtaattta aatttaagag ttgcttttac agttaacaat ggaatatgcc      2700
ttctctgcta tgtctgaaaa tagaagctat ttattatgag cttctacagg tattttaaa     2760
tagagcaagc atgttgaatt taaaatatga ataaccccac ccaacaattt tcagtttatt    2820
ttttgctttg gtcgaacttg gtgtgtgttc atcacccatc agttatttgt gagggtgttt    2880
attctatatg aatattgttt catgtttgta tgggaaaatt gtagctaaac atttcattgt    2940
ccccagtctg caaaagaagc acaattctat tgctttgtct tgcttatagt cattaaatca    3000
ttactttttac atatattgct gttacttctg ctttctttaa aaatatagta aaggatgttt   3060
tatgaagtca caagatacat atatttttat tttgacctaa atttgtacag tcccattgta   3120
agtgttgttt ctaattatag atgtaaaatg aaatttcatt tgtaattgga aaaaatccaa    3180
taaaaaggat attcatttag aaaatagcta agatctttaa taaaaatttg atatgaaaag   3240
cacaatgtgc agaagttatg gaaaacctat agaggattac aacaggtaaa cgttaaagag    3300
aatacattgc tgacttatag tgatgtggct aagaagtaca tgctttgttg taaaattgct    3360
tgaaagccca ttgaaagatg tatctgttta tttacagtct ttgaagtaaa agttaccaat    3420
gtttgccaat aaaaa                                                     3435

<210> SEQ ID NO 42
<211> LENGTH: 8888
<212> TYPE: DNA
<213> ORGANISM: Homo sapiens

<400> SEQUENCE: 42
actggggtgg cgcgctacct ctgcggagaa ggatctgaca gtgttccgga gccggggcga     60
gcagccaaaa ggcccgcgga gtcgcgctgg gccgccccgg cgcagctgaa ccgggggccg   120
cgcctgccag gccgacgggt ctggcccagc ctggcgccaa ggggttcgtg cgctgtggag   180
acgcggaggg tcgaggcggc gcggcctgag tgaaacccaa tggaaaaagc atgacatttta 240
gaagtagaag acttagcttc aaatccctac tccttcactt actaattttg tgatttggaa   300
atatccgcgc aagatgttga cgttgcagac ttggctagtg caagccttgt ttatttttcct 360
caccactgaa tctacaggtg aacttctaga tccatgtggt tatatcagtc ctgaatctcc   420
agttgtacaa cttcattcta atttcactgc agtttgtgtg ctaaaggaaa aatgtatgga   480
```

```
ttatttttcat gtaaatgcta attacattgt ctggaaaaca aaccatttta ctattcctaa    540
ggagcaatat actatcataa acagaacagc atccagtgtc acctttacag atatagcttc    600
attaaatatt cagctcactt gcaacattct tacattcgga cagcttgaac agaatgttta    660
tggaatcaca ataatttcag gcttgcctcc agaaaaacct aaaaatttga gttgcattgt    720
gaacgagggg aagaaaatga ggtgtgagtg ggatggtgga agggaaacac acttggagac    780
aaacttcact ttaaaatctg aatgggcaac acacaagttt gctgattgca aagcaaaacg    840
tgacaccccc acctcatgca ctgttgatta ttctactgtg tattttgtca acattgaagt    900
ctgggtagaa gcagagaatg cccttgggaa ggttacatca gatcatatca attttgatcc    960
tgtatataaa gtgaagccca atccgccaca taatttatca gtgatcaact cagaggaact   1020
gtctagtatc ttaaaattga catggaccaa cccaagtatt aagagtgtta taatactaaa   1080
atataacatt caatatagga ccaaagatgc ctcaacttgg agccagattc ctcctgaaga   1140
cacagcatcc acccgatctt cattcactgt ccaagacctt aaaccttta cagaatatgt    1200
gtttaggatt cgctgtatga aggaagatgg taagggatac tggagtgact ggagtgaaga   1260
agcaagtggg atcacctatg aagatagacc atctaaagca ccaagtttct ggtataaaat   1320
agatccatcc catactcaag ctacagaac tgtacaactc gtgtggaaga cattgcctcc    1380
ttttgaagcc aatggaaaaa tcttggatta tgaagtgact ctcacaagat ggaaatcaca   1440
tttacaaaat tacacagtta atgccacaaa actgacagta aatctcacaa atgatcgcta   1500
tctagcaacc ctaacagtaa gaaatcttgt tggcaaatca gatgcagctg ttttaactat   1560
ccctgcctgt gactttcaag ggaacttagc agagagcaaa tgctatttga taacagttac   1620
tccagtatat gctgatggac caggaagccc tgaatccata aaggcatacc ttaaacaagc   1680
tccaccttcc aaaggaccta ctgttcggac aaaaaaagta gggaaaaacg aagctgtctt   1740
agagtgggac caacttcctg ttgatgttca gaatggattt atcagaaatt atactatatt   1800
ttatagaacc atcattggaa atgaaactgc tgtgaatgtg gattcttccc acacagaata   1860
tacattgtcc tcttttgacta gtgacacatt gtacatggta cgaatggcag catacacaga   1920
tgaaggtggg aaggatggtc cagaattcac ttttactacc ccaaagtttg ctcaaggaga   1980
aattgaagcc atagtcgtgc ctgtttgctt agcattccta ttgacaactc ttctgggagt   2040
gctgttctgc tttaataagc gagacctaat taaaaacac atctggccta atgttccaga   2100
tccttcaaag agtcatattg cccagtggtc acctcacact cctccaaggc acaattttaa   2160
ttcaaaagat caaatgtatt cagatggcaa tttcactgat gtaagtgttg tggaaataga   2220
agcaaatgac aaaaagcctt ttccagaaga tctgaaatca ttggacctgt tcaaaaagga   2280
aaaaattaat actgaaggac acagcagtgg tattggggg tcttcatgca tgtcatcttc   2340
taggccaagc atttctagca gtgatgaaaa tgaatcttca caaacactt cgagcactgt    2400
ccagtattct accgtggtac acagtggcta cagacaccaa gttccgtcag tccaagtctt   2460
ctcaagatcc gagtctaccc agcccttgtt agattcagag gagcggccag aagatctaca   2520
attagtagat catgtagatg gcggtgatgg tattttgccc aggcaacagt acttcaaaca   2580
gaactgcagt cagcatgaat ccagtccaga tatttcacat tttgaaaggt caaagcaagt   2640
ttcatcagtc aatgaggaag attttgttag acttaaacag cagatttcag atcatatttc   2700
acaatcctgt ggatctgggc aaatgaaaat gtttcaggaa gtttctgcag cagatgcttt   2760
tggtccaggt actgagggac aagtagaaag atttgaaaca gttggcatgg aggctgcgac   2820
tgatgaaggc atgcctaaaa gttacttacc acagactgta cggcaaggcg gctacatgcc   2880
```

```
tcagtgaagg actagtagtt cctgctacaa cttcagcagt acctataaag taaagctaaa    2940
atgattttat ctgtgaattc agattttaaa aagtcttcac tctctgaaga tgatcatttg    3000
cccttaagga caaaaatgaa ctgaagtttc acatgagcta tttccattcc agaatatctg    3060
ggattctact ttaagcacta cataaactga ctttatcctc agactagctg aatgattttg    3120
tgctgtttca ggatgtttgc actgaagaaa aacagaaagc ttatctgaaa tttataaaac    3180
tttttgtttt gctacataga aaacagaagg tatttgaata ataagcagtg atatgcttag    3240
tgagcacagc tatactgatt ttgattagaa tagtcatcag agtggcttag ggacagttaa    3300
tataaagag gagcaaggtg tagaccatca tctacttctg ctaaaataac ttaaaaagag     3360
gtccataggc cataactaca tgagcccagc ttttgtaatc tgacaaaaaa atgaggagca    3420
gcttcgtgta tatcagtgta cacggtattc cttaggtccc ttccattggt agtgatgctg    3480
cgagttatta ctggagaaaa ggaattctag agctttaact tggcagatta aaagtactca    3540
tttttttattc atcaataatt agtaatctca ctagttttca aaatttgca tattattgac    3600
aacctctttg aagatgcatt tcacaaactc aacagagtgc catgataaga gctagggatc    3660
ccccaaacta tctcaagcat ctaaaaaatt gccatttta aaggcttaaa ttgtagtagt     3720
aaggggaaa acaggaagta gtagtaaagg ggaaaaaaa ccaataaagc atctaaaaaa      3780
ttggcatgtt aaaaggctta aattgctaat gtgtgtatat atatatat atatacacac     3840
acatatcatt gacttttctt aagacttcag agtactgggt agatgaacac tttatacagt    3900
atatatcttc agcttaaatt tgttttgagt attttttta tttttaaata gtaggcaaa      3960
gatttaaatt tttttatttt tagtaaatgt ttgaggcaca ctaagacaac ttgggcaata    4020
tttgccaaaa caaacagaa ccccaaaaaa tgtacatctt gttcttagca aatatcatta     4080
ttgtagagac acttaataaa gagatggtat tttaatgtct gcagttctga ggtagggtgg    4140
aacttagttc tacattgtga tttaggaatt tttaaaacct ttttcttca agggagaagt     4200
gacccaggcc tcgagtttag tgctaaagcc gctagtgtac ttatgctgtc ccctaaccac    4260
cacgtgcgat atggaagcag atgctaaata taggggtttt cttagaaagt aagaggaaat    4320
tagcaagcgt tattagtgat tgactactgc tatcaagtga attcaaagga aacaggtttt    4380
tatgccatat ttaagttaca gaaccaggc atgcttagaa tagtttctag aggttattgg     4440
agaatagaaa gctaagaaaa cttggtatac atttacaatg gaaatataat tacacttttt    4500
actctcagaa tattgttcac attagacttc ctgtttatct tttatattct tgcatttata    4560
taatgcctca tcctttcaaa gttctttcac atattatatg atcttcttta tgaaaaaaat    4620
agatgtttca ttctgatata ttcagtttcc cactttaggc aaaagtagat taatagaatg    4680
acgaattcaa agtagatgag gaaaatcagg cacagagaag taaggtagg gatagaccca     4740
aatttacaca acaagataat gacatctcca gcttttaagt tgatcatcaa aggctgggct    4800
ggatttgtct tgctgtatgt gtcaggaaat ttatacctat tacattttcc attttctcaa    4860
aatttaagtc acatgactaa tatttagctg caactttcct cataacaaat agtgtcatga    4920
agaatgttgt agtgtgaagt ttgtacattt cagggtcaga tatacaatat gaactcttaa    4980
tctacaggaa tgagaatgga ggatcattga aggccatgat ataaacaaat ttgcatgttg    5040
aagcctgtat aaaacatggt acagtgagtg aatataccccc catccccaag aacactttat   5100
acatattaaa tggatatatg attactgtgc aaaaattcat tctggaaatg aacatatatt    5160
tgagcactaa tatgtaatgt acacctgccc taaggagaaa ataaattata aaactttta    5220
```

```
cattcaaaat tactttccca agcatgtctt agaataatct atgtgttgat gcatgtaaat    5280
tgtactttag gtaggcaaag aaatctggtt atttatgtaa aaactagtct aataaagtta    5340
gttagtggct ttatcacttt aaatctttag tgtccaaaag tggtgtttaa agtaatagca    5400
catcagaaaa ccttgtctgg acaaaactag ttcactcact gcttctgcac ctgcagttgc    5460 tcccttttagg gttataaaat aatgacccaa atgttacatg tgttgatatt ataacttgtc    5520
agttactgat gtctgtggta tcctaccctc atctctgaaa gggataatac tgaataatta    5580
ttagaaaact ataaaacttc acactttgta ccattaaaac ctaaaatttt aatcttgtcc    5640
ttttttacta tggatcagtc ggcactcggg aacagcagca aggaaaaaaa gcaaatttca    5700
ttcacatgtt ctgtgttcat acctcttctc tacctaattg ttcatttaaa tttcagcctt    5760
attccttgat aagggatttt accacatgaa gtcatccagt gaccctagct cttattgtga    5820
agttagtgga gtatacttag aaatgttaca actttaaaat gttacaaaac attcattaaa    5880
gctcatattt aaagtagagc atctagtttg agaaatagaa atcaattatt aaagatgtct    5940 ttttctacc catttaacta gttaaaacca tgacatgtaa atgtagaagt agaataatca    6000
tagaattccc taaatatttt ctgtttacta acatatattg accaagtaca tcaagcagga    6060
gagatcttcc ttcattctgt tatagtccac atcattctaa ttttgctcag ttgttattaa    6120
gagcatattc ctaaaccata cacttttgtt tcaataaagt tttattttgt tgagatgaat    6180
aaaataacaa agttataagc tgcataagac aaaagttcaa ttgttcaaaa aaatttact    6240 gggatagctt tctattacag gtattgttag attatattgt gctgataaga ttactttcta    6300
aaaaatttgt acttttctgt aaattaaaag aatatggagt cataaaatgg caagtgtttt    6360
aggattagcc taaaattgga cattgtcatt gatttcaaag aaggtatgaa ctagcagtct    6420
tacagcctaa ttcttctttg gactggtcct tggcagcagt tccttttcag actcgataaa    6480
cagaattcag atgatgtaag tcaaaacaaa actttacaaa gccaagcgta ttatcttttg    6540
cattaaccta ttttttttcca tcatacatgc tactagtatg tgcattagca tgatattctc    6600
atatacattg cattaaaaat taaaggtgg cagctcaggg tgagctcttc tgttgctcat    6660
ttgttcctaa atttttaagg gcttttttctc agtcaatagt ttgtacaaac tggttagttt    6720
aacttcatta cccatttcat taaagttgat gggtcgtgtg atgagatgca tttaaggccg    6780
atagtgatag atgtttttttt tatttcttga acacaggctt tgtctgaatg atgttctttt    6840
atctcttgaa cacaagcttt gaatgataac tacaggtttt aagtgctgtt acattaatac    6900
cataatgtga tgtgttagaa acaaagggat atttcaaagg tagatatttg aaaattctct    6960
agtctcaata tgtatgtgta ttgaatatac tctaaaaata aatgtgcaat ttgctagtag    7020
gacaatgcag tgactgacta gcattaggta tgtttctttt atatcctagc tatgtcccac    7080
tttcttctaa gtgcaatcct ttcatgttca cttgctgttt taccccatct actctaactt    7140
catttggaag gcttgtctag agtatagcat gtatttttac ctttgcagtg aattgcatgt    7200
gctaattgta accacagcta ttttatgtt gacataactc caaatgttat attaaatgtt    7260
ctattatata ttagctctaa tcccttaagt aaattttaag aaataaatac ttgttcaaat    7320 ttttttttctg tatgtggtta ctatcatctg actatgcata tttgtaacag catttatcat    7380
tagtggtgtt agctaaataa gcatcttagt gtaaatgaga tgcttcgtgt gggttttgtg    7440
acattttaaa tgcataatg gaatgtgatt taaaagaaaa ccagtacact atcttggtct    7500
taataacata gaatggagat ggcaaattta tccactagtt ttccagattt actatttaat    7560
agctgaggtc tgaaatcgta gcatcctccc tcctagtgga cattaaaaaa aaaaaaaaa    7620
```

```
aaaaaaacct acttggttgt caagagccca agtatggagg tgctgcgcca tcttgtggcc      7680
tgtctgtgcc caccctgcac tctgctggag tctccatcct tgttgcagtg agacttgaag      7740
ttcaagattg atacatggca tcctcctgct acttcttgag gttactaagt agtatatgaa      7800
actaatcagt cagcaagtcc acctggaagg aaaagaaaat ctcaactatt aatgtgcctt      7860
cacattgtga ttttgtctaa aaaatgtag  tgagtcaaaa aacccacaag ccagccaaca      7920
gtaactcctt cacatatata ccagagttta tagaaataac atgtcagctt tgggctatgt      7980
gctcctttgt ttaaaatctt ctatttggtt atggcttgta taggctcaag cctgatttct      8040
ttaaggtgtg gtggctcatc ttatcctaat gtgtatgata gatacagtcc atcctgcttt      8100
ggaaaagatt atgtaactcc ttgagagcat actctttctc tagcccaaag gcagtgagag      8160
agttttcttg ttcaggattg cttaactttc catttaagct ttttcttttt aaattaatac      8220
aaacttctac actttcaaaa tacgaaatat attacaactg cgtataggct cttccatact      8280
taagtccagt gctgggcaa gttaatggag tgaaagacta caagcaaaga ggaactgagg      8340
tagaaaaaga agaatgtgtg aaagcagcag gaagctcagc caactcgaaa gcagggtgaa      8400
cagcttgagt cctgttgctg ctgatcgggg ttggctcttg gacaacttag taagatcatg      8460
gaaaggctgc ttgggttctc catagaaaag ttctgtctcc atcaagggag gaaaatgtac      8520
ctttcaactc aaaattcaat atttgttttt aaatatagct attttcccca accgctaaag      8580
attttcaaca gatacgaagc cagagcttag ttttagaaac ctgtggacat tcaaacctga      8640
ttctttattc cctgtgacta tggttatgtc attttacatg tcaaaaaagt gtatctagaa      8700
ttgtcatttc ttattttga gcttttttta gtgagaatta tccctcact taaatggctt        8760 tttatttaaa catctgtgca ttctgtatga aattgtagtc tttctgggat aacatggtga      8820
gctatatggt ggtaatccac acacacaaaa ataaaagcca aaaaaaaaacc aaaaaaaaaa     8880 aaaaaaaa                                                                8888
```

<210> SEQ ID NO 43
<211> LENGTH: 8988
<212> TYPE: DNA
<213> ORGANISM: Homo sapiens

<400> SEQUENCE: 43

```
actggggtgg cgcgctacct ctgcggagaa ggatctgaca gtgttccgga gccggggcga       60
gcagccaaaa ggcccgcgga gtcgcgctgg gccgccccgg cgcagctgaa ccggggggccg     120 cgcctgccag gccgacgggt ctgggcccagc ctggcgccaa ggggttcgtg cgctgtggag     180
acgcggaggg tcgaggcggc gcggcctgag tgaaacccaa tggaaaaagc atgacattta      240
gaagtagaag acttagcttc aaatccctac tccttcactt actaattttg tgatttggaa      300
atatccgcgc aagatgttga cgttgcagac ttggctagtg caagccttgt ttattttcct      360
caccactgaa tctacaggtg aacttctaga tccatgtggt tatatcagtc ctgaatctcc      420
agttgtacaa cttcattcta atttcactgc agtttgtgtg ctaaaggaaa aatgtatgga      480
ttattttcat gtaaatgcta attacattgt ctggaaaaca aaccatttta ctattcctaa      540
ggagcaatat actatcataa acagaacagc atccagtgtc acctttacag atatagcttc      600
attaaatatt cagctcactt gcaacattct tacattcgga cagcttgaac agaatgtttta     660 tggaatcaca ataatttcag gcttgcctcc agaaaaacct aaaaatttga gttgcattgt      720
gaacgagggg aagaaaatga ggtgtgagtg ggatggtgga agggaaacac acttggagac     780
```

```
aaacttcact ttaaaatctg aatgggcaac acacaagttt gctgattgca aagcaaaacg      840
tgacaccccc acctcatgca ctgttgatta ttctactgtg tattttgtca acattgaagt      900
ctgggtagaa gcagagaatg cccttgggaa ggttacatca gatcatatca attttgatcc      960
tgtatataaa gtgaagccca atccgccaca taatttatca gtgatcaact cagaggaact     1020
gtctagtatc ttaaaattga catggaccaa cccaagtatt aagagtgtta taatactaaa     1080
atataacatt caatatagga ccaaagatgc ctcaacttgg agccagattc ctcctgaaga     1140
cacagcatcc acccgatctt cattcactgt ccaagacctt aaacctttta cagaatatgt     1200
gtttaggatt cgctgtatga aggaagatgg taagggatac tggagtgact ggagtgaaga     1260
agcaagtggg atcacctatg aagataacat tgcctccttt tgaagccaat ggaaaaatct     1320
tggattatga agtgactctc acaagatgga aatcacattt acaaaattac acagttaatg     1380
ccacaaaact gacagtaaat ctcacaaatg atcgctatct agcaacccta acagtaagaa     1440
atcttgttgg caaatcagat gcagctgttt taactatccc tgcctgtgac tttcaagcta     1500
ctcaccctgt aatggatctt aaagcattcc ccaaagataa catgctttgg gtggaatgga     1560
ctactccaag ggaatctgta aagaaatata tacttgagtg gtgtgtgtta tcagataaag     1620
caccctgtat cacagactgg caacaagaag atggtaccgt gcatcgcacc tatttaagag     1680
ggaacttagc agagagcaaa tgctatttga taacagttac tccagtatat gctgatggac     1740
caggaagccc tgaatccata aaggcatacc ttaaacaagc tccaccttcc aaaggaccta     1800
ctgttcggac aaaaaaagta gggaaaaacg aagctgtctt agagtgggac caacttcctg     1860
ttgatgttca aatggatttt atcagaaatt atactatatt ttatagaacc atcattggaa     1920
atgaaactgc tgtgaatgtg gattcttccc acacagaata tacattgtcc tctttgacta     1980
gtgacacatt gtacatggta cgaatggcag catacacaga tgaaggtggg aaggatggtc     2040
cagaattcac ttttactacc ccaaagtttg ctcaaggaga aattgaagcc atagtcgtgc     2100
ctgtttgctt agcattccta ttgacaactc ttctgggagt gctgttctgc tttaataagc     2160
gagacctaat taaaaaacac atctggccta atgttccaga tccttcaaag agtcatattg     2220
cccagtggtc acctcacact cctccaaggc acaattttaa ttcaaaagat caaatgtatt     2280
cagatggcaa tttcactgat gtaagtgttg tggaaataga agcaaatgac aaaaagcctt     2340
ttccagaaga tctgaaatca ttggacctgt tcaaaaagga aaaattaat actgaaggac     2400 acagcagtgg tattggggg tcttcatgca tgtcatcttc taggccaagc atttctagca     2460
gtgatgaaaa tgaatcttca caaaacactt cgagcactgt ccagtattct accgtggtac     2520
acagtggcta cagacaccaa gttccgtcag tccaagtctt ctcaagatcc gagtctaccc     2580
agcccttgtt agattcagag gagcggccag aagatctaca attagtagat catgtagatg     2640
gcggtgatgg tattttgccc aggcaacagt acttcaaaca gaactgcagt cagcatgaat     2700
ccagtccaga tatttcacat tttgaaaggt caaagcaagt ttcatcagtc aatgaggaag     2760
attttgttag acttaaacag cagatttcag atcatatttc acaatcctgt ggatctgggc     2820
aaatgaaaat gtttcaggaa gtttctgcag cagatgcttt tggtccaggt actgagggac     2880
aagtagaaag atttgaaaca gttggcatgg aggctgcgac tgatgaaggc atgcctaaaa     2940
gttacttacc acagactgta cggcaaggcg gctacatgcc tcagtgaagg actagtagtt     3000
cctgctacaa cttcagcagt acctataaag taaagctaaa atgattttat ctgtgaattc     3060
agattttaaa aagtcttcac tctctgaaga tgatcatttg cccttaagga caaaaatgaa     3120
ctgaagtttc acatgagcta tttccattcc agaatatctg ggattctact ttaagcacta     3180
```

```
cataaactga ctttatcctc agactagctg aatgattttg tgctgtttca ggatgtttgc    3240
actgaagaaa aacagaaagc ttatctgaaa tttataaaac tttttgtttt gctacataga    3300
aaacagaagg tatttgaata ataagcagtg atatgcttag tgagcacagc tatactgatt    3360
ttgattagaa tagtcatcag agtggcttag ggacagttaa tataaaagag gagcaaggtg    3420
tagaccatca tctacttctg ctaaaataac ttaaaagag gtccataggc cataactaca     3480
tgagcccagc ttttgtaatc tgacaaaaaa atgaggagca gcttcgtgta tatcagtgta    3540
cacggtattc cttaggtccc ttccattggt agtgatgctg cgagttatta ctggagaaaa    3600
ggaattctag agctttaact tggcagatta aaagtactca ttttttattc atcaataatt    3660
agtaatctca ctagttttca aaatttgca tattattgac aacctctttg aagatgcatt     3720
tcacaaactc aacagagtgc catgataaga gctaggatc ccccaaacta tctcaagcat     3780 ctaaaaatt gccatttta aaggcttaaa ttgtagtagt aaaggggaaa acaggaagta      3840
gtagtaaagg ggaaaaaaaa ccaataaagc atctaaaaaa ttggcatgtt aaaaggctta    3900
aattgctaat gtgtgtatat atatatatat atatacacac acatatcatt gacttttctt    3960
aagacttcag agtactgggt agatgaacac tttatacagt atatatcttc agcttaaatt    4020
tgttttgagt atttttttta tttttaaata agtaggcaaa gatttaaatt tttttatttt    4080
tagtaaatgt ttgaggcaca ctaagacaac ttgggcaata tttgccaaaa caaacagaa     4140 ccccaaaaaa tgtacatctt gttcttagca aatatcatta ttgtagagac acttaataaa    4200
gagatggtat tttaatgtct gcagttctga ggtagggtgg aacttagttc tacattgtga    4260
tttaggaatt tttaaaacct ttttcttca agggagaagt gacccaggcc tcgagtttag     4320
tgctaaagcc gctagtgtac ttatgctgtc ccctaaccac cacgtgcgat atggaagcag    4380
atgctaaata tagggttttt cttagaaagt aagaggaaat tagcaagcgt tattagtgat    4440
tgactactgc tatcaagtga attcaaagga aacaggtttt tatgccatat ttaagttaca    4500
gaaaccaggc atgcttagaa tagtttctag aggttattgg agaatagaaa gctaagaaaa    4560
cttggtatac atttacaatg gaaatataat tacactttt actctcagaa tattgttcac     4620
attagacttc ctgtttatct tttatattct tgcatttata taatgcctca tccttttcaaa   4680 gttctttcac atattatatg atcttcttta tgaaaaaaat agatgtttca ttctgatata    4740 ttcagttttcc cactttaggc aaaagtagat taatagaatg acgaattcaa agtagatgag   4800
gaaaatcagg cacagagaag taaaggtagg gatagaccca aatttacaca acaagataat    4860
gacatctcca gcttttaagt tgatcatcaa aggctgggct ggatttgtct tgctgtatgt    4920
gtcaggaaat ttatacctat tacatttttcc attttctcaa aatttaagtc acatgactaa   4980
tatttagctg caacttttcct cataacaaat agtgtcatga agaatgttgt agtgtgaagt   5040
ttgtacattt cagggtcaga tatacaatat gaactcttaa tctacaggaa tgagaatgga    5100
ggatcattga aggccatgat ataaacaaat ttgcatgttg aagcctgtat aaaacatggt    5160
acagtgagtg aatataccc catccccaag aacactttat acatattaaa tggatatatg     5220
attactgtgc aaaaattcat tctggaaatg aacatatatt tgagcactaa tatgtaatgt    5280
acacctgccc taaggagaaa ataaattata aaacttttta cattcaaaat tactttccca    5340
agcatgtctt agaataatct atgtgttgat gcatgtaaat tgtactttag gtaggcaaag    5400
aaatctggtt atttatgtaa aaactagtct aataaagtta gttagtggct ttatcacttt    5460
aaatctttag tgtccaaaag tggtgtttaa agtaatagca catcagaaaa ccttgtctgg    5520
```

```
acaaaactag ttcactcact gcttctgcac ctgcagttgc tcccttttagg gttataaaat    5580
aatgacccaa atgttacatg tgttgatatt ataacttgtc agttactgat gtctgtggta    5640
tcctaccctc atctctgaaa gggataatac tgaataatta ttagaaaact ataaaacttc    5700
acactttgta ccattaaaac ctaaaatttt aatcttgtcc ttttttacta tggatcagtc    5760
ggcactcggg aacagcagca aggaaaaaaa gcaaatttca ttcacatgtt ctgtgttcat    5820
acctcttctc tacctaattg ttcatttaaa tttcagcctt attccttgat aagggatttt    5880
accacatgaa gtcatccagt gaccctagct cttattgtga agttagtgga gtatacttag    5940
aaatgttaca actttaaaat gttacaaaac attcattaaa gctcatattt aaagtagagc    6000
atctagtttg agaaatagaa atcaattatt aaagatgtct ttttctacc catttaacta     6060
gttaaaacca tgacatgtaa atgtagaagt agaataatca tagaattccc taaaatattt    6120
ctgtttacta acatatattg accaagtaca tcaagcagga gagatcttcc ttcattctgt    6180
tatagtccac atcattctaa ttttgctcag ttgttattaa gagcatattc ctaaaccata    6240
cactttgtt tcaataaagt tttattttgt tgagatgaat aaaataacaa agttataagc     6300
tgcataagac aaaagttcaa ttgttcaaaa aaaatttact gggatagctt tctattacag    6360
gtattgttag attatattgt gctgataaga ttactttcta aaaaatttgt acttttctgt    6420
aaattaaaag aatatggagt cataaaatgg caagtgttttt aggattagcc taaaattgga   6480
cattgtcatt gatttcaaag aaggtatgaa ctagcagtct tacagcctaa ttcttctttg    6540
gactggtcct tggcagcagt tcctttcag actcgataaa cagaattcag atgatgtaag     6600
tcaaacaaa actttacaaa gccaagcgta ttatcttttg cattaaccta ttttttttcca    6660
tcatacatgc tactagtatg tgcattagca tgatattctc atatacattg cattaaaaat    6720
taaaaggtgg cagctcaggg tgagctcttc tgttgctcat ttgttcctaa attttttaagg   6780
gcttttctc agtcaatagt ttgtacaaac tggttagttt aacttcatta cccatttcat     6840
taaagttgat gggtcgtgtg atgagatgca tttaaggccg atagtgatag atgttttttt    6900
tatttcttga acacaggctt tgtctgaatg atgttctttt atctcttgaa cacaagcttt    6960
gaatgataac tacaggtttt aagtgctgtt acattaatac cataatgtga tgtgttagaa    7020
acaaagggat atttcaaagg tagatatttg aaaattctct agtctcaata tgtatgtgta    7080
ttgaatatac tctaaaaata aatgtgcaat ttgctagtag gacaatgcag tgactgacta    7140
gcattaggta tgtttctttt tatatcctagc tatgtcccac tttcttctaa gtgcaatcct   7200
ttcatgttca cttgctgttt taccccatct actctaactt catttggaag gcttgtctag    7260
agtatagcat gtattttttac ctttgcagtg aattgcatgt gctaattgta accacagcta   7320
tttttatgtt gacataactc caaatgttat attaaatgtt ctattatata ttagctctaa    7380
tcccttaagt aaattttaag aaataaatac ttgttcaaat ttttttttctg tatgtggtta   7440
ctatcatctg actatgcata tttgtaacag catttatcat tagtggtgtt agctaaataa    7500
gcatcttagt gtaaatgaga tgcttcgtgt gggttttgtg acatttttaaa tgacataatg   7560
gaatgtgatt taaagaaaa ccagtacact atcttggtct taataacata gaatggagat     7620
ggcaaattta tccactagtt ttccagattt actatttaat agctgaggtc tgaaatcgta    7680
gcatcctccc tcctagtgga cattaaaaaa aaaaaaaaa aaaaaaccct acttggttgt     7740
caagagccca agtatggagg tgctgcgcca tcttgtggcc tgtctgtgcc caccctgcac    7800
tctgctggag tctccatcct tgttgcagtg agacttgaag ttcaagattg atacatggca    7860
tcctcctgct acttcttgag gttactaagt agtatatgaa actaatcagt cagcaagtcc    7920
```

```
acctggaagg aaaagaaaat ctcaactatt aatgtgcctt cacattgtga ttttgtctaa    7980
aaaaatgtag tgagtcaaaa aacccacaag ccagccaaca gtaactcctt cacatatata    8040
ccagagttta tagaaataac atgtcagctt tgggctatgt gctcctttgt ttaaaatctt    8100
ctatttggtt atggcttgta taggctcaag cctgatttct ttaaggtgtg gtggctcatc    8160
ttatcctaat gtgtatgata gatacagtcc atcctgcttt ggaaaagatt atgtaactcc    8220
ttgagagcat actcttttctc tagcccaaag gcagtgagag agttttcttg ttcaggattg    8280
cttaactttc catttaagct ttttcttttt aaattaatac aaacttctac actttcaaaa    8340
tacgaaatat attacaactg cgtataggct cttccatact taagtccagt gcttgggcaa    8400
gttaatggag tgaaagacta caagcaaaga ggaactgagg tagaaaaaga agaatgtgtg    8460
aaagcagcag gaagctcagc caactcgaaa gcagggtgaa cagcttgagt cctgttgctg    8520
ctgatcgggg ttggctcttg gacaacttag taagatcatg gaaaggctgc ttgggttctc    8580
catagaaaag ttctgtctcc atcaagggag gaaaatgtac cttttcaactc aaaattcaat    8640
atttgttttt aaatatagct attttcccca accgctaaag attttcaaca gatacgaagc    8700
cagagcttag ttttagaaac ctgtggacat tcaaacctga ttctttattc cctgtgacta    8760
tggttatgtc attttacatg tcaaaaaagt gtatctagaa ttgtcatttc ttattttttga    8820
gcttttttta gtgagaatta tcccctcact taaatggctt tttatttaaa catctgtgca    8880
ttctgtatga aattgtagtc tttctgggat aacatggtga gctatatggt ggtaatccac    8940
acacacaaaa ataaaagcca aaaaaaaacc aaaaaaaaaa aaaaaaa                  8988

<210> SEQ ID NO 44
<211> LENGTH: 9071
<212> TYPE: DNA
<213> ORGANISM: Homo sapiens

<400> SEQUENCE: 44
actggggtgg cgcgctacct ctgcggagaa ggatctgaca gtgttccgga gccggggcga      60
gcagccaaaa ggcccgcgga gtcgcgctgg gccgccccgg cgcagctgaa ccggggggccg     120
cgcctgccag gccgacgggt ctggcccagc ctggcgccaa ggggttcgtg cgctgtggag     180
acgcggaggg tcgaggcggc gcggcctgag tgaaacccaa tggaaaaagc atgacattta     240
gaagtagaag acttagcttc aaatccctac tccttcactt actaattttg tgatttggaa     300
atatccgcgc aagatgttga cgttgcagac ttggctagtg caagccttgt ttattttcct     360
caccactgaa tctacaggtg aacttctaga tccatgtggt tatatcagtc ctgaatctcc     420
agttgtacaa cttcattcta atttcactgc agtttgtgtg ctaaaggaaa aatgtatgga     480
ttattttcat gtaaatgcta attacattgt ctggaaaaca aaccatttta ctattcctaa     540
ggagcaatat actatcataa acagaacagc atccagtgtc accttttacag atatagcttc     600
attaaatatt cagctcactt gcaacattct tacattcgga cagcttgaac agaatgttta     660
tggaatcaca ataatttcag gcttgcctcc agaaaaacct aaaaatttga gttgcattgt     720
gaacgagggg aagaaaatga ggtgtgagtg ggatggtgga agggaaacac acttggagac     780
aaacttcact ttaaaatctg aatgggcaac acacaagttt gctgattgca aagcaaaacg     840
tgacaccccc acctcatgca ctgttgatta ttctactgtg tattttgtca acattgaagt     900
ctgggtagaa gcagagaatg ccccttgggaa ggttacatca gatcatatca attttgatcc     960
tgtatataaa gtgaagccca atccgccaca taatttatca gtgatcaact cagaggaact    1020
```

```
gtctagtatc ttaaaattga catggaccaa cccaagtatt aagagtgtta taatactaaa    1080
atataacatt caatatagga ccaaagatgc ctcaacttgg agccagattc ctcctgaaga    1140
cacagcatcc acccgatctt cattcactgt ccaagacctt aaaccttta cagaatatgt    1200 gtttaggatt cgctgtatga aggaagatgg taagggatac tggagtgact ggagtgaaga    1260
agcaagtggg atcacctatg aagatagacc atctaaagca ccaagtttct ggtataaaat    1320
agatccatcc catactcaag ctacagaac tgtacaactc gtgtggaaga cattgcctcc    1380
ttttgaagcc aatggaaaaa tcttggatta tgaagtgact ctcacaagat ggaaatcaca    1440
tttacaaaat tacacagtta atgccacaaa actgacagta aatctcacaa atgatcgcta    1500
tctagcaacc ctaacagtaa gaaatcttgt tggcaaatca gatgcagctg ttttaactat    1560
ccctgcctgt gactttcaag ctactcaccc tgtaatggat cttaaagcat cccccaaaga    1620
taacatgctt tgggtggaat ggactactcc aagggaatct gtaaagaaat atatacttga    1680
gtggtgtgtg ttatcagata aagcaccctg tatcacagac tggcaacaag aagatggtac    1740
cgtgcatcgc acctatttaa gagggaactt agcagagagc aaatgctatt tgataacagt    1800
tactccagta tatgctgatg gaccaggaag ccctgaatcc ataaaggcat accttaaaca    1860
agctccacct tccaaaggac ctactgttcg gacaaaaaaa gtagggaaaa acgaagctgt    1920
cttagagtgg gaccaacttc ctgttgatgt tcagaatgga tttatcagaa attatactat    1980 atttataga accatcattg gaaatgaaac tgctgtgaat gtggattctt cccacacaga    2040
atatacattg tcctctttga ctagtgacac attgtacatg gtacgaatgg cagcatacac    2100
agatgaaggt gggaaggatg gtccagaatt cactttact accccaaagt ttgctcaagg    2160
agaaattgaa gccatagtcg tgcctgtttg cttagcattc ctattgacaa ctcttctggg    2220
agtgctgttc tgctttaata gcgagacct aattaaaaaa cacatctggc ctaatgttcc    2280
agatccttca aagagtcata ttgcccagtg gtcacctcac actcctccaa ggcacaattt    2340
taattcaaaa gatcaaatgt attcagatgg caatttcact gatgtaagtg ttgtggaaat    2400
agaagcaaat gacaaaaagc cttttccaga agatctgaaa tcattggacc tgttcaaaaa    2460
ggaaaaaatt aatactgaag gacacagcag tggtattggg gggtcttcat gcatgtcatc    2520
ttctaggcca agcatttcta gcagtgatga aatgaatct tcacaaaaca cttcgagcac    2580
tgtccagtat tctaccgtgg tacacagtgg ctacagacac caagttccgt cagtccaagt    2640
cttctcaaga tccgagtcta cccagccctt gttagattca gaggagcggc cagaagatct    2700
acaattagta gatcatgtag atggcggtga tggtatttg cccaggcaac agtacttcaa    2760
acagaactgc agtcagcatg aatccagtcc agatatttca cattttgaaa ggtcaaagca    2820
agtttcatca gtcaatgagg aagattttgt tagacttaaa cagcagattt cagatcatat    2880
ttcacaatcc tgtggatctg gcaaatgaa atgtttcag gaagtttctg cagcagatgc    2940
ttttggtcca ggtactgagg acaagtagaa agatttgaa acagttggca tggaggctgc    3000
gactgatgaa ggcatgccta aaagttactt accacagact gtacggcaag gcggctacat    3060
gcctcagtga aggactagta gttcctgcta caacttcagc agtacctata agtaaagct    3120 aaaatgattt tatctgtgaa ttcagatttt aaaaagtctt cactctctga agatgatcat    3180
ttgcccttaa ggacaaaaat gaactgaagt ttcacatgag ctatttccat tccagaatat    3240
ctgggattct actttaagca ctacataaac tgactttatc ctcagactag ctgaatgatt    3300
ttgtgctgtt tcaggatgtt tgcactgaag aaaaacagaa agcttatctg aaatttataa    3360
aactttttgt tttgctacat agaaaacaga aggtatttga ataataagca gtgatatgct    3420
```

```
tagtgagcac agctatactg attttgatta gaatagtcat cagagtggct tagggacagt   3480
taatataaaa gaggagcaag gtgtagacca tcatctactt ctgctaaaat aacttaaaaa   3540
gaggtccata ggccataact acatgagccc agcttttgta atctgacaaa aaaatgagga   3600
gcagcttcgt gtatatcagt gtacacggta ttccttaggt cccttccatt ggtagtgatg   3660
ctgcgagtta ttactggaga aaaggaattc tagagcttta acttggcaga ttaaaagtac   3720
tcatttttta ttcatcaata attagtaatc tcactagttt tcaaaaattt gcatattatt   3780
gacaacctct ttgaagatgc atttcacaaa ctcaacagag tgccatgata agagctaggg   3840
atcccccaaa ctatctcaag catctaaaaa attgccattt ttaaaggctt aaattgtagt   3900
agtaaagggg aaaacaggaa gtagtagtaa aggggaaaaa aaaccaataa agcatctaaa   3960
aaattggcat gttaaaaggc ttaaattgct aatgtgtgta tatatatata tatatataca   4020
cacacatatc attgactttt cttaagactt cagagtactg ggtagatgaa cactttatac   4080
agtatatatc ttcagcttaa atttgttttg agtattttt ttattttaa ataagtaggc   4140 aaagatttaa attttttat ttttagtaaa tgtttgaggc acactaagac aacttgggca   4200
atatttgcca aaacaaaaca gaaccccaaa aaatgtacat cttgttctta gcaaatatca   4260
ttattgtaga gacacttaat aaagagatgg tattttaatg tctgcagttc tgaggtaggg   4320
tggaacttag ttctacattg tgatttagga attttaaaa cctttttct tcaagggaga   4380 agtgacccag gcctcgagtt tagtgctaaa gccgctagtg tacttatgct gtcccctaac   4440
caccacgtgc gatatggaag cagatgctaa atatagggt tttcttagaa agtaagagga   4500
aattagcaag cgttattagt gattgactac tgctatcaag tgaattcaaa ggaaacaggt   4560
ttttatgcca tatttaagtt acagaaacca ggcatgctta gaatagtttc tagaggttat   4620
tggagaatag aaagctaaga aaacttggta tacatttaca atggaaatat aattacactt   4680
tttactctca gaatattgtt cacattagac ttcctgttta tcttttatat tcttgcattt   4740
atataatgcc tcatcctttc aaagttcttt cacatattat atgatcttct ttatgaaaaa   4800
aatagatgtt tcattctgat atattcagtt tcccactta ggcaaaagta gattaataga   4860
atgacgaatt caaagtagat gaggaaaatc aggcacagag aagtaaaggt agggatagac   4920
ccaaatttac acaacaagat aatgacatct ccagctttta agttgatcat caaaggctgg   4980
gctggatttg tcttgctgta tgtgtcagga aatttatacc tattcatttt tccattttct   5040
caaaatttaa gtcacatgac taatatttag ctgcaacttt cctcataaca aatagtgtca   5100
tgaagaatgt tgtagtgtga agtttgtaca tttcagggtc agatatacaa tatgaactct   5160
taatctacag gaatgagaat ggaggatcat tgaaggccat gatataaaca aatttgcatg   5220
ttgaagcctg tataaaacat ggtacagtga gtgaatatac ccccatcccc aagaacactt   5280
tatacatatt aaatggatat atgattactg tgcaaaaatt cattctggaa atgaacatat   5340
atttgagcac taatatgtaa tgtacacctg ccctaaggag aaaataaatt ataaaacttt   5400
ttacattcaa aattactttc ccaagcatgt cttagaataa tctatgtgtt gatgcatgta   5460
aattgtactt taggtaggca agaaatctg gttatttatg taaaaactag tctaataaag   5520
ttagttagtg gctttatcac tttaaatctt tagtgtccaa aagtggtgtt taagtaata   5580 gcacatcaga aaaccttgtc tggacaaaac tagttcactc actgcttctg cacctgcagt   5640
tgctcccttt agggttataa aataatgacc caaatgttac atgtgttgat attataactt   5700
gtcagttact gatgtctgtg gtatcctacc ctcatctctg aaagggataa tactgaataa   5760
```

```
ttattagaaa actataaaac ttcacacttt gtaccattaa aacctaaaat tttaatcttg    5820 tccttttta  ctatggatca gtcggcactc gggaacagca gcaaggaaaa aaagcaaatt    5880
tcattcacat gttctgtgtt catacctctt ctctacctaa ttgttcattt aaatttcagc    5940
cttattcctt gataagggat tttaccacat gaagtcatcc agtgaccta  gctcttattg    6000 tgaagttagt ggagtatact tagaaatgtt acaactttaa aatgttacaa acattcatt     6060 aaagctcata tttaaagtag agcatctagt ttgagaaata gaaatcaatt attaaagatg    6120 tctttttct  acccatttaa ctagttaaaa ccatgacatg taaatgtaga agtagaataa    6180
tcatagaatt ccctaaaata tttctgttta ctaacatata ttgaccaagt acatcaagca    6240
ggagagatct tccttcattc tgttatagtc cacatcattc taattttgct cagttgttat    6300
taagagcata ttcctaaacc atacactttt gtttcaataa agttttattt tgttgagatg    6360
aataaaataa caaagttata agctgcataa gacaaaagtt caattgttca aaaaaatt     6420 actgggatag ctttctatta caggtattgt tagattatat tgtgctgata agattacttt    6480 ctaaaaatt  tgtactttc  tgtaaattaa aagaatatgg agtcataaaa tggcaagtgt    6540
tttaggatta gcctaaaatt ggacattgtc attgattca  aagaaggtat gaactagcag    6600
tcttacagcc taattcttct ttggactggt ccttggcagc agttcctttt cagactcgat    6660
aaacagaatt cagatgatgt aagtcaaaac aaaactttac aaagccaagc gtattatctt    6720
ttgcattaac ctatttttt  ccatcataca tgctactagt atgtgcatta gcatgatatt    6780
ctcatataca ttgcattaaa aattaaaagg tggcagctca gggtgagctc ttctgttgct    6840
catttgttcc taaatttta  agggctttt  ctcagtcaat agtttgtaca aactggttag    6900
tttaacttca ttacccattt cattaaagtt gatgggtcgt gtgatgagat gcatttaagg    6960
ccgatagtga tagatgtttt ttttatttct tgaacacagg ctttgtctga atgatgttct    7020
tttatctctt gaacacaagc tttgaatgat aactacaggt tttaagtgct gttacattaa    7080
taccataatg tgatgtgtta gaaacaaagg gatatttcaa aggtagatat ttgaaaattc    7140
tctagtctca atatgtatgt gtattgaata tactctaaaa ataaatgtgc aatttgctag    7200
taggacaatg cagtgactga ctagcattag gtatgtttct tttatatcct agctatgtcc    7260
cactttcttc taagtgcaat cctttcatgt tcacttgctg ttttaccca  tctactctaa    7320 cttcatttgg aaggcttgtc tagagtatag catgtatttt tacctttgca gtgaattgca    7380
tgtgctaatt gtaaccacag ctattttat  gttgacataa ctccaaatgt tatattaaat    7440
gttctattat atattagctc taatcccta  agtaaattt  aagaaataaa tacttgttca    7500 aatttttt   ctgtatgtgg ttactatcat ctgactatgc atatttgtaa cagcatttat    7560
cattagtggt gttagctaaa taagcatctt agtgtaaatg agatgcttcg tgtgggtttt    7620
gtgacatttt aaatgacata atggaatgtg atttaaaaga aaaccagtac actatcttgg    7680
tcttaataac atagaatgga gatggcaaat ttatccacta gttttccaga tttactattt    7740
aatagctgag gtctgaaatc gtagcatcct ccctcctagt ggacattaaa aaaaaaaaa     7800 aaaaaaaaa  cctacttggt tgtcaagagc ccaagtatgg aggtgctgcg ccatcttgtg    7860
gcctgtctgt gcccaccctg cactctgctg gagtctccat ccttgttgca gtgagacttg    7920
aagttcaaga ttgatacatg gcatcctcct gctacttctt gaggttacta agtagtatat    7980
gaaactaatc agtcagcaag tccacctgga aggaaaagaa aatctcaact attaatgtgc    8040
cttcacattg tgattttgtc taaaaaatg  tagtgagtca aaaaacccac aagccagcca    8100
acagtaactc cttcacatat ataccagagt ttatagaaat aacatgtcag ctttgggcta    8160
```

```
tgtgctcctt tgtttaaaat cttctatttg gttatggctt gtataggctc aagcctgatt    8220
tctttaaggt gtggtggctc atcttatcct aatgtgtatg atagatacag tccatcctgc    8280
tttggaaaag attatgtaac tccttgagag catactcttt ctctagccca aaggcagtga    8340
gagagttttc ttgttcagga ttgcttaact ttccatttaa gcttttttctt tttaaattaa   8400 tacaaacttc tacactttca aaatacgaaa tatattacaa ctgcgtatag gctcttccat    8460
acttaagtcc agtgcttggg caagttaatg gagtgaaaga ctacaagcaa agaggaactg    8520
aggtagaaaa agaagaatgt gtgaaagcag caggaagctc agccaactcg aaagcagggt    8580
gaacagcttg agtcctgttg ctgctgatcg gggttggctc ttggacaact tagtaagatc    8640
atggaaaggc tgcttgggtt ctccatagaa aagttctgtc tccatcaagg gaggaaaatg    8700
tacctttcaa ctcaaaattc aatatttgtt tttaaatata gctatttttcc ccaaccgcta   8760 aagatttttca acagatacga agccagagct tagttttaga aacctgtgga cattcaaacc   8820 tgattccttta ttccctgtga ctatggttat gtcattttac atgtcaaaaa agtgtatcta   8880
gaattgtcat ttcttattttt tgagctttttt ttagtgagaa ttatcccctc acttaaatgg  8940 cttttttatttt aaacatctgt gcattctgta tgaaattgta gtctttctgg ataacatgg   9000 tgagctatat ggtggtaatc cacacacaca aaaataaaag ccaaaaaaaa accaaaaaaa    9060
aaaaaaaaaa a                                                        9071

<210> SEQ ID NO 45
<211> LENGTH: 3829
<212> TYPE: DNA
<213> ORGANISM: Homo sapiens

<400> SEQUENCE: 45
caggcagcgc tgcgtcctgc tgcgcacgtg ggaagccctg gccccggcca ccccgcgat      60 gccgcgcgct ccccgctgcc gagccgtgcg ctccctgctg cgcagccact accgcgaggt    120
gctgccgctg gccacgttcg tgcggcgcct ggggccccag ggctggcggc tggtgcagcg    180
cggggacccg gcggctttcc gcgcgctggt ggcccagtgc ctggtgtgcg tgccctggga    240
cgcacggccg cccccccgccg ccccctcctt ccgccaggtg tcctgcctga aggagctggt   300
ggcccgagtg ctgcagaggc tgtgcgagcg cggcgcgaag aacgtgctgg ccttcggctt    360
cgcgctgctg gacggggccc gcgggggccc ccccgaggcc ttcaccacca gcgtgcgcag    420
ctacctgccc aacacggtga ccgacgcact gcggggagc ggggcgtggg ggctgctgct    480
gcgccgcgtg ggcgacgacg tgctggttca cctgctggca cgctgcgcgc tctttgtgct    540
ggtggctccc agctgcgcct accaggtgtg cgggccgccg ctgtaccagc tcggcgctgc    600
cactcaggcc cggcccccgc cacacgctag tggacccccga aggcgtctgg gatgcgaacg    660
ggcctggaac catagcgtca gggaggccgg ggtccccctg ggcctgccag ccccgggtgc    720
gaggaggcgc gggggcagtg ccagccgaag tctgccgttg cccaagaggc ccaggcgtgg    780
cgctgcccct gagccggagc ggacgcccgt tgggcagggg tcctgggccc acccgggcag    840
gacgcgtgga ccgagtgacc gtggtttctg tgtggtgtca cctgccagac ccgccgaaga    900
agccacctct ttgagggtg cgctctctgg cacgcgccac tccacccat ccgtgggccg      960 ccagcaccac gcgggccccc catccacatc gcggccacca cgtccctggg acacgccttg   1020
tcccccggtg tacgccgaga ccaagcactt cctctactcc tcaggcgaca aggagcagct   1080
gcggccctcc ttcctactca gctctctgag gcccagcctg actggcgctc ggaggctcgt   1140
```

-continued

```
ggagaccatc tttctgggtt ccaggccctg gatgccaggg actccccgca ggttgccccg    1200
cctgccccag cgctactggc aaatgcggcc cctgtttctg gagctgcttg ggaaccacgc    1260
gcagtgcccc tacggggtgc tcctcaagac gcactgcccg ctgcgagctg cggtcacccc    1320
agcagccggt gtctgtgccc gggagaagcc ccagggctct gtggcggccc ccaggaggag    1380
ggacacagac ccccgtcgcc tggtgcagct gctccgccag cacagcagcc cctggcaggt    1440
gtacggcttc gtgcgggcct gcctgcgccg gctggtgccc ccaggcctct ggggctccag    1500
gcacaacgaa cgccgcttcc tcaggaacac caagaagttc atctccctgg ggaagcatgc    1560
caagctctcg ctgcaggagc tgacgtggaa gatgagcgtg cgggactgcg cttggctgcg    1620
caggagccca ggggttggct gtgttccggc cgcagagcac cgtctgcgtg aggagatcct    1680
ggccaagttc ctgcactggc tgatgagtgt gtacgtcgtc gagctgctca ggtctttctt    1740
ttatgtcacg gagaccacgt tcaaaagaa caggctcttt ttctaccgga agagtgtctg    1800
gagcaagttg caaagcattg gaatcagaca gcacttgaag agggtgcagc tgcgggagct    1860
gtcggaagca gaggtcaggc agcatcggga agccaggccc gccctgctga cgtccagact    1920
ccgcttcatc cccaagcctg acgggctgcg gccgattgtg aacatggact acgtcgtggg    1980
agccagaacg ttccgcagag aaaagagggc cgagcgtctc acctcgaggg tgaaggcact    2040
gttcagcgtg ctcaactacg agcgggcgcg gcgccccggc ctcctgggcg cctctgtgct    2100
gggcctggac gatatccaca gggcctggcg caccttcgtg ctgcgtgtgc gggcccagga    2160
cccgccgcct gagctgtact ttgtcaaggt ggatgtgacg ggcgcgtacg acaccatccc    2220
ccaggacagg ctcacggagg tcatcgccag catcatcaaa ccccagaaca cgtactgcgt    2280
gcgtcggtat gccgtggtcc agaaggccgc ccatgggcac gtccgcaagg ccttcaagag    2340
ccacgtctct accttgacag acctccagcc gtacatgcga cagttcgtgg ctcacctgca    2400
ggagaccagc ccgctgaggg atgccgtcgt catcgagcag agctcctccc tgaatgaggc    2460
cagcagtggc ctcttcgacg tcttcctacg cttcatgtgc caccacgccg tgcgcatcag    2520
gggcaagtcc tacgtccagt gccaggggat cccgcagggc tccatcctct ccacgctgct    2580
ctgcagcctg tgctacggcg acatggagaa caagctgttt gcggggattc ggcgggacgg    2640
gctgctcctg cgtttggtgg atgatttctt gttggtgaca cctcacctca cccacgcgaa    2700
aaccttcctc agctatgccc ggacctccat cagagccagt ctcaccttca accgcggctt    2760
caaggctggg aggaacatgc gtcgcaaact cttttgggtc ttgcggctga gtgtcacag    2820
cctgtttctg gatttgcagg tgaacagcct ccagacggtg tgcaccaaca tctacaagat    2880
cctcctgctg caggcgtaca ggtttcacgc atgtgtgctg cagctcccat tcatcagca    2940
agtttggaag aaccccacat ttttcctgcg cgtcatctct gacacggcct ccctctgcta    3000
ctccatcctg aaagccaaga acgcagggat gtcgctgggg gccaagggcg ccgccggccc    3060
tctgccctcc gaggccgtgc agtggctgtg ccaccaagca ttcctgctca agctgactcg    3120
acaccgtgtc acctacgtgc cactcctggg gtcactcagg acagcccaga cgcagctgag    3180
tcggaagctc ccggggacga cgctgactgc cctggaggcc gcagccaacc cggcactgcc    3240
ctcagacttc aagaccatcc tggactgatg ccaccccgcc cacagccagg ccgagagcag    3300
acaccagcag ccctgtcacg ccgggctcta cgtcccaggg agggagggc ggcccacacc    3360
caggcccgca ccgctgggag tctgaggcct gagtgagtgt ttggccgagg cctgcatgtc    3420
cggctgaagg ctgagtgtcc ggctgaggcc tgagcgagtg tccagccaag gctgagtgt    3480
ccagcacacc tgccgtcttc acttccccac aggctggcgc tcggctccac cccagggcca    3540
```

```
gcttttcctc accaggagcc cggcttccac tccccacata ggaatagtcc atccccagat    3600
tcgccattgt tcacccctcg ccctgccctc ctttgccttc accccacc atccaggtgg     3660 agaccctgag aaggaccctg ggagctctgg gaatttggag tgaccaaagg tgtgccctgt    3720
acacaggcga ggaccctgca cctggatggg ggtccctgtg ggtcaaattg ggggaggtg     3780 ctgtgggagt aaaatactga atatatgagt ttttcagttt tgaaaaaaa               3829
```

<210> SEQ ID NO 46
<211> LENGTH: 4018
<212> TYPE: DNA
<213> ORGANISM: Homo sapiens

<400> SEQUENCE: 46

```
caggcagcgc tgcgtcctgc tgcgcacgtg ggaagccctg gccccggcca ccccgcgat       60 gccgcgcgct ccccgctgcc gagccgtgcg ctccctgctg cgcagccact accgcgaggt    120
gctgccgctg ccacgttcg tgcggcgcct ggggccccag ggctggcggc tggtgcagcg     180
cggggacccg gcggctttcc gcgcgctggt ggcccagtgc ctggtgtgcg tgccctggga    240
cgcacggccg ccccccgccg ccccctcctt ccgccaggtg tcctgcctga aggagctggt    300
ggcccgagtg ctgcagaggc tgtgcgagcg cggcgcgaag aacgtgctgg ccttcggctt    360
cgcgctgctg acggggccc gcgggggccc cccgaggcc ttcaccacca gcgtgcgcag     420
ctacctgccc aacacggtga ccgacgcact gcggggagc ggggcgtggg ggctgctgct    480
gcgccgcgtg ggcgacgacg tgctggttca cctgctggca cgctgcgcgc tctttgtgct    540
ggtggctccc agctgcgcct accaggtgtg cgggccgccg ctgtaccagc tcggcgctgc    600
cactcaggcc cggcccccgc cacacgctag tggaccccga aggcgtctgg gatgcgaacg    660
ggcctggaac catagcgtca gggaggccgg ggtcccctg ggcctgccag ccccgggtgc     720
gaggaggcgc ggggcagtg ccagccgaag tctgccgttg cccaagaggc ccaggcgtgg    780
cgctgcccct gagccggagc ggacgcccgt tgggcagggg tcctgggccc acccgggcag    840
gacgcgtgga ccgagtgacc gtggtttctg tgtggtgtca cctgccagac ccgccgaaga    900
agccacctct ttggagggtg cgctctctgg cacgcgccac tcccacccat ccgtgggccg    960
ccagcaccac gcgggccccc catccacatc gcggccacca cgtccctggg acacgccttg   1020 tccccggtg tacgccgaga ccaagcactt cctctactcc tcaggcgaca aggagcagct    1080
gcggccctcc ttcctactca gctctctgag gcccagcctg actggcgctc ggaggctcgt   1140
ggagaccatc tttctgggtt ccaggccctg gatgccaggg actccccgca ggttgccccg   1200
cctgccccag cgctactggc aaatgcggcc cctgtttctg gagctgcttg ggaaccacgc   1260
gcagtgcccc tacggggtgc tcctcaagac gcactgcccg ctgcgagctg cggtcacccc    1320
agcagccggt gtctgtgccc gggagaagcc cagggctct gtggcggccc ccgaggagga    1380
ggacacagac ccccgtcgcc tggtgcagct gctccgccag cacagcagcc cctggcaggt    1440
gtacggcttc gtgcgggcct gcctgcgccg gctggtgccc ccaggcctct ggggctccag   1500
gcacaacgaa cgccgcttcc tcaggaacac caagaagttc atctccctgg ggaagcatgc   1560
caagctctcg ctgcaggagc tgacgtggaa gatgagcgtg cgggactgcg cttggctgcg   1620
caggagccca ggggttggct gtgttccggc cgcagagcac cgtctgcgtg aggagatcct    1680
ggccaagttc ctgcactggc tgatgagtgt gtacgtcgtc gagctgctca ggtcttttctt   1740 ttatgtcacg gagaccacgt ttcaaaagaa caggctcttt ttctaccgga agagtgtctg    1800
```

```
gagcaagttg caaagcattg aatcagaca gcacttgaag agggtgcagc tgcgggagct    1860
gtcggaagca gaggtcaggc agcatcggga agccaggccc gccctgctga cgtccagact    1920
ccgcttcatc cccaagcctg acgggctgcg gccgattgtg aacatggact acgtcgtggg    1980
agccagaacg ttccgcagag aaaagagggc cgagcgtctc acctcgaggg tgaaggcact    2040
gttcagcgtg ctcaactacg agcgggcgcg gcgccccggc ctcctgggcg cctctgtgct    2100
gggcctggac gatatccaca gggcctggcc caccttcgtg ctgcgtgtgc gggcccagga    2160
cccgccgcct gagctgtact ttgtcaaggt ggatgtgacg ggcgcgtacg acaccatccc    2220
ccaggacagg ctcacggagg tcatcgccag catcatcaaa cccagaacaa cgtactgcgt    2280
gcgtcggtat gccgtggtcc agaaggccgc ccatgggcac gtccgcaagg ccttcaagag    2340
ccacgtctct accttgacag acctccagcc gtacatgcga cagttcgtgg ctcacctgca    2400
ggagaccagc ccgctgaggg atgccgtcgt catcgagcag agctcctccc tgaatgaggc    2460
cagcagtggc ctcttcgacg tcttcctacg cttcatgtgc caccacgccg tgcgcatcag    2520
gggcaagtcc tacgtccagt gccaggggat cccgcagggc tccatcctct ccacgctgct    2580
ctgcagcctg tgctacggcg acatggagaa caagctgttt gcggggattc ggcgggacgg    2640
gctgctcctg cgtttggtgg atgatttctt gttggtgaca cctcacctca cccacgcgaa    2700
aaccttcctc aggaccctgg tccgaggtgt ccctgagtat ggctgcgtgg tgaacttgcg    2760
gaagacagtg gtgaacttcc ctgtagaaga cgaggccctg ggtggcacgg cttttgttca    2820
gatgccggcc cacggcctat tccctggtgt cggcctgctg ctggatacccc ggaccctgga    2880 ggtgcagagc gactactcca gctatgcccg gacctccatc agagccagtc tcaccttcaa    2940
ccgcggcttc aaggctggga ggaacatgcg tcgcaaactc tttggggtct gcggctgaa    3000 gtgtcacagc ctgtttctgg atttgcaggt gaacagcctc cagacggtgt gcaccaacat    3060
ctacaagatc ctcctgctgc aggcgtacag gtttcacgca tgtgtgctgc agctcccatt    3120
tcatcagcaa gtttggaaga ccccacatt tttcctgcgc gtcatctctg acacggcctc    3180
cctctgctac tccatcctga agccaagaa cgcagggatg tcgctggggg ccaagggcgc    3240
cgccggccct ctgccctccg aggccgtgca gtggctgtgc caccaagcat tcctgctcaa    3300
gctgactcga caccgtgtca cctacgtgcc actcctgggg tcactcagga cagcccagac    3360
gcagctgagt cggaagctcc cggggacgac gctgactgcc ctggaggccg cagccaaccc    3420
ggcactgccc tcagacttca agaccatcct ggactgatgg ccacccgccc acagccaggc    3480
cgagagcaga caccagcagc cctgtcacgc cgggctctac gtcccaggga gggaggggcg    3540
gcccacaccc aggcccgcac cgctgggagt ctgaggcctg agtgagtgtt tggccgaggc    3600
ctgcatgtcc ggctgaaggc tgagtgtccg gctgaggcct gagcgagtgt ccagccaagg    3660
gctgagtgtc cagcacacct gccgtcttca cttccccaca ggctggcgct cggctccacc    3720
ccagggccag ctttttcctca ccaggagccc ggcttccact ccccacatag gaatagtcca    3780
tccccagatt cgccattgtt caccccttcgc cctgccctcc tttgccttcc acccccacca    3840
tccaggtgga ccctgagaa aggaccctgg gagctctggg aatttggagt gaccaaaggt    3900
gtgccctgta cacaggcgag gaccctgcac ctggatgggg gtccctgtgg gtcaaattgg    3960
ggggaggtgc tgtgggagta aaatactgaa tatatgagtt tttcagttttt gaaaaaaa    4018
```

<210> SEQ ID NO 47
<211> LENGTH: 4635
<212> TYPE: DNA
<213> ORGANISM: Homo sapiens

<400> SEQUENCE: 47

```
attctttgga atactactgc tagaagtctg acttaagacc cagcttatgg gccacatggc      60
acccagctgc ttctgcagag aaggcaggcc actgatgggt acagcaaagt gtggtgctgc     120
tggccaagcc aaagacccgt gtaggatgac tgggcctctg cccttgtgg gtgttgccac     180
tgtgcttgag tgcctggtga agaatgtgat gggatcacta gcatgtctgc ggagagcggc     240
cctgggacga gattgagaaa tctgccagta atggggatg gactagaaac ttcccaaatg     300
tctacaacac aggcccaggc ccaaccccag ccagccaacg cagccagcac caacccccg      360
cccccagaga cctccaaccc taacaagccc aagaggcaga ccaaccaact gcaatacctg     420
ctcagagtgg tgctcaagac actatggaaa caccagtttg catggccttt ccagcagcct     480
gtggatgccg tcaagctgaa cctccctgat tactataaga tcattaaaac gcctatggat     540
atgggaacaa taagaagcg cttggaaaac aactattact ggaatgctca ggaatgtatc     600
caggacttca acactatgtt tacaaattgt tacatctaca acaagcctgg agatgacata     660
gtcttaatgg cagaagctct ggaaaagctc ttcttgcaaa aataaatga gctacccaca     720
gaagaaaccg agatcatgat agtccaggca aaaggaagag gacgtgggag gaaagaaaca     780
gggacagcaa aacctggcgt ttccacggta ccaaacacaa ctcaagcatc gactcctccg     840
cagacccaga cccctcagcc gaatcctcct cctgtgcagg ccacgcctca cccttccct      900
gccgtcaccc cggacctcat cgtccagacc cctgtcatga cagtggtgcc tccccagcca     960
ctgcagacgc cccgccagt gccccccag ccacaacccc cacccgctcc agctccccag      1020
cccgtacaga gccacccacc catcatcgcg gccacccac agcctgtgaa gacaaagaag     1080
ggagtgaaga ggaaagcaga caccaccacc cccaccacca ttgacccat tcacgagcca     1140
ccctcgctgc ccccggagcc caagaccacc aagctgggcc agcggcggga gagcagccgg     1200
cctgtgaaac ctccaaagaa ggacgtgccc gactctcagc agcacccagc accagagaag     1260
agcagcaagg tctcggagca gctcaagtgc tgcagcggca tcctcaagga gatgtttgcc     1320
aagaagcacg ccgcctacgc ctggccctcc tacaagcctg tggacgtgga ggcactgggc     1380
ctacacgact actgtgacat catcaagcac cccatggaca tgagcacaat caagtctaaa     1440
ctggaggccc gtgagtaccg tgatgctcag gagtttggtg ctgacgtccg attgatgttc     1500
tccaactgct ataagtacaa ccctcctgac catgaggtgg tggccatggc ccgcaagctc     1560
caggatgtgt tcgaaatgcg ctttgccaag atgccggacg agcctgagga gccagtggtg     1620
gccgtgtcct ccccggcagt gcccctccc accaaggttg tggccccgcc ctcatccagc     1680
gacagcagca gcgatagctc ctcggacagt gacagttcga ctgatgactc tgaggaggag     1740
cgagcccagc ggctggctga gctccaggag cagctcaaag ccgtgcacga gcagcttgca     1800
gccctctctc agccccagca gaacaaacca agaaaaagg agaaagacaa gaaggaaaag     1860
aaaaaagaaa agcacaaaag gaaagaggaa gtggaagaga taaaaaag caaagccaag      1920
gaacctcctc ctaaaaagac gaagaaaaat aatagcagca acagcaatgt gagcaagaag     1980
gagccagcgc ccatgaagag caagcccct cccacgtatg agtcggagga agaggacaag      2040
tgcaagccta tgtcctatga ggagaagcgg cagctcagct ggacatcaa caagctcccc     2100
ggcgagaagc tgggccgcgt ggtgcacatc atccagtcac gggagccctc cctgaagaat     2160
tccaaccccg acgagattga aatcgacttt gagaccctga gccgtccac actgcgtgag     2220
ctggagcgct atgtcacctc ctgtttgcgg aagaaaagga aacctcaagc tgagaaagtt     2280
```

```
gatgtgattg ccggctcctc caagatgaag ggcttctcgt cctcagagtc ggagagctcc    2340
agtgagtcca gctcctctga cagcgaagac tccgaaacag gtcctgccta atcattggac    2400
acggactctt aataaaacgg tcttcagttc cagattcctt cccagcaagc tatagcttaa    2460
gtccattttc ttccgtgaaa gggacaggac tccatcaagt tatggaattc ctcagagccc    2520
tgggcctgtc ccccggggtg gattagtcat gtccagcagc acacgcctag tcccgccttc    2580
gggaaggctg cctgcctggc cagccgccca ggcctctctg tgtaaagact gcctggctgt    2640
cctgcccagc cttcctggtt ctctggggtc ctctgggtgg gtggcatctc ctggagggtg    2700
atgacaatcc ccaacacatg cattcatgtg gtgctactct gtgtgcaaag ccagaccccca   2760 agtatgtttt ctctctttgt cccatccctc tttttctggg actttggacc ctaactactt    2820
ccctcctgaa ccttgcagtg acatcagtcc aggagagctc tcgttcagtg tgcggaagaa    2880
cactctgacc tctagagctg tcctagataa ggagtgggag ctttagaggc aaggcctcta    2940
gaccctggaa ggctcagtga ggctcttccc acagcatgct tctcactggt gccctgtaag    3000
gctcgagcca ccgctgactc tgagcctttt ggagtctttc ctccttcgtc tccattgttc    3060
ccgtgcattt ccaaaagctt aagttgcctg gtgggcattt cccccagtttc tttggcctcc    3120 gtcttctcaa gtcacatagg gaaagtacct cctggaacca ggctgcagta tgcaggacct    3180
gccaggcagg cactggtgaa gggccttggg cctatcatcc ccccaacccc acctcaccc    3240 acccgcctcc tctagtgggg tgagtctggg ctggtggacc agagagggtg tcacagaccc    3300
tcagggactg ccccatggac acctctgact ggtgttaaca gtgtgaacat tttccccgtc    3360
ttcagtccct tagaatgacg acagccctg ggttgggc aggcgagtgt ggccacatca    3420
tccaagccct cccagagaca caaataggct tttttgctct aaaaataaat accagccctt    3480
ttttggtcac aaatccagca tctcagcaga aaactgcctg acatgaaaag tccctgagg    3540 aactgcatct gcgtttcagg ggcttttcat tttttctcct tttttaaagt gtagattgtg    3600
ggtgcttcct agaggcctgc cttcttctgg aactggaagt gggctatcac catgggcaag    3660
cccttgggtg caggctcccc acctgcctgg gaactctggc agctctcctc agctccttgg    3720
gcttgagcag ctgcaactgc cccagatttg ctgtggaagc aggggctagc cctggcctca    3780
ccagggcctc ccggggccct gcattgatgc tcaggagttc ctgggctgct cttgatcctt    3840
tctgggcatc cagcttccag ttaagctctg tttgccaaac aaactattct cagctgccct    3900
ttggcctgcg cctgatgtgt tcctgttgca gtcccgcctg cctgagacag gagcaggcag    3960
gagagccttc atgcccagat tcccacagga caattgggga gctgctggca ttgtctttct    4020
gggaagattc tgctttcttg gaccaaatgg cagcctgatt accagtgtcg ggcctgcatg    4080
ctgcccccga cacacgcacg cacgcgcaca cacgtgtgca catgggccat agccacaagc    4140
cagctctcct ccagggtcct ttcaacctcg ctgtccaggg accctgtcct tcttgcccgt    4200
ggggcttcca tctggcagag aacgttcagg gcttgttgaa cttgaaagct cattagactt    4260
aagctgtcac ctgtgcttgg tgccccagga acagccagag gaacagtgc ccactcactt    4320 cttgttggca gcctcctgtg caggaagtgc cagccgggcc tcgacgcacc agctggctgt    4380
gggtcctgag gaggggcggg aggcggccgc tcagtgcaga tggggactcc tctcctctgc    4440
cctgacctta ccctccatta cctccttcac tggagtgggg ctgggggtg ggtggaatca    4500 gtgtttaat cggattttta aaaaacattt tatttctttg tacaattacc atcctatgta    4560
aagatgaaat ttgtgttgag ttgaagattg tcatggaata aagatcacac cgtacttgag    4620
gccatcttca tgtaa                                                     4635
```

<210> SEQ ID NO 48
<211> LENGTH: 1050
<212> TYPE: DNA
<213> ORGANISM: Homo sapiens

<400> SEQUENCE: 48

```
acacacacac acccctcccc tgccatccct ccccggactc cggctccggc tccgattgca      60
atttgcaacc tccgctgccg tcgccgcagc agccaccaat tcgccagcgg ttcaggtggc     120
tcttgcctcg atgtcctagc ctaggggccc ccgggccgga cttggctggg ctcccttcac     180
cctctgcgga gtcatgaggg cgaacgacgc tctgcaggtg ctgggcttgc ttttcagcct     240
ggcccggggc tccgaggtgg gcaactctca ggcagtgtgt cctgggactc tgaatggcct     300
gagtgtgacc ggcgatgctg agaaccaata ccagacactg tacaagctct acgagaggtg     360
tgaggtggtg atggggaacc ttgagattgt gctcacggga cacaatgccg acctctcctt     420
cctgcagtgg attcgagaag tgacaggcta tgtcctcgtg gccatgaatg aattctctac     480
tctaccattg cccaacctcc gcgtggtgcg agggacccag gtctacgatg gaagtttgc      540
catcttcgtc atgttgaact ataacaccaa ctccagccac gctctgcgcc agctccgctt     600
gactcagctc accggtcagt tcccgatggt tccttctggc ctcacccctc agccagccca     660
agactggtac ctccttgatg atgacccaag actgctcact ctaagtgcct cttccaaggt     720
gcctgtcacc ttggccgctg tctaaaggtc cattgctccc taagcaatag agggccccca     780
gtaggggag ctaggggcat ctgctccagg gaaaggaacc ctgtgtcctt gtggggctgg      840
agtcagagct ggatctgtta accgtttttc taatttcaaa gtacagtgta ccggaggcca     900
ggcctgatgg cttacacctg taatcccagc attttgggag gccaaggagg gcagatcact     960
tgagatcagg agtttgagac cagcctggcc aacatggcga aaccctgtct ctactaaaaa    1020
tacaaaaaaa taaataaaa taaaaaatta                                      1050
```

<210> SEQ ID NO 49
<211> LENGTH: 1038
<212> TYPE: DNA
<213> ORGANISM: Homo sapiens

<400> SEQUENCE: 49

```
atttgaggcc atataaagtc acctgaggcc ctctccacca cagcccacca gtgaccacga      60
aggctgtgct gcttgccctg ttgatggcag gcttggccct gcagccaggc actgccctgc     120
tgtgctactc ctgcaaagcc caggtgagca acgaggactg cctgcaggtg gagaactgca     180
cccagctggg ggagcagtgc tggaccgcgc gcatccgcgc agttggcctc ctgaccgtca     240
tcagcaaagg ctgcagcttg aactgcgtgg atgactcaca ggactactac gtgggcaaga     300
agaacatcac gtgctgtgac accgacttgt gcaacgccag cggggcccat gccctgcagc     360
cggctgctgc catccttgcg ctgctccctg cactcggcct gctgctctgg gacccggcc      420
agctctaggc tctgggggc cccgctgcag cccacactgg gtgtggtgcc ccaggcctct     480
gtgccactcc tcacacaccc ggcccagtgg gagcctgtcc tggttcctga ggcacatcct     540
aacgcaagtc tgaccatgta tgtctgcgcc cctgtccccc accctgaccc tcccatggcc     600
ctctccagga ctcccacccg gcagatcggc tctattgaca cagatccgcc tgcagatggc     660
ccctccaacc ctctctgctg ctgtttccat ggcccagcat tctccaccct taaccctgtg     720
ctcaggcacc tcttccccca ggaagccttc cctgcccacc ccatctatga cttgagccag     780
```

| | | |
|---|---|---|
| gtctggtccg tggtgtcccc cgcacccagc aggggacagg cactcaggag ggcccggtaa | 840 | |
| aggctgagat gaagtggact gagtagaact ggaggacagg agtcgacgtg agttcctggg | 900 | |
| agtctccaga gatggggcct ggaggcctgg aggaagggc caggcctcac attcgtgggg | 960 | |
| ctccctgaat ggcagcctca gcacagcgta ggcccttaat aaacacctgt tggataagcc | 1020 | |
| agaaaaaaaa aaaaaaaa | 1038 | |

<210> SEQ ID NO 50
<211> LENGTH: 2723
<212> TYPE: DNA
<213> ORGANISM: Homo sapiens

<400> SEQUENCE: 50

| | | |
|---|---|---|
| ggcggcgctt gattgggctg gggggccaa ataaaagcga tggcgattgg gctgccgcgt | 60 | |
| ttggcgctcg gtccggtcgc gtccgacacc cggtgggact cagaaggcag tggagcccg | 120 | |
| gcggcggcgg cggcggcgcg cggggcgac gcgcggaac aacgcgagtc ggcgcgcggg | 180 | |
| acgaagaata atcatgggcc agactggaa gaaatctgag aagggaccag tttgttggcg | 240 | |
| gaagcgtgta aaatcagagt acatgcgact gagacagctc aagaggttca gacgagctga | 300 | |
| tgaagtaaag agtatgttta gttccaatcg tcagaaaatt ttggaaagaa cggaaatctt | 360 | |
| aaaccaagaa tggaaacagc gaaggataca gcctgtgcac atcctgactt ctgtgagctc | 420 | |
| attgcgcggg actaggagt gttcggtgac cagtgacttg gattttccaa cacaagtcat | 480 | |
| cccattaaag actctgaatg cagttgcttc agtacccata atgtattctt ggtctcccct | 540 | |
| acagcagaat tttatggtgg aagatgaaac tgttttacat aacattcctt atatgggaga | 600 | |
| tgaagtttta gatcaggatg gtactttcat tgaagaacta ataaaaaatt atgatgggaa | 660 | |
| agtacacggg gatagagaat gtgggtttat aaatgatgaa attttgtgg agttggtgaa | 720 | |
| tgcccttggt caatataatg atgatgacga tgatgatgat ggagacgatc ctgaagaaag | 780 | |
| agaagaaaag cagaaagatc tggaggatca ccgagatgat aaagaaagcc gcccacctcg | 840 | |
| gaaatttcct tctgataaaa ttttgaagc catttcctca atgtttccag ataagggcac | 900 | |
| agcagaagaa ctaaaggaaa aatataaaga actcaccgaa cagcagctcc caggcgcact | 960 | |
| tcctcctgaa tgtacccca acatagatgg accaaatgct aaatctgttc agagagagca | 1020 | |
| aagcttacac tccttttcata cgcttttctg taggcgatgt tttaaatatg actgcttcct | 1080 | |
| acatcgtaag tgcaattatt cttttcatgc aacacccaac acttataagc ggaagaacac | 1140 | |
| agaaacagct ctagacaaca aaccttgtgg accacagtgt taccagcatt tggagggagc | 1200 | |
| aaaggagttt gctgctgctc tcaccgctga gcggataaag accccaccaa aacgtccagg | 1260 | |
| aggccgcaga agaggacggc ttcccaataa cagtagcagg cccagcaccc ccaccattaa | 1320 | |
| tgtgctggaa tcaaaggata cagacagtga tagggaagca gggactgaaa cggggggaga | 1380 | |
| gaacaatgat aaagaagaag aagagaagaa agatgaaact tcgagctcct ctgaagcaaa | 1440 | |
| ttctcggtgt caaacaccaa taaagatgaa gccaaatatt gaacctcctg agaatgtgga | 1500 | |
| gtggagtggt gctgaagcct caatgtttag agtcctcatt ggcacttact atgacaattt | 1560 | |
| ctgtgccatt gctaggttaa ttgggaccaa aacatgtaga caggtgtatg agtttagagt | 1620 | |
| caaagaatct agcatcatag ctccagctcc cgctgaggat gtggatactc ctccaaggaa | 1680 | |
| aaagaagagg aaaacaccggt tgtgggctgc acactgcaga aagatacagc tgaaaaagga | 1740 | |
| cggctcctct aaccatgttt acaactatca accctgtgat catccacggc agccttgtga | 1800 | |
| cagttcgtgc ccttgtgtga tagcacaaaa ttttttgtgaa aagttttgtc aatgtagttc | 1860 | |

-continued

```
agagtgtcaa aaccgctttc cgggatgccg ctgcaaagca cagtgcaaca ccaagcagtg    1920
cccgtgctac ctggctgtcc gagagtgtga ccctgacctc tgtcttactt gtggagccgc    1980
tgaccattgg gacagtaaaa atgtgtcctg caagaactgc agtattcagc ggggctccaa    2040
aaagcatcta ttgctggcac catctgacgt ggcaggctgg gggattttta tcaaagatcc    2100
tgtgcagaaa aatgaattca tctcagaata ctgtggagag attatttctc aagatgaagc    2160
tgacagaaga gggaaagtgt atgataaata catgtgcagc tttctgttca acttgaacaa    2220
tgattttgtg gtggatgcaa cccgcaaggg taacaaaatt cgttttgcaa atcattcggt    2280
aaatccaaac tgctatgcaa aagttatgat ggttaacggt gatcacagga taggtatttt    2340
tgccaagaga gccatccaga ctggcgaaga gctgttttt gattacagat acagccaggc    2400
tgatgccctg aagtatgtcg gcatcgaaag agaaatggaa atcccttgac atctgctacc    2460
tcctccccc tcctctgaaa cagctgcctt agcttcagga acctcgagta ctgtgggcaa    2520
tttagaaaaa gaacatgcag tttgaaattc tgaatttgca aagtactgta agaataattt    2580
atagtaatga gtttaaaaat caactttta ttgccttctc accagctgca aagtgttttg    2640
taccagtgaa ttttttgcaat aatgcagtat ggtacatttt tcaactttga ataaagaata    2700
cttgaacttg tccttgttga atc                                            2723
```

<210> SEQ ID NO 51
<211> LENGTH: 2261
<212> TYPE: DNA
<213> ORGANISM: Homo sapiens

<400> SEQUENCE: 51

```
gagaagaaag ccagtgcgtc tctgggcgca ggggccagtg gggctcggag gcacaggcac     60
cccgcgacac tccaggttcc ccgacccacg tccctggcag ccccgattat ttacagcctc    120
agcagagcac ggggcggggg cagaggggcc cgcccgggag ggctgctact tcttaaaacc    180
tctgcgggct gcttagtcac agccccccctt gcttgggtgt gtccttcgct cgctccctcc    240
ctccgtctta ggtcactgtt ttcaacctcg aataaaaact gcagccaact tccgaggcag    300
cctcattgcc cagcggaccc cagcctctgc caggttcggt ccgccatcct cgtcccgtcc    360
tccgccggcc cctgccccgc gcccagggat cctccagctc ctttcgcccg cgccctccgt    420
tcgctccgga caccatggac aagttttggt ggcacgcagc ctggggactc tgcctcgtgc    480
cgctgagcct ggcgcagatc gatttgaata taacctgccg cttttgcaggt gtattccacg    540
tggagaaaaa tggtcgctac agcatctctc ggacggaggc cgctgacctc tgcaaggctt    600
tcaatagcac cttgcccaca atggcccaga tggagaaagc tctgagcatc ggatttgaga    660
cctgcaggta tgggttcata gaagggcacg tggtgattcc ccggatccac ccaactcca     720
tctgtgcagc aaacaacaca ggggtgtaca tcctcacatc caacacctcc cagtatgaca    780
catattgctt caatgcttca gctccacctg aagaagattg tacatcagtc acagacctgc    840
ccaatgcctt tgatggacca attaccataa ctattgttaa ccgtgatggc acccgctatg    900
tccagaaagg agaatacaga acgaatcctg aagacatcta ccccagcaac cctactgatg    960
atgacgtgag cagcggctcc tccagtgaaa ggagcagcac ttcaggaggt tacatctttt   1020
acacctttc tactgtacac cccatcccag acgaagacag tcctggatc accgacagca   1080
cagacagaat ccctgctacc agagaccaag acacattcca ccccagtggg gggtcccata   1140
ccactcatgg atctgaatca gatggacact cacatgggag tcaagaaggt ggagcaaaca   1200
```

```
caacctctgg tcctataagg acaccccaaa ttccagaatg gctgatcatc ttggcatccc   1260
tcttggcctt ggctttgatt cttgcagttt gcattgcagt caacagtcga agaagttgaa   1320
gagattcagg ttatagcata agaagagcac tgtttcatcg tcttcttgct gttaggaggt   1380
ctatgaagca gagaagaact tcctttgga aaacaactaa atgaagacag tcacctcgct   1440
agaactgaca catgggctgt ttttatattc ttgaaggcca ctctctccct acctgaacca   1500
agacctatag gtttacatgt tatttacatt ttatatataa tatatatata tatatataca   1560
catacattat atatacacaa tagtaattct agcaacagag gaaatgacct ttaacagggg   1620
tataaatcta aatttataaa agtataaatc taaatttctt acccaagaca ctttaaagat   1680
acattatttt tctccaggac gtaattcata ggaatattaa gccttttgta aatgtccctt   1740
tagatggttt ctcataaggt aaaagaaact tatttccaag caggaccacc tttattgtgt   1800
ccccagatca cctcacaggg cagaaaaatg cccctcagtc tgggagaaga cctagagaga   1860
attatggact ccttactggt ttttggaaag caaccaacag ctaattccaa caccatgggc   1920
agcccataca gtctctaatt atctgagaaa atcaaatgat gctgttacaa taattacgct   1980
ggtacaagtt aataaaagtg ccatgttaca gtcaaacagc tatgttgcta tctataccat   2040
tgagggcata gttttaaaaa gtagttatgc tacctgattg tataaggaac aaaactgaga   2100 gaaaaatct aaaaggccgc ctatgattga atggaaagat ttttttttagt tgaatttaaa   2160 taatgtgact tgggggagcc tttacaaaga gtctttatac ctcccttcag cttcctcatt   2220
ttcccttgga ttacttttgc tcaattaaat atgaatttcc t                       2261
```

<210> SEQ ID NO 52
<211> LENGTH: 4542
<212> TYPE: DNA
<213> ORGANISM: Homo sapiens

<400> SEQUENCE: 52

```
gagaagaaag ccagtgcgtc tctgggcgca ggggccagtg gggctcggag gcacaggcac     60
cccgcgacac tccaggttcc ccgacccacg tccctggcag cccgattat ttacagcctc    120 agcagagcac ggggcggggg cagaggggcc cgcccgggag ggctgctact tcttaaaacc    180
tctgcgggct gcttagtcac agcccccctt gcttgggtgt gtccttcgct cgctccctcc    240
ctccgtctta ggtcactgtt ttcaacctcg aataaaaact gcagccaact tccgaggcag    300
cctcattgcc cagcggaccc cagcctctgc caggttcggt ccgccatcct cgtcccgtcc    360
tccgccggcc cctgccccgc gcccagggat cctccagctc ctttcgcccg cgccctccgt    420
tcgctccgga caccatggac aagttttggt ggcacgcagc ctggggactc tgcctcgtgc    480
cgctgagcct ggcgcagatc gatttgaata taacctgccg cttttgcaggt gtattccacg    540 tggagaaaaa tggtcgctac agcatctctc ggacggaggc cgctgacctc tgcaaggctt    600
tcaatagcac cttgcccaca atggcccaga tggagaaagc tctgagcatc ggatttgaga    660
cctgcaggta tgggttcata gaagggcacg tggtgattcc ccggatccac cccaactcca    720
tctgtgcagc aaacaacaca ggggtgtaca tcctcacatc caacacctcc cagtatgaca    780
catattgctt caatgcttca gctccacctg aagaagattg tacatcagtc acagacctgc    840
ccaatgcctt tgatggacca attaccataa ctattgttaa ccgtgatggc acccgctatg    900
tccagaaagg agaatacaga acgaatcctg aagacatcta ccccagcaac cctactgatg    960
atgacgtgag cagcggctcc tccagtgaaa ggagcagcac ttcaggaggt tacatctttt   1020 acacctttttc tactgtacac cccatcccag acgaagacag tccctggatc accgacagca   1080
```

```
cagacagaat ccctgctacc agacactcac atgggagtca agaaggtgga gcaaacacaa    1140
cctctggtcc tataaggaca ccccaaattc cagaatggct gatcatcttg gcatccctct    1200
tggccttggc tttgattctt gcagtttgca ttgcagtcaa cagtcgaaga aggtgtgggc    1260
agaagaaaaa gctagtgatc aacagtggca atggagctgt ggaggacaga aagccaagtg    1320
gactcaacgg agaggccagc aagtctcagg aaatggtgca tttggtgaac aaggagtcgt    1380
cagaaactcc agaccagttt atgacagctg atgagacaag gaacctgcag aatgtggaca    1440
tgaagattgg ggtgtaacac ctacaccatt atcttggaaa gaaacaaccg ttggaaacat    1500
aaccattaca gggagctggg acacttaaca gatgcaatgt gctactgatt gtttcattgc    1560
gaatcttttt tagcataaaa ttttctactc tttttgtttt ttgtgttttg ttctttaaag    1620
tcaggtccaa tttgtaaaaa cagcattgct ttctgaaatt agggcccaat taataatcag    1680
caagaatttg atcgttccag ttcccacttg gaggcctttc atccctcggg tgtgctatgg    1740
atggcttcta acaaaaacta cacatatgta ttcctgatcg ccaacctttc ccccaccagc    1800
taaggacatt tcccagggtt aatagggcct ggtccctggg aggaaatttg aatgggtcca    1860
ttttgccctt ccatagccta atccctgggc attgctttcc actgaggttg ggggttgggg    1920
tgtactagtt acacatcttc aacagacccc ctctagaaat ttttcagatg cttctgggag    1980
acacccaaag ggtgaagcta tttatctgta gtaaactatt tatctgtgtt tttgaaatat    2040
taaaccctgg atcagtcctt tgatcagtat aatttttttaa agttactttg tcagaggcac    2100
aaaagggttt aaactgattc ataataaata tctgtacttc ttcgatcttc accttttgtg    2160
ctgtgattct tcagtttcta aaccagcact gtctgggtcc ctacaatgta tcaggaagag    2220
ctgagaatgg taaggagact cttctaagtc ttcatctcag agaccctgag ttccccactca    2280
gacccactca gccaaatctc atggaagacc aaggagggca gcactgtttt tgttttttgt    2340
tttttgtttt tttttttttga cactgtccaa aggttttcca tcctgtcctg gaatcagagt    2400
tggaagctga ggagcttcag cctcttttat ggtttaatgg ccacctgttc tctcctgtga    2460
aaggctttgc aaagtcacat taagtttgca tgacctgtta tccctggggc cctatttcat    2520
agaggctggc cctattagtg atttccaaaa acaaatggaa agtgccttttt gatgtcttac    2580
aataagagaa gaagccaatg gaaatgaaag agattggcaa aggggaagga tgatgccatg    2640
tagatcctgt ttgacatttt tatggctgta tttgtaaact taaacacacc agtgtctgtt    2700
cttgatgcag ttgctattta ggatgagtta agtgcctggg gagtccctca aaaggttaaa    2760
gggattccca tcattggaat cttatcacca gataggcaag tttatgacca aacaagagag    2820
tactggcttt atcctctaac ctcatatttt ctcccacttg gcaagtcctt tgtggcatt    2880
attcatcagt cagggtgtcc gattggtcct agaacttcca aaggctgctt gtcatagaag    2940
ccattgcatc tataaagcaa cggctcctgt taaatggtat ctccttttctg aggctcctac    3000
taaaagtcat ttgttaccta aacttatgtg cttaacaggc aatgcttctc agaccacaaa    3060
gcagaaagaa gaagaaaagc tcctgactaa atcagggctg gcttagaca gagttgatct    3120
gtagaatatc tttaaaggag agatgtcaac tttctgcact attcccagcc tctgctcctc    3180
cctgtctacc ctctcccctc cctctctccc tccacttcac cccacaatct tgaaaaactt    3240
cctttctctt ctgtgaacat cattggccag atccattttc agtggtctgg atttcttttt    3300
attttctttt caacttgaaa gaaactggac attaggccac tatgtgttgt tactgccact    3360
agtgttcaag tgcctcttgt tttcccagag atttcctggg tctgccagag gcccagacag    3420
```

```
gctcactcaa gctctttaac tgaaaagcaa caagccactc caggacaagg ttcaaaatgg    3480
ttacaacagc ctctacctgt cgccccaggg agaaagggt agtgatacaa gtctcatagc    3540
cagagatggt tttccactcc ttctagatat tcccaaaaag aggctgagac aggaggttat    3600
tttcaatttt attttggaat taaatacttt tttcccttta ttactgttgt agtccctcac    3660
ttggatatac ctctgttttc acgatagaaa taagggaggt ctagagcttc tattccttgg    3720
ccattgtcaa cggagagctg gccaagtctt cacaaaccct tgcaacattg cctgaagttt    3780
atggaataag atgtattctc actcccttga tctcaagggc gtaactctgg aagcacagct    3840
tgactacacg tcattttttac caatgatttt caggtgacct gggctaagtc atttaaactg    3900
ggtctttata aaagtaaaag gccaacattt aattattttg caaagcaacc taagagctaa    3960
agatgtaatt tttcttgcaa ttgtaaatct tttgtgtctc ctgaagactt cccttaaaat    4020
tagctctgag tgaaaaatca aagagacaa aagcatctt cgaatccata tttcaagcct    4080
ggtagaattg gcttttctag cagaaccttt ccaaaagttt tatattgaga ttcataacaa    4140
caccaagaat tgattttgta gccaacattc attcaatact gttatatcag aggagtagga    4200
gagaggaaac atttgactta tctggaaaag caaaatgtac ttaagaataa gaataacatg    4260
gtccattcac ctttatgtta tagatatgtc tttgtgtaaa tcatttgttt tgagttttca    4320
aagaatagcc cattgttcat tcttgtgctg tacaatgacc actgttattg ttactttgac    4380
ttttcagagc acacccttcc tctggttttt gtatatttat tgatggatca ataataatga    4440
ggaaagcatg atatgtatat tgctgagttg aaagcactta ttggaaaata ttaaaaggct    4500
aacattaaaa gactaaagga aacagaaaaa aaaaaaaaa aa                        4542

<210> SEQ ID NO 53
<211> LENGTH: 4809
<212> TYPE: DNA
<213> ORGANISM: Homo sapiens

<400> SEQUENCE: 53
gagaagaaag ccagtgcgtc tctgggcgca ggggccagtg gggctcggag gcacaggcac      60
cccgcgacac tccaggttcc ccgacccacg tccctggcag ccccgattat ttacagcctc     120
agcagagcac ggggcggggg cagaggggcc cgcccgggag ggctgctact tcttaaaacc     180
tctgcgggct gcttagtcac agccccccctt gcttgggtgt gtccttcgct cgctccctcc     240
ctccgtctta ggtcactgtt ttcaacctcg aataaaaact gcagccaact tccgaggcag     300
cctcattgcc cagcggaccc cagcctctgc caggttcggt ccgccatcct cgtcccgtcc     360
tccgccggcc cctgccccgc gcccagggat cctccagctc ctttcgcccg cgccctccgt     420
tcgctccgga caccatggac aagttttggt ggcacgcagc ctggggactc tgcctcgtgc     480
cgctgagcct ggcgcagatc gatttgaata taacctgccg ctttgcaggt gtattccacg     540
tggagaaaaa tggtcgctac agcatctctc ggacggaggc cgctgacctc tgcaaggctt     600
tcaatagcac cttgcccaca atggcccaga tggaaaagc tctgagcatc ggatttgaga     660
cctgcaggta tgggttcata gaagggcacg tggtgattcc ccggatccac cccaactcca     720
tctgtgcagc aaacaacaca ggggtgtaca tcctcacatc caacacctcc cagtatgaca     780
catattgctt caatgcttca gctccacctg aagaagattg tacatcagtc acagacctgc     840
ccaatgcctt tgatggacca attaccataa ctattgttaa ccgtgatggc acccgctatg     900
tccagaaagg agaatacaga acgaatcctg aagcatctca ccccagcaac cctactgatg     960
atgacgtgag cagcggctcc tccagtgaaa ggagcagcac ttcaggaggt tacatctttt    1020
```

```
acaccttttc tactgtacac cccatcccag acgaagacag tccctggatc accgacagca    1080
cagacagaat ccctgctacc aataggaatg atgtcacagg tggaagaaga gacccaaatc    1140
attctgaagg ctcaactact ttactggaag gttatacctc tcattaccca cacacgaagg    1200
aaagcaggac cttcatccca gtgacctcag ctaagactgg gtcctttgga gttactgcag    1260
ttactgttgg agattccaac tctaatgtca atcgttcctt atcaggagac caagacacat    1320
tccaccccag tgggggtcc cataccactc atggatctga atcagatgga cactcacatg    1380
ggagtcaaga aggtggagca aacacaacct ctggtcctat aaggacaccc caaattccag    1440
aatggctgat catcttggca tccctcttgg ccttggcttt gattcttgca gtttgcattg    1500
cagtcaacag tcgaagaagg tgtgggcaga agaaaaagct agtgatcaac agtggcaatg    1560
gagctgtgga ggacagaaag ccaagtggac tcaacggaga ggccagcaag tctcaggaaa    1620
tggtgcattt ggtgaacaag gagtcgtcag aaactccaga ccagtttatg acagctgatg    1680
agacaaggaa cctgcagaat gtggacatga agattgggtg taacaccta caccattatc    1740 ttggaaagaa acaaccgttg gaaacataac cattacaggg agctgggaca cttaacagat    1800
gcaatgtgct actgattgtt tcattgcgaa tcttttttag cataaaattt tctactcttt    1860
ttgttttttg tgttttgttc tttaaagtca ggtccaattt gtaaaaacag cattgctttc    1920
tgaaattagg gcccaattaa taatcagcaa gaatttgatc gttccagttc ccacttggag    1980
gcctttcatc cctcgggtgt gctatggatg gcttctaaca aaaactacac atatgtattc    2040
ctgatcgcca acctttcccc caccagctaa ggacatttcc cagggttaat agggcctggt    2100
ccctgggagg aaatttgaat gggtccattt tgcccttcca tagcctaatc cctgggcatt    2160
gctttccact gaggttgggg gttggggtgt actagttaca catcttcaac agaccccctc    2220
tagaaatttt tcagatgctt ctgggagaca cccaaagggt gaagctattt atctgtagta    2280
aactatttat ctgtgttttt gaaatattaa accctggatc agtcctttga tcagtataat    2340
tttttaaagt tactttgtca gaggcacaaa agggtttaaa ctgattcata ataaatatct    2400
gtacttcttc gatcttcacc ttttgtgctg tgattcttca gtttctaaac cagcactgtc    2460
tgggtcccta caatgtatca ggaagagctg agaatggtaa ggagactctt ctaagtcttc    2520
atctcagaga ccctgagttc ccactcagac ccactcagcc aaatctcatg gaagaccaag    2580
gagggcagca ctgttttttgt tttttgtttt ttgtttttt tttttgacac tgtccaaagg    2640
ttttccatcc tgtcctggaa tcagagttgg aagctgagga gcttcagcct ctttatggt    2700 ttaatggcca cctgttctct cctgtgaaag gctttgcaaa gtcacattaa gtttgcatga    2760
cctgttatcc ctggggccct atttcataga ggctggccct attagtgatt ccaaaaaca    2820 atatggaagt gccttttgat gtcttacaat aagagaagaa gccaatggaa atgaaagaga    2880
ttggcaaagg ggaaggatga tgccatgtag atcctgtttg acatttttat ggctgtattt    2940
gtaaacttaa acacaccagt gtctgttctt gatgcagttg ctatttagga tgagttaagt    3000
gcctggggag tccctcaaaa ggttaaaggg attcccatca ttggaatctt atcaccagat    3060
aggcaagttt atgaccaaac aagagagtac tggctttatc ctctaacctc atattttctc    3120
ccacttggca agtcctttgt ggcatttatt catcagtcag ggtgtccgat tggtcctaga    3180
acttccaaag gctgcttgtc atagaagcca ttgcatctat aaagcaacgg ctcctgttaa    3240
atggtatctc ctttctgagg ctcctactaa aagtcatttg ttacctaaac ttatgtgctt    3300
aacaggcaat gcttctcaga ccacaaagca gaaagaagaa gaaagctcc tgactaaatc    3360
```

| | |
|---|---|
| agggctgggc ttagacagag ttgatctgta aatatctttt aaaggagaga tgtcaacttt | 3420 |
| ctgcactatt cccagcctct gctcctccct gtctaccctc tccctccct ctctccctcc | 3480 |
| acttcacccc acaatcttga aaaacttcct ttctcttctg tgaacatcat tggccagatc | 3540 |
| cattttcagt ggtctggatt tctttttatt ttcttttcaa cttgaaagaa actggacatt | 3600 |
| aggccactat gtgttgttac tgccactagt gttcaagtgc ctcttgtttt cccagagatt | 3660 |
| tcctgggtct gccagaggcc cagacaggct cactcaagct cttaactga aaagcaacaa | 3720 |
| gccactccag gacaaggttc aaaatggtta caacagcctc tacctgtcgc cccagggaga | 3780 |
| aaggggtagt gatacaagtc tcatagccag agatggtttt ccactccttc tagatattcc | 3840 |
| caaaagagg ctgagacagg aggttatttt caattttatt ttggaattaa atactttttt | 3900 |
| ccctttatta ctgttgtagt ccctcacttg gatatacctc tgttttcacg atagaaataa | 3960 |
| gggaggtcta gagcttctat tccttggcca ttgtcaacgg agagctggcc aagtcttcac | 4020 |
| aaacccttgc aacattgcct gaagtttatg gaataagatg tattctcact cccttgatct | 4080 |
| caaggcgta actctggaag cacagcttga ctacacgtca tttttaccaa tgattttcag | 4140 |
| gtgacctggg ctaagtcatt taaactgggt ctttataaaa gtaaaaggcc aacatttaat | 4200 |
| tattttgcaa agcaacctaa gagctaaaga tgtaattttt cttgcaattg taaatctttt | 4260 |
| gtgtctcctg aagacttccc ttaaaattag ctctgagtga aaaatcaaaa gagacaaaag | 4320 |
| acatcttcga atccatattt caagcctggt agaattggct tttctagcag aacctttcca | 4380 |
| aaagttttat attgagattc ataacaacac caagaattga ttttgtagcc aacattcatt | 4440 |
| caatactgtt atatcagagg agtaggagag aggaaacatt tgacttatct ggaaaagcaa | 4500 |
| aatgtactta agaataagaa taacatggtc cattcacctt tatgttatag atatgtcttt | 4560 |
| gtgtaaatca tttgttttga gttttcaaag aatagcccat tgttcattct tgtgctgtac | 4620 |
| aatgaccact gttattgtta ctttgacttt tcagagcaca cccttcctct ggttttgta | 4680 |
| tatttattga tggatcaata ataatgagga aagcatgata tgtatattgc tgagttgaaa | 4740 |
| gcacttattg gaaatatta aaaggctaac attaaaagac taaggaaac agaaaaaaaa | 4800 |
| aaaaaaaaa | 4809 |

```
<210> SEQ ID NO 54
<211> LENGTH: 3985
<212> TYPE: DNA
<213> ORGANISM: Homo sapiens

<400> SEQUENCE: 54
```

| | |
|---|---|
| gagaagaaag ccagtgcgtc tctgggcgca ggggccagtg gggctcggag gcacaggcac | 60 |
| cccgcgacac tccaggttcc ccgacccacg tccctggcag cccgattat ttacagcctc | 120 |
| agcagagcac ggggcggggg cagaggggcc cgcccgggag ggctgctact tcttaaaacc | 180 |
| tctgcgggct gcttagtcac agccccccctt gcttgggtgt gtccttcgct cgctccctcc | 240 |
| ctccgtctta ggtcactgtt ttcaacctcg aataaaaact gcagccaact tccgaggcag | 300 |
| cctcattgcc cagcggaccc cagcctctgc caggttcggt ccgccatcct cgtcccgtcc | 360 |
| tccgccggcc cctgccccgc gcccagggat cctccagctc ctttcgcccg cgccctccgt | 420 |
| tcgctccgga caccatggac aagttttggt ggcacgcagc ctggggactc tgcctcgtgc | 480 |
| cgctgagcct ggcgcagatc gatttgaata taacctgccg cttttgcaggt gtattccacg | 540 |
| tggagaaaaa tggtcgctac agcatctctc ggacggaggc cgctgacctc tgcaaggctt | 600 |
| tcaatagcac cttgcccaca atggcccaga tggagaaagc tctgagcatc ggatttgaga | 660 |

```
cctgcagttt gcattgcagt caacagtcga agaaggtgtg ggcagaagaa aaagctagtg      720
atcaacagtg gcaatggagc tgtggaggac agaaagccaa gtggactcaa cggagaggcc      780
agcaagtctc aggaaatggt gcatttggtg aacaaggagt cgtcagaaac tccagaccag      840
tttatgacag ctgatgagac aaggaacctg cagaatgtgg acatgaagat tggggtgtaa      900
cacctacacc attatcttgg aaagaaacaa ccgttggaaa cataaccatt acagggagct      960
gggacactta acagatgcaa tgtgctactg attgtttcat tgcgaatctt ttttagcata     1020
aaattttcta ctcttttttgt tttttgtgtt ttgttcttta aagtcaggtc caatttgtaa     1080
aaacagcatt gctttctgaa attagggccc aattaataat cagcaagaat ttgatcgttc     1140
cagttcccac ttggaggcct ttcatccctc gggtgtgcta tggatggctt ctaacaaaaa     1200
ctacacatat gtattcctga tcgccaacct ttcccccacc agctaaggac atttcccagg     1260
gttaataggg cctggtccct ggggaggaaat ttgaatgggt ccattttgcc cttccatagc     1320
ctaatccctg ggcattgctt tccactgagg ttgggggttg gggtgtacta gttacacatc     1380
ttcaacagac cccctctaga aatttttcag atgcttctgg gagacaccca aagggtgaag     1440
ctatttatct gtagtaaact atttatctgt gttttgaaaa tattaaaccc tggatcagtc     1500
ctttgatcag tataattttt taaagttact ttgtcagagg cacaaaaggg tttaaactga     1560
ttcataataa atatctgtac ttcttcgatc ttcaccttt gtgctgtgat tcttcagttt      1620
ctaaaccagc actgtctggg tccctacaat gtatcaggaa gagctgagaa tggtaaggag     1680
actcttctaa gtcttcatct cagagaccct gagttccac tcagacccac tcagccaaat      1740
ctcatggaag accaaggagg gcagcactgt ttttgttttt tgtttttgt ttttttttt       1800 tgacactgtc caaaggtttt ccatcctgtc ctggaatcag agttggaagc tgaggagctt     1860
cagcctcttt tatggtttaa tggccacctg ttctctcctg tgaaaggctt tgcaaagtca     1920
cattaagttt gcatgacctg ttatccctgg ggccctattt catagaggct ggccctatta     1980
gtgatttcca aaaacaatat ggaagtgcct tttgatgtct tacaataaga gaagaagcca     2040
atggaaatga aagagattgg caaaggggaa ggatgatgcc atgtagatcc tgttttgacat    2100 ttttatggct gtatttgtaa acttaaacac accagtgtct gttcttgatg cagttgctat     2160
ttaggatgag ttaagtgcct ggggagtccc tcaaaaggtt aaagggattc ccatcattgg     2220
aatcttatca ccagataggc aagtttatga ccaaacaaga gagtactggc tttatcctct     2280
aacctcatat tttctcccac ttggcaagtc ctttgtggca tttattcatc agtcagggtg     2340
tccgattggt cctagaactt ccaaaggctg cttgtcatag aagccattgc atctataaag     2400
caacggctcc tgttaaatgg tatctccttt ctgaggctcc tactaaaagt catttgttac     2460
ctaaacttat gtgcttaaca ggcaatgctt ctcagaccac aaagcagaaa gaagaagaaa     2520
agctcctgac taaatcaggg ctgggcttag acagagttga tctgtagaat atctttaaag     2580
gagagatgtc aactttctgc actattccca gcctctgctc ctccctgtct accctctccc     2640
ctccctctct ccctccactt caccccacaa tcttgaaaaa cttcctttct cttctgtgaa     2700
catcattggc cagatccatt ttcagtggtc tggattcttt tttattttct tttcaacttg     2760
aaagaaactg acattaggc cactatgtgt tgttactgcc actagtgttc aagtgcctct      2820
tgttttccca gagatttcct gggtctgcca gaggcccaga caggctcact caagctcttt     2880
aactgaaaag caacaagcca ctccaggaca aggttcaaaa tggttacaac agcctctacc     2940
tgtcgcccca gggagaaagg ggtagtgata caagtctcat agccagagat ggttttccac     3000
```

```
tccttctaga tattcccaaa agaggctga gacaggaggt tattttcaat tttattttgg      3060
aattaaatac ttttttccct ttattactgt tgtagtccct cacttggata tacctctgtt      3120
ttcacgatag aaataaggga ggtctagagc ttctattcct tggccattgt caacggagag      3180
ctggccaagt cttcacaaac ccttgcaaca ttgcctgaag tttatggaat aagatgtatt      3240
ctcactccct tgatctcaag gcgtaactc tggaagcaca gcttgactac acgtcatttt       3300
taccaatgat tttcaggtga cctgggctaa gtcatttaaa ctgggtcttt ataaaagtaa      3360
aaggccaaca tttaattatt ttgcaaagca acctaagagc taaagatgta attttttcttg     3420 caattgtaaa tcttttgtgt ctcctgaaga cttcccttaa aattagctct gagtgaaaaa      3480
tcaaaagaga caaaagacat cttcgaatcc atatttcaag cctggtagaa ttggcttttc      3540
tagcagaacc tttccaaaag ttttatattg agattcataa caacaccaag aattgatttt      3600
gtagccaaca ttcattcaat actgttatat cagaggagta ggagagagga aacatttgac      3660
ttatctggaa aagcaaaatg tacttaagaa taagaataac atggtccatt caccttttatg    3720 ttatagatat gtctttgtgt aaatcatttg ttttgagttt tcaaagaata gcccattgtt     3780
cattcttgtg ctgtacaatg accactgtta ttgttacttt gacttttcag agcacaccct      3840
tcctctggtt tttgtatatt tattgatgga tcaataataa tgaggaaagc atgatatgta      3900
tattgctgag ttgaaagcac ttattggaaa atattaaaag gctaacatta aaagactaaa      3960
ggaaacagaa aaaaaaaaa aaaaa                                             3985

<210> SEQ ID NO 55
<211> LENGTH: 4605
<212> TYPE: DNA
<213> ORGANISM: Homo sapiens

<400> SEQUENCE: 55
gagaagaaag ccagtgcgtc tctgggcgca ggggccagtg gggctcggag gcacaggcac        60
cccgcgacac tccaggttcc ccgacccacg tccctggcag cccgattat ttacagcctc        120 agcagagcac ggggcggggg cagaggggcc cgccgggag ggctgctact tcttaaaacc        180
tctgcgggct gcttagtcac agcccccctt gcttgggtgt gtccttcgct cgctccctcc       240
ctccgtctta ggtcactgtt ttcaacctcg aataaaaact gcagccaact tccgaggcag       300
cctcattgcc cagcggaccc cagcctctgc caggttcggt ccgccatcct cgtcccgtcc       360
tccgccggcc cctgccccgc gcccagggat cctccagctc ctttcgcccg cgccctccgt      420
tcgctccgga caccatggac aagttttggt ggcacgcagc ctgggactc tgcctcgtgc        480 cgctgagcct ggcgcagatc gatttgaata taacctgccg ctttgcaggt gtattccacg       540
tggagaaaaa tggtcgctac agcatctctc ggacggaggc cgctgacctc tgcaaggctt       600
tcaatagcac cttgcccaca atggcccaga tggagaaagc tctgagcatc ggatttgaga      660
cctgcaggta tgggttcata gaagggcacg tggtgattcc ccggatccac cccaactcca      720
tctgtgcagc aaacaacaca ggggtgtaca tcctcacatc caacacctcc cagtatgaca      780
catattgctt caatgcttca gctccacctg aagaagattg tacatcagtc acagacctgc      840
ccaatgcctt tgatggacca ttaccataa ctattgttaa ccgtgatggc acccgctatg       900
tccagaaagg agaatacaga acgaatcctg aagcatcta ccccagcaac cctactgatg       960
atgacgtgag cagcggctcc tccagtgaaa ggagcagcac ttcaggaggt tacatcttt       1020 acaccttttc tactgtacac cccatcccag acgaagacag tcctggatc accgacagca      1080 cagacagaat ccctgctacc agagaccaag acacattcca ccccagtggg ggtcccata      1140
```

-continued

```
ccactcatgg atctgaatca gatggacact cacatgggag tcaagaaggt ggagcaaaca      1200
caacctctgg tcctataagg acaccccaaa ttccagaatg gctgatcatc ttggcatccc      1260
tcttggcctt ggctttgatt cttgcagttt gcattgcagt caacagtcga agaaggtgtg      1320
ggcagaagaa aaagctagtg atcaacagtg gcaatggagc tgtggaggac agaaagccaa      1380
gtggactcaa cggagaggcc agcaagtctc aggaaatggt gcatttggtg aacaaggagt      1440
cgtcagaaac tccagaccag tttatgacag ctgatgagac aaggaacctg cagaatgtgg      1500
acatgaagat tggggtgtaa cacctacacc attatcttgg aaagaaacaa ccgttggaaa      1560
cataaccatt acagggagct gggacactta acagatgcaa tgtgctactg attgtttcat      1620
tgcgaatctt ttttagcata aaattttcta ctcttttttgt tttttgtgtt tgttctttta     1680
aagtcaggtc caatttgtaa aaacagcatt gctttctgaa attagggccc aattaataat      1740
cagcaagaat ttgatcgttc cagttcccac ttggaggcct ttcatccctc gggtgtgcta      1800
tggatggctt ctaacaaaaa ctacacatat gtattcctga tcgccaacct ttcccccacc      1860
agctaaggac atttcccagg gttaataggg cctggtccct gggaggaaat ttgaatgggt      1920
ccattttgcc cttccatagc ctaatccctg gcattgcttt ccactgagg ttggggttg       1980 gggtgtacta gttacacatc ttcaacagac cccctctaga aattttttcag atgcttctgg     2040 gagacaccca aagggtgaag ctatttatct gtagtaaact atttatctgt gttttttgaaa    2100 tattaaaccc tggatcagtc ctttgatcag tataattttt taaagttact ttgtcagagg      2160
cacaaaaggg tttaaactga ttcataataa atatctgtac ttcttcgatc ttcacctttt      2220
gtgctgtgat tcttcagttt ctaaaccagc actgtctggg tccctacaat gtatcaggaa      2280
gagctgagaa tggtaaggag actcttctaa gtcttcatct cagagaccct gagttcccac      2340
tcagacccac tcagccaaat ctcatggaag accaaggagg gcagcactgt ttttgttttt      2400
tgttttttgt ttttttttt tgacactgtc caaaggtttt ccatcctgtc ctggaatcag       2460
agttggaagc tgaggagctt cagcctcttt tatggtttaa tggccacctg ttctctcctg      2520
tgaaaggctt tgcaaagtca cattaagttt gcatgacctg ttatccctgg ggccctattt      2580
catagaggct ggccctatta gtgatttcca aaaacaatat ggaagtgcct tttgatgtct      2640
tacaataaga gaagaagcca atggaaatga aagagattgg caaggggaa ggatgatgcc       2700 atgtagatcc tgtttgacat tttatggct gtatttgtaa acttaaacac accagtgtct       2760
gttcttgatg cagttgctat ttaggatgag ttaagtgcct ggggagtccc tcaaaaggtt      2820
aaagggattc ccatcattgg aatcttatca ccagataggc aagtttatga ccaaacaaga      2880
gagtactggc tttatcctct aacctcatat tttctcccac ttggcaagtc ctttgtggca     2940
tttattcatc agtcagggtg tccgattggt cctagaactt ccaaaggctg cttgtcatag     3000
aagccattgc atctataaag caacggctcc tgttaaatgg tatctccttt ctgaggctcc     3060
tactaaaagt catttgttac ctaaacttat gtgcttaaca ggcaatgctt ctcagaccac     3120
aaagcagaaa gaagaagaaa agctcctgac taaatcaggg ctgggcttag acagagttga     3180
tctgtagaat atcttaaaag gagagatgtc aactttctgc actattccca gcctctgctc     3240
ctccctgtct accctctccc ctccctctct ccctccactt caccccacaa tcttgaaaaa     3300
cttcctttct cttctgtgaa catcattggc cagatccatt ttcagtggtc tggatttctt    3360
tttattttct tttcaacttg aaagaaactg gacattaggc cactatgtgt tgttactgcc     3420
actagtgttc aagtgcctct tgtttttccca gagatttcct gggtctgcca gaggcccaga    3480
```

| | |
|---|---|
| caggctcact caagctcttt aactgaaaag caacaagcca ctccaggaca aggttcaaaa | 3540 |
| tggttacaac agcctctacc tgtcgcccca gggagaaagg ggtagtgata caagtctcat | 3600 |
| agccagagat ggttttccac tccttctaga tattcccaaa aagaggctga gacaggaggt | 3660 |
| tattttcaat tttatttttgg aattaaatac ttttttccct ttattactgt tgtagtccct | 3720 |
| cacttggata tacctctgtt ttcacgatag aaataaggga ggtctagagc ttctattcct | 3780 |
| tggccattgt caacggagag ctggccaagt cttcacaaac ccttgcaaca ttgcctgaag | 3840 |
| tttatggaat aagatgtatt ctcactccct tgatctcaag ggcgtaactc tggaagcaca | 3900 |
| gcttgactac acgtcatttt taccaatgat tttcaggtga cctgggctaa gtcatttaaa | 3960 |
| ctgggtcttt ataaaagtaa aaggccaaca tttaattatt ttgcaaagca acctaagagc | 4020 |
| taaagatgta atttttcttg caattgtaaa tcttttgtgt ctcctgaaga cttcccttaa | 4080 |
| aattagctct gagtgaaaaa tcaaaagaga caaaagacat cttcgaatcc atatttcaag | 4140 |
| cctggtagaa ttggcttttc tagcagaacc tttccaaaag ttttatattg agattcataa | 4200 |
| caacaccaag aattgatttt gtagccaaca ttcattcaat actgttatat cagaggagta | 4260 |
| ggagagagga acatttgac ttatctggaa aagcaaaatg tacttaagaa taagaataac | 4320 |
| atggtccatt caccttatg ttatagatat gtctttgtgt aaatcatttg ttttgagttt | 4380 |
| tcaaagaata gcccattgtt cattcttgtg ctgtacaatg accactgtta ttgttacttt | 4440 |
| gacttttcag agcacaccct tcctctgtt tttgtatatt tattgatgga tcaataataa | 4500 |
| tgaggaaagc atgatatgta tattgctgag ttgaaagcac ttattggaaa atattaaaag | 4560 |
| gctaacatta aaagactaaa ggaaacagaa aaaaaaaaa aaaaa | 4605 |

<210> SEQ ID NO 56
<211> LENGTH: 5001
<212> TYPE: DNA
<213> ORGANISM: Homo sapiens

<400> SEQUENCE: 56

| | |
|---|---|
| gagaagaaag ccagtgcgtc tctgggcgca ggggccagtg gggctcggag gcacaggcac | 60 |
| cccgcgacac tccaggttcc ccgacccacg tccctggcag ccccgattat ttacagcctc | 120 |
| agcagagcac ggggcggggg cagaggggcc cgcccgggag ggctgctact tcttaaaacc | 180 |
| tctgcgggct gcttagtcac agcccccctt gcttgggtgt gtccttcgct cgctccctcc | 240 |
| ctccgtctta ggtcactgtt ttcaacctcg aataaaaact gcagccaact tccgaggcag | 300 |
| cctcattgcc cagcggaccc cagcctctgc caggttcggt ccgccatcct cgtcccgtcc | 360 |
| tccgccggcc cctgccccgc gcccagggat cctccagctc ctttcgcccg cgccctccgt | 420 |
| tcgctccgga caccatggac aagttttggt ggcacgcagc ctgggactc tgcctcgtgc | 480 |
| cgctgagcct ggcgcagatc gatttgaata taacctgccg ctttgcaggt gtattccacg | 540 |
| tggagaaaaa tggtcgctac agcatctctc ggacggaggc cgctgacctc tgcaaggctt | 600 |
| tcaatagcac cttgcccaca atgggccaga tggaaaagc tctgagcatc ggatttgaga | 660 |
| cctgcaggta tgggttcata gaagggcacg tggtgattcc ccggatccac cccaactcca | 720 |
| tctgtgcagc aaacaacaca ggggtgtaca tcctcacatc caacacctcc cagtatgaca | 780 |
| catattgctt caatgcttca gctccacctg aagaagattg tacatcagtc acagacctgc | 840 |
| ccaatgcctt tgatggacca attaccataa ctattgttaa ccgtgatggc acccgctatg | 900 |
| tccagaaagg agaatacaga acgaatcctg aagcatcta ccccagcaac cctactgatg | 960 |
| atgacgtgag cagcggctcc tccagtgaaa ggagcagcac ttcaggaggt tacatctttt | 1020 |

```
acaccttttc tactgtacac cccatcccag acgaagacag tccctggatc accgacagca    1080
cagacagaat ccctgctacc aatatggact ccagtcatag tataacgctt cagcctactg    1140
caaatccaaa cacaggtttg gtggaagatt tggacaggac aggacctctt tcaatgacaa    1200
cgcagcagag taattctcag agcttctcta catcacatga aggcttggaa gaagataaag    1260
accatccaac aacttctact ctgacatcaa gcaataggaa tgatgtcaca ggtggaagaa    1320
gagacccaaa tcattctgaa ggctcaacta ctttactgga aggttatacc tctcattacc    1380
cacacacgaa ggaaagcagg accttcatcc cagtgacctc agctaagact gggtcctttg    1440
gagttactgc agttactgtt ggagattcca actctaatgt caatcgttcc ttatcaggag    1500
accaagacac attccacccc agtgggggggt cccataccac tcatggatct gaatcagatg    1560
gacactcaca tgggagtcaa gaaggtggag caaacacaac ctctggtcct ataaggacac    1620
cccaaattcc agaatggctg atcatcttgg catccctctt ggccttggct ttgattcttg    1680
cagtttgcat tgcagtcaac agtcgaagaa ggtgtgggca gaagaaaaag ctagtgatca    1740
acagtggcaa tggagctgtg gaggacagaa agccaagtgg actcaacgga gaggccagca    1800
agtctcagga aatggtgcat ttggtgaaca aggagtcgtc agaaactcca gaccagttta    1860
tgacagctga tgagacaagg aacctgcaga atgtggacat gaagattggg gtgtaacacc    1920
tacaccatta tcttggaaag aaacaaccgt tggaaacata accattacag ggagctggga    1980
cacttaacag atgcaatgtg ctactgattg tttcattgcg aatctttttt agcataaaat    2040
tttctactct ttttgttttt tgtgttttgt tctttaaagt caggtccaat ttgtaaaaac    2100
agcattgctt tctgaaatta gggcccaatt aataatcagc aagaatttga tcgttccagt    2160
tcccacttgg aggcctttca tccctcgggt gtgctatgga tggcttctaa caaaaactac    2220
acatatgtat tcctgatcgc caacctttcc cccaccagct aaggacattt cccagggtta    2280
atagggcctg gtccctggga ggaaatttga atgggtccat tttgcccttc catagcctaa    2340
tccctgggca ttgcttttcca ctgaggttgg gggttggggt gtactagtta cacatcttca    2400
acagaccccc tctagaaatt tttcagatgc ttctgggaga cacccaaagg gtgaagctat    2460
ttatctgtag taaactattt atctgtgttt ttgaaatatt aaaccctgga tcagtccttt    2520
gatcagtata attttttaaa gttactttgt cagaggcaca aaagggttta aactgattca    2580
taataaatat ctgtacttct tcgatcttca ccttttgtgc tgtgattctt cagtttctaa    2640
accagcactg tctgggtccc tacaatgtat caggaagagc tgagaatggt aaggagactc    2700
ttctaagtct tcatctcaga gaccctgagt tcccactcag acccactcag ccaaatctca    2760
tggaagacca aggagggcag cactgttttt gttttttgtt tttgtttttt ttttttgac    2820 actgtccaaa ggttttccat cctgtcctgg aatcagagtt ggaagctgag gagcttcagc    2880
ctcttttatg gtttaatggc cacctgttct ctcctgtgaa aggctttgca aagtcacatt    2940
aagtttgcat gacctgttat ccctgggggcc ctatttcata gaggctggcc ctattagtga    3000
tttccaaaaa caatatggaa gtgccttttg atgtcttaca ataagagaag aagccaatgg    3060
aaatgaaaga gattggcaaa ggggaaggat gatgccatgt agatcctgtt tgacattttt    3120
atggctgtat ttgtaaactt aaacacacca gtgtctgttc ttgatgcagt tgctatttag    3180
gatgagttaa gtgcctgggg agtccctcaa aaggttaaag ggattcccat cattggaatc    3240
ttatcaccag ataggcaagt ttatgaccaa acaagagagt actggcttta tcctctaacc    3300
tcatattttc tcccacttgg caagtccttt gtggcattta ttcatcagtc agggtgtccg    3360
```

| | |
|---|---:|
| attggtccta gaacttccaa aggctgcttg tcatagaagc cattgcatct ataaagcaac | 3420 |
| ggctcctgtt aaatggtatc tccttttctga ggctcctact aaaagtcatt tgttacctaa | 3480 |
| acttatgtgc ttaacaggca atgcttctca gaccacaaag cagaaagaag aagaaaagct | 3540 |
| cctgactaaa tcagggctgg gcttagacag agttgatctg tagaatatct ttaaaggaga | 3600 |
| gatgtcaact ttctgcacta ttcccagcct ctgctcctcc ctgtctaccc tctccctcc | 3660 |
| ctctctccct ccacttcacc ccacaatctt gaaaaacttc ctttctcttc tgtgaacatc | 3720 |
| attggccaga tccattttca gtggtctgga tttcttttta ttttcttttc aacttgaaag | 3780 |
| aaactggaca ttaggccact atgtgttgtt actgccacta gtgttcaagt gcctcttgtt | 3840 |
| ttcccagaga tttcctgggt ctgccagagg cccagacagg ctcactcaag ctctttaact | 3900 |
| gaaaagcaac aagccactcc aggacaaggt tcaaaatggt tacaacagcc tctacctgtc | 3960 |
| gccccaggga gaaggggta gtgatacaag tctcatagcc agagatggtt ttccactcct | 4020 |
| tctagatatt cccaaaaaga ggctgagaca ggaggttatt ttcaattta ttttggaatt | 4080 |
| aaatactttt ttccctttat tactgttgta gtccctcact tggatatacc tctgttttca | 4140 |
| cgatagaaat aagggaggtc tagagcttct attccttggc cattgtcaac ggagagctgg | 4200 |
| ccaagtcttc acaaaccctt gcaacattgc ctgaagtta tggaataaga tgtattctca | 4260 |
| ctcccttgat ctcaagggcg taactctgga agcacagctt gactacacgt catttttacc | 4320 |
| aatgattttc aggtgacctg ggctaagtca tttaaactgg gtcttatataa agtaaaagg | 4380 |
| ccaacattta attatttgc aaagcaacct aagagctaaa gatgtaattt tcttgcaat | 4440 |
| tgtaaatctt ttgtgtctcc tgaagacttc ccttaaaatt agctctgagt gaaaaatcaa | 4500 |
| aagagacaaa agacatcttc gaatccatat ttcaagcctg gtagaattgg ctttttctagc | 4560 |
| agaacctttc caaagttttt atattgagat tcataacaac accaagaatt gattttgtag | 4620 |
| ccaacattca ttcaatactg ttatatcaga ggagtaggag agaggaaaca tttgacttat | 4680 |
| ctggaaaagc aaaatgtact taagaataag aataacatgg tccattcacc tttatgttat | 4740 |
| agatatgtct ttgtgtaaat catttgttt gagttttcaa agaatagccc attgttcatt | 4800 |
| cttgtgctgt acaatgacca ctgttattgt tactttgact tttcagagca caccttcct | 4860 |
| ctggtttttg tatatttatt gatggatcaa taataatgag gaaagcatga tatgtatatt | 4920 |
| gctgagttga aagcacttat tggaaaatat taaaaggcta acattaaaag actaaaggaa | 4980 |
| acagaaaaaa aaaaaaaaaa a | 5001 |

```
<210> SEQ ID NO 57
<211> LENGTH: 5619
<212> TYPE: DNA
<213> ORGANISM: Homo sapiens

<400> SEQUENCE: 57
```

| | |
|---|---:|
| gagaagaaag ccagtgcgtc tctgggcgca ggggccagtg gggctcggag gcacaggcac | 60 |
| cccgcgacac tccaggttcc ccgacccacg tccctggcag ccccgattat ttacagcctc | 120 |
| agcagagcac ggggcggggg cagaggggcc cgccgggag ggctgctact tcttaaaacc | 180 |
| tctgcgggct gcttagtcac agccccccctt gcttgggtgt gtccttcgct cgctccctcc | 240 |
| ctccgtctta ggtcactgtt ttcaacctcg aataaaaact gcagccaact tccgaggcag | 300 |
| cctcattgcc cagcggaccc cagcctctgc caggttcggt ccgccatcct cgtcccgtcc | 360 |
| tccgccggcc cctgccccgc gcccagggat cctccagctc ctttcgcccg cgccctccgt | 420 |
| tcgctccgga caccatggac aagttttggt ggcacgcagc ctggggactc tgcctcgtgc | 480 |

```
cgctgagcct ggcgcagatc gatttgaata taacctgccg ctttgcaggt gtattccacg    540
tggagaaaaa tggtcgctac agcatctctc ggacggaggc cgctgacctc tgcaaggctt    600
tcaatagcac cttgcccaca atggcccaga tggagaaagc tctgagcatc ggatttgaga    660
cctgcaggta tgggttcata aagggcacg tggtgattcc ccggatccac cccaactcca     720
tctgtgcagc aaacaacaca ggggtgtaca tcctcacatc aacacctcc cagtatgaca     780 catattgctt caatgcttca gctccacctg aagaagattg tacatcagtc acagacctgc    840
ccaatgcctt tgatggacca attaccataa ctattgttaa ccgtgatggc acccgctatg    900
tccagaaagg agaatacaga acgaatcctg aagcatccta ccccagcaac cctactgatg    960
atgacgtgag cagcggctcc tccagtgaaa ggagcagcac ttcaggaggt tacatctttt   1020 acacctttc tactgtacac cccatcccag acgaagacag tccctggatc accgacagca    1080
cagacagaat ccctgctacc agtacgtctt caaataccat ctcagcaggc tgggagccaa   1140 atgaagaaa tgaagatgaa agagacagac acctcagttt ttctggatca ggcattgatg    1200
atgatgaaga ttttatctcc agcaccattt caaccacacc acgggctttt gaccacacaa   1260
aacagaacca ggactggacc cagtggaacc caagccattc aaatccggaa gtgctacttc   1320
agacaaccac aaggatgact gatgtagaca gaaatggcac cactgcttat gaaggaaact   1380
ggaacccaga agcacaccct cccctcattc accatgagca tcatgaggaa gagagaccc    1440 cacattctac aagcacaatc caggcaactc ctagtagtac aacggaagaa acagctaccc   1500
agaaggaaca gtggtttggc aacagatggc atgaggata tcgccaaaca cccaaagaag    1560
actcccattc gacaacaggg acagctgcag cctcagctca taccagccat ccaatgcaag   1620
gaaggacaac accaagccca gaggacagtt cctggactga tttcttcaac ccaatctcac   1680
accccatggg acgaggtcat caagcaggaa gaaggatgga tatggactcc agtcatagta   1740
taacgcttca gcctactgca aatccaaaca caggtttggt ggaagatttg gacaggacag   1800
gacctctttc aatgacaacg cagcagagta attctcagag cttctctaca tcacatgaag   1860
gcttggaaga agataaagac catccaacaa cttctactct gacatcaagc aataggaatg   1920
atgtcacagg tggaagaaga gacccaaatc attctgaagg ctcaactact ttactggaag   1980
gttatacctc tcattaccca cacacgaagg aaagcaggac cttcatccca gtgacctcag   2040
ctaagactgg gtccttttgga gttactgcag ttactgttgg agattccaac tctaatgtca   2100
atcgttcctt atcaggagac caagacacat tccaccccag tgggggtcc cataccactc     2160 atggatctga atcagatgga cactcacatg ggagtcaaga aggtggagca acacaaacct    2220
ctggtcctat aaggacaccc caaattccag aatggctgat catcttggca tccctcttgg    2280
ccttggcttt gattcttgca gtttgcattg cagtcaacag tcgaagaagg tgtgggcaga   2340 agaaaagct agtgatcaac agtggcaatg gagctgtgga ggacagaaag ccaagtggac   2400
tcaacggaga ggccagcaag tctcaggaaa tggtgcattt ggtgaacaag gagtcgtcag   2460
aaactccaga ccagtttatg acagctgatg agacaaggaa cctgcagaat gtggacatga   2520
agattggggt gtaacaccta caccattatc ttggaaagaa acaaccgttg gaaacataac   2580
cattacaggg agctgggaca cttaacagat gcaatgtgct actgattgtt tcattgcgaa   2640 tctttttag cataaaattt tctactcttt ttgttttttg tgttttgttc tttaaagtca     2700
ggtccaattt gtaaaacag cattgctttc tgaaattagg gcccaattaa taatcagcaa    2760
gaatttgatc gttccagttc ccacttggag gcctttcatc cctcgggtgt gctatggatg   2820
```

```
gcttctaaca aaaactacac atatgtattc ctgatcgcca acctttcccc caccagctaa    2880
ggacatttcc cagggttaat agggcctggt ccctgggagg aaatttgaat gggtccattt    2940
tgcccttcca tagcctaatc cctgggcatt gctttccact gaggttgggg gttggggtgt    3000
actagttaca catcttcaac agacccctc tagaaatttt tcagatgctt ctgggagaca    3060
cccaaagggt gaagctattt atctgtagta aactatttat ctgtgttttt gaaatattaa    3120
accctggatc agtcctttga tcagtataat tttttaaagt tactttgtca gaggcacaaa    3180
agggtttaaa ctgattcata ataaatatct gtacttcttc gatcttcacc ttttgtgctg    3240
tgattcttca gtttctaaac cagcactgtc tgggtcccta caatgtatca ggaagagctg    3300
agaatggtaa ggagactctt ctaagtcttc atctcagaga ccctgagttc ccactcagac    3360
ccactcagcc aaatctcatg gaagaccaag gagggcagca ctgttttttgt ttttttgtttt    3420 ttgttttttt ttttttgacac tgtccaaagg ttttccatcc tgtcctggaa tcagagttgg    3480
aagctgagga gcttcagcct cttttatggt ttaatggcca cctgttctct cctgtgaaag    3540
gctttgcaaa gtcacattaa gtttgcatga cctgttatcc ctggggccct atttcataga    3600
ggctggccct attagtgatt tccaaaaaca atatggaagt gccttttgat gtcttacaat    3660
aagagaagaa gccaatggaa atgaaagaga ttggcaaagg ggaaggatga tgccatgtag    3720
atcctgtttg acattttat ggctgtattt gtaaacttaa acacaccagt gtctgttctt    3780
gatgcagttg ctatttagga tgagttaagt gcctggggag tccctcaaaa ggttaaaggg    3840
attcccatca ttggaatctt atcaccagat aggcaagttt atgaccaaac aagagagtac    3900
tggctttatc ctctaacctc atattttctc ccacttggca agtcctttgt ggcatttatt    3960
catcagtcag ggtgtccgat tggtcctaga acttccaaag gctgcttgtc atagaagcca    4020
ttgcatctat aaagcaacgg ctcctgttaa atggtatctc ctttctgagg ctcctactaa    4080
aagtcatttg ttacctaaac ttatgtgctt aacaggcaat gcttctcaga ccacaaagca    4140
gaaagaagaa gaaaagctcc tgactaaatc agggctgggc ttagacagag ttgatctgta    4200
gaatatcttt aaaggagaga tgtcaacttt ctgcactatt cccagcctct gctcctccct    4260
gtctaccctc tcccctcccc ctctccctcc acttcaccc acaatcttga aaaacttcct    4320
ttctcttctg tgaacatcat tggccagatc cattttcagt ggtctggatt tcttttatt    4380 ttcttttcaa cttgaaagaa actggacatt aggccactat gtgttgttac tgccactagt    4440
gttcaagtgc ctcttgttttt cccagagatt tcctgggtct gccagaggcc cagacaggct    4500
cactcaagct ctttaactga aaagcaacaa gccactccag acaaggttc aaaatggtta    4560 caacagcctc tacctgtcgc cccagggaga aagggtagt gatacaagtc tcatagccag    4620
agatggtttt ccactccttc tagatattcc caaaaagagg ctgagacagg aggttatttt    4680 caatttatt ttggaattaa atactttttt ccctttatta ctgttgtagt ccctcacttg    4740
gatatacctc tgttttcacg atagaaataa gggaggtcta gagcttctat tccttggcca    4800
ttgtcaacgg agagctggcc aagtcttcac aaacccttgc aacattgcct gaagtttatg    4860
gaataagatg tattctcact cccttgatct caagggcgta actctggaag cacagcttga    4920
ctacacgtca ttttaccaa tgattttcag gtgacctggg ctaagtcatt taaactgggt    4980
ctttataaaa gtaaaaggcc aacatttaat tattttgcaa agcaacctaa gagctaaaga    5040
tgtaattttt cttgcaattg taaatctttt gtgtctcctg aagacttccc ttaaaattag    5100
ctctgagtga aaaatcaaaa gagacaaaag acatcttcga atccatattt caagcctggt    5160
agaattggct tttctagcag aacctttcca aaagtttat attgagattc ataacaacac    5220
```

| | |
|---|---|
| caagaattga ttttgtagcc aacattcatt caatactgtt atatcagagg agtaggagag | 5280 |
| aggaaacatt tgacttatct ggaaaagcaa aatgtactta agaataagaa taacatggtc | 5340 |
| cattcacctt tatgttatag atatgtcttt gtgtaaatca tttgttttga gttttcaaag | 5400 |
| aatagcccat tgttcattct tgtgctgtac aatgaccact gttattgtta ctttgacttt | 5460 |
| tcagagcaca cccttcctct ggttttgta tatttattga tggatcaata ataatgagga | 5520 |
| aagcatgata tgtatattgc tgagttgaaa gcacttattg gaaatatta aaaggctaac | 5580 |
| attaaaagac taaggaaac agaaaaaaaa aaaaaaaa | 5619 |

<210> SEQ ID NO 58
<211> LENGTH: 5748
<212> TYPE: DNA
<213> ORGANISM: Homo sapiens

<400> SEQUENCE: 58

| | |
|---|---|
| gagaagaaag ccagtgcgtc tctgggcgca ggggccagtg gggctcggag gcacaggcac | 60 |
| cccgcgacac tccaggttcc ccgacccacg tccctggcag ccccgattat ttacagcctc | 120 |
| agcagagcac ggggcggggg cagaggggcc cgcccgggag ggctgctact tcttaaaacc | 180 |
| tctgcgggct gcttagtcac agccccctt gcttgggtgt gtccttcgct cgctccctcc | 240 |
| ctccgtctta ggtcactgtt ttcaacctcg aataaaaact gcagccaact tccgaggcag | 300 |
| cctcattgcc cagcggaccc cagcctctgc caggttcggt ccgccatcct cgtcccgtcc | 360 |
| tccgccggcc cctgccccgc gcccagggat cctccagctc cttttcgcccg cgccctccgt | 420 |
| tcgctccgga caccatggac aagttttggt ggcacgcagc ctggggactc tgcctcgtgc | 480 |
| cgctgagcct ggcgcagatc gatttgaata taacctgccg ctttgcaggt gtattccacg | 540 |
| tggagaaaaa tggtcgctac agcatctctc ggacggaggc cgctgacctc tgcaaggctt | 600 |
| tcaatagcac cttgcccaca atggcccaga tggagaaagc tctgagcatc ggatttgaga | 660 |
| cctgcaggta tgggttcata gaagggcacg tggtgattcc ccggatccac cccaactcca | 720 |
| tctgtgcagc aaacaacaca ggggtgtaca tcctcacatc caacacctcc cagtatgaca | 780 |
| catattgctt caatgcttca gctccacctg aagaagattg tacatcagtc acagacctgc | 840 |
| ccaatgcctt tgatggacca attaccataa ctattgttaa ccgtgatggc acccgctatg | 900 |
| tccagaaagg agaatacaga acgaatcctg aagcatcta ccccagcaac cctactgatg | 960 |
| atgacgtgag cagcggctcc tccagtgaaa ggagcagcac ttcaggaggt tacatctttt | 1020 |
| acacctttc tactgtacac cccatcccag acgaagacac tccctggatc accgacagca | 1080 |
| cagacagaat ccctgctacc actttgatga gcactagtgc tacagcaact gagacagcaa | 1140 |
| ccaagaggca agaaacctgg gattggtttt catggttgtt tctaccatca gagtcaaaga | 1200 |
| atcatcttca cacaacaaca caaatggctg gtacgtcttc aaataccatc tcagcaggct | 1260 |
| gggagccaaa tgaagaaaat gaagatgaaa gagacagaca cctcagtttt tctggatcag | 1320 |
| gcattgatga tgatgaagat tttatctcca gcaccatttc aaccacacca cgggcttttg | 1380 |
| accacacaaa acagaaccag gactggaccc agtggaaccc aagccattca aatccggaag | 1440 |
| tgctacttca caaccacaca aggatgactg atgtagacag aaatggcacc actgcttatg | 1500 |
| aaggaaactg gaaccagaa gcacacctc ccctcattca ccatgagcat catgaggaag | 1560 |
| aagagacccc acattctaca agcacaatcc aggcaactcc tagtagtaca acggaagaaa | 1620 |
| cagctaccca gaaggaacag tggttggca acagatggca tgagggatat cgccaaacac | 1680 |

-continued

| | |
|---|---|
| ccaaagaaga ctcccattcg acaacaggga cagctgcagc ctcagctcat accagccatc | 1740 |
| caatgcaagg aaggacaaca ccaagcccag aggacagttc ctggactgat ttcttcaacc | 1800 |
| caatctcaca ccccatggga cgaggtcatc aagcaggaag aaggatggat atggactcca | 1860 |
| gtcatagtat aacgcttcag cctactgcaa atccaaacac aggtttggtg aagatttgg | 1920 |
| acaggacagg acctctttca tgacaacgc agcagagtaa ttctcagagc ttctctacat | 1980 |
| cacatgaagg cttggaagaa gataaagacc atccaacaac ttctactctg acatcaagca | 2040 |
| ataggaatga tgtcacaggt ggaagaagag acccaaatca ttctgaaggc tcaactactt | 2100 |
| tactggaagg ttatacctct cattacccac acacgaagga aagcaggacc ttcatcccag | 2160 |
| tgacctcagc taagactggg tcctttggag ttactgcagt tactgttgga gattccaact | 2220 |
| ctaatgtcaa tcgttcctta tcaggagacc aagacacatt ccaccccagt ggggggtccc | 2280 |
| ataccactca tggatctgaa tcagatggac actcacatgg gagtcaagaa ggtggagcaa | 2340 |
| acacaacctc tggtcctata aggacacccc aaattccaga atggctgatc atcttggcat | 2400 |
| ccctcttggc cttggctttg attcttgcag tttgcattgc agtcaacagt cgaagaaggt | 2460 |
| gtgggcagaa gaaaaagcta gtgatcaaca gtggcaatgg agctgtggag gacagaaagc | 2520 |
| caagtggact caacgagag gccagcaagt ctcaggaaat ggtgcatttg gtgaacaagg | 2580 |
| agtcgtcaga aactccagac cagtttatga cagctgatga gacaaggaac ctgcagaatg | 2640 |
| tggacatgaa gattggggtg taacacctac accattatct ggaaagaaa caaccgttgg | 2700 |
| aaacataacc attacaggga gctgggacac ttaacagatg caatgtgcta ctgattgttt | 2760 |
| cattgcgaat cttttttagc ataaaatttt ctactctttt tgttttttgt gttttgttct | 2820 |
| ttaaagtcag gtccaatttg taaaaacagc attgctttct gaaattaggg cccaattaat | 2880 |
| aatcagcaag aatttgatcg ttccagttcc cacttggagg cctttcatcc ctcgggtgtg | 2940 |
| ctatggatgg cttctaacaa aaactacaca tatgtattcc tgatcgccaa cctttccccc | 3000 |
| accagctaag acatttccc agggttaata gggcctggtc cctgggagga aatttgaatg | 3060 |
| ggtccatttt gcccttccat agcctaatcc ctgggcattg cttttccactg aggttggggg | 3120 |
| ttggggtgta ctagttacac atcttcaaca gaccccctct agaaattttt cagatgcttc | 3180 |
| tgggagacac ccaaagggtg aagctattta tctgtagtaa actatttatc tgtgttttg | 3240 |
| aaatattaaa ccctggatca gtcctttgat cagtataatt ttttaaagtt actttgtcag | 3300 |
| aggcacaaaa gggtttaaac tgattcataa taaatatctg tacttcttcg atcttcacct | 3360 |
| tttgtgctgt gattcttcag tttctaaacc agcactgtct gggtccctac aatgtatcag | 3420 |
| gaagagctga gaatggtaag gagactcttc taagtcttca tctcagagac cctgagttcc | 3480 |
| cactcagacc cactcagcca aatctcatgg aagaccaagg agggcagcac tgtttttgtt | 3540 |
| ttttgttttt tgttttttt ttttgacact gtccaaaggt tttccatcct gtcctggaat | 3600 |
| cagagttgga agctgaggag cttcagcctc ttttatggtt taatggccac ctgttctctc | 3660 |
| ctgtgaaagg ctttgcaaag tcacattaag tttgcatgac ctgttatccc tggggcccta | 3720 |
| tttcatagag gctggcccta ttagtgattt ccaaaaacaa tatggaagtg ccttttgatg | 3780 |
| tcttacaata agagaagaag ccaatggaaa tgaaagagat tggcaaaggg aaggatgat | 3840 |
| gccatgtaga tcctgtttga cattttatg gctgtatttg taaacttaaa cacaccagtg | 3900 |
| tctgttcttg atgcagttgc tatttaggat gagttaagtg cctggggagt ccctcaaaag | 3960 |
| gttaaaggga ttcccatcat tggaatctta tcaccagata ggcaagttta tgaccaaaca | 4020 |
| agagagtact ggctttatcc tctaacctca tattttctcc cacttggcaa gtccttttgtg | 4080 |

```
gcatttattc atcagtcagg gtgtccgatt ggtcctagaa cttccaaagg ctgcttgtca    4140
tagaagccat tgcatctata aagcaacggc tcctgttaaa tggtatctcc tttctgaggc    4200
tcctactaaa agtcatttgt tacctaaact tatgtgctta acaggcaatg cttctcagac    4260
cacaaagcag aaagaagaag aaaagctcct gactaaatca gggctgggct tagacagagt    4320
tgatctgtag aatatcttta aaggagagat gtcaactttc tgcactattc ccagcctctg    4380
ctcctccctg tctaccctct cccctccctc tctccctcca cttcacccca caatcttgaa    4440
aaacttcctt tctcttctgt gaacatcatt ggccagatcc attttcagtg gtctggattt    4500 cttttttattt tcttttcaac ttgaaagaaa ctggacatta ggccactatg tgttgttact    4560
gccactagtg ttcaagtgcc tcttgttttc ccagagattt cctgggtctg ccagaggccc    4620
agacaggctc actcaagctc tttaactgaa aagcaacaag ccactccagg acaaggttca    4680
aaatggttac aacagcctct acctgtcgcc ccagggagaa aggggtagtg atacaagtct    4740
catagccaga gatggttttc cactccttct agatattccc aaaaagaggc tgagacagga    4800
ggttattttc aattttattt tggaattaaa tacttttttc cctttattac tgttgtagtc    4860
cctcacttgg atatacctct gttttcacga tagaaataag ggaggtctag agcttctatt    4920
ccttggccat tgtcaacgga gagctggcca agtcttcaca aacccttgca acattgcctg    4980
aagtttatgg aataagatgt attctcactc ccttgatctc aagggcgtaa ctctggaagc    5040
acagcttgac tacacgtcat ttttaccaat gattttcagg tgacctgggc taagtcattt    5100
aaactgggtc tttataaaag taaaaggcca acatttaatt attttgcaaa gcaacctaag    5160
agctaaagat gtaatttttc ttgcaattgt aaatcttttg tgtctcctga agacttccct    5220
taaaattagc tctgagtgaa aaatcaaaag agacaaaaga catcttcgaa tccatatttc    5280
aagcctggta gaattggctt ttctagcaga accttttccaa aagtttttata ttgagattca    5340 taacaacacc aagaattgat tttgtagcca acattcattc aatactgtta tatcagagga    5400
gtaggagaga ggaaacattt gacttatctg gaaaagcaaa atgtacttaa gaataagaat    5460
aacatggtcc attcaccttt atgttataga tatgtctttg tgtaaatcat tgttttgag     5520 ttttcaaaga atagcccatt gttcattctt gtgctgtaca atgaccactg ttattgttac    5580
tttgactttt cagagcacac ccttcctctg gttttttgtat atttattgat ggatcaataa    5640
taatgaggaa agcatgatat gtatattgct gagttgaaag cacttattgg aaaatattaa    5700
aaggctaaca ttaaaagact aaaggaaaca gaaaaaaaaa aaaaaaaa                  5748
```

<210> SEQ ID NO 59
<211> LENGTH: 1333
<212> TYPE: DNA
<213> ORGANISM: Homo sapiens

<400> SEQUENCE: 59

```
gtggcggcgg cgaaggtggc ggcggctcgg ccagtactcc cggccccgc  catttcggac     60 tgggagcgag cgcggcgcag gcactgaagg cggcggcggg gccagaggct cagcggctcc    120
caggtgcggg agagaggcct gctgaaaatg actgaatata aacttgtggt agttggagct    180
ggtggcgtag gcaagagtgc cttgacgata cagctaatte agaatcattt tgtggacgaa    240
tatgatccaa caatagagga ttcctacagg aagcaagtag taattgatgg agaaacctgt    300
ctcttggata ttctcgacac agcaggtcat gaggagtaca gtgcaatgag ggaccagtac    360
atgaggactg ggagggctt tctttgtgta tttgccataa ataatactaa atcatttgaa    420
```

```
gatattcacc attatagaga acaaattaaa agagttaagg actctgaaga tgtacctatg      480
gtcctagtag gaaataaatg tgatttgcct tctagaacag tagacacaaa acaggctcag      540
gacttagcaa gaagttatgg aattccttt attgaaacat cagcaaagac aagacagggt      600
```
(note: line at 600 — second block reads "aattcctttt")
```
gttgatgatg ccttctatac attagttcga gaaattcgaa acataaaga aaagatgagc        660 aaagatggta aaagaagaa aaagaagtca aagacaaagt gtgtaattat gtaaatacaa       720
tttgtacttt tttcttaagg catactagta caagtggtaa tttttgtaca ttacactaaa      780
ttattagcat ttgttttagc attacctaat tttttcctg ctccatgcag actgttagct       840
tttaccttaa atgcttattt taaaatgaca gtggaagttt tttttcctc gaagtgccag       900 tattcccaga gttttggttt tgaactagc aatgcctgtg aaaagaaac tgaataccta       960 agatttctgt cttggggttt tggtgcatg cagttgatta cttcttattt ttcttaccaa      1020
ttgtgaatgt tggtgtgaaa caaattaatg aagcttttga atcatcccta ttctgtgttt     1080
tatctagtca cataaatgga ttaattacta atttcagttg agaccttcta attggttttt     1140
actgaaacat tgagggaaca caaatttatg ggcttcctga tgatgattct tctaggcatc     1200
atgtcctata gtttgtcatc cctgacgaat gtaaagttac actgttcaca aaggttttgt     1260 ctccttca  ctgctattag tcatggtcac tctccccaaa atattatatt ttttctataa     1320 aaaaaaaaa aaa                                                         1333

<210> SEQ ID NO 60
<211> LENGTH: 3769
<212> TYPE: DNA
<213> ORGANISM: Homo sapiens

<400> SEQUENCE: 60
aaaagatttt aacaagtata aaaaattctc ataggaatta aatgtagtct ccctgtgtca       60
gactgctctt tcatagtata actttaaatc ttttcttcaa cttgagtctt tgaagatagt      120
tttaattctg cttgtgacat taaaagatta tttgggccag ttatagctta ttaggtgttg      180
aagagaccaa ggttgcaagg ccaggccctg tgtgaacctt tgagctttca tagagagttt      240
cacagcatgg actgtgtccc cacggtcatc cagtgttgtc atgcattggt tagtcaaaat      300
ggggagggac tagggcagtt tggatagctc aacaagatac aatctcactc tgtggtggtc      360
ctgctgacaa atcaagagca ttgcttttgt ttccttaagaa acaaactct ttttaaaaa      420 ttacttttaa atattaactc aaaagttgag attttggggt ggtggtgtgc caagacatta      480
attttttttt aaacaatgaa gtgaaaaagt tttacaatct ctaggtttgg ctagttctct      540
taacactggt taaattaaca ttgcataaac acttttcaag tctgatccat atttaataat      600
gctttaaaat aaaaataaaa acaatccttt tgataaattt aaaatgttac ttattttaaa      660
ataaatgaag tgagatggca tggtgaggtg aaagtatcac tggactagga agaaggtgac      720
ttaggttcta gataggtgtc ttttaggact ctgattttga ggacatcact tactatccat      780
ttcttcatgt taaaagaagt catctcaaac tcttagtttt tttttttac aactatgtga       840 tttatattcc atttacataa ggatacactt atttgtcaag ctcagcacaa tctgtaaatt      900
tttaacctat gttacaccat cttcagtgcc agtcttgggc aaaattgtgc aagaggtgaa      960
gtttatattt gaatatccat tctcgtttta ggactcttct tccatattag tgtcatcttg     1020
cctccctacc ttccacatgc cccatgactt gatgcagttt taatacttgt aattccccta     1080
accataagat ttactgctgc tgtggatatc tccatgaagt tttcccactg agtcacatca     1140
gaaatgccct acatcttatt tcctcagggc tcaagagaat ctgacagata ccataaaggg     1200
```

-continued

```
atttgaccta atcactaatt ttcaggtggt ggctgatgct ttgaacatct ctttgctgcc    1260
caatccatta gcgacagtag gattttttcaa acctggtatg aatagacaga accctatcca    1320
gtggaaggag aatttaataa agatagtgct gaaagaattc cttaggtaat ctataactag    1380
gactgctcct ggtaacagta atacattcca ttgttttagt aaccagaaat cttcatgcaa    1440
tgaaaaatac tttaattcat gaagcttact tttttttttt ttggtgtcag agtctcgctc    1500
ttgtcaccca ggctggaatg cagtggcgcc atctcagctc actgcaacct ccatctccca    1560
ggttcaagcg attctcgtgc ctcggcctcc tgagtagctg ggattacagg cgtgtgccac    1620
tacactcaac taatttttgt attttttagga gagacggggt ttcaccctgt tggccaggct    1680
ggtctcgaac tcctgacctc aagtgattca cccaccttgg cctcataaac ctgttttgca    1740
gaactcattt attcagcaaa tatttattga gtgcctacca gatgccagtc accgcacaag    1800
gcactgggta tatggtatcc ccaaacaaga gacataatcc cggtccttag gtagtgctag    1860
tgtggtctgt aatatcttac taaggccttt ggtatacgac ccagagataa cacgatgcgt    1920
attttagttt tgcaaagaag gggtttggtc tctgtgccag ctctataatt gttttgctac    1980
gattccactg aaactcttcg atcaagctac tttatgtaaa tcacttcatt gttttaaagg    2040
aataaacttg attatattgt tttttatttt ggcataactg tgattctttt aggacaatta    2100
ctgtacacat taaggtgtat gtcagatatt catattgacc caaatgtgta atattccagt    2160
tttctctgca taagtaatta aaatatactt aaaaattaat agtttatctt gggtacaaat    2220
aaacaggtgc ctgaactagt tcacagacaa ggaaacttct atgtaaaaat cactatgatt    2280
tctgaattgc tatgtgaaac tacagatctt tggaacactg tttaggtagg gtgttaagac    2340
ttacacagta cctcgtttct acacagagaa agaaatggcc atacttcagg aactgcagtg    2400
cttatgaggg gatatttagg cctcttgaat ttttgatgta gatgggcatt tttttaaggt    2460
agtggttaat tacctttatg tgaactttga atggtttaac aaaagatttg ttttgtaga    2520 gattttaaag ggggagaatt ctagaaataa atgttaccta attattacag ccttaaagac    2580
aaaaatcctt gttgaagttt ttttaaaaaa agctaaatta catagactta ggcattaaca    2640
tgtttgtgga agaatatagc agacgtatat tgtatcattt gagtgaatgt tcccaagtag    2700
gcattctagg ctctatttaa ctgagtcaca ctgcatagga atttagaacc taactttttat    2760 aggttatcaa aactgttgtc accattgcac aattttgtcc taatatatac atagaaactt    2820 tgtgggcat gttaagttac agtttgcaca agttcatctc atttgtattc cattgatttt    2880 tttttttcttc taaacatttt ttcttcaaac agtatataac ttttttttagg ggatttttt    2940 ttagacagca aaaactatct gaagatttcc atttgtcaaa agtaatgat ttcttgataa    3000 ttgtgtagta atgtttttta gaacccagca gttaccttaa agctgaattt atatttagta    3060
acttctgtgt taatactgga tagcatgaat tctgcattga gaaactgaat agctgtcata    3120
aaatgaaact ttctttctaa agaaagatac tcacatgagt tcttgaagaa tagtcataac    3180
tagattaaga tctgtgtttt agtttaatag tttgaagtgc ctgtttggga taatgatagg    3240
taatttagat gaattaggg gaaaaaaaag ttatctgcag atatgttgag ggcccatctc    3300 tcccccaca ccccccacaga gctaactggg ttacagtgtt ttatccgaaa gtttccaatt    3360
ccactgtctt gtgttttcat gttgaaaata cttttgcatt tttccttga gtgccaattt    3420 cttactagta ctatttctta atgtaacatg tttacctgga atgtatttta actatttttg    3480
tatagtgtaa actgaaacat gcacattttt tgtacattgt gctttctttt gtgggacata    3540
```

-continued

| tgcagtgtga tccagttgtt ttccatcatt tggttgcgct gacctaggaa tgttggtcat | 3600 |
| atcaaacatt aaaaatgacc actcttttaa ttgaaattaa cttttaaatg tttataggag | 3660 |
| tatgtgctgt gaagtgatct aaaatttgta atattttgt catgaactgt actactccta | 3720 |
| attattgtaa tgtaataaaa atagttacag tgacaaaaaa aaaaaaaaa | 3769 |

<210> SEQ ID NO 61
<211> LENGTH: 1693
<212> TYPE: DNA
<213> ORGANISM: Homo sapiens

<400> SEQUENCE: 61

| ctaggcggcg gccgcggcgg cggaggcagc agcggcggcg gcagtggcgg cggcgaaggt | 60 |
| ggcggcggct cggccagtac tcccggcccc agccatttcg gactgggagc gagcgcggcg | 120 |
| caggcactga aggcggcggc ggggccagag gctcagcggc tcccaggcct gctgaaaatg | 180 |
| actgaataaa cttgtggtag ttggagctgg tggcgtaggc aagagtgcct tgacgataca | 240 |
| gctaattcag aatcattttg tggacgaata tgatcgaaca atagaggtgt tattaagcag | 300 |
| tatgtaaaaa gtccttacaa tacttaatac attaagaaaa catacaattt caagaggaaa | 360 |
| tccccgagta atacattatt gacattttca gcagttctag ttatattgag aagagcatct | 420 |
| catggaattg gcagaatgaa gatggagatt aaatgagatg atgtttgtaa tatgcttatg | 480 |
| acagtatctg gcatataagt aagggctcag taaatgttga ctgctgtaat tactattaat | 540 |
| agtaatatga ttacctttag taaaagttat tagtttcttt aggttttttg tttactacaa | 600 |
| tatagtaaac aaaatctata cttggaatgt atatattgtt ttgttttgat acatggaata | 660 |
| tgtctctgtg tcagagtcac tgcctgagtt ggaaaaccca tactcgagta tgttaaaagg | 720 |
| tgaacacact gaataattta gttattaatt ataatgaaa aatgacaaac ttgatgttct | 780 |
| ggttaatgag gttatcttat cttgaatgag ttagcttttta aattcctcaa ataaaggca | 840 |
| tttaataaac caggaaacac ttcattaaaa aaattatgca agtcagtgta aaagaagatt | 900 |
| aaaattccac atgggcaaag gacacacgtt ggcgataaat atgcagataa gaaaaaaaac | 960 |
| ctatataaca ttattactcc tcaaagaaat tggtatgaaa acaataaaaa tgtgtagctt | 1020 |
| atcaaaccaa caaaaattta aaaatatgaa atccatttta agtaatgata aatgggtgc | 1080 |
| actcttagtg ctttatagaa tagtagtata atgaacctca tgtgtgtacc aacagctctt | 1140 |
| tcatatctta acatttagca acatttgatt tagctctttc ttttttccaa gatagaaaag | 1200 |
| ttaatattgt tgaagactcc tgcattcttt tccctagtct tatttttcttc cctcccataa | 1260 |
| atgtgttaaa atctctgtgt gtattgtttt ggttgtattt ttacataaaa ctttacatat | 1320 |
| tatataaaat ttaattgaag gtaaaattta ttaaattatt cttaatatat attgtaattt | 1380 |
| aaaaattaac agcttcattg tcttgataaa atttatggta tcttaaacat gtgcttgttt | 1440 |
| ttctaagaga acattgaaac atagatttta aaacaaattg ttgaaagatt aaaaaatctg | 1500 |
| cctttgcaca ctgttacatt gaaagtgggg catttgtcgt gaacattcat ttcaaatatg | 1560 |
| tagtatcttc agaatatttg agaaggattt gtattatata attgaaaaat ctgttaaatt | 1620 |
| gtatttatgt taactgctta attctaataa aatttccatt catttttag tatctgcaaa | 1680 |
| aaaaaaaaaa aaa | 1693 |

<210> SEQ ID NO 62
<211> LENGTH: 567
<212> TYPE: DNA
<213> ORGANISM: Homo sapiens

<400> SEQUENCE: 62

```
atgactgaat ataaacttgt ggtagttgga gctggtggcg taggcaagag tgccttgacg      60
atacagctaa ttcagaatca ttttgtggac gaatatgatc caacaataga ggattcctac     120
aggaagcaag tagtaattga tggagaaacc tgtctcttgg atattctcga cacagcaggt     180
catgaggagt acagtgcaat gagggaccag tacatgagga ctggggaggg ctttctttgt     240
gtatttgcca taaataatac taaatcattt gaagatattc accattatag agaacaaatt     300
aaaagagtta aggactctga agatgtacct atggtcctag taggaaataa atgtgatttg     360
ccttctagaa cagtagacac aaaacaggct caggacttag caagaagtta tggaattcct     420
tttattgaaa catcagcaaa gacaagacag ggtgttgatg atgccttcta tacattagtt     480
cgagaaattc gaaaacataa agaaaagatg agcaaagatg gtaaaaagaa gaaaaagaag     540
tcaaagacaa agtgtgtaat tatgtag                                         567
```

<210> SEQ ID NO 63
<211> LENGTH: 53713
<212> TYPE: DNA
<213> ORGANISM: Homo sapiens

<400> SEQUENCE: 63

```
caaagtataa tgaaataagt gtccagtaag gataaagtgc agagtaagtg aattaagcag      60
cacccattca tgtgttcaaa ttcctgccag agtcaaaagg ttgtgctgaa gtagagtcca     120
tgaaagcatc gtagatggct cctcctgctc aagttcccct gctctgcgtc ctgctactct     180
ggccacaacc gtctggaccc agggttgaca cacaaacaaa cacaataatc ttttagccag     240
acataaagaa ggccagccac caatcaggaa aattgtgtcc cataaaggcc cttcctattg     300
aacagtgaat gacagacatg gccagatctt ctctcttgga atgctttgaa tgttagtcac     360
agagagtgac cactagaagc acagatagca gtagaagcta agactacatg aaaaagcagt     420
ggacagatgg tgatttatga gaatggcaaa attactagag tcataggcaa tggatacttg     480
ttaatgaagg gatgagcagg gccccacagc ctgttgctgg ctcacaagtg cagttgattg     540
ctggactgaa cagcagctct ccgcctgatg atagggtttt ttaaagtgtc cttattgcct     600
taaagtaaat cctcagcatt tgcagtgctc tgagggtgtc ctagcatttt ataccttttt     660
tctaagagcc caggtaacat aagggtactc ctgttgttct ggctttaatt ctatctgcag     720
aagagggttt cttgtgaaag aaagggtcag tatggtcttt tatctgtaca gcagataaaa     780
agggtatgta cgtgcacacc tttgtacgtg gctgccttcc caggacagtc tgacagtaga     840
gggtagaaac ttcagttgta gctgagagca ggcctggaat ccccatgctt atacttttta     900
tttcctcccc ccttttccat tgtgatcaca ggctacttca gtgtgcttgt ccttggagag     960
agcaagggaa gggagagcca gggagactgt tcaagggagc caccaggctc gagaaagagg    1020
aaccctgaa gacagtagaa agtgcaggtg ccaagaattt gaatatctac atcagagttt     1080
ctcaatgtgc acacagtgaa ctaccagttt aggatcattt gatttgctaa aaatgaagat    1140
tactggtcta ccttagacca actgaataaa atatctgggt gaggggccta ggaacttgca    1200
tttttggtag gcatggcagg tgattcctaa agcatttacc cttgagacct ctatgttaag    1260
gaaagaaagg taatgttgca aggaggtggt gccggcttct aagaaagtac ccaggactga    1320
acggcagaaa gacctgacat accatatgta taaattgctg tggaagtgaa aaggaaagag    1380
aaagtgtctg aggtaaaact ggagtgtggg gtgcgtggaa caaatggttg gatgcagatt    1440
```

| | | | | | |
|---|---|---|---|---|---|
| tgctttacga | atcatgagcc | tagatgataa | ctgagaccat | gtggatggat | taggtttctg | 1500 |
| ctaatgccag | aatttttata | atcagcataa | aagtgctata | taaagctttc | ccctcttcta | 1560 |
| tattatagtc | cttttaagat | gtatggaaca | tcaactatag | gaagaacatc | atattcacag | 1620 |
| ctgtaagagg | aaacaagaac | ttatcatgca | cttgatgttg | tacaaaataa | atctgtgatt | 1680 |
| tatgcttgag | tgaccacaaa | gtagcataca | cataagcgca | aattcattca | tttaagaatt | 1740 |
| ccttgtgtct | attatgtacg | agataagtat | ctctgagctg | cacgaatgt | ggcttatcag | 1800 |
| aaggtgacct | aagtttcaaa | gcagattttg | ttaagatgaa | gacagagatt | gacaggaggt | 1860 |
| ttaagacact | ctgtctaaag | taaagattta | gagtcacaga | gttcatggat | taggatttag | 1920 |
| aatccacaga | gggtccacag | attcactcat | tcaacattcc | ataaatattt | attgaatgcc | 1980 |
| ttttgtgtc | agagactgtc | ttaggtgctg | gaaatttagc | agtaaatgaa | acagaccaaa | 2040 |
| acccatgccc | tcatggagct | tacattctga | tggtagagag | acaagaaaac | aaaatagata | 2100 |
| gtgtattatt | gaaggtgatg | agagctctgg | agaaaaagta | ggaaaagaga | cagatctggg | 2160 |
| acaagggcga | aattacagta | tcaaagatga | tcttttagg | gaagatctcc | ttttaaaaac | 2220 |
| actttggaac | aaagatttaa | atgaggtgcc | agaggggtag | caagtgcata | ttccctgagg | 2280 |
| aagacgcctg | cctggcattt | tcaaggaaca | gccagtaacc | aatgtttatc | tacgtaagta | 2340 |
| aggaagggag | aacagtagga | tgagagttca | gagaagaggg | tagggatat | caaataattt | 2400 |
| aaggccatgt | aggatttttg | agaagaattt | tgcttttatg | tcaagtggaa | tgagggccac | 2460 |
| tgatgatctg | ggagtagagt | gactatgatc | cgacatgaag | tatactccat | tttttaacta | 2520 |
| tgtgaacttg | tgccaacgtt | ttaacctcta | aatctgtttc | gtcatttgta | aaacggtaaa | 2580 |
| aagtattta | cctcataagg | ttgtcgtgat | gattaaataa | gatgatacga | taagtgcaaa | 2640 |
| agatttagct | tgtacttaac | atagagtagg | cacattttct | ccccttccct | gtctttcact | 2700 |
| tttctcttct | gccccttcca | cctggcgcta | ggaggggag | actggaataa | accttgcaga | 2760 |
| ttacagcccg | tgtaagagta | gaaaggaaag | gatgacagtt | gatgtaaagc | cttggttaac | 2820 |
| agacataata | gctgggattt | aaattcagct | ttattggtgg | tttatgatgt | ggactagagg | 2880 |
| aatggaactg | aaagtctcgg | aggaggggcg | atcctatcag | gtacaggcgc | tgcttttcca | 2940 |
| gccctcaatc | ctcaagactc | tcccaagata | catttctagg | tagtttatca | acacagactc | 3000 |
| cgggtatgct | agcatgttta | attgccccat | tgtttaatgt | cttaactcca | cgaactttaa | 3060 |
| ctgattaatc | tgtcttctaa | ttaatgtttg | aatgactctc | ctcaggtcta | aactaccaag | 3120 |
| gccatctcta | cttaaaaaca | gttgtctttt | gtttgtgatt | tcaggggccc | tgggtataag | 3180 |
| cgaagtccct | gtttagagac | cttgtgatgg | gttcaaaata | tcaagaaaga | tagcaaaata | 3240 |
| tcacaagcct | cctgacccga | gaagattagc | gttgaaaggg | tctgtcgtgt | ttgtttgggc | 3300 |
| ctggggctaa | attcccagcc | caagtgctga | ggctgataat | aatcggggcg | gcgatcagac | 3360 |
| agccccggtg | tgggaaatcg | tccgcccggt | ctccctaagt | cccgaagtc | gcctcccact | 3420 |
| tttggtgact | gcttgtttat | ttacatgcag | tcaatgatag | taaatggatg | cgcgccagta | 3480 |
| taggccgacc | ctgagggtgg | cggggtgctc | ttcgcagctt | ctctgtggag | accggtcagc | 3540 |
| ggggcggcgt | ggccgctcgc | ggcgtctccc | tggtggcatc | cgcacagccc | gccgcggtcc | 3600 |
| ggtcccgctc | cgggtcagaa | ttggcggctg | cggggacagc | cttgcggcta | ggcaggggc | 3660 |
| gggccgccgc | gtgggtccgg | cagtccctcc | tcccgccaag | gcgccgccca | gaccccgctct | 3720 |
| ccagccggcc | cggctcgcca | ccctagaccg | ccccagccac | cccttcctcc | gcggcccgg | 3780 |
| ccccgctcc | tccccgccg | gccggcccg | gccccctcct | tctccccgcc | ggcgctcgct | 3840 |

```
gcctccccct cttccctctt cccacaccgc cctcagccgc tccctctcgt acgcccgtct   3900
gaagaagaat cgagcgcgga acgcatcgat agctctgccc tctgcggccg cccggccccg   3960
aactcatcgg tgtgctcgga gctcgatttt cctaggcggc ggccgcggcg gcggaggcag   4020
cagcggcggc ggcagtggcg gcggcgaagg tggcggcggc tcggccagta ctcccggccc   4080
ccgccatttc ggactgggag cgagcgcggc gcaggcactg aaggcggcgg cggggccaga   4140
ggctcagcgg ctcccaggtg cgggagagag gtacggagcg gaccacccct cctgggcccc   4200
tgcccgggtc ccgaccctct ttgccggcgc cgggcgggc cggcggcgag tgaatgaatt   4260
aggggtcccc ggaggggcgg gtgggggcg cgggcgcggg gtcggggcgg gctgggtgag   4320
aggggtctgc aggggggagg cgcgcggacg cggcggcgcg gggagtgagg aatgggcggt   4380
gcggggctga ggagggtgag gctggaggcg gtcgccgctg gtgctgcttc ctggacgggg   4440
aacccctcc ttcctcctcc ccgagagccg cggctggagg cttctgggga gaaactcggg   4500
ccgggccggc tgcccctcgg agcggtgggg tgcggtggag gttactcccg cggcgccccg   4560
gcctcccctc cccctctccc cgctcccgca cctcttgcct ccctttccag cactcggctg   4620
cctcggtcca gccttccctg ctgcatttgg catctctagg acgaaggtat aaacttctcc   4680
ctcgagcgca ggctggacgg atagtggtcc ttttccgtgt gtaggggatg tgtgagtaag   4740
aggggaggtc acgttttgga agagcatagg aaagtgctta gagaccactg tttgaggtta   4800
ttgtgtttgg aaaaaaatgc atctgcctcc gagttcctga atgctcccct cccccatgta   4860
tgggctgtga cattgctgtg gccacaaagg aggaggtgga ggtagagatg gtggaagaac   4920
aggtggccaa caccctacac gtagagcctg tgacctacag tgaaaaggaa aaagttaatc   4980
ccagatggtc tgttttgctt ggtcaagtta aacccgaaga aaacccgcag agcagaagca   5040
aggcttttttc cttgctagtt gagtgtagac agcaatagca aaaatagtac ttgaagttta   5100
atttacctgt tcttgtcctt tcccctattt cttatgtatt accctcatcc cctcgtctct   5160
tttatactac cctcattttg cagatgtgtt ctacatctca agagttatta cagtactcca   5220
aaacagcact tacatgattt tttaaactta cagaggaatt gtagcaatcc accagctaac   5280
cgcctgaaat agacttaaac atgtgcatct cctttttttt tttttttttg agacacagtc   5340
tcgctctgtt gcccaggctg gagtgcaatg gcgcggtatc ggctcactga aacctccgcc   5400
tcctgggttc aagcaattct cctgcctcag cctcccgagt agctgggact agtaggtgca   5460
cgccaccatg cccagctaat ttttgtattt ttagtagaga cagagtttca tcatgttggt   5520
caggatggtc tccatctgct ctgttgccca ggctggagtg cagtggcgcc gtctcggctc   5580
actgcaacct ctgcctcctg cattcaagca attctcctgc ctcagcctcc cgaataactg   5640
ggattacagg tgtctgctgc catgcccggc taattttttg tattttagt agagacgggg   5700
gtttcaccat gttggtcagg ctggtctaga actcctgacc tcgtgatctg cccgcctcgg   5760
cctcccaaca gtggcatgtg catcttatag ctgaagtcta agccttctta aatcttgaga   5820
tccatcaaaa cagacaggtt ttctaattgt tatacaatgt atatgttatg tttataatag   5880
aaatcatttt acaaataagt tataaatggg aaagtctat ttgtaattat cagctcagaa   5940
ttaaccataa aactggtgtc actgaagtga ctgaggtcca aaatgctgac tctgcatgtt   6000
atagactaca gatatcaaat atggttgcta acaatagttt actttgagac tgtagccatc   6060
cacagtatat ttgcttttaa gagatggtag atggtaattc agttttatga aaataaaaaa   6120
tgaattttct tccattacaa aattgttgga ttcgagtcca gtccactcct tactagcttt   6180
```

```
tctaactctc ggtgagggat ccccctcccag cccatgatct tcatttggta agactccttt    6240
ggaacccagt tctctctagt ggatttaaat gtgatttggt tttaaaaatc tcattcaagg    6300
aatttttttt ttttctggaa acaaccaccg cataaacaag taaaccggaa gatacatgtg    6360
gctctgaatt catatatata cacaaactct aatccaatgt ctgtccacag tatttcctag    6420
gctagtaaac ttttttggcct taacgacccc tctaccctct ttgttttttt gagagagaga    6480
gtctcactct gtcacccagg ccggaatgca gtggcgcgat ctcggcccgc tactacctcc    6540
gactctcagg ctcaagcgat tctcccgcct cagcttcccg agtagccggg attacaggct    6600
cccgccaccg ggctaattgt attttttagat acgggatttc accatgttgg ccaggctggt    6660
ctcgacctcc tgacctcagg tgatccgccc gcctaagcct cccaaagtgc tgggattaca    6720
ggccaccaca cccggcctac actcttaaaa attatcgaag gggccgggca cattggctct    6780
tatctgtaat cccagcactt tgggagactg aggcgggagg atcgcttgag gccaggagtt    6840
ggagaccagc gtactcaaca tagtgagacc ttgttataaa gaaaaaaaaa atccaggatt    6900
aaaaaaaatc tttgatttgt ttgggattta ttaatattta ccgtattgga aattaaaaca    6960 atttttttaaa atgtattcat ttaaaaataa taagcccatt acttggtaac atgaataaaa    7020 tatttttatga aaaataacta ttttccaaaa caaaaccaaa acttagaaaa gtggtattgt    7080
ttcacacttc agtaaatctc tttaatgatg tggcttaata gaagatatgg attcttatat    7140
ctgcatctgc attcaatcta ttatgatcac acatctggaa aacttgtgaa agaatgggag    7200 ttaaagggt aaaggacatc ttaatgttat tatgaaaaca gttttgaccct cttgcacacc    7260 agaaaagtct tagtaacctg aggggttcct agaccacatt ttgagaactg ttttaggcta    7320
tgcaaactgg ttgggggggag gttggggtag gcagagagct agaagataca ttttagtgta    7380
attctcctca tctattccta attgctttgg cctacatttg aaataaagcg tggaggcaaa    7440
cgggataaga tacatgtttg tagtggttgt taacttcacc ctagacaagc agccaataag    7500
tctaggtaga gcagagtaag gcggggaact atgccgtgac cgtgtgtgat acaattttc    7560 tagcctgtgg tgcttttttgc ggcagggctt aggagtaagg ttagtatgtt atcattggg    7620 aaaccaaatt attattttgg gtcttcagtc aattatgatg ctgtgtatat ttagtgttta    7680
tctacaatat atgcacattc attaatttgg agctactcat cctataataa atagttgtgc    7740
atttactccc attttttct gcatttctct ccttatttat aattatgtgt tacatgaggg    7800
aaaggaggtg aaattaaaca ttcatattat ttcaaaaaat ttgaaacaac taactaaaaa    7860
atatgtttta ttttctgtat ggtgtttgtt atacaatctg tcaatattca tgcacctctt    7920
gggagacagt gtatgaaaag caaagagtaa cagtcacatg gattactgat tactgagata    7980
tattcacttg catcttttttt ttttttttgag acggagtggc tctgtcgccc aggctggagt    8040
gcagtggcgt gatctcggct cactgcaagc tccgcctcct gggttcacgc cattcttctg    8100
cctcagcctc ccaagtagct gggactacag gcgcccgcca ccgcgccgg ctaatttttt    8160 tatattttta gtagagacgg ggtttcaccg ggttagccag gatggtcttg atctcctgac    8220
ctcgtgatcc accctcctcg gcctcccaaa gtgctaggat tataggcgtg agccaccgtg    8280
cccggctcac ttgcatctct taacagctgt tttcttacta aaacagtgt ttatctctaa    8340 tcttttttgtt tgtttgtttg ttttgagatg gagtcttact ccgtcaccca atctggagtg    8400
cagtggcgtg atctgggctc actgcaacct ctgcctcccg ggttcaagtg attctccttc    8460
ctcagcctcc ccagtagcta ggactacagg agagcgccac cacgcctgat taatttttgt    8520 attttttagta gagagagggt ttcaccatat tggccaggct ggtcttgaac tcctggcctc    8580
```

```
aggtgatcca cccgccttgg cctctgaaag tgctgggatt acaggcatga gccgccgcac   8640
ccggctttct aatctttatc ttttttttgtg cagcggtgat acaggattat gtattgtact   8700
gaacagttaa ttcggagttc tcttggtttt tagctttatt ttccccagag attttttttt   8760
tttttttttt ttttgagacg gagtcttgct ctatcgccag gctggagtgc agtggcgcca   8820
tctcggctca ttgcaacctc ggactccxat ttccccxaga gatatttcac acattaaaat   8880
gtcgtcaaat attgttcttc tttgcctcag tgtttaaatt tttatttccc catgacacaa   8940
tccagcttta tttgacactc attctctcaa ctctcatctg attcttactg ttaatattta   9000
tccaagagaa ctactgccat gatgctttaa aagttttct gtagctgttg catattgact   9060
tctaacactt agaggtgggg gtccactagg aaaactgtaa caataagagt ggagatagct   9120
gtcagcaact tttgtgaggg tgtgctacag ggtgtagagc actgtgaagt ctctacatga   9180
gtgaagtcat gatatgatcc tttgagagcc tttagccgcc gcagaacagc agtctggcta   9240
tttagataga acaacttgat tttaagataa aagaactgtc tatgtagcat ttatgcattt   9300
ttcttaagcg tcgatggagg agtttgtaaa tgaagtacag ttcattacga tacacgtctg   9360
cagtcaactg gaattttcat gattgaattt tgtaaggtat tttgaaataa ttttttcatat  9420 aaaggtgagt ttgtattaaa aggtactggt ggagtatttg atagtgtatt aaccttatgt   9480
gtgacatgtt ctaatatagt cacattttca ttattttat tataaggcct gctgaaaatg   9540
actgaatata aacttgtggt agttggagct ggtggcgtag gcaagagtgc cttgacgata   9600
cagctaattc agaatcattt tgtggacgaa tatgatccaa caatagaggt aaatcttgtt   9660
ttaatatgca tattactggt gcaggaccat tcttgatac agataaaggt ttctctgacc   9720
attttcatga gtacttatta caagataatt atgctgaaag ttaagttatc tgaaatgtac   9780
cttgggtttc aagttatatg taaccattaa tatgggaact ttactttcct tgggagtatg   9840
tcagggtcca tgatgttcac tctctgtgca ttttgattgg aagtgtattt cagagtttcg   9900
tgagagggta gaaatttgta tcctatctgg acctaaaaga caatcttttt attgtaactt   9960
ttatttttat gggtttcttg gtattgtgac atcatatgta aaggttagat ttaattgtac  10020
tagtgaaata taattgtttg atggttgatt tttttaaact tcatcagcag tatttttccta 10080 tcttcttctc aacattagag aacctacaac taccgataaa attttacaaa atgaattatt  10140
tgcctaaggt gtgqtttata taaaggtact attaccaact ttacctttgc tttgttgtca   10200
tttttaaatt tactcaagga aatactagga tttaaaaaaaa aattccttga gtaaatttaa   10260
attgttatca tgttttgag gattattttc agatttttt agtttaatga aaatttacca    10320
aagtaaagac cagcagcaga atgataagta aagacctgta agacaccttg aaggtcatgg   10380
agtagaactt ccatcccaag cagatgagga tttatttaat ctcaaagacc tccaggaggg   10440
gacattcccc aactgtcctt gttaactcat tttcagaaca tatttattag catattttac   10500
atgtaatttg gatcttcatg ttaaatttaa catcagtgga gatggaaaat aagcatatcg   10560
ccttgtcttt gaaatagccc tatattgtta gattgtttct taggcttctt taccctgggt   10620
taagcagtcc taatacttta gcatttattc tacatctagt gtactaattt aaaaaaaatca  10680 gttctgaaaa atttctaaga actttcttca agttccaagc tgtgaaatct agaacaggtc   10740
aaagtgcctt attaacgtac tgtactgtgt agtgtcttga agagacactt tgcgctgagg   10800
caagttctga gggcattggg tggccttggg aagatattta tgcagtttag aacctggaga   10860
attgattaga taactaatca taaggaaacg tcacatattt ttggtactat aaaaaagtgg   10920
```

```
agaaataatg cctatttgca aagatttgat ttaaacatag aaacaacttt atttggcttc   10980
caattttaag aatttacagc agtaaagggg aacagtctaa ttgaagtaga ctgcctatgc   11040
aatagtctct gtatatttac ttttgacaag ttaattcaat gtgtactata gttttgtttc   11100
tttgaagagg tttgaatagt gcacccattt taatctgtat tgcaaattca gggttacttg   11160
gcagactcta ctatttaaat cagatgtaaa aggaagtttt aatataattc actttatgcc   11220
tgaaagtttt cctgggattt tggaaggtga ttttactgga aatgctgtct gtcttccctg   11280
aaaatctgag aaattccatt acactttgtt tccaatcaga ggtcatgagt gctatatgag   11340
tatatacagc atgacgtcat gaatgtgata aagtgggtta ggaacctttt tgctaatgat   11400
tgttaaaatg caatataaat gttgaagaaa taaagctaac agttaagcct ttatttgggc   11460
ggaaggctga aaaagtttat aaacttaaac ctataactct gcttatgatt tctgccaaac   11520
cagaagactt gactctggga agcattggtt acctgtgaac tttgaaactg acggtccctg   11580
acgtagttta gtcacctggg aaaaggtatc tgagattatc tcttatctcc caagttacag   11640
tgagtctctg agggaactga cacattacat taagttcttg gtgtagttaa actgtaagaa   11700
aggcaggaga acttagtagt taaatagttg gttaaatgga aatgctgact ccatgttatt   11760
gtaaaaagtt aaaaatttag gaggatatgg ggatttcact gccattgcag gttttgattg   11820
gtatttacca atccgtgtgg gtcagagaga aaattagaaa ggatatgact gcacattttg   11880
gaattattag cagttttttct acatttaaaa tggaaataaa ttttttaaaa atttaaatca   11940
agtaatactg tattttttgg tgatttagat ttttcaaaat ttacactaag agatagtaag   12000
gagggtggct attgtttctt tcaataatgt ctctgagagg ttgtaactca tctaaggata   12060
cgtagctaat aagtggtagg atttcaattt aaattctctg agaccaagtt aagtagaatt   12120
tgcactgtac tcttgtataa cttttttaaaa ctgaaaatta gctatctttc aaattaagaa   12180
aatatttact aatggagact aattcagatt tgtaagtata ccaaaatttg aacttagcct   12240
gctatctaat ggcaacttag tggcagaggt atgatgtaaa atcattcagg tatgacacat   12300
agatggagta tgtttgtatt cgaggctgtg cacataatca cctttacttg tattgtgaag   12360
tatatattgt tatctttat gaagcccact aaagagataa tgaaatacct cgttattagg   12420
gcaagattat tgaaaactca aaatagcccc caaacacaat acttggctag aaatatatac   12480
ctttatagtt cagagatcat ttattatcaa aaccctgaag ttttttttct aaggtaaaat   12540
ttggtggaag aggaaaagtc tcgttttaaa aaaatgtagg tagttacaga gatcagaatg   12600
attagttgat cacttaccaa atatatatta agtatctact gtatataata tgctagtaag   12660
aataaatata gcaggaagta ttttttccca ggctctaatt gtttgacatc agcatgcttt   12720
tattgtggca cttataattc agttcaagta ttatgcccct cttgatgga acagtttcct   12780 attcagtaag gaagaccaga ttaatcattg gattggtttg tttcatcttt agtgttctga   12840
gctgtagagt atttatttac caaggtttat tttaattttt atttatttt tattttccca   12900 tgttcattgt agaattcatt ttacctacga atgaagtatg tagattatag agagaaaatt   12960
tgtaaaatta aactgatact gaagactggt ataagaaaag ccttatgtaa tttgtaagct   13020
gctattcttc tgagtttata catatatctt tagtaatcaa tgagggatgg ttgggtgact   13080
gccctccagg ggacatttgg caacatctgg agatgttttt ggttgccaca acttggggag   13140
agagtactgc tactggcatc tattgagtag atgctattac tttaaatggc aaagctgcag   13200
ttacctttgc accaacctaa tattaaactt cctgcagtgc acgggaaagc ccccacaaca   13260
gggttatctg accccaaacc tcaatggtgt taagatccaa accttgatat gttaacctgt   13320
```

```
agctttaaac atcctttaaa ttgtcaaatt catgtccctg acataaggtt tatgttagat   13380
tttcaagtat aacaaagatt taaactttaa cttttgtacg ttaatgatat gttagcttac   13440
tccagtcttc tattaaaaca ttctgttttt aaaatcagag acacacagca attttataaa   13500
tcatttctct tcaaggctgt gaagctctcc ccacttttgt gagtgccctc tactggtcaa   13560
attatttgct ttataacaag taacagtgaa atcctaagtt tgtgtagttt cgctgtttaa   13620
attatgggtg gcatcaattt ataaatatat tcgttttatt taaaagtctt atatgattga   13680
tttcgtatca tttttgctct ctgctaatat taatataaag attactgtct gtattagtta   13740
ggcctaacta gtaggtgag tatagtgaac taagaaagga aacgaggcag tatataagaa    13800
aatagggtgg ttcagttgtt aacacttact gagcttactt tgttgaaggg actaaaaggc   13860
agcagtgtgg ctctctgagc ttctttgcat gcactcagga gctgcttaat ggagtccaag   13920
gcttggtggt gtgttacagg ggatgatagg agggtcctat tcagaagtgg caaattgtga   13980
aagtgcacat tttgtagagt tttataggac tgtagaatag ttgtgagcac ctgattttta   14040
gaataaacag aaaactcagg tactgtattt aggtcaaatt aagaataagt atttattaag   14100
acctgaatat aaaactttac tggtcatggt ttttttctac cttgggtttt tataaatcca   14160
aagatttaaa aacatacaaa tggaagttgg taatggaatt aagtgaaagg aaaaaatgat   14220
tttatggttt ggaatctcct aagattctgg ttttaacaat acaactaatt ccttaatcct   14280
agaaatgttc ttcactgccc actttgtacc atgcagtctt cctgtgggct agagatacac   14340
tgaggcgcaa aacagaccag attcctgcct tcatggagct tattagtttt aggtatctct   14400
agatttcttg taatacctat tacaatgcct gcacatcagt tcattcatgt gggttcaacg   14460
tagtactcag tacatggcaa attcaagttt tacttttcgg aacttcatgg atttttttcc   14520
tcagaatatc ttttatccat aattggttga atctgtagat gcagtaccca tggatatgga   14580
tggcccactt tattttgaag agcagtgttt ctaggcaatc atgctaatta tatatgactt   14640
aatttagagg ctttatactt aagagcatta catttctggc gtctcttaac cattattatt   14700
tcataatgtg taggttatgg aacagttaaa ttattgggat cttaatatag aaattagtag   14760
aaataagcca gatatggtgg ctcatgcctg taatcttagc actttgggag gctgaggcta   14820
ttcgctgtac tattttttac tacttttcta taggtttgaa attttttcaa aataaaacat   14880
tgaaaaaagt aaggtaggta gtgtgtccct ccttaatcct ttcaaatatt ttattttcac   14940
tatttctatt aatttttttt tttgttttg agatggagtc tcgctctgtt gcccaggctg    15000
gagtgcagtg gcgcgatctt ggctcactgc agcctccacc tcctgggttc agccattct   15060 cctgcctcag cctcctgggt agctggtatt acaggcatgc accaccacac ccaattactt   15120
tttgtatttt tagtagagac ggggtttcac catgttggcc aggctagtct cgaactcctg   15180
acctcgtgat ctgcccgcct cagcagtgtc actgcttcta gaccgttttc aaggcacaga   15240
gcttagaaat gcatgttact aagaaatcaa gagttaacta tttttcacct tctttctccc   15300
gcagtgagaa ccctggttct accctgtttc tccttgtgta aattttaatg ctaaactata   15360
cacttgtgaa ataaaaatga taatgtcatt cttaaattat ggatcttgca gtgttatcta   15420
agtaacatag attgagtgat ttaactttag gtttccttaa ttgtggaatt tggataaata   15480
ttttcacccc ttgagaaaag tgagactcct ttctcatcat cagagtatcc ttaaaccatt   15540
aaggcaaaca tttgggaaaa aactgagcta tctggctgca taaaaattaa gtttctttta   15600
acaaagatag aagacaaatg aaaacctaga aaaaccattt ggttcaagta acaggaagct   15660
```

```
atcttatata tgaattagag aaaagcaaac acacaaatag aaaaaaaggg atgggggta    15720 ctaaagatat aaatagcttg tctaccaaaa aagaaataaa ataaataaca tgaacatata    15780
aaaagacact tacttcatga atgtgatgca agttcaaaca ataaataaca tttctgtact    15840
ttcatattgg ctaaggttaa aatgataact gctaggaagg gtatggagaa gtgtgcgcct    15900
tgcactgtag tgggagtata gaccctcaga cttatggag gtcagtctgg aaatatgttt    15960
caaaatgtaa actacatgtc ctttgaccag gtaattcaac ttcttgaaat ttatccaagg    16020
atttaattgg ataaatgttt aagatgtata tataagaatg tttactgcag tgttgtttat    16080
gattttaaaa aaatggaaat catcttcatg tctaccaata gagaatgggt gaataaatta    16140
tggtatgtcc atatatacaa attacatagt tgttggaaat attaggtaga tttagatata    16200
ctgatgttca aaaatgtcca ttatgtaagt gaagctgggt cacagcacct tgtgttgagt    16260
atgatttcat ctagaaacaa aattactccc tcatcctttg ttgtgtttta gttttttaaa    16320
ataagcttat accattgggc tgggggaaaa gtaaatactc gttttggaga gagaaaaggg    16380
cactaaagtt tcagataccg ttagattatt tcatgcttat ttttcaagcc tcaataaatt    16440
acataattca catgtagtct tggattaagg aaattgctat taaggctaaa taaataatat    16500
gagaggtata taatataaaa tatgaacatt atattggcat taagattgga tccacggtca    16560
ttccagcctc tcattcttac ctggacttca agtgatcact tgtgggcaaa tgccatctga    16620
cttgaacagg ttacacatgt atgctcatta tatcgttatt ttcaaaattt gtcatataaa    16680
ttttccttga gttcattcag atttttgaac tagtttttc tcttgggagt agtacacact    16740
taattctctc tagtactaag ctaatgttca ccattcttat aatttaagt atccagcatt    16800 tagtaaagaa gtctttgttt tctttatcct tacttttagt gaatgtctta gtttttaatt    16860
gaaaattctg ccatgaaaat aagctcttta acatcttcac tccctaatca aaacagaaat    16920
ccttcatagc cttcagttgt agctatcctt ccctgtgatt tgtccagctc cattatattt    16980
attttgaaat atggtgacca gttttgcaaa attatttcaa ctgtaggtgc ccagtgattt    17040
tgtaaggaga agatactgtt tctgaacagt tctcagtagc cagtggcctg ccctactttt    17100
ttggcctgcg tgtagtatat aaaataatgc agttaacttt ttatagcact tttcatttta    17160
taaagagatt ttcatggtct ttaatattaa tctatgtata aagtcctgta tgcagtttta    17220
cctactttca cagctgaagg aacaatagct tagagaagat gtgagataaa gtagtttgcc    17280
caagcccata gcacaaataa gtgaagttct tcggctgtcc atggatcgaa gactcccaag    17340
tctatctcta gcctggactt ctgtcctgag caccagacat gtatgtatat caagatgcct    17400
gcaggtcata tccaccagga caacccatga gtacagggaa ttcaacatgc ccaatatcac    17460
tcatcttttc cttcgccctc ccctttgtac tcatcccctg tcggtaagct ctgttatttt    17520
aaaaaattga aatgtattca catagcatac aatttacact tttcaagtgt acatggtttt    17580
tagtatattc acaagggttg tgcagtcatt actactaatt ccagaatgtt attatcaccc    17640
caaaagtccc acatccatta gcagccactc cccaatccct tctcccacca gcctctaaaa    17700
actgctaatt tttccatctc tgtggatttg tccactctga ttatttcata taaagagaat    17760
cgtacagacg tggcctttg tgtctggcat cctccacaca ggatgatatt tcagagttc    17820 gtctatgttt ttgcttgttg atcattcctt cattcctttt tctggctgaa taatactctg    17880
ttatatggat ataccttatt ttgtttatct gttcatttga tgggcatttg agtgatttcc    17940 tcttttggc aattttgaat aatgccacta taaacattta tgtacacgtt tttgtgtgac    18000
catatgtttt cacttctctc gggtgtatat ctaaggtaca gttgctgggt tatatggtag    18060
```

```
ctctgtctttgacttttga ggaactgcca agtggttttg gtagtgattg tactgtttac   18120
attcctacca acaattttac ctaagtattt ctcaaatcta tttaatcttt tcggtccata   18180
ctgctgttgc tgccttagtt cagattttgt catttcttgt ataattcgt agctcatctc    18240
ccagtctctg ctcccctctc tcctccctc ccccttcttc tctctcttat ttccacccat    18300
ttttaacatt tatagaagtc aaagtctag ttcagaaagc agaaccaca ctagatattt     18360
cagcacagag aactaattag gtgttggaag actgaaaggc aaaaaacac tgaagtaaca    18420
cagtaacatc aagaatgggc actactccta agattcaggg aatgctggga agatttgggg   18480
tttatcagaa ctggaagctc agaggagggg ccccttgtcg ctgaggctta atccctgcag   18540
aggtgccttt ggctgctact ggtgaatctg agtgggtatg gatgagtcag tgtctgggaa   18600
gggccaaaac attttgtccc tttctataat ttgtcatgat aatgctagta atgaatctga   18660
tctcccttcc tattttaaaa accttttagt gattttgtat aggatgaagt ttaaaactcc   18720
ttacttaata tacacatgac cctccgtaag ctggccctg cttgattgtc cagtttcact    18780
tcttggtgct tattctaagg cctctaagcc ttagagatcc tctaagcctt tgagatcccc   18840
aaaccctgga ctgcggactg gtacccacct gtgtggcctg tgaggaactg ggctgcacag   18900
ccggaaggag gtgagcatta cttgccttag ctcctgtcag atcggcagca ttagattcta   18960
ataggagcgt gaaccgtgtt gtgaactgcc catgcaagga tctaggttgc atactcctta   19020
ggagaatcta actaatgctt gatggtctga ggtgaaacag tttcatcctg aaatcacccc   19080
caactcggtc cttggaaaaa ttgtcttcca cgaaactggt ccctgatgcc ggaaaagttg   19140
gggaccgctg ttctaagcta aagttatatg gagctccttg gttctgtgtc ctcaacatgc   19200
tgttctatgt ttttacatt ctgtttgctc cttcctgctt ggaatgtcct tcccctcccc    19260
gtctttctta atgcatacaa agttgatctc tcctgtgtgc caccattgta cttcgtcttg   19320
catatggtgt tacattcatt ttatttaat tatttattta cgttcatgtc tcttccactc    19380
accttagttg cttgaggtca gaaactatat aatgtgtgac acggaatgtg acacctagat   19440
tttcaataag tgtttctatg atacaaggga gactgatgtg ggtagatggg aatgaactca   19500
tcaacctctg tttacatacc ctaaattccc tgtttcttcc ctattataat tctgacagtc   19560
tacaacagtc tttgatggct tataaacgga aagtgcggaa cacatcattc tacagtgaat   19620
ttaaataacc tttcggaaga gtaacgtaaa gtacttgagc attaattgag taaaagtttc   19680
tcatcttttc ctacaggtgt tattaagcag tatgtaaaaa gtccttacaa tacttaatac   19740
attaagaaaa catacaattt caagaggaaa tccccgagta atacattatt gacattttca   19800
gcagttctag ttatattgag aagagcatct catggaattg gcagaatgaa gatggagatt   19860
aaatgagatg atgtttgtaa tatgcttatg acagtatctg gcatataagt aagggctcag   19920
taaatgttga ctgctgtaat tactattaat agtaatatga ttacctttag taaaagttat   19980
tagtttcttt aggttttttg tttactacaa tatagtaaac aaaatctata cttggaatgt   20040
atatattgtt ttgttttgat acatggaata tgtctctgtg tcagagtcac tgcctgagtt   20100
ggaaaaccca tactcgagta tgttaaaagg tgaacacact gaataattta gttattaatt   20160
ataatggaaa aatgacaaac ttgatgttct ggttaatgag gttatcttat cttgaatgag   20220
ttagctttta aattcctcaa ataaaggca tttaataaac caggaaacac ttcattaaaa    20280
aaattatgca agtcagtgta aaagaagatt aaaattccac atgggcaaag gacacacgtt   20340
ggcgataaat atgcagataa gaaaaaaaac ctatataaca ttattactcc tcaaagaaat   20400
```

```
tggtatgaaa acaataaaaa tgtgtagctt atcaaaccaa caaaaattta aaaatatgaa   20460
atccatttta agtaatgata aaatgggtgc actcttagtg ctttatagaa tagtagtata   20520
atgaacctca tgtgtgtacc aaccagctct ttcatatctt aacatttagc aacatttgat   20580
ttagctcttt cttttttcca agatagaaaa gttaatattg ttgaagactc ctgcattctt   20640
ttccctagtc ttattttctt ccctcccata aatgtgttaa aatctctgtg tgtattgttt   20700
tggttgtatt tttacataaa actttacata ttatataaaa tttaattgaa ggtaaaattt   20760
attaaattat tcttaatata tattgtaatt taaaaattaa cagcttcatt gtcttgataa   20820
aatttatggt atcttaaaca tgtgcttgtt tttctaagag aacattgaaa catagatttt   20880
aaaacaaatt gttgaaagat taaaaaatct gcctttgcac actgttacat tgaaagtggg   20940
gcatttgtcg tgaacattca tttcaaatat gtagtatctt cagaatattt gagaaggatt   21000
tgtattatat aattgaaaaa tctgttaaat tgtatttatg ttaactgctt aattctaata   21060
aaatttccat tcatttttta gtatctgcat atatttacat caaatggatt cattcactta   21120
tttaagaggc agtactaatt acctatagcg ttcaagactg ttaggtagag ggtgtgtagt   21180
ggtgagtaca acaggcgtga gccctaccaa cacggagttt aaagcctagt agaggatata   21240
gacttaaaca atttcacaag taaatacata attacaaatt ataatacatg ctatgaagga   21300
aacataggag gtaccagaga aggaagagtg cttttgcattt ttatttttaa gaccgaagag   21360
tgctattgga ggactttgag caagtgaatg acatgatcta acctaccttc gttcattcat   21420
tcattcattc atttttcttcc ttcctggctc aagcagtcct cccacctgag ctccccaaat   21480
agctgggact acaggtacac actaccacac ctaattttt tttgtatttt ttgtatttttt  21540 gatgggattt taccatgttg gccaggctgg tcttgaactc ttgacctcag gtgatccacc   21600
tgtctcggcc tcccaaggtg ttgggattat aggtgcctag cccatggtgc ctagccctaa   21660
cctacattta taaactatca cttgctgctg tgtggagact atattgtgag attaacagca   21720
gggatacctg ctaggaagca attgctgcag attgcctgag acaaaatagt tatcatggac   21780 taggggatg gtgttggtgg tggtggtagg tggttggatg taggatatat tttgaagata   21840
ggtaaatggt gcaagattat gggtcagttt taaatgctta agtaaatttt ctttgtaaga   21900
cattttagga tgccatgtta agaatctctt tataactgtc atttaaaaaa aaaccacata   21960
ttttcttagc ataatttccc atagtaacat tactatgtca aaggctatga acatttgaat   22020
gactttagat aaatactgta attgctttcc aaaaatattg tgcttattat gtcaccagaa   22080
atgtttgaat tctgtctaca attcagtctt gccagtatag tacatttcat ttagaaaaat   22140
tttttactat gtagatggaa aaaataatat tttagctggg agtggggga ctatggggaa    22200 taactttcct tcatttaata ttttattgtg agttagttta agttacttta ttttatcgta   22260
gtttcctaag gctacaaatt agtaaccttg gtaacttatg tacctaattt aaaagtttac   22320 tttttgaaa ggctggaaat actaattaaa aacgtaacac cttcatcctt gtctttgctc    22380
cattattaac tagtttcatt acagaatctc tgtgttttaa aatcagatgg gttttcataa   22440
ccagtacttt ctcagagtgg taaatttaaa aaaatatata aagagaataa ataatatttg   22500
ttgagaatac ttcaaataat gtgaagagtt attaacttac agcaggagtt ggcaaacttt   22560
tctataaagg gccatatggg tctttgtcac aaagtcttgg gttttgtttt tgtttttttt   22620
aaacagctat ttaactattc ctagctaatg ggcaatacaa aaacagtggg caagatttgg   22680
cctgtgggca gtagcttgct gaaacctttat ttagactcta aattttttga aagagtctac   22740
attgatgcat attttttttt cttcctccaa atacagttga cccttgaaca acatgcgttt   22800
```

```
gagtgaccat gggtccactt gtgatacacg ttttttccc aaccaaatgc agatatggag    22860
ggctgacttt tcatataacct ggatgttcct gggccaactg taggactaga ggctgggggg   22920
ggtcttggaa ccaatgccgt gtgtatacca gggatgactg tttcttatgg cctgacctga   22980
agttggaaca gaatctttat taatatataa ttttttgttgc gtttgttttc tctttatatt   23040
tatccattct ttttagatcg tatttcattt aacactttt cttctttagt ttttaccaag    23100
ttgcactgaa aatagctcag tgactaattg cacttctaag agtgaggacc ctagttaaaa   23160
ttaactctaa aaatactgaa tttttaacct aaaccttttg tttctaatca acagtattat   23220
ttatgagtag gttatagatt actttgaaac ggaatgtgtc tcagaacttt gctatcgata   23280
tttttaaggt ctggtaggga aaagataata ggaatgagat ttatcagtga ataggggact   23340
gctttcccag tttctcggtc gcactggtgt attcaccatg gaagcatctt atgaaatatg   23400
tacataaact actaatatcc cacattacag gttgactatt ctttatctga aatgcttagg   23460
acctagaagt attttttggat tttggttttt cagagtaggg atactcagcc tacattggta   23520
agtaaagaat gtgaggtgac aggctgggcg cgatggttga cgcctgtaat cccagcactt   23580
tgggaggccg aggcggatca cctgaggtca ggagttgaag accagcctgg ccaatctgta   23640
ctaaaaatac aaaaattagc tggacacagt ggcacgtgcc agtagtccca gctactcagg   23700
aggctgaggt aggagaatcg cttgaacctg ggaggcggag gttgcagtga ctcgagatcg   23760
tgtcactgcc ctccagccta ggcaacagag caagactcca tctcaaaaaa aaaaaaaaaaa   23820 aaaaaaaaa agaatgtgag gtggcagcaa taggtaggaa gagtctttgg tcagctttac   23880
atgctctgta gccatgcctg ggtaatgggt tgactctaag actctgtgct ttgctcccac   23940
ctcctgcttt ttcattactc tttagaatgg ttttttaattt gtgatctata ggagttcttt   24000
caagtattta ataagagaat aggctaaatt aagtaaatgt caactgaatg ctcaaatctc   24060
tactaaagag cctcttatttt agaaaataaa tatccatctt ttttttctga ctggtgagat   24120
aattaatttt tattacagat ggtttggaaa ataccatatg ctttaaaaga taagcacaaa   24180
attatagtct aatatgtagg ttttcatact ttaaaaaatt gaaaaccaaa gaaaaacatt   24240
taacatagca tctagtacaa agaaaagaga taagcaagag ataaatgtct ttttttggga   24300
agagttttgc tgttgttgcc caggctggag tgcaatggca caatctcagc tcaccgtaac   24360
ctccacctcc cgggttcaag tgattctcct gcctcagcct cccgagtagc tgggattaca   24420
gtcatgcacc accaggccca ggtaattttg tatgtttagt agagatgggg tttctccgtg   24480
ttggtcaggc tgatctcaaa ctcccgacct caggtgatct gcccaccttg cctcccaaa    24540 gtgctgggat tacagacatg agccatcgca cccggccaag ataaatgtct tttaaattat   24600
ctccattaaa gacataacct ttataacatt ttgatgtata tattaccagt tttaaacac   24660 atagtagatt tgtataaata cataaacaca tattattgtg atcatgctgc acttagacat   24720
ctttatattc tcccttatact gtaaacattt tgaaatactt tactaacaac atttgtaatg   24780
accattcttt ctctctttct ccctctgata gaatggtcta cagagtaatt cataaactaa   24840
acatacttta gaggctgggc gcagtggctc atgcctgtaa tcccagcact tgagaggct    24900 gaggcgtgca gatcacgagg tcaggagtta gagaccagcc tgactaacat ggtgaaaccc   24960
catctctact aaaaaaacag tacaaaaatt agccgggcgt ggtggcgtgc acctagaatc   25020
ccagctactc aagaggctga ggcaggagaa tcactcgagc ccaggaggca gaggttgtag   25080
tgagccgaga ttgcaccaca gcactccagc ctgggcgaca gagcgagact ccatctcaaa   25140
```

| | | | | | |
|---|---|---|---|---|---|
| aaaaaaaaaa | aaagatacat | taatactata | gcctacatgt | ggaacattaa | gaaaataatt | 25200 |
| gcttttatgt | ttatgcttta | tacctgttgt | tagccctgct | tcttatttca | tgatttcatg | 25260 |
| gcttcacatt | gtaacatccc | tttaccatat | tttttgagga | ctgttttggc | agaatgtgtg | 25320 |
| aaatcttgag | cagaagtatt | acccaaaagt | cagaagaaaa | tcagattttt | atttcaagat | 25380 |
| tctgttaaag | ttacccactc | ccttcttta | cttaatctta | tagttgcagt | tctctctctt | 25440 |
| tttagaaaag | aaaaaagagg | cccctcagga | tttgcagatg | aaacaatatt | gctctttaga | 25500 |
| gatatccatc | tggctgttag | attatttttc | cacagttttc | agaagtggat | gaggccatta | 25560 |
| gaatcttgag | tattgcccat | ttccttatgt | gtgcctttga | ctatagataa | aatagatgca | 25620 |
| tgacaattat | ttataagttg | attgattttt | cttgtcattt | aaatcatctt | gaataataga | 25680 |
| gttggtagag | ctatcccatt | tttgaaatta | ttttgttttg | tcataaactt | tttgttacca | 25740 |
| gcatgtacac | ttgcattgtt | gactctccat | ataatacctt | taaaaatttt | ttttttgtgg | 25800 |
| taaaatatgc | ataacataaa | gtttaccatg | gtagttttct | ttcatttgtt | ttgttttgt | 25860 |
| ttttttgaga | cggagccttg | ctctgttgcc | aggctggagt | gcagtggagc | gatcttggct | 25920 |
| cactgcaacc | tccgcctccc | gggttcaagc | aattcccctg | cctcagcctc | ctgagtagct | 25980 |
| gggactacag | gcgcccgcca | ccacgcccgg | ctaatatttt | gtattttaat | agagatgggg | 26040 |
| tttcaccatg | ttggccagga | tgttcttgat | ctcctgacct | catgatccgc | ccacctcggc | 26100 |
| ctcccaaagt | gttgggattg | caagtgtgag | ccaccgcgcc | tagaccatgg | tagttaattt | 26160 |
| taagtgttca | attcagtgac | cttaagtgtg | ttcataatgt | tgtgcaacca | tcaccatgtt | 26220 |
| gtctaaccat | tagcactatc | tgttttgaga | acttttttt | atcatcccaa | attagaattc | 26280 |
| tgtacctgtc | aaatagtccc | cagtaatcct | ccctccccca | gcccctggta | atctgtagtc | 26340 |
| tacttttcgt | cttttgaat | ttgcctattt | taggttcctc | atataagtgg | aattatgtgg | 26400 |
| tatttgtcct | tttgtgttgg | cttacttcat | ttagcataat | gttttcaagg | ttcatctgtg | 26460 |
| ttgtagcatg | tatatacagg | ttgaagcatc | cgttatccaa | aatggttgtg | accagaagtg | 26520 |
| gtttggattt | cagatttttt | ttttggattt | tggaatattc | atagatactt | aactggttca | 26580 |
| gcatccctcg | tccaaaaatc | caaaatcaga | tggagctcag | tggctcatgc | ttgtaatccc | 26640 |
| aacacgttgg | gtggccaagg | caggaggatc | gcttgagccc | aggagttcaa | ccagcctgag | 26700 |
| caacacaaga | ccctatctct | ccaaaaaaaa | aaaaaaaaa | aaaagatga | agaaaaaaa | 26760 |
| aatccaaaat | caaatgctcc | agtgagcatt | tccttttagc | atcatgtcag | gctctaaaag | 26820 |
| ttacaggttt | tggagcattt | tggatttcag | attttggat | taacctgcat | taatgctcaa | 26880 |
| cctatatgaa | attttattcc | ttttatggc | tgaataatgt | tccactgtat | gtatatacta | 26940 |
| cattttgttt | atccattcat | ctgttaacag | acacttaagt | tatttccaca | ttttgggtat | 27000 |
| tataaatagt | gctgctgcga | acattggtgt | acatgtatct | gtttgagtcc | ctgttttag | 27060 |
| ttattttggt | tatataccta | ggaatggaat | tgctgatcat | atggtaattc | tgtgtttaac | 27120 |
| tttttgagga | actaccactg | ttttccacaa | tggcatcacc | attttacatt | cccaccagca | 27180 |
| atgcacaaag | atttcagtgt | ctgtatcctt | gctaacactt | attttccatt | ttttgagttt | 27240 |
| ttttgttttg | tttttttaat | aatagccaat | cctaatgggt | atgtggtagc | atctcatggt | 27300 |
| tttgatttta | ttttcctgac | tattgatgat | gttgagcatc | ttttcaggtg | cttagtggcc | 27360 |
| atttgtccgt | catctttgga | gcaggaacaa | tgtcttttca | agtcctttgc | ccatttttaa | 27420 |
| attgaatttt | ttgttgttga | gttgtatata | acacctttt | tgaagtaaaa | ggtgcactgt | 27480 |
| aataatccag | actgtgtttc | tcccttctca | ggattcctac | aggaagcaag | tagtaattga | 27540 |

```
tggagaaacc tgtctcttgg atattctcga cacagcaggt caagaggagt acagtgcaat    27600
gagggaccag tacatgagga ctggggaggg cttcctttgt gtatttgcca taaataatac    27660
taaatcattt gaagatattc accattatag gtgggtttaa attgaatata ataagctgac    27720
attaaggagt aattatagtt tttattttt gagtctttgc taatgccatg catataatat     27780
ttaataaaaa ttttaaata atgtttatga ggtaggtaat atccctgttt tataaatgaa     27840
gttcttgggg gattagagca gtggagtaac ttgctccaga ctgcatcggt agtggtggtg    27900
ctgggattga aacctaggcc tgtttgactc cacagccttc tgtactcttg actattctac    27960
aaaagcaaga ctttaaactt tttagataca tcattaaaaa agaaaaccat aaaaaagaat    28020
atgaaaagat gatttgagat ggtgtcactt taacagtctt aaaagcaatc gtgtgtatag    28080
catagaattg cttggattgg ataaacagtg gcattatata ttttaaaaaa taaaagtttt    28140
gaaagattga agaatttggg cattacagtt ctcttaaatc tgacaaagct gcataaaact    28200
attaaaataa tcattattat actattttat attctatttc tttgagggtt tagttttcca    28260
aaaactacat attaagcaaa tgaatcactc agtggctatg tcatataata acgagttagc    28320
ctagttataa gaagtttaac attttatttt agaacattgt tacagcatgt ttactgtata    28380
gtctagtaat agaggaaaag acatttgggt gggtggtagt ggtagtattt ttatagagga    28440
gttaccaaat ttcagctcta ttatccaagt ttacccagct aatggtgttc ggaaccggga    28500
atttgagcca attctgactc tgttgtctgc tctgctcctt cttttgtgct gtgtctttga    28560
aagtcaccta aaattgtgag ggaatgtaat ttcaccccaa atttagagtt tatgcacttg    28620
ttatattgaa aatgattaac atgtagaagg gcttttaatg gaataagtgg tgtagtaact    28680
tcagtgttgc ctacctagaa atcaaaatct ttctagttgt ccactttgtt ttttgaaaaa    28740
gtaatatgaa aattatgtta atgctttaat tcaggttttt gtaaaatatt ttttatcttt    28800
acacatttaa catacgtttc taaaattata gtctgttata tagcactttg ggtctagaat    28860
ttttcagtag tttctgtttt actattatga tctacctgca tattaaccta ttaggttata    28920
gttttactat acttctaggt atttgatctt ttgagagaga tacaaggttt ctgtttaaaa    28980
aggtaaagaa acaaaataac tagtagaaga aggaaggaaa atttggtgta gtggaaacta    29040
ggaattacat tgttttcttt cagccaaatt ttatgacaaa agttgtggac aggttttgaa    29100
agatatttgt gttactaatg actgtgctat aactttttt tctttcccag agaacaaatt    29160
aaaagagtta aggactctga agatgtacct atggtcctag taggaaataa atgtgatttg    29220
ccttctagaa cagtagacac aaaacaggct caggacttag caagaagtta tggaattcct    29280
tttattgaaa catcagcaaa gacaagacag gtaagtaaca ctgaaataaa tacagatctg    29340
ttttctgcaa aatcataact gttatgtcat ttaatatatc agttttctc tcaattatgc     29400 tatactagga aataaaacaa tatttagtaa atgttttgt ctcttgagag gcattgctt      29460 cttaatccag tgtccatggt actgcttttg gctttggttt cttctacat tgaaaatttc     29520 tcttcaattc tgagcacatg ttaacattta gaattcaaga ggtgggatt ttttttttccc    29580 atggttacat atatatat atatatatat atatatatat atatatatat atatataaag     29640
aacagggcaa caaattttg cgttttctat ttcggtagta cttttaaacc attatgtcat     29700
gtttctaggt taaacgttgt tgtatttgaa gaatttact ttggcagaat ttttttgagg     29760
atgtgtttat ttctggagaa aggtctcatt aaagaaagac aatacccaga aagccaacag    29820
aaattctgtt actcatttaa tgcatttttc tgacaaaaat tattgccaga gagaacctga    29880
```

```
attttgtttc aaaaatcatc tttgttttaa aaatgacttt ttcttcaggt aaaataaaat    29940
aatttcagtt gctattattt aacctgtttg tatgaagagt ttaacatata ggaaatgaat    30000
acataaagat aggaaggaat taattgttat atgtagtcat atgtctctta atgacaggga    30060
tactttctaa gaaatacatt gttaggtgat tttgtcattg tgcaaacatc atagaatata    30120
cttacacaaa ccttggtagt ataacctact atacacctgg gatatgtagt atagtctctt    30180
gccccaggga tacaaacctg tacagtatgt aactgtacta atgactataa ggcaattgtt    30240
aacacaatgg taagttttgt gtgtctaaac ctacacttgg gctaccctaa gtttatatat    30300 tttttttaaat ttctgttcaa taataaatta accttacttt actgtaactt tttaaacttt    30360 ttaattttc ctaacatttt gacttttgta atacagctta aaacacacat tatacagcta    30420
tacaaatttt tctttcctta tatctttatt ctgtaagctt ttttccatat ttaaaatttt    30480
ttgtttgttt ttacttatta aacttttttg ttaaaaacta agacatgcat gcacattaac    30540
ctaggcctac acagggtcag gaccatcaat atcattgtct tccacttcca catcttgtcc    30600
cactggaaga tcttcagggg cagtaacaca cgtggagctg tcatctccta taataacatt    30660
gccttctttt ggaataccte ctgaaggacc tatccaaggc tgtttatagt aacttttttt    30720
tttttttttt tttttttttt agtaaatagg aggagtacac tataaaataa caatataggt    30780
gctataccat tatacaactg acagtgcagt aggtttgttt acaccagcat caccacaaac    30840
acgtgagcaa tgtgtcgtac tacagtgtta ggatggctat aacatcacta agcaatagga    30900
acttttaaac tccattataa tcttatggga ccactatcac atatgcaatc tcctgtggac    30960
caaaatgtca ttatgtggta catgactgta ctaagaaatt gatccatcta tattccatca    31020 attgtttag ggcttttttct ggttacattt acctgtgagc ccagaaaacc agttttgtag    31080
aaattaactt ctgtaatgct aggagttaaa aaaaattgct gaacaacttt tacattgtta    31140
aacatttaaa aacaagcgtt ctagaagttt atcaaatttc ataaaggtgc aaaaatgtaa    31200
atgtaaatca ttatccagct aatatatatg ttgtatttcc ctagtaggag agcatatgta    31260
cctcttccta gttatacaaa tttgatatat agtaaagaaa cagtaaattc tacttcaagt    31320
cattttggga ggattaaaaa ctgaatttct ctagtttgac cattgtacag atttatctgg    31380 caatttact aaaacctgat ttataggtta aacttggtgt atatcatata tcactttact    31440
ttagaggaat taagatttca cataaatcca tttccaggtt ccaaagacca ggaagaggct    31500 tggttttgt ttttctttt actgtcttta cagtctcctt gacttttctt aggagagaag    31560
gtactgagaa aacatgattc taatatttat tatttttct tccaacattt tcttatgaaa    31620
cattttcaaa tacaaaattg agttttattt aaaacatttg caaatatact acctagattc    31680
taccattgtt gttttatatt tgctttactt acaacttttta aaagatgctt tttataccac    31740
tgaacatttt agcttacatt tcacaaagaa aagaaaaaat ttaagagact ttgcataatg    31800
ttttaagggg ttgcagtaaa gaagtgcttc ttatattttc ttatgcatac aaatcagctg    31860
ggcttattaa aatccagatt ctaattcaga aggtttaggt ggggaccgag tctgcatttc    31920
taacaaactc ctaggtggta ttttttcttgg tacttggacc atactttgag tagaaaagca    31980
gtagaggaca taaaaagagt cttgttagtc ccactttgtt gctgtccact tctcatttga    32040
taatatccta aaatagctgt gtctcctttt tggtggttgt atgattacta cctcagaagt    32100
actaattgat tcttgctatt tgaccttaat actttaatat aacacagcat tcatatttga    32160
tcagaaaact atctggcttc cttttataag agattttttag gttttataca gttttgtggc    32220
cttgggtttt tttgtttgat ttgttttttt gaaggtatat aatatgtaag tagataaaca    32280
```

```
aatttgattt gtagacattt ttatgtggat catctaatta aaaatggagg gatacagtat    32340
gaaagaatac ttgtacttct taacagagca ctcaaccttt cttttacatc ctgtttcact    32400
gatgttatta tgtaatttat gttgctaaac tataaattag atatttaatt tctgttcttt    32460
gatttccttt tattattaaa tggacttgtt gatttgccta gaaattaatt tgcctttcaa    32520
aagtcttatt aatcttcctc cgttgaaatt aatttgatat ttgcatgctt ctggaagact    32580
ttaaagagct attccgagta actgtagaga ttataaaatg aaatatggga attttaataa    32640
attttacatc tccagttact ggtgaaaatg tcaagtcctc ctttctgcag agtattttgt    32700
tactcatctg ttattcagct tatttattta tttatttatt tatttatttt tctttctttc    32760
ttgttttttt tttttgagac ggagtcttgc tttgtcgccc aggctggagt acagtggtgg    32820
gatcttggct cactgcaggc tccgcctccc gggttcacac cattcttctg cctcagcctc    32880
ccaagtagct gggactacag gcacccgcca ccatgccttg ctaaattttt gtatttttag    32940
tagagacggg tttcactgtg ttagccagga tggtctcgat ctcttgacct cgtgatccac    33000
ctgcctcggc ctcccaaagt gctgggatta caggcatgag ccaccgcgcc tggcccttat    33060 ttgttttta aacaaaatta gtgtgcatat ccttgttgta ttttatcggc aagttgtttt    33120
atgccctaac ttttggggtc ttgatcatga gcctaaaaca cgtaaacacc caaaagaat    33180 tatattccgg ttaaaggaac aaaacattca tttagaagtt ctcatccatg taaatcagag    33240
gctggcaaat attttctgta aagggccaag atagtaaatg ttttaggctt tgagggccac    33300
aagtggtatc tgttgcattt ttttttaatt atgaccctt aaaatgcaaa aatcgttgtt    33360
agcttgtgca tagtataaaa ataggctggc cgcatgctgt ggctcatgcc tgtaatccca    33420
gaaatgaggt gggaagccga ggtgggcaca ccacctgagg tcaggagttc gaggccagcc    33480
tggccaacgt ggttgaaacc ccgtctctac taaaaataca aaacttagcc aggcgtggtg    33540
gcgggtgcct gttatcctgg ctactcaagg ggctgaggca gtagaattgc ttgaacctga    33600
gaggcagagg ctgtagtgag cccagatcaa gccagtgcac accagcctgg acgaccgagc    33660
gagactctgt ctcaaaaaaa aaaaaaaaag gctgtggctg catttggtcc attggctgta    33720
atatgctgat tcctaattct ctgggtaact ttagtgtttg attagctact agaagttagg    33780
ttaaactttt gtattttaca ggctaacttt aataatctta aagtaaaact taacatagtt    33840
catggaaagg aaatagaaat tttaccctag tactcttttt ttttttttt tttttttttg    33900 aggcagagtc tccctctgtc acccaggctg gagtgcagtg gtgggatctt ggctgattgc    33960
aacctcctcc tcctgggttc aagcaattct tgtgcctcag cctcccgagc agctgggact    34020
acaggcacgc accaccacac ctgactgatt tttgtatttt tagtagagac agggtttcgc    34080
catgttggcc aggctggtct tgaactcctg gcatcaagtg atcctcccat ctgagcctcc    34140
cagtgtgctg ggattacaga cgtgagtcac tgtgcctggt ctctagtatt ttttttttt    34200 ttgagacggt ctcactgttg ccaggctgga gtgcagtggc gcgatcctgg ctcactgcaa    34260
cctccgcttc ccggattcaa gcgattttcc tgcctcagcc tctgagtag ctgggactat    34320 gggtgcacac caccacgccc agctaatttt tgtatttta gtagagacgg ggtttcacca    34380
tgttggccaa tatggtctca atctcttgac ctcgtgatct gcccgtctcg gcctcccaaa    34440
gtgctgggat tacaggcgtg agccactgtg cccagctgta cttttttaaga taagaattgc    34500 agggtatata tttttaccaa cttaataact tataatttta aaaagctaat tacttggcta    34560
gaatataatg cgttacatat tctttacact cagttcagtc catatctgaa aggcaaatag    34620
```

```
aattattttc tgctagtaca ttgtgtagtc cctatgttcc tagtgtataa ggactgttac    34680
ctagttcaca tttatctggg ttgttgacag attttcctgg tcccttggga cagtgcatgg    34740
ccatgttggc aaaagctgtc aaaattgaaa cattgacacc atgagaattg tgtgttttcc    34800
agtctgctaa aatcaaaagt gggagggttc agtaaggtga ataacagaag cagagttttc    34860
ggggtatctg ttactcctca ttcggctttt ctgctctctg ggggtctcaa tttaaatata    34920
atgtgaaaat tagttttacg aacctaaaaa tgttgagtga ttcatttcct ggttttgttg    34980
ttaatttcta gatatttaaa ttaattgtta gaagaacccc gttaaagaat gctttgcaaa    35040
acaacctcct tatgtgctat gtctctgttt aatagtagtt gagtttgtgt acatgagatc    35100
aatattttga actatagctt tttatgagtt aaaaattgac ggaacagtta ctgtgcactt    35160
gctgtgcacc atggtagtct cccaagtagt ggttttctg catttcaata gtacatgaga    35220
taggctgtgg gtggcaaggt ttcttgagaa agtgagggat gcacagttgg gttttagaat    35280
acatcttgtt cctccatgcc cttccccacc aaaaggctgg tagtcttgca tttgtatata    35340
gttagggtat ttgatgtgtt gcttccttga cagagttttg caagaatttg cagatttaac    35400
aggaacaaaa acttacttaa aacaaaatct cttagtaaaa gcatagtcta gcaagattta    35460
gaatgatact ttggctaaca gtactttctc tatatggagt gctttgtttc catagcctca    35520
caagtatgtt ttcagataat agttgagttg aaaatgttgt caatctcttg attttaaaaa    35580
atttacatat ttaaagttgt atacttttgt tcctacgtat tttcagttgt tcttaaagtt    35640
taataagtga catttgaaaa tgagtatatg tgtataaaaa caaaagtagg ctaggcacgg    35700
tggctcatgc ctataatcct agcactttgg gaggctgagg caggcggatc acaaggtcag    35760
gagtttgaga ccagcctggg caatatggtg aaacccccct ctactaaaaa tacaaaaatt    35820
agctgggtgt ggtggtgcat gcctgtagtc ccagctactc aggaggctga ggcaggagaa    35880
tcgcttgaac ccggaggtgg cggttgcagt gagccgagat tgcaccactg cagtccagcc    35940
tgggcggcag agcgagactc catctcaaaa aaaaaaaca aaaaagaaa aagttaaaaa    36000 aaaacaaaaa accccccacaa aatgagtata tgtggcaaca agtcctattc tcaaaaaaat    36060
tattgtgtgc tagttaagag cttaatgagt agccagtcgg tattaaatat ctgtttcagc    36120
tatattttat ctttaaaaat tatctacaga ttttggaatg tgaaaaacta gtgttttgtt    36180
tcataggtat atactgtagg cattttaaaa ataagagcca gtgccagtgg tttacagtgt    36240
acacaaggat aatgttctca tgttctcttg atgtcagtat gactttaaag catattatca    36300
agaaataact aagtctgaaa aactgtggta aataactggt actctaaaac ctaagtttct    36360
tattactaaa aataagaaat ggtaaaagtc accctgtgct gttaattata tgagccactg    36420
aggtcctgac actgaattct tggtggtgga taataatctc ttctttttaa ttattggctt    36480
ccaattctct ctgcattgct ggaaacaaaa atcatatatt tcactattgg tggtggggat    36540
gctgtcactg aaaagtagaa cacattcata ttgattttag atagacacat tcatattgat    36600
tttagaaata agttaaaatc aaaatttgct tctgctaaat tagtagagga ccaatactgt    36660
ttttctcctt catagtatgt tttggtactt ctacattgac attataactt ttttttttt    36720 aaacagaaat agaagtttac attcttagaa aatttatgaa aatatgagct ttacctggt    36780 ttgtgtgtgt gcgtatatat atacacatat ttttaaattt cttacattga ttttcaaatt    36840
gaaagagaac catttgtgaa agtatcttaa cagagctcat gctttacatt ttacatgcta    36900
caaagttatt ttagtgcctt aaattatttta tgttgcttat taatgaaaat tttggataca    36960
taattttttc aagacaaagg taaaaataat aaacccttt cttctgagga ttaatgataa    37020
```

```
atataaactt taaaacgatt aaaaaaattt ttttagagac agggtcttgc tctgttgccc   37080
agactgaagt gcagtggtgc agtcatagct caatgaagcc tcaaactcct gggcccaggc   37140
aaccctcctg cctcagcctt ttgagtagct gggacttcag gctcatgcca acatgcctaa   37200
tttatcttat ttttagtaga gatgaggtct caaactcctg gcatctcttg ccctctcaaa   37260
gtgctggtac tacaggcatt agtcaccaca cctgacactt aaaatctttt atatacaggt   37320
gtaagtgggt atctaactta aagtgccaac gaatgtagtt gaaagtttgt agttggctta   37380
gctaactagt taactaaatt gattccatta aaaataagat aagactgctc ttagaatata   37440
atgatttttg ttattcgtta aatataaata tatcactgga tagtatatgt taatgacttg   37500
agatacgcat tttaacatat aatcacgtta cttaaatgcc tgcctttgaa ctgaaactta   37560
acattatgaa tttaaattaa agtttgactt tagaggtaaa tttctgtact ttactaaagc   37620
agttcttaat ataattctga gatttctaaa aattagtgtg ccctaaagaa ttgaggtgtg   37680
tttttcttaa ctactgtagg cagtagatgt acagatgact tctgcatgca aaaattaagc   37740
cctagccatt ggtttacttc aactaatact tagttgccaa ttctctgtgt gtgattgaat   37800
ttaaaactgc aaatggtact ggtgatacat taacttttta ggtgctaggt ccactttgtt   37860
acatttggtt cagtagaaac attgatgtta ccaatctcag aaagctaaaa tatgtatgcc   37920
aatccccaaa ttaggtaatt tattcttaat tttaagataa aagaatagaa ttcccttaaa   37980
attaaatgtg gagtaaaata taccagcttt aaaaaatatt caccttctg ttagaagaat    38040
gaacataata ttcatctttt taatttgcac tatatataga ttaatatttc tgtgtatttc   38100
tctgtgcccc tactttgatg gtatgctttt ctgaacaaac tagcagcaca gttaactaag   38160
cactttgccc cgtttgatga ctgcctaatt ttctagattg gaaaatatta aaaacttta    38220
tctccatatg gccaatatat gattgtacct gttgtcatag ctctcttatg tttaagcaag   38280
aaaaacccta ttaagagtat ttaaattaga atggaaggca cacagccagt atgattgaac   38340
actgttctaa aaattatttt taagacttgt agtaaggcca ggtttggtgg ctcatggctg   38400
taatcccagc ccttaggagg ccaaggtggg cggatcactt gtgctcagga gtttgagacc   38460
agcccgggca acatggcaaa accctgtctc tacgaaaaat acaaaaatca gtcaggtgtg   38520
gtggtgcttg cctgtagtcc cagctatttg agaggctgag gcaggggat cacctagcct    38580
gggaggtcga ggctgcagtc atgatcgtgc cattgcactc catcctgggc aacccagtga   38640
gaccctgtct ctaaaacaaa aaaataaaaa aagaacttgt agtaaggata caaaatgctc   38700
ctattttgtg tgtgtcctt aattcatgat gtttttatat tatggtaagc agctctcatt    38760
taagatttta ataatgtaat taaacatgta cagaagaccc agtctcagct tcacttgtat   38820
accctggaaa tagactgaaa ggtgttaaaa tttaagataa aactcaaggt tccagtttct   38880
tgactcacct ttgagattct tttatgtttt tgttgttttt taacaaaggt ttcacgtcca   38940
tattttacca tttttcttct cattctcccc tggaggaggg tgtgggaatc gatagtatat   39000
aaatcacttt tttcctaagt caaagaagta atttaaagct aacttcagtt taggctttaa   39060
ttccaggact agcaaactaa aatggttgca ttaattgaca aacagatgct aatacctgtg   39120
tttaggcttg tcataatctc tcctaattcc taatttaaaa attttaaaat ttaattccat   39180
tagaaaacaa aactgacttt taagaacaaa ccaggattct agcccatatt ttaaaactgc   39240
atcctcagtt ttattcaaac agtctgatgt ctgttttaaaa aaaaaaaaat ctcaagctca   39300
taatctcaaa cttcttgcac atggctttcc cagtaaatta ctcttaccaa tgcaacagac   39360
```

```
tttaaagaag ttgtgtttta caatgcagag agtggaggat gcttttttata cattggtgag    39420 agagatccga caatacagat tgaaaaaaat cagcaaagaa gaaaagactc ctggctgtgt    39480
gaaaattaaa aaatgcatta taatgtaatc tggtaagttt aagttcagca cattaatttt    39540
ggcagaaagc agatgtcttt taaaggtaac aaggtggcaa ccactttaga actacttagg    39600
tgtagtattc taacttgaag tattaaaaga taagaaactt gtttccataa ttagtacatt    39660
tatttttaat ctagtgggaa ttaattataa ttgagacaat tttgatggct gtagtagact    39720
aatctatatt tggcataaag tctaatgatt taatgagtct taagtaaact aaatatttgg    39780
aaactgatat ttacctttat ttttaaggga aaagttttga gataatcagc agcttttttt    39840
tttttttttt tttttttagt agggagaaaa agatatgagc tatagtagac agcagtaata    39900
ttgaatggcc cagaaggtgg gaaaaagcca ctcttaaatg tattttttct tttggatatt    39960
ttacaagcaa ataataactt ctgcctaagt tcgccatctc agtggcatca gcagcacagc    40020
actttcttat cccagtgaga aacctgggaa tttaggatg actcctaccg ccctcttttc    40080
cccctggttt ggaagtatcc acaaattcct gtgacgttac attctgtgtc ttttatgtca    40140
tcattagttc aggccccctat catttcttgt tggactgtta gaacctccta tttggtttac    40200
cagttgctgc catcattcat tgtgaaaccg gagagataca ctttaaagaa atgtcatttt    40260
tggccgggcg cggtggctca cgcctgtaat cccagcactt gggaggcct aggcgggtga    40320 tcacctgagg tcaggagttc aagaccagcc tggctaacat ggtgaaaccc tatttctact    40380
aaaaatacaa aaattagcc gggcgtggtg gcacgtgcct gtaatcccag ctacttggga    40440
ggctgaggca ggagaattgc ttgaacctgg gaggcagagg ttgcagtgag ctgagaatgc    40500
accattgcac tccagcttga gcaacaagag cgaaactctg tctcaaaaaa aaaaaaaaaa    40560
agtcatttta gctatagaat aaaatctcat gttccacatg tgttgcagat agtccttact    40620
accttcccac cactccagct cttttttggt cttatatcta aaaacgtcat cttgcctgaa    40680
tttcttttgt tcttctataa ataaatacca tgttatttcc taccttccct tgagtcttgg    40740
ctcttgtttg gaatgccagt attttatcc ctagtcttac taattagcta acactctcat    40800
gattccccag tctcctactc tctaaaaacc tttcttaaa cccttagact aggcatggag    40860
cccttcctgt gtattcccag aatactattc ttaactatta tatgcttccc atgttatgtt    40920
gaaataacta acctcttctg tttcattcct atattacttg acagcaaaat cttagccaga    40980
attacatatt tttaatcttt gcacacccat tgcctagtaa ggttcctggg acatagtaac    41040
tacccagtaa atatttattg cgtggaattc tcattttcgt ttctaaaccc gtattaaact    41100
ctgtcttgct cagaaaatac ttcactaggt atcataaagt tcatggcaga gcttaagctt    41160
tggatgcata ttgtttgtaa tatatcatgt tcttaagaat aggcaataaa attacagttt    41220
tcaaaaacta ctacatttat tatatttatt acaagttggt gttctttatt acatgaattt    41280
taggtatttc ccaaaagtat aaaatataca tttgaatagt agactcaatc ccaaaagata    41340
ctacgtggtg tactaatcta ctaaactcag aaacaaagca tgactggcat taatttttgt    41400
tgaaatttat gaactctgaa tgttttttgaa tatcattctg taaagcaata ttttgcaatt    41460
aaagcaattt tgcatgttaa attttaccac aacctctaaa atattgcaaa tttaacaata    41520
cagtttgaaa agttacacat tttaaataac agtaccatga ccagatttag gtggtggttt    41580 taattttttta ttttctcctc ctattgtctc accattagat gatttaaaaa atagaattgt    41640
ttagagtaaa ataagtgtta tgctctaatt tatatttaaa atgaaggttt aagcacgtac    41700
tattctaaaa tttctaattt gtgcaaatta tgttttatac agtgactgta ggtgaatgtc    41760
```

```
acaattgttt gatgtgacga atccttgttt ttcagtacac gtggaagtaa ttcatataaa    41820
agagaagtat acttggtaat taaaaattta aaattaaata caatttaaaa aaaaatttat    41880
ttgacaagct ggctgtggtg tgtgtgcctg tagtatcagc tgcttgggag cctgaggcag    41940
gaggattgcc tgaccccagg agtttgaggt tgaaggagc tatgatgtg ccatggcact      42000 gtagcctagg caacagaaag agactccatc tcttaaaaaa agtaaaaata aaaaatttt     42060 ggcacaggga cagtggctca cacttataat gccagaactt taggagtcca cagcgcgagg   42120
actgcttgag gccaggagtt taagaccaga ctgggcaacg taatgagacc ccacctttag    42180
gaaataaata cataaataaa aatttgacaa tgataaacat atataaatta gcttttctta    42240
gtcctgaaaa agataatgtt atgtgtatgt gtgagaatga ttagttctca tatgagaaaa    42300
aaagaattca ttgctctgtg taggttgtga catttccttc acgattgaaa ttaattaatt    42360
tttttttatt acttatttat ttttaaaata gagacaggtt cttgctgtgt tgcccaggct    42420
ggtctcaaac tcctggcctc aagcagttct cctgcctcag cctcccaaat tgctgtgact    42480
gtaggtgtga gccactgcac tgggccaaaa ttacttaatt ttaacaagat gatgtagaga    42540
ggagagttca ttgcaacata agcctagaat cttgtcaga atcttaggaa gtaatgtttt     42600
caaattctgt gttttcacca taaaatgtgt cttctctgtg tccatcacat ggttttcat     42660 tgttttctgc tttaccattt tagtaccatt ggcattttc ttcattgtaa agtagtaga     42720 aatggagtag attacataag gatgtgatca gagggaattt attcattcag ggtaagggag    42780
ttagatcctc ttttaagatt ctatcacatt ctaagggttt atgattctaa actgtcaagt    42840
aaattgtcaa gtgctggcaa gctacagaat aatttttatt gtatcattgg aaattttccc    42900
ctctatatgt gttaaagagt ttagcctgaa gggatacata cacatacata tatgtaatca    42960
aaccttgatg gtattgtatt gctgataaat tatttcttac cacttttcct ttctcctgtg    43020
ggagaaacaa aagcatatgt ttgtgtagta tcagtaatga tattagagag tgggaaacat    43080
cagtgagtgc agtttgggga ctttattgga gactttcact agtgctcaaa taaataatgc    43140 tggttttat cctactgttt gcttaatgtg gactagcctc ttattcccat tctatgttta     43200
cctctcttaa aatattggtc acgctttctt gaattataga tctattagga aaattcatga    43260
actgtagcta attttcattg ttcatgctcc agatttattt tgaaatatcg ttaatcttag    43320
tagtacagta aaggagaaat accacttaac attttttgtt tttttttctt tgagacagag    43380
tcatgctctg tcacccagtc tggagtgcag tggtgctatc tcggctcact gcaatgcact    43440
tcgcctctcc gggttcagca attctcctgc ctcagcctcc tgagtagctg ggattacagg    43500
cacctgctac cacacccagc taattttgt atttttagta gagacagggt ttcaccatgt     43560
tggccaggct ggtctgaaac tcctcacctc aagtgatcca cccgtcttgg cctcccaaag    43620
tgctgggatt acaggcttga gccaccgcac cccgcccact taacatttta aattaatttc    43680
aagataatat cacttgaata tttttacaca tataattttt ttaatacatt tatttacaca    43740
gtttataata tcctacaaag tgattacaat gagtaaaaac ccagttttca ttgttcctaa    43800
agtggcttga tttatacaac ttaatgtgtt gggtatttgt ttctaagact ccctctgctg    43860
tctaggtttg gaagtattgt gaggttaaca gattttcttt ttatagttac tactcagttg    43920
aacaggcttt aaaatacaga gagaatcata tttttcttc attttttgct tttatttata    43980
tttttctttt aattggagac atgacaagaa ttgacttgtg tatggatctt gcataattta    44040
agtactgcag gtttaaaatc tactctacta ccagtttgag agtgccattt ttcacactgt    44100
```

```
agattattag gttgaaaagt attatggctt aaaatcgctt ttagccatta aatttaaata  44160
accttgcttt aatcataaat agatggtggt cacaatgact aactgttaaa ctctttgaag  44220
acaggatatt tggctttata tggcaagctt ttgaatacaa cagaaattaa aactttatgg  44280
gatagaaaga atctcctcca aattggtaaa ctataagacc tttcaaatga tttagctaat  44340
ttctccacaa atctgaggta ttagtgtttt ttttaaagtg gtattctcct gtgttggggt  44400
cactttaaac cttttcctta atgataaata tatgaattga aactaatccc ttaatatata  44460
tcatttgaaa actgaaataa tatgtttaga tactgtttac ttgttgataa attattggaa  44520
taggatgttc gaatactgtt tacttcttgg taaatttta aatccaatgg attttacgta  44580
agtatagaac tggagctcaa atactgttac tgtgtgtgaa gatatatgaa catagtttac  44640
agttgcatgg cttatatcta aagtccagaa acataaggac aattaagtgt acacacacac  44700
acatgcattt ggattttgat gacttaggtt tgccaatgtg gaaaaaatag tagcaaatta  44760
agttctcctg tgaaaaagtc gttacctta t ttaaaattct gtgccattgg ttatccttgt  44820
cttttgtgaa aattagtgtt cctgtttata atattgacaa acacctatg cggatgacat  44880 ttaagaattc taaaagtcct aatatatgta atatatattc agttgcctga agagaaacat  44940
aaagaatcct ttcttaatat ttttttccatt aatgaaattt gttacctgta cacatgaagc  45000
catcgtatat attcacattt taatactttt tatgtatttc agggtgttga tgatgccttc  45060
tatacattag ttcgagaaat tcgaaaacat aaagaaaaga tgagcaaaga tggtaaaaag  45120
aagaaaaaga agtcaaagac aaagtgtgta attatgtaaa tacaatttgt actttttct  45180 taaggcatac tagtacaagt ggtaattttt gtacattaca ctaaattatt agcatttgtt  45240
ttagcattac ctaatttttt tcctgctcca tgcagactgt tagcttttac cttaaatgct  45300 tatttttaaaa tgacagtgga agttttttt tcctctaagt gccagtattc ccagagtttt  45360 ggttttgaa ctagcaatgc ctgtgaaaaa gaaactgaat acctaagatt tctgtcttgg  45420
ggcttttggt gcatgcagtt gattacttct tatttttctt accaattgtg aatgttggtg  45480
tgaaacaaat taatgaagct tttgaatcat ccctattctg tgtttttatct agtcacataa  45540 atggattaat tactaatttc agttgagacc ttctaattgg tttttactga aacattgagg  45600
gaacacaaat ttatgggctt cctgatgatg attcttctag gcatcatgtc ctatagtttg  45660
tcatccctga tgaatgtaaa gttacactgt tcacaaaggt tttgtctcct ttccactgct  45720
attagtcatg gtcactctcc ccaaaatatt atatttttc tataaaaaga aaaaaatgga  45780
aaaaaattac aaggcaatgg aaactattat aaggccattt cctttcaca ttagataaat  45840 tactataaag actcctaata gcttttcctg ttaaggcaga cccagtatga aatggggatt  45900
attatagcaa ccattttggg gctatattta catgctacta aattttata ataattgaaa  45960 agatttaac aagtataaaa aattctcata ggaattaaat gtagtctccc tgtgtcagac  46020
tgctctttca tagtataact ttaaatcttt tcttcaactt gagtctttga agatagtttt  46080
aattctgctt gtgacattaa aagattattt gggccagtta tagcttatta ggtgttgaag  46140
agaccaaggt tgcaaggcca ggccctgtgt gaaccttga gctttcatag agagtttcac  46200
agcatggact gtgtccccac ggtcatccag tgttgtcatg cattggttag tcaaaatggg  46260
gagggactag ggcagtttgg atagctcaac aagatacaat ctcactctgt ggtggtcctg  46320
ctgacaaatc aagagcattg cttttgtttc ttaagaaaac aaactctttt ttaaaaatta  46380
cttttaaata ttaactcaaa agttgagatt ttggggtggt ggtgtgccaa gacattaatt  46440 tttttttaa acaatgaagt gaaaaagttt tacaatctct aggtttggct agttctctta  46500
```

```
acactggtta aattaacatt gcataaacac ttttcaagtc tgatccatat ttaataatgc   46560
tttaaaataa aaataaaaac aatccttttg ataaatttaa aatgttactt attttaaaat   46620
aaatgaagtg agatggcatg gtgaggtgaa agtatcactg gactaggaag aaggtgactt   46680
aggttctaga taggtgtctt ttaggactct gattttgagg acatcactta ctatccattt   46740
cttcatgtta aaagaagtca tctcaaactc ttagttttt ttttttacaa ctatgtaatt    46800
tatattccat ttacataagg atacacttat ttgtcaagct cagcacaatc tgtaaatttt   46860
taacctatgt tacaccatct tcagtgccag tcttgggcaa aattgtgcaa gaggtgaagt   46920
ttatatttga atatccattc tcgttttagg actcttcttc catattagtg tcatcttgcc   46980
tccctacctt ccacatgccc catgacttga tgcagtttta atacttgtaa ttcccctaac   47040
cataagattt actgctgctg tggatatctc catgaagttt tcccactgag tcacatcaga   47100
aatgccctac atcttatttc ctcagggctc aagagaatct gacagatacc ataaagggat   47160
ttgacctaat cactaatttt caggtggtgg ctgatgcttt gaacatctct ttgctgccca   47220
atccattagc gacagtagga tttttcaaac ctggtatgaa tagacagaac cctatccagt   47280
ggaaggagaa tttaataaag atagtgctga aagaattcct taggtaatct ataactagga   47340
ctactcctgg taacagtaat acattccatt gttttagtaa ccagaaatct tcatgcaatg   47400
aaaaatactt taattcatga agcttacttt ttttttttgg tgtcagagtc tcgctcttgt   47460
cacccaggct ggaatgcagt ggcgccatct cagctcactg caacctccat ctcccaggtt   47520
caagcgattc tcgtgcctcg gcctcctgag tagctgggat tacaggcgtg tgccactaca   47580
ctcaactaat ttttgtattt ttaggagaga cggggtttca ccctgttggc caggctggtc   47640
tcgaactcct gacctcaagt gattcaccca ccttggcctc ataaacctgt tttgcagaac   47700
tcatttattc agcaaatatt tattgagtgc ctaccagatg ccagtcaccg cacaaggcac   47760
tgggtatatg gtatccccaa acaagagaca taatcccggt ccttaggtag tgctagtgtg   47820
gtctgtaata tcttactaag gcctttggta tacgacccag agataacacg atgcgtattt   47880
tagttttgca aagaaggggt ttggtctctg tgccagctct ataattgttt tgctacgatt   47940
ccactgaaac tcttcgatca agctacttta tgtaaatcac ttcattgttt taaggaata    48000 aacttgatta tattgttttt ttatttggca taactgtgat tcttttagga caattactgt   48060
acacattaag gtgtatgtca gatattcata ttgacccaaa tgtgtaatat tccagttttc   48120
tctgcataag taattaaaat atacttaaaa attaatagtt ttatctgggt acaaataaac   48180
aggtgcctga actagttcac agacaaggaa acttctatgt aaaaatcact atgatttctg   48240
aattgctatg tgaaactaca gatctttgga acactgttta ggtagggtgt taagacttac   48300
acagtacctc gtttctacac agagaaagaa atggccatac ttcaggaact gcagtgctta   48360 tgagggata tttaggcctc ttgaattttt gatgtagatg ggcattttt taaggtagtg     48420 gttaattacc tttatgtgaa ctttgaatgg tttaacaaaa gatttgtttt tgtagagatt   48480
ttaaaggggg agaattctag aaataaatgt tacctaatta ttacagcctt aaagacaaaa   48540
atccttgttg aagtttttt aaaaaaagct aaattacata gacttaggca ttaacatgtt    48600
tgtggaagaa tatagcagac gtatattgta tcatttgagt gaatgttccc aagtaggcat   48660
tctaggctct atttaactga gtcacactgc ataggaattt agaacctaac ttttataggt   48720
tatcaaaact gttgtcacca ttgcacaatt ttgtcctaat atatacatag aaactttgtg   48780
gggcatgtta agttacagtt tgcacaagtt catctcattt gtattccatt gatttttttt   48840
```

```
ttcttctaaa catttttttct tcaaacagta tataactttt tttaggggat ttttttttag    48900
acagcaaaaa ctatctgaag atttccattt gtcaaaaagt aatgatttct tgataattgt    48960
gtagtaatgt tttttagaac ccagcagtta ccttaaagct gaatttatat ttagtaactt    49020
ctgtgttaat actggatagc atgaattctg cattgagaaa ctgaatagct gtcataaaat    49080
gaaactttct ttctaaagaa agatactcac atgagttctt gaagaatagt cataactaga    49140
ttaagatctg tgttttagtt taatagtttg aagtgcctgt ttgggataat gataggtaat    49200
ttagatgaat ttaggggaaa aaaaagttat ctgcagatat gttgagggcc catctctccc    49260
cccacacccc cacagagcta actgggttac agtgttttat ccgaaagttt ccaattccac    49320
tgtcttgtgt tttcatgttg aaaatacttt tgcattttc ctttgagtgc caatttctta    49380
ctagtactat ttcttaatgt aacatgttta cctggaatgt attttaacta ttttttgtata    49440
gtgtaaactg aaacatgcac attttttgta cattgtgctt tcttttgtgg gacatatgca    49500
gtgtgatcca gttgttttcc atcatttggt tgcgctgacc taggaatgtt ggtcatatca    49560
aacattaaaa atgaccactc ttttaattga aattaacttt taaatgttta taggagtatg    49620
tgctgtgaag tgatctaaaa tttgtaatat ttttgtcatg aactgtacta ctcctaatta    49680
ttgtaatgta ataaaaatag ttacagtgac tatgagtgtg tatttattca tgaaatttga    49740
actgtttgcc ccgaaatgga tatggaatac tttataagcc atagacacta tagtataccaa   49800
gtgaatcttt tatgcagctt gttagaagta tcctttattt ctaaaaggtg ctgtggatat    49860
tatgtaaagg cgtgtttgct taaacttaaa accatattta gaagtagatg caaaacaaat    49920
ctgcctttat gacaaaaaaa tataggataa cattattttat ttatttcctt ttatcaaaga   49980
aggtaattga tacacaacag gtgacttggt tttaggccca aaggtagcag cagcaacatt    50040
aataatggaa ataattgaat agttagttat gtatgttaat gccagtcacc agcaggctat    50100
ttcaaggtca gaagtaatga ctccatacat attatttatt tctataacta catttaaatc    50160
attaccagga actgtttgtt ttgtagtgaa ccttgagtat gtgctgttaa tataccaaat    50220
tgggtgaaaa aataagggat tcctttcaaa agttaagaga agtaagtgtg taagaaatta    50280
ttttgcttat taaatgttcg gtaaatggca ttctcttgtc agtaaaatgg agaaataagc    50340
taaaaataat tggctaagtc ctattaagtt agaggattaa gtgtattata ttttcattca    50400
aaattgggtg ctcattaatt tatgatcggt agtatagcta aattgctatg tttgtatcaa    50460
aattgagcat aaagttgctg atactttctc cgtatgaaca gaagttgaaa cctatttagt    50520
tcagtagggc agctcaggga ttttttttaca caacatgtat atcttcccat tttaagttag    50580
aattatttta caacatctgg tatacataaa cagctggcac tgatagctaa attaaagtag    50640
taatgatcaa ttagttttgt tggtatctga ataatagcgt tgtttcatag ctctgtatttt  50700
cctaaggaag tacaaagctt ctagctcttt cattacaaat tcgccctgtg caataagttc    50760
tttgatcttc tctggattct tcacatcttt gttttttaagg aaaatgttct tcaaacgctt    50820
tttaaaatag tctgctcctt ttggatagtc tcgtccaaga tacagcagct tcaaaaagaa    50880
agattatata tttctaaaca atccatgtca tataataaca tttttataaa attggcaaca    50940
taattactta catttttata aagttttagt acttctcctc ttaaagaatt ggccattttc    51000
atttatcatg taaattatcc acttttatgc ataacatacc taaagaaagg aaaattttttt   51060
tgcaattagc tgcattgtag tcttaaaaaa ataaaaaaag gttatacaca ttgagaaaat    51120
ggtaaccttt tttacattca ataaatattt cttgataact ttttcgttcc acgtactggg    51180
atatagttat aaacacttcc gataaaatta cctgctgtca taattgacgt tttcctatgg    51240
```

```
gagacataag caaagacaat tgtgattgtg agaagtcaca tgaaggaaat gagaaagtgg   51300
attgtcatca cagataggta cgtgtacctc cttttatgcc acagtggaat gagttaaact   51360
agatttaaat tccagttgca taatgtacag attaattaac cttgctgagc ctgagttttc   51420
cttatcaaca aacaagagat tatctttacc ctgctctcaa ggcaaggcca gagccacttg   51480
aaggacattg agcagaagcc tgatcaaatg ctgatgggtg cttatccaaa gggaggctga   51540
aaactagcag aaactgggtg agttaagcag gttggaatag tagatgggca gtaagattgg   51600
tggtgaagag gccaaatgaa caacctgtaa gagggtgtcc ctgaggaaca ggcaaaatca   51660
tgcttcttta tgtgtaatgt gttaactcta ctttgtagag gaggctccaa acttaaaggc   51720
atcatgacag tctaaaccta gaaataatt cccactacct gttagagttg aatagtaagc    51780
tcttaacatt gcatcctatc aggtggatgc aactgcaatt tgttccattg tgattgataa   51840
ctttgattac ccaattaatg tatttgctaa gattgtccat tgtaaaatta tttctccaag   51900
gaacctagtc cttttaatgg agaatagcat ttagaaacta taatctggat ggaatgcttt   51960
agaaaccaag gtctgggtgc taaaaatgct aatcaccatg ggactgtcac tgttcccagg   52020
tcctctaagt gacaaagctg caagtgtata tacatacgga tttaggtgtt gtatgtgtgt   52080 atgacttta tattaatctc catataatct gctacctaac attcaattcc aatactacag    52140
ggtttatttt catttcccct ctttacatgg gtttaatact cttgctgaac agtgagaagt   52200
ctggttccca cttgtcctta ataaatttac tttttataat catcacccct tctctcacta   52260
tgtaatcaaa atcctcttgc tgtcaccatt cggcgcacac actctactct ctgagctctg   52320
ccacctaatg ccagagtgcc actgccacca tcccacatgc atggtcttct cttccccctt   52380
tcccccaacc taccccttctt gggctcaagc aacttacact gcaccatttc ctccctcctg   52440
ggtaaggctc accttttgtt cccattccaa aaacctgtgc caccatttcc ttcacccctaa  52500 taggatgccc tcctcatccc ctgctaggct gctgctgtgc acaagtccct accccagag    52560 gccctcctca ctgcatttgg gctccagtat cccctgctgg gctactacct tgccagcctt   52620
tctctcgccc ccaccttccc cagatgcctg ccttgctcag ccccacgtaa tgacttttgg   52680
actgaattac tctgataggc aagcaggaag caactttttt tttttgaga tggattcttg    52740 ctctgtcccc aagctggagt gcagtggtgc catctcagct cactgcaacc tccacctccc   52800
tggttcaagc aattcccctg cctcagtctc cccagtaagc tgggactacg tgtgcgcgcc   52860
accacgcctg gctaattttt ttttttttt tttttgtatt tcagtagaga cggggtttca   52920
ccatgttggc cgggatggtc ttgatctcct caccttgtga tccacccacc ttggcctccc   52980
aaagtgctgg gattacaggc gtgagccacc gtgcccggcc gcaacttata tttttaaaat   53040
aggcttttag atcagtttta agggttattt tatagttaac tagcagaaaa tgtggattaa   53100
aattacagta ccatactcaa ttaaaaatca tgcgctacat aatttaagtt ctcctgttaa   53160
cttctgtttg ggttgaaccc cgaagtacaa tagtgtagat tctcattgtg acctcacctg   53220 ccccttttagg cattttgcaa aatttacacc ttttacaatt tgaaaggcag ggtgccagtg  53280
ccttcatgta tttcatttaa tctgaaattt ttatacgtat tagacataga aactgcataa   53340
aatatgaatg tacaaattaa agtaaaatat acatctgggt acccatcatt caagttatga   53400
aacaaaagtc ttagaagccc ccatgtgccc ctctccaatt gcttctcctt ccccatctct   53460
accaagatag cctctaatga cttcctgctt attctcttta gttttcccag cactcatgaa   53520
cattgcccta aatatttaat tttggcaatt tgagcagcaa gcacgaatct agcaaggaaa   53580
```

```
agggcaacaa tgctgctgtt aattaaagcc aaacagccct agtctggctt taccttctcc     53640
aggctttctg gatcccttct agagaagtta atttgcaatg tcatgagtga atactgggct     53700
cctcacaact gaa                                                        53713

<210> SEQ ID NO 64
<211> LENGTH: 49663
<212> TYPE: DNA
<213> ORGANISM: Homo sapiens

<400> SEQUENCE: 64
cctcatggag cttacattct gatggtagag agacaagaaa acaaaataga tagtgtatta       60
ttgaaggtga tgagagctct ggagaaaaag taggaaaaga gacagatctg ggacaagggc      120
gaaattacag tatcaaagat gatcttttta gggaagatct ccttttaaaa acactttgga      180
acaaagattt aaatgaggtg ccagaggggt agcaagtgca tattccctga ggaagacgcc      240
tgcctggcat tttcaaggaa cagccagtaa ccaatgttta tctacgtaag taaggaaggg      300
agaacagtag gatgagagtt cagagaagag ggtaggggat atcaaataat ttaaggccat      360
gtaggatttt tgagaagaat tttgctttta tgtcaagtgg aatgagggcc actgatgatc      420
tgggagtaga gtgactatga tccgacatga agtatactcc attttttaac tatgtgaact      480
tgtgccaacg ttttaacctc taaatctgtt tcgtcatttg taaaacggta aaaagtattt      540
tacctcataa ggttgtcgtg atgattaaat aagatgatac gataagtgca aaagatttag      600
cttgtactta acatagagta ggcacatttt ctcccttcc ctgtctttca cttttctctt       660
ctgccccttc cacctggcgc taggagggggg agactgaat aaaccttgca gattacagcc      720
cgtgtaagag tagaaaggaa aggatgacag ttgatgtaaa gccttggtta acagacataa      780
tagctgggat ttaaattcag ctttattggt ggtttatgat gtggactaga ggaatggaac      840
tgaaagtctc ggaggagggg cgatcctatc aggtacaggc gctgctttc cagccctcaa       900 tcctcaagac tctcccaaga tacatttcta ggtagtttat caacacagac tccgggtatg      960
ctagcatgtt taattgcccc attgtttaat gtcttaactc cacgaacttt aactgattaa     1020
tctgtcttct aattaatgtt tgaatgactc tcctcaggtc taaactacca aggccatctc     1080
tacttaaaaa cagttgtctt ttgtttgtga tttcaggggc cctgggtata agcgaagtcc     1140
ctgtttagag accttgtgat gggttcaaaa tatcaagaaa gatagcaaaa tatcacaagc     1200
ctcctgaccc gagaagatta gcgttgaaag ggtctgtcgt gtttgtttgg gcctggggct     1260
aaattcccag cccaagtgct gaggctgata ataatcgggg cggcgatcag acagccccgg     1320
tgtgggaaat cgtccgcccg gtctccctaa gtccccgaag tcgcctccca cttttggtga     1380
ctgcttgttt atttacatgc agtcaatgat agtaaatgga tgcgcgccag tataggccga     1440
ccctgagggt ggcggggtgc tcttcgcagc ttctctgtgg agaccggtca gcggggcggc     1500
gtggccgctc gcggcgtctc cctggtggca tccgcacagc ccgccgcggt ccggtcccgc     1560
tccgggtcag aattggcggc tgcggggaca gccttgcggc taggcagggg gcgggccgcc     1620
gcgtgggtcc ggcagtccct cctcccgcca aggcgccgcc cagacccgct ctccagccgg     1680
cccggctcgc cacccctagac cgcccagcc acccccttcct ccgccggccc ggcccccgct    1740
cctcccccgc cggcccggcc cggccccctc cttctccccg ccggcgctcg ctgcctcccc     1800
ctcttccctc ttcccacacc gccctcagcc gctccctctc gtacgccgt ctgaagaaga      1860 atcgagcgcg gaacgcatcg atagctctgc cctctgcgc cgcccggccc cgaactcatc      1920
ggtgtgctcg gagctcgatt ttcctaggcg gcggccgcgg cggcggaggc agcagcggcg     1980
```

```
gcggcagtgg cggcggcgaa ggtggcggcg gctcggccag tactcccggc ccccgccatt   2040
tcggactggg agcgagcgcg gcgcaggcac tgaaggcggc ggcggggcca gaggctcagc   2100
ggctcccagg tgcgggagag aggtacggag cggaccaccc ctcctgggcc cctgcccggg   2160
tcccgaccct ctttgccggc gccggcgggg ccggcggcg agtgaatgaa ttaggggtcc    2220
ccggaggggc gggtgggggg cgcgggcgcg gggtcggggc gggctggggtg agaggggtct  2280 gcagggggga ggcgcgcgga cgcggcggcg cggggagtga ggaatgggcg gtgcggggct   2340
gaggagggtg aggctggagg cggtcgccgc tggtgctgct tcctggacgg ggaacccctt   2400
ccttcctcct ccccgagagc cgcggctgga ggcttctggg gagaaactcg ggccgggccg   2460
gctgcccctc ggagcggtgg ggtgcggtgg aggttactcc cgcggcgccc cggcctcccc   2520 tcccctctc cccgctcccg cacctcttgc ctccctttcc agcactcggc tgcctcggtc    2580
cagccttccc tgctgcattt ggcatctcta ggacgaaggt ataaacttct ccctcgagcg   2640
caggctggac ggatagtggt ccttttccgt gtgaggggga tgtgtgagta agaggggagg   2700
tcacgttttg aagagcata ggaaagtgct tagagaccac tgtttgaggt tattgtgttt    2760
ggaaaaaaat gcatctgcct ccgagttcct gaatgctccc ctcccccatg tatgggctgt   2820
gacattgctg tggccacaaa ggaggaggtg gaggtagaga tggtggaaga acaggtggcc   2880
aacaccctac acgtagagcc tgtgacctac agtgaaaagg aaaaagttaa tcccagatgg   2940
tctgttttgc ttggtcaagt taaacccgaa gaaaacccgc agagcagaag caaggctttt   3000
tccttgctag ttgagtgtag acagcaatag caaaaatagt acttgaagtt taatttacct   3060
gttcttgtcc tttcccctat ttcttatgta ttaccctcat cccctcgtct cttttatact   3120
accctcattt tgcagatgtg ttctacatct caagagttat tacagtactc caaaacagca   3180
cttacatgat tttttaaact tacagaggaa ttgtagcaat ccaccagcta accgcctgaa   3240
atagacttaa acatgtgcat ctcctttttt tttttttttt tgagacacag tctcgctctg   3300
ttgcccaggc tggagtgcaa tggcgcgta tcggctcact gaaacctccg cctcctgggt    3360
tcaagcaatt ctcctgcctc agcctcccga gtagctggga ctagtaggtg cacgccacca   3420
tgcccagcta attttgtat ttttagtaga gacagagttt catcatgttg gtcaggatgg    3480
tctccatctg ctctgttgcc caggctggag tgcagtggcg ccgtctcggc tcactgcaac   3540
ctctgcctcc tgcattcaag caattctcct gcctcagcct cccgaataac tgggattaca   3600
ggtgtctgct gccatgcccg gctaatttttt tgtattttta gtagagacgg ggtttcacc   3660 atgttggtca ggctggtcta gaactcctga cctcgtgatc tgcccgcctc ggcctcccac   3720
agtggcatgt gcatcttata gctgaagtct aagccttctt aaatcttgag atccatcaaa   3780
acagacaggt tttctaattg ttatacaatg tatatgttat gtttataata gaaatcattt   3840
tacaaataag ttataaatgg gaaaggtcta tttgtaatta tcagctcaga attaaccata   3900
aaactggtgt cactgaagtg actgaggtcc aaaatgctga ctctgcatgt tatagactac   3960
agatatcaaa tatggttgct aacaatagtt tactttgaga ctgtagccat ccacagtata   4020
tttgctttta agagatggta gatggtaatt cagtttatg aaaaataaaa atgaattttc     4080
ttccattaca aaattgttgg attcgagtcc agtccactcc ttactagctt ttctaactct   4140
cggtgaggga tcccctccca gcccatgatc ttcatttggt aagactcctt tggaacccag   4200
ttctctctag tggatttaaa tgtgatttgg ttttaaaaat ctcattcaag gaatttttt    4260 tttttctgga aacaaccacc gcataaacaa gtaaaccgga agatacatgt ggctctgaat   4320
```

```
tcatatatat acacaaactc taatccaatg tctgtccaca gtatttccta ggctagtaaa    4380 cttttttggcc ttaacgaccc ctctaccctc tttgtttttt tgagagagag agtctcactc   4440
tgtcacccag gccggaatgc agtggcgcga tctcggcccg ctactacctc cgactctcag    4500
gctcaagcga ttctcccgcc tcagcttccc gagtagccgg gattacaggc tcccgccacc    4560
gggctaattg tattttaga tacgggattt caccatgttg gccaggctgg tctcgacctc     4620
ctgacctcag gtgatccgcc cgcctaagcc tcccaaagtg ctgggattac aggcaccac     4680 acccggccta cactcttaaa aattatcgaa ggggccgggc acattggctc ttatctgtaa    4740
tcccagcact tgggagact gaggcgggag gatcgcttga ggccaggagt tggagaccag     4800
cgtactcaac atagtgagac cttgttataa agaaaaaaaa aatccaggat taaaaaaaat    4860
ctttgatttg tttgggattt attaatattt accgtattgg aaattaaaac aatttttaaa    4920
aatgtattca tttaaaaata ataagcccat tacttggtaa catgaataaa atattttatg    4980
aaaaataact attttccaaa acaaaaccaa aacttagaaa agtggtattg tttcacactt    5040
cagtaaatct ctttaatgat gtggcttaat agaagatatg gattcttata tctgcatctg    5100
cattcaatct attatgatca cacatctgga aaacttgtga aagaatggga gttaaaaggg    5160
taaaggacat cttaatgtta ttatgaaaac agttttgacc tcttgcacac cagaaaagtc    5220 ttagtaaccct gaggggttcc tagaccacat tttgagaact gttttaggct atgcaaactg    5280
gttgggggga ggttggggta ggcagagagc tagaagatac attttagtgt aattctcctc    5340
atctattcct aattgctttg gcctacattt gaaataaagc gtggaggcaa acgggataag    5400
atacatgttt gtagtggttg ttaacttcac cctagacaag cagccaataa gtctaggtag    5460
agcagagtaa ggcggggaac tatgccgtga ccgtgtgtga tacaattttt ctagcctgtg    5520 gtgcttttg cggcagggct taggagtaag gttagtatgt tatcatttgg gaaaccaaat    5580
tattattttg ggtcttcagt caattatgat gctgtgtata tttagtgttt atctacaata    5640
tatgcacatt cattaatttg gagctactca tcctataata aatagttgtg catttactcc    5700
catttttttc tgcatttctc tccttattta taattatgtg ttacatgagg gaaaggaggt    5760
gaaattaaac attcatatta tttcaaaaaa tttgaaacaa ctaactaaaa aatatgtttt    5820
attttctgta tggtgtttgt tatacaatct gtcaatattc atgcacctct tgggagacag    5880
tgtatgaaaa gcaaagagta acagtcacat ggattactga ttactgagat atattccactt   5940 gcatcttttt tttttttgga gacggagtgg ctctgtcgcc caggctggag tgcagtggcg    6000
tgatctcggc tcactgcaag ctccgcctcc tgggttcacg ccattcttct gcctcagcct    6060
cccaagtagc tgggactaca ggcgcccgcc accacgcccg gctaattttt ttatattttt    6120
agtagagacg ggtttcacc gggttagcca ggatggtctt gatctcctga cctcgtgatc     6180
caccctcctc ggcctcccaa agtgctagga ttataggcgt gagccaccgt gcccggctca    6240
cttgcatctc ttaacagctg ttttcttact aaaaacagtg tttatctcta atcttttgt     6300 ttgtttgttt gttttgagat ggagtcttac tccgtcaccc aatctggagt gcagtggcgt    6360
gatctgggct cactgcaacc tctgcctccc gggttcaagt gattctcctt cctcagcctc    6420
cccagtagct aggactacag gagagcgcca ccacgcctga ttaattttg tatttttagt     6480 agagagaggg tttcaccata ttggccaggc tggtcttgaa ctcctggcct caggtgatcc    6540
acccgccttg gcctcgaaa gtgctgggat tacaggcatg agccgccgca cccggctttc     6600 taatcttat cttttttgt gcagcggtga tacaggatta tgtattgtac tgaacagtta      6660
attcggagtt ctcttggttt ttagctttat tttccccaga gattttttt tttttttttt    6720
```

```
tttttgagac ggagtcttgc tctatcgcca ggctggagtg cagtggcgcc atctcggctc    6780
attgcaacct cggactccta ttttccccag agatatttca cacattaaaa tgtcgtcaaa    6840
tattgttctt ctttgcctca gtgtttaaat ttttatttcc ccatgacaca atccagcttt    6900
atttgacact cattctctca actctcatct gattcttact gttaatattt atccaagaga    6960
actactgcca tgatgcttta aaagtttttc tgtagctgtt gcatattgac ttctaacact    7020
tagaggtggg ggtccactag gaaaactgta acaataagag tggagatagc tgtcagcaac    7080
ttttgtgagg gtgtgctaca gggtgtagag cactgtgaag tctctacatg agtgaagtca    7140
tgatatgatc ctttgagagc ctttagccgc cgcagaacag cagtctggct atttagatag    7200
aacaacttga ttttaagata aagaactgt ctatgtagca tttatgcatt tttcttaagc    7260
gtcgatggag gagtttgtaa atgaagtaca gttcattacg atacacgtct gcagtcaact    7320
ggaattttca tgattgaatt ttgtaaggta ttttgaaata attttcata taaaggtgag    7380 tttgtattaa aaggtactgg tggagtattt gatagtgtat taaccttatg tgtgacatgt    7440
tctaatatag tcacattttc attattttta ttataaggcc tgctgaaaat gactgaatat    7500
aaacttgtgg tagttggagc tggtggcgta ggcaagagtg ccttgacgat acagctaatt    7560
cagaatcatt ttgtggacga atatgatcca acaatagagg taaatcttgt tttaatatgc    7620
atattactgg tgcaggacca ttctttgata cagataaagg tttctctgac cattttcatg    7680
agtacttatt acaagataat tatgctgaaa gttaagttat ctgaaatgta ccttgggttt    7740
caagttatat gtaaccatta atatgggaac tttactttcc ttgggagtat gtcagggtcc    7800
atgatgttca ctctctgtgc attttgattg gaagtgtatt tcagagtttc gtgagagggt    7860
agaaatttgt atcctatctg gacctaaaag acaatctttt tattgtaact tttattttta    7920
tgggtttctt ggtattgtga catcatatgt aaaggttaga tttaattgta ctagtgaaat    7980
ataattgttt gatggttgat tttttaaac ttcatcagca gtattttcct atcttcttct    8040
caacattaga gaacctacaa ctaccggata aattttacaa aatgaattat ttgcctaagg    8100
tgtggtttat ataaaggtac tattaccaac tttaccttg ctttgttgtc atttttaaat    8160
ttactcaagg aaatactagg atttaaaaaa aaattccttg agtaaattta aattgttatc    8220 atgttttga ggattatttt cagattttt tagtttaatg aaaatttacc aaagtaaaga    8280
ccagcagcag aatgataagt aaagacctgt aagcacactt gaaggtcatg gagtagaact    8340
tccatcccaa gcagatgagg atttatttaa tctcaaagac ctccaggagg ggacattccc    8400
caactgtcct tgttaactca ttttcagaac atatttatta gcatatttta catgtaattt    8460
ggatcttcat gttaaattta acatcagtgg agatggaaaa taagcatatc gccttgtctt    8520
tgaaatagcc ctatattgtt agattgtttc ttaggcttct ttaccctggg ttaagcagtc    8580
ctaatacttt agcatttatt ctacatctag tgtactaatt taaaaaaatc agttctgaaa    8640
aatttctaag aactttcttc aagttccaag ctgtgaaatc tagaacaggt caaagtgcct    8700
tattaacgta ctgtactgtg tagtgtcttg aagagacact ttgcgctgag gcaagttctg    8760
agggcattgg gtggccttgg gaagatattt atgcagttta gaacctggag aattgattag    8820
ataactaatc ataaggaaac gtcacatatt tttggtacta taaaaaagtg gagaaataat    8880
gcctatttgc aaagatttga tttaaacata gaaacaactt tatttggctt ccaattttaa    8940
gaatttacag cagtaaaggg gaacagtcta attgaagtag actgcctatg caatagtctc    9000
tgtatattta cttttgacaa gttaattcaa tgtgtactat agttttgttt ctttgaagag    9060
```

```
gtttgaatag tgcacccatt ttaatctgta ttgcaaattc agggttactt ggcagactct   9120
actatttaaa tcagatgtaa aaggaagttt taatataatt cactttatgc ctgaaagttt   9180
tcctgggatt ttggaaggtg attttactgg aaatgctgtc tgtcttccct gaaaatctga   9240
gaaattccat tacactttgt ttccaatcag aggtcatgag tgctatatga gtatatacag   9300
catgacgtca tgaatgtgat aaagtgggtt aggaaacctt ttgctaatga ttgttaaaat   9360
gcaatataaa tgttgaagaa ataaagctaa cagttaagcc tttatttggg cggaaggctg   9420
aaaaagttta taaacttaaa cctataactc tgcttatgat ttctgccaaa ccagaagact   9480
tgactctggg aagcattggt tacctgtgaa ctttgaaact gacggtccct gacgtagttt   9540
agtcacctgg gaaaaggtat ctgagattat ctcttatctc ccaagttaca gtgagtctct   9600
gagggaactg acacattaca ttaagttctt ggtgtagtta aactgtaaga aaggcaggag   9660
aacttagtag ttaaatagtt ggttaaatgg aaatgctgac tccatgttat tgtaaaaagt   9720
taaaaattta ggaggatatg gggatttcac tgccattgca ggttttgatt ggtatttacc   9780
aatccgtgtg ggtcagagag aaaattagaa aggatatgac tgcacatttt ggaattatta   9840 gcagttttc tacatttaaa atggaaataa attttttaaa aatttaaatc aagtaatact    9900 gtatttttg gtgatttaga tttttcaaaa tttacactaa gagatagtaa ggagggtggc    9960
tattgtttct ttcaataatg tctctgagag gttgtaactc atctaaggat acgtagctaa  10020
taagtggtag gatttcaatt taaattctct gagaccaagt taagtagaat ttgcactgta  10080
ctcttgtata acttttaaa actgaaaatt agctatcttt caaattaaga aaatatttac   10140
taatggagac taattcagat ttgtaagtat accaaaattt gaacttagcc tgctatctaa  10200
tggcaactta gtggcagagg tatgatgtaa aatcattcag gtatgacaca tagatggagt  10260
atgtttgtat tcgaggctgt gcacataatc acctttactt gtattgtgaa gtatatattg  10320
ttatctttta tgaagcccac taaagagata atgaaatacc tcgttattag ggcaagatta  10380
ttgaaaactc aaaatagccc ccaaacacaa tacttggcta gaaatatata cctttatagt  10440
tcagagatca tttattatca aaaccctgaa gttttttttc taaggtaaaa tttggtggaa  10500
gaggaaaagt ctcgttttaa aaaaatgtag gtagttacag agatcagaat gattagttga  10560
tcacttacca aatatatatt aagtatctac tgtatataat atgctagtaa gaataaatat  10620
agcaggaagt attttttccc aggctctaat tgtttgacat cagcatgctt ttattgtggc  10680
acttataatt cagttcaagt attatgcccc tctttgatgg aacagtttcc tattcagtaa  10740
ggaagaccag attaatcatt ggattggttt gtttcatctt tagtgttctg agctgtagag  10800
tatttattta ccaaggttta ttttaatttt tattttattt ttattttttcc atgttcattg  10860 tagaattcat tttacctacg aatgaagtat gtagattata gagagaaaat ttgtaaaatt  10920
aaactgatac tgaagactgg tataagaaaa gccttatgta atttgtaagc tgctattctt  10980
ctgagtttat acatatatct ttagtaatca atgagggatg gttgggtgac tgccctccag  11040
gggacatttg gcaacatctg gagatgtttt tggttgccac aacttgggga gagagtactg  11100
ctactggcat ctattgagta gatgctatta ctttaaatgg caaagctgca gttacctttg  11160
caccaaccta atattaaact tcctgcagtg cacgggaaag cccccacaac agggttatct  11220
gaccccaaac ctcaatggtg ttaagatcca aaccttgata tgttaacctg tagctttaaa  11280
catcctttaa attgtcaaat tcatgtccct gacataaggt ttatgttaga ttttcaagta  11340
taacaaagat ttaaacttta acttttgtac gttaatgata tgttagctta ctccagtctt  11400
ctattaaaac attctgtttt taaaatcaga gacacacagc aatttttataa atcatttctc  11460
```

```
ttcaaggctg tgaagctctc cccactttg tgagtgccct ctactggtca aattatttgc    11520
tttataacaa gtaacagtga aatcctaagt ttgtgtagtt tcgctgttta aattatgggt    11580
ggcatcaatt tataaatata ttcgttttat ttaaaagtct tatatgattg atttcgtatc    11640
atttttgctc tctgctaata ttaatataaa gattactgtc tgtattagtt aggcctaact    11700
aagtaggtga gtatagtgaa ctaagaaagg aaacgaggca gtatataaga aaatagggtg    11760
gttcagttgt taacacttac tgagcttact ttgttgaagg gactaaaagg cagcagtgtg    11820
gctctctgag cttctttgca tgcactcagg agctgcttaa tggagtccaa ggcttggtgg    11880
tgtgttacag gggatgatag gagggtccta ttcagaagtg gcaaattgtg aaagtgcaca    11940
ttttgtagag ttttatagga ctgtagaata gttgtgagca cctgatttt agaataaaca    12000
gaaaactcag gtactgtatt taggtcaaat taagaataag tatttattaa gacctgaata    12060
taaaacttta ctggtcatgg ttttttcta ccttgggttt ttataaatcc aaagatttaa    12120
aaacatacaa atggaagttg gtaatggaat taagtgaaag gaaaaaatga ttttatggtt    12180
tggaatctcc taagattctg gttttaacaa tacaactaat tccttaatcc tagaaatgtt    12240
cttcactgcc cactttgtac catgcagtct tcctgtgggc tagagataca ctgaggcgca    12300
aaacagacca gattcctgcc ttcatggagc ttattagttt taggtatctc tagatttctt    12360
gtaataccta ttacaatgcc tgcacatcag ttcattcatg tgggttcaac gtagtactca    12420
gtacatggca aattcaagtt ttacttttcg gaacttcatg gattttttc ctcagaatat    12480
cttttatcca taattggttg aatctgtaga tgcagtaccc atggatatgg atggcccact    12540
ttatttgaa gagcagtgtt tctaggcaat catgctaatt atatatgact taatttagag    12600
gcttatact taagagcatt acatttctgg cgtctcttaa ccattattat ttcataatgt    12660
gtaggttatg gaacagttaa attattggga tcttaatata gaaattagta gaaataagcc    12720
agatatggtg gctcatgcct gtaatctag cactttggga ggctgaggct attcgctgta    12780
ctatttttta ctacttttct ataggtttga aattttttca aaataaaaca ttgaaaaaag    12840
taaggtaggt agtgtgtccc tccttaatcc tttcaaatat tttattttca ctatttctat    12900
taatttttt ttttgttttt gagatggagt ctcgctctgt tgcccaggct ggagtgcagt    12960
ggcgcgatct tggctcactg cagcctccac ctcctgggtt ccagccattc tcctgcctca    13020
gcctcctggg tagctggtat tacaggcatg caccaccaca cccaattact ttttgtattt    13080
ttagtagaga cggggtttca ccatgttggc caggctagtc tcgaactcct gacctcgtga    13140
tctgcccgcc tcagcagtgt cactgcttct agaccgtttt caaggcacag agcttagaaa    13200
tgcatgttac taagaaatca agagttaact attttccacc ttctttctcc cgcagtgaga    13260
accctggttc taccctgttt ctccttgtgt aaatttaat gctaaactat acacttgtga    13320
aataaaaatg ataatgtcat tcttaaatta tggatcttgc agtgttatct aagtaacata    13380
gattgagtga tttaacttta ggtttcctta tttgtggaat ttggataaat attttcacc    13440
cttgagaaaa gtgagactcc tttctcatca tcagagtatc cttaaaccat taaggcaaac    13500
atttgggaaa aaactgagct atctggctgc ataaaaatta gtttctttt aacaaagata    13560
gaagacaaat gaaaacctag aaaaaccatt tggttcaagt aacaggaagc tatcttatat    13620
atgaattaga gaaaagcaaa cacacaaata gaaaaaaagg gatgggggt actaaagata    13680
taaatagctt gtctaccaaa aagaaataa aataaataac atgaacatat aaaaagacac    13740
ttacttcatg aatgtgatgc aagttcaaac aataaataac atttctgtac tttcatattg    13800
```

```
gctaaggtta aaatgataac tgctaggaag ggtatggaga agtgtgcgcc ttgcactgta   13860
gtgggagtat agaccctcag actttatgga ggtcagtctg gaaatatgtt tcaaaatgta   13920
aactacatgt cctttgacca ggtaattcaa cttcttgaaa tttatccaag gatttaattg   13980
gataaatgtt taagatgtat atataagaat gtttactgca gtgttgttta tgattttaaa   14040
aaaatggaaa tcatcttcat gtctaccaat agagaatggg tgaataaatt atggtatgtc   14100
catatataca aattacatag ttgttggaaa tattaggtag atttagatat actgatgttc   14160
aaaaatgtcc attatgtaag tgaagctggg tcacagcacc ttgtgttgag tatgatttca   14220
tctagaaaca aaattactcc ctcatccttt gttgtgtttt agttttttaa aataagctta   14280
taccattggg ctgggggaaa agtaaatact cgttttggag agagaaaagg gcactaaagt   14340
ttcagatacc gttagattat ttcatgctta tttttcaagc ctcaataaat tacataattc   14400
acatgtagtc ttggattaag gaaattgcta ttaaggctaa ataataata tgagaggtat   14460 ataatataaa atatgaacat tatattggca ttaagattgg atccacggtc attccagcct   14520
ctcattctta cctggacttc aagtgatcac ttgtgggcaa atgccatctg acttgaacag   14580
gttacacatg tatgctcatt atatcgttat tttcaaaatt tgtcatataa attttccttg   14640
agttcattca gattttgaa ctagtttttt ctcttgggag tagtacacac ttaattctct   14700
ctagtactaa gctaatgttc accattctta taattttaag tatccagcat ttagtaaaga   14760
agtctttgtt ttctttatcc ttacttttag tgaatgtctt agtttttaat tgaaaattct   14820
gccatgaaaa taagctcttt aacatcttca ctccctaatc aaaacagaaa tccttcatag   14880
ccttcagttg tagctatcct tccctgtgat ttgtccagct ccattatatt tattttgaaa   14940
tatggtgacc agttttgcaa aattattca actgtaggtg cccagtgatt ttgtaaggag   15000
aagatactgt ttctgaacag ttctcagtag ccagtggcct gcccctactt tttggcctgc   15060
gtgtagtata taaaataatg cagttaactt tttatagcac ttttcatttt ataaagagat   15120
tttcatggtc tttaatatta atctatgtat aaagtcctgt atgcagtttt acctactttc   15180
acagctgaag gaacaatagc ttagagaaga tgtgagataa agtagtttgc ccaagcccat   15240
agcacaaata agtgaagttc ttcggctgtc catggatcga agactcccaa gtctatctct   15300
agcctggact tctgtcctga gcaccagaca tgtatgtata tcaagatgcc tgcaggtcat   15360
atccaccagg acaacccatg agtacaggga attcaacatg cccaatatca ctcatctttt   15420
ccttcgccct ccccttttgta ctcatcccct gtcggtaagc tctgttattt taaaaaattg   15480
aaatgtattc acatagcata caatttacac ttttcaagtg tacatggttt ttagtatatt   15540
cacaagggtt gtgcagtcat tactactaat tccagaatgt tattatcacc ccaaaagtcc   15600
cacatccatt agcagccact ccccaatccc ttctcccacc agcctctaaa aactgctaat   15660
ttttccatct ctgtggattt gtccactctg attatttcat ataaagagaa tcgtacagac   15720 gtggccttt gtgtctggca tcctccacac aggatgatat tttcagagtt cgtctatgtt   15780
tttgcttgtt gatcattcct tcattccttt ttctggctga ataatactct gttatatgga   15840
tataccttat tttgtttatc tgttcatttg atgggcattt gagtgatttc ctcttttttgg   15900 caattttgaa taatgccact ataaacattt atgtacacgt ttttgtgtga ccatatgttt   15960
tcacttctct cgggtgtata tctaaggtac agttgctggg ttatatggta gctctgtctt   16020 tgacttttg aggaactgcc aagtggtttt ggtagtgatt gtactgttta cattcctacc   16080
aacaatttta cctaagtatt tctcaaatct atttaatctt ttcggtccat actgctgttg   16140
ctgccttagt tcagattttg tcatttcttg taataattcg tagctcatct cccagtctct   16200
```

```
gctcccctct ctccctccct ccccttctt ctctctctta tttccaccca tttttaacat   16260
ttatagaagt caaaagtcta gttcagaaag cagaaaccac actagatatt tcagcacaga   16320
gaactaatta ggtgttggaa gactgaaagg caaaaaaaca ctgaagtaac acagtaacat   16380
caagaatggg cactactcct aagattcagg gaatgctggg aagatttggg gtttatcaga   16440
actggaagct cagaggaggg gcccttgtc gctgaggctt aatccctgca gaggtgcctt   16500
tggctgctac tggtgaatct gagtgggtat ggatgagtca gtgtctggga agggccaaaa   16560
cattttgtcc ctttctataa tttgtcatga taatgctagt aatgaatctg atctcccttc   16620 ctatttaaa aaccttttag tgattttgta taggatgaag tttaaaactc cttacttaat   16680
atacacatga ccctccgtaa gctggcccct gcttgattgt ccagtttcac ttcttggtgc   16740
ttattctaag gcctctaagc cttagagatc ctctaagcct ttgagatccc caaaccctgg   16800
actgcggact ggtacccacc tgtgtggcct gtgaggaact gggctgcaca gccggaagga   16860
ggtgagcatt acttgcctta gctcctgtca gatcggcagc attagattct aataggagcg   16920
tgaaccgtgt tgtgaactgc ccatgcaagg atctaggttg catactcctt aggagaatct   16980
aactaatgct tgatggtctg aggtgaaaca gtttcatcct gaaatcaccc ccaactcggt   17040
ccttggaaaa attgtcttcc acgaaactgg tccctgatgc cggaaaagtt ggggaccgct   17100
gttctaagct aaagttatat ggagctcctt ggttctgtgt cctcaacatg ctgttctatg   17160 tttttacat tctgtttgct ccttcctgct tggaatgtcc ttcccctccc cgtctttctt   17220
aatgcataca aagttgatct ctcctgtgtg ccaccattgt acttcgtctt gcatatggtg   17280
ttacattcat tttatttaa ttatttattt acgttcatgt ctcttccact caccttagtt   17340
gcttgaggtc agaaactata taatgtgtga cacggaatgt gacacctaga ttttcaataa   17400
gtgtttctat gatacaaggg agactgatgt gggtagatgg gaatgaactc atcaacctct   17460
gtttacatac cctaaattcc ctgtttcttc cctattataa ttctgacagt ctacaacagt   17520
ctttgatggc ttataaacgg aaagtgcgga acacatcatt ctacagtgaa tttaaataac   17580
ctttcggaag agtaacgtaa agtacttgag cattaattga gtaaaagttt ctcatctttt   17640
cctacaggtg ttattaagca gtatgtaaaa agtccttaca atacttaata cattaagaaa   17700
acatacaatt tcaagaggaa atccccgagt aatacattat tgacattttc agcagttcta   17760
gttatattga gaagagcatc tcatggaatt ggcagaatga agatggagat taatgagat   17820 gatgtttgta atatgcttat gacagtatct ggcatataag taagggctca gtaaatgttg   17880
actgctgtaa ttactattaa tagtaatatg attaccttta gtaaaagtta ttagtttctt   17940 taggttttt gtttactaca atatagtaaa caaaatctat acttggaatg tatatattgt   18000 tttgtttga tacatggaat atgtctctgt gtcagagtca ctgcctgagt tggaaaaccc   18060
atactcgagt atgttaaaag gtgaacacac tgaataattt agttattaat tataatggaa   18120
aaatgacaaa cttgatgttc tggttaatga ggttatctta tcttgaatga gttagctttt   18180
aaattcctca aaataaaggc atttaataaa ccaggaaaca cttcattaaa aaaattatgc   18240
aagtcagtgt aaaagaagat taaaattcca catgggcaaa ggacacacgt tggcgataaa   18300
tatgcagata agaaaaaaaa cctatataac attattactc ctcaaagaaa ttggtatgaa   18360
aacaataaaa atgtgtagct tatcaaacca acaaaaattt aaaaatatga aatccatttt   18420
aagtaatgat aaaatgggtg cactcttagt gctttataga atagtagtat aatgaacctc   18480
atgtgtgtac caaccagctc tttcatatct taacatttag caacatttga tttagctctt   18540
```

```
tcttttttcc aagatagaaa agttaatatt gttgaagact cctgcattct tttccctagt    18600
cttattttct tccctcccat aaatgtgtta aaatctctgt gtgtattgtt ttggttgtat    18660
ttttacataa aactttacat attatataaa atttaattga aggtaaaatt tattaaatta    18720
ttcttaatat atattgtaat ttaaaaatta acagcttcat tgtcttgata aaatttatgg    18780
tatcttaaac atgtgcttgt ttttctaaga gaacattgaa acatagattt taaaacaaat    18840
tgttgaaaga ttaaaaaatc tgcctttgca cactgttaca ttgaaagtgg ggcatttgtc    18900
gtgaacattc atttcaaata tgtagtatct tcagaatatt tgagaaggat ttgtattata    18960
taattgaaaa atctgttaaa ttgtatttat gttaactgct taattctaat aaaatttcca    19020
ttcattttt agtatctgca tatatttaca tcaaatggat tcattcactt atttaagagg     19080
cagtactaat tacctatagc gttcaagact gttaggtaga gggtgtgtag tggtgagtac    19140
aacaggcgtg agccctacca acacggagtt taaagcctag tagaggatat agacttaaac    19200
aatttcacaa gtaaatacat aattacaaat tataatacat gctatgaagg aaacatagga    19260
ggtaccagag aaggaagagt gctttgcatt tttatttta agaccgaaga gtgctattgg     19320
aggactttga gcaagtgaat gacatgatct aacctacctt cgttcattca ttcattcatt    19380
cattttcttc cttcctggct caagcagtcc tcccacctga gctccccaaa tagctgggac    19440
tacaggtaca cactaccaca cctaattttt ttttgtattt tttgtatttt tgatgggatt    19500
ttaccatgtt ggccaggctg gtcttgaact cttgacctca ggtgatccac ctgtctcggc    19560
ctcccaaggt gttgggatta taggtgccta gcccatggtg cctagcccta acctacattt    19620
ataaactatc acttgctgct gtgtggagac tatattgtga gattaacagc agggatacct    19680
gctaggaagc aattgctgca gattgcctga gacaaaatag ttatcatgga ctaggggat    19740
ggtgttggtg gtggtggtag gtggttggat gtaggatata ttttgaagat aggtaaatgg    19800
tgcaagatta tgggtcagtt ttaaatgctt aagtaaattt tctttgtaag acattttagg    19860
atgccatgtt aagaatctct ttataactgt catttaaaaa aaaaccacat attttcttag    19920
cataatttcc catagtaaca ttactatgtc aaaggctatg aacatttgaa tgactttaga    19980
taaatactgt aattgctttc caaaatatt gtgcttatta tgtcaccaga aatgtttgaa     20040
ttctgtctac aattcagtct tgccagtata gtacatttca tttagaaaaa ttttttacta    20100
tgtagatgga aaaataata ttttagctgg gagtgggggg actatgggga ataactttcc     20160
ttcattaat attttattgt gagttagttt aagttacttt attttatcgt agtttcctaa     20220
ggctacaaat tagtaacctt ggtaacttat gtacctaatt taaaagttta ctttttttgaa   20280
aggctggaaa tactaattaa aaacgtaaca ccttcatcct tgtctttgct ccattattaa    20340
ctagtttcat tacagaatct ctgtgtttta aaatcagatg ggttttcata accagtactt    20400
tctcagagtg gtaaatttaa aaaatatat aaagagaata ataatatttt gttgagaata     20460
cttcaaataa tgtgaagagt tattaactta cagcaggagt tggcaaactt ttctataaag    20520
ggccatatgg gtctttgtca caaagtcttg ggttttttgtt tttgtttttt taaacagcta   20580
tttaactatt cctagctaat gggcaataca aaaacagtgg gcaagatttg gcctgtgggc    20640
agtagcttgc tgaaaccctta tttagactct aaatttttg aaagagtcta cattgatgca    20700
tattttttt tcttcctcca aatacagttg acccttgaac aacatgcgtt tgagtgacca    20760
tgggtccact tgtgatacac gttttttttcc caaccaaatg cagatatgga gggctgactt    20820
ttcatatacc tggatgttcc tgggccaact gtaggactag aggctggggg gggtcttgga    20880
accaatgccg tgtgtatacc agggatgact gtttcttatg gcctgacctg aagttggaac    20940
```

```
agaatcttta ttaatatata attttttgttg cgtttgtttt ctctttatat ttatccattc   21000
tttttagatc gtatttcatt taacactttt tcttctttag ttttaccaa gttgcactga    21060 aaatagctca gtgactaatt gcacttctaa gagtgaggac cctagttaaa attaactcta   21120
aaaatactga attttaacc taaaccttt gtttctaatc aacagtatta tttatgagta     21180
ggttatagat tactttgaaa cggaatgtgt ctcagaactt tgctatcgat attttaagg    21240 tctggtaggg aaaagataat aggaatgaga tttatcagtg aatagggac tgctttccca    21300 gtttctcggt cgcactggtg tattcaccat ggaagcatct tatgaaatat gtacataaac   21360
tactaatatc ccacattaca ggttgactat tctttatctg aaatgcttag gacctagaag   21420
tatttttgga ttttggtttt tcagagtagg gatactcagc ctacattggt aagtaaagaa   21480
tgtgaggtga caggctgggc gcgatggttg acgcctgtaa tcccagcact tgggaggcc    21540 gaggcggatc acctgaggtc aggagttgaa gaccagcctg gccaatctgt actaaaata   21600 caaaaattag ctggacacag tggcacgtgc cagtagtccc agctactcag gaggctgagg   21660
taggagaatc gcttgaacct gggaggcgga ggttgcagtg actcgagatc gtgtcactgc   21720
cctccagcct aggcaacaga gcaagactcc atctcaaaaa aaaaaaaaaa aaaaaaaaa    21780 aagaatgtga ggtggcagca ataggtagga agagtctttg gtcagcttta catgctctgt   21840
agccatgcct gggtaatggg ttgactctaa gactctgtgc tttgctccca cctcctgctt   21900
tttcattact ctttagaatg gttttttaatt tgtgatctat aggagttctt tcaagtattt   21960
aataagagaa taggctaaat taagtaaatg tcaactgaat gctcaaatct ctactaaaga   22020
gcctcttatt tagaaaataa atatccatct ttttttctg actggtgaga taattaattt    22080
ttattacaga tggtttggaa aataccatat gctttaaaag ataagcacaa aattatagtc   22140
taatatgtag gttttcatac tttaaaaaat tgaaaccaa agaaaaacat ttaacatagc    22200
atctagtaca aagaaaagag ataagcaaga gataaatgtc ttttttggga cagagtttg    22260 ctgttgttgc ccaggctgga gtgcaatggc acaatctcag ctcaccgtaa cctccacctc   22320
ccgggttcaa gtgattctcc tgcctcagcc tcccgagtag ctgggattac agtcatgcac   22380
caccaggccc aggtaatttt gtatgtttag tagagatggg gtttctccgt gttggtcagg   22440
ctgatctcaa actcccgacc tcaggtgatc tgcccacctt ggcctcccaa agtgctggga   22500
ttacagacat gagccatcgc acccggccaa gataaatgtc ttttaaatta tctccattaa   22560
agacataacc tttataacat tttgatgtat atattaccag tttttaaaca catagtagat   22620
ttgtataaat acataaacac atattattgt gatcatgctg cacttagaca tctttatatt   22680
ctccttatac tgtaaacatt ttgaaatact ttactaacaa catttgtaat gaccattctt    22740
tctctctttc tccctctgat agaatggtct acagagtaat tcataaacta aacatacttt   22800
agaggctggg cgcagtggct catgcctgta atcccagcac tttgagaggc tgaggcgtgc   22860
agatcacgag gtcaggagtt agagaccagc ctgactaaca tggtgaaacc ccatctctac   22920
taaaaaaaca gtacaaaaat tagccgggcg tggtggcgtg cacctagaat cccagctact   22980
caagaggctg aggcaggaga atcactcgag cccaggaggc agaggttgta gtgagccgag   23040
attgcaccac agcactccag cctgggcgac agagcgagac tccatctcaa aaaaaaaaa    23100 aaaagataca ttaatactat agcctacatg tggaacatta agaaaataat tgcttttatg   23160
tttatgcttt atacctgttg ttagccctgc ttccttatttc atgatttcat ggcttcacat   23220
tgtaacatcc ctttaccata ttttttgagg actgttttgg cagaatgtgt gaaatcttga   23280
```

```
gcagaagtat acccaaaag tcagaagaaa atcagatttt tatttcaaga ttctgttaaa    23340
gttacccact cccttctttt acttaatctt atagttgcag ttctctctct ttttagaaaa    23400
gaaaaagag gcccctcagg atttgcagat gaaacaatat tgctctttag agatatccat    23460
ctggctgtta gattattttt ccacagtttt cagaagtgga tgaggccatt agaatcttga    23520
gtattgccca tttccttatg tgtgcctttg actatagata aaatagatgc atgacaatta    23580
tttataagtt gattgatttt tcttgtcatt taaatcatct tgaataatag agttggtaga    23640
gctatcccat ttttgaaatt attttgtttt gtcaataact ttttgttacc agcatgtaca    23700
cttgcattgt tgactctcca tataatacct ttaaaaaatt ttttttttgtg gtaaaatatg    23760
cataacataa agtttaccat ggtagttttc tttcatttgt tttgttttg ttttttttgag    23820
acggagcctt gctctgttgc caggctggag tgcagtggag cgatcttggc tcactgcaac    23880
ctccgcctcc cgggttcaag caattcccct gcctcagcct cctgagtagc tgggactaca    23940
ggcgcccgcc accacgcccg gctaatattt tgtattttaa tagagatggg gtttcaccat    24000
gttggccagg atgttcttga tctcctgacc tcatgatccg cccacctcgg cctcccaaag    24060
tgttgggatt gcaagtgtga gccaccgcgc ctagaccatg gtagttaatt ttaagtgttc    24120
aattcagtga ccttaagtgt gttcataatg ttgtgcaacc atcaccatgt tgtctaacca    24180
ttagcactat ctgttttgag aacttttttt tatcatccca aattagaatt ctgtacctgt    24240
caaatagtcc ccagtaatcc tccctcccc agccctggt aatctgtagt ctacttttcg    24300
tcttttgaa tttgcctatt ttaggttcct catataagtg gaattatgtg gtatttgtcc    24360
ttttgtgttg gcttacttca tttagcataa tgttttcaag gttcatctgt gttgtagcat    24420
gtatacag gttgaagcat ccgttatcca aaatggttgt gaccagaagt ggtttggatt    24480
tcagatttt ttttttggatt ttggaatatt catagatact taactggttc agcatccctc    24540
gtccaaaaat ccaaaatcag atggagctca gtggctcatg cttgtaatcc caacacgttg    24600
ggtggccaag gcaggaggat cgcttgagcc caggagttca accagcctga gcaacacaag    24660
accctatctc tccaaaaaaa aaaaaaaaa aaaaagatg aaagaaaaaa aaatccaaaa    24720
tcaaatgctc cagtgagcat ttccttttag catcatgtca ggctctaaaa gttacaggtt    24780
ttggagcatt ttggatttca gattttttgga ttaacctgca ttaatgctca acctatatga    24840
aattttattc ctttttatgg ctgaataatg ttccactgta tgtatatact acattttgtt    24900
tatccattca tctgttaaca gacacttaag ttatttccac attttgggta ttataaatag    24960
tgctgctgcg aacattggtg tacatgtatc tgtttgagtc cctgtttta gttatttgg    25020
ttatatacct aggaatggaa ttgctgatca tatggtaatt ctgtgtttaa cttttttgagg    25080
aactaccact gttttccaca atggcatcac cattttacat tcccaccagc aatgcacaaa    25140
gatttcagtg tctgtatcct tgctaacact tattttccat tttttgagtt tttttgtttt    25200
gtttttttaa taatagccaa tcctaatggg tatgtggtag catctcatgg ttttgatttt    25260
attttcctga ctattgatga tgttgagcat cttttcaggt gcttagtggc catttgtccg    25320
tcatctttgg agcaggaaca atgtcttttc aagtcctttg cccatttta aattgaattt    25380
tttgttgttg agtgtatat aacacctttt ttgaagtaaa aggtgcactg taataatcca    25440
gactgtgttt ctcccttctc aggattccta caggaagcaa gtagtaattg atggagaaac    25500
ctgtctcttg gatattctcg acacagcagg tcaagaggag tacagtgcaa tgagggacca    25560
gtacatgagg actggggagg gctttctttg tgtatttgcc ataaataata ctaaatcatt    25620
tgaagatatt caccattata ggtgggttta aattgaatat aataagctga cattaaggag    25680
```

```
taattatagt ttttattttt tgagtctttg ctaatgccat gcatataata tttaataaaa  25740 attttaaat aatgtttatg aggtaggtaa tatccctgtt ttataaatga agttcttggg   25800
ggattagagc agtggagtaa cttgctccag actgcatcgg tagtggtggt gctgggattg   25860
aaacctaggc ctgtttgact ccacagcctt ctgtactctt gactattcta caaaagcaag   25920
actttaaact ttttagatac atcattaaaa aagaaaacca taaaaaagaa tatgaaaaga   25980
tgatttgaga tggtgtcact ttaacagtct taaaagcaat cgtgtgtata gcatagaatt   26040
gcttggattg gataaacagt ggcattatat attttaaaaa ataaaagttt tgaaagattg   26100
aagaatttgg gcattacagt tctcttaaat ctgacaaagc tgcataaaac tattaaaata   26160
atcattatta tactatttta tattctattt ctttgagggt ttagttttcc aaaaactaca   26220
tattaagcaa atgaatcact cagtggctat gtcatataat aacgagttag cctagttata   26280
agaagtttaa cattttattt aagaacattg ttacagcatg tttactgtat agtctagtaa   26340
tagaggaaaa gacatttggg tgggtggtag tggtagtatt tttatagagg agttaccaaa   26400
tttcagctct attatccaag tttacccagc taatggtgtt cggaaccggg aatttgagcc   26460
aattctgact ctgttgtctg ctctgctcct tcttttgtgc tgtgtctttg aaagtcacct   26520
aaaattgtga gggaatgtaa tttcacccca aatttagagt ttatgcactt gttatattga   26580
aaatgattaa catgtagaag ggcttttaat ggaataagtg gtgtagtaac ttcagtgttg   26640
cctacctaga aatcaaaatc tttctagttg tccactttgt tttttgaaaa agtaaatatga  26700 aaattatgtt aatgctttaa ttcaggtttt tgtaaaatat tttttatctt tacacattta   26760
acatacgttt ctaaaattat agtctgttat atagcacttt gggtctagaa ttttttcagta  26820 gtttctgttt tactattatg atctacctgc atattaacct attaggttat agttttacta   26880
tacttctagg tatttgatct tttgagagag atacaaggtt tctgtttaaa aaggtaaaga   26940
aacaaaataa ctagtagaag aaggaaggaa aatttggtgt agtggaaact aggaattaca   27000
ttgttttctt tcagccaaat tttatgacaa aagttgtgga caggttttga aagatatttg   27060
tgttactaat gactgtgcta taactttttt ttctttccca gagaacaaat taaaagagtt   27120
aaggactctg aagatgtacc tatggtccta gtaggaaata aatgtgattt gccttctaga   27180
acagtagaca caaacaggc tcaggactta gcaagaagtt atggaattcc tttttattgaa  27240 acatcagcaa agacaagaca ggtaagtaac actgaaataa atacagatct gttttctgca   27300
aaatcataac tgttatgtca tttaatatat cagttttttct ctcaattatg ctatactagg   27360
aaataaaaca atatttagta aatgttttg tctcttgaga gggcattgct tcttaatcca   27420
gtgtccatgg tactgctttt ggctttggtt tcttttctaca ttgaaaattt ctcttcaatt   27480
ctgagcacat gttaacattt agaattcaag aggtggggat tttttttttcc catggttaca   27540 tatatatata tatatatata tatatatata tatatatata tatatataaa gaacagggca   27600 acaaatttt gcgttttcta tttcggtagt acttttaaac cattatgtca tgtttctagg   27660
ttaaacgttg ttgtatttga agaattttac tttggcagaa ttttttttgag gatgtgttta   27720 tttctggaga aaggtctcat taagaaaaga caatacccag aaagccaaca gaaattctgt   27780
tactcattta atgcattttt ctgacaaaaa ttattgccag agagaacctg aatttgtttt   27840
caaaaatcat ctttgtttta aaatgacttt ttcttcagg taaaataaaa taattcagt    27900 tgctattatt taacctgttt gtatgaagag tttaacatat aggaaatgaa tacataaaga   27960
taggaaggaa ttaattgtta tatgtagtca tatgtctctt aatgacaggg atactttcta   28020
```

```
agaaatacat tgttaggtga tttttgtcatt gtgcaaacat catagaatat acttacacaa    28080
accttggtag tataacctac tatacacctg ggatatgtag tatagtctct tgccccaggg    28140
atacaaacct gtacagtatg taactgtact aatgactata aggcaattgt taacacaatg    28200
gtaagttttg tgtgtctaaa cctacacttg ggctaccta agtttatata ttttttaaa     28260 tttctgttca ataataaatt aaccttactt tactgtaact ttttaaactt tttaattttt    28320
cctaacattt tgacttttgt aatacagctt aaaacacaca ttatacagct atacaaattt    28380
ttctttcctt atatctttat tctgtaagct tttttccata tttaaaattt tttgtttgtt    28440
tttacttatt aaactttttt gttaaaaact aagacatgca tgcacattaa cctaggccta    28500
cacagggtca ggaccatcaa tatcattgtc ttccacttcc acatcttgtc ccactggaag    28560
atcttcaggg gcagtaacac acgtggagct gtcatctcct ataataacat tgccttcttt    28620
tggaatacct cctgaaggac ctatccaagg ctgtttatag ttaactttt tttttttttt    28680 tttttttttt tagtaaatag gaggagtaca ctataaaata acaatatagg tgctatacca    28740
ttatacaact gacagtgcag taggtttgtt tacaccagca tcaccacaaa cacgtgagca    28800
atgtgtcgta ctacagtgtt aggatggcta taacatcact aagcaatagg aactttaaa    28860 ctccattata atcttatggg accactatca catatgcaat ctcctgtgga ccaaaatgtc    28920
attatgtggt acatgactgt actaagaaat tgatccatct atattccatc aatttgttta    28980 gggcttttc tggttacatt tacctgtgag cccagaaaac cagttttgta gaattaact     29040 tctgtaatgc taggagttaa aaaaaattgc tgaacaactt ttacattgtt aaacatttaa    29100
aaacaagcgt tctagaagtt tatcaaattt cataaaggtg caaaaatgta aatgtaaatc    29160
attatccagc taatatatat gttgtatttc cctagtagga gagcatatgt acctcttcct    29220
agttatacaa atttgatata tagtaaagaa acagtaaatt ctacttcaag tcattttggg    29280
aggattaaaa actgaatttc tctagtttga ccattgtaca gatttatctg gcaattttac    29340
taaaacctga tttataggtt aaacttggtg tatatcatat atcactttac tttagaggaa    29400
ttaagatttc acataaatcc atttccaggt tccaaagacc aggaagaggc ttggttttg    29460 tttttctttt tactgtcttt acagtctcct tgacttttct taggagagaa ggtactgaga    29520
aaacatgatt ctaatattta ttatttttc ttccaacatt ttcttatgaa acattttcaa    29580
atacaaaatt gagttttatt taaaacattt gcaaatatac tacctagatt ctaccattgt    29640
tgttttatat ttgctttact tacaactttt aaaagatgct ttttatacca ctgaacatt     29700 tagcttacat ttcacaaaga aaagaaaaaa tttaagagac tttgcataat gttttaaggg    29760
gttgcagtaa agaagtgctt cttatattt cttatgcata caaatcagct gggcttatta    29820
aaatccagat tctaattcag aaggtttagg tggggaccga gtctgcattt ctaacaaact    29880
cctaggtggt attttcttg gtacttggac catactttga gtagaaaagc agtagaggac    29940
ataaaaagag tcttgttagt cccactttgt tgctgtccac ttctcatttg ataatatcct    30000
aaaatagctg tgtctccttt ttggtggttg tatgattact acctcagaag tactaattga    30060
ttcttgctat ttgaccttaa tactttaata taacacagca ttcatatttg atcagaaaac    30120
tatctggctt ccttttataa gagattttta ggttttatac agttttgtgg ccttgggttt    30180
ttttgtttga tttgtttttt tgaaggtata taatatgtaa gtagataaac aaatttgatt    30240
tgtagacatt tttatgtgga tcatctaatt aaaaatggag ggatacagta tgaaagaata    30300
cttgtacttc ttaacagagc actcaacctt tcttttacat cctgtttcac tgatgttatt    30360
atgtaattta tgttgctaaa ctataaaatta gatatttaat ttctgttctt tgatttcctt    30420
```

```
ttattattaa atggacttgt tgatttgcct agaaattaat ttgcctttca aaagtcttat    30480
taatcttcct ccgttgaaat taatttgata tttgcatgct tctggaagac tttaaagagc    30540
tattccgagt aactgtagag attataaaat gaaatatggg aattttaata aattttacat    30600
ctccagttac tggtgaaaat gtcaagtcct cctttctgca gagtattttg ttactcatct    30660
gttattcagc ttatttattt atttatttat ttatttattt ttctttcttt cttgtttttt    30720
tttttgaga cggagtcttg ctttgtcgcc caggctggag tacagtggtg ggatcttggc    30780
tcactgcagg ctccgcctcc cgggttcaca ccattcttct gcctcagcct cccaagtagc    30840
tgggactaca ggcacccgcc accatgcctt gctaaatttt tgtattttta gtagagacgg    30900
gtttcactgt gttagccagg atggtctcga tctcttgacc tcgtgatcca cctgcctcgg    30960
cctcccaaag tgctgggatt acaggcatga gccaccgcgc ctggcccta tttgtttttt     31020
aaacaaaatt agtgtgcata tccttgttgt attttatcgg caagttgttt tatgccctaa    31080
cttttggggt cttgatcatg agcctaaaac acgtaaacac ccaaaaagaa ttatattccg    31140
gttaaaggaa caaaacattc atttagaagt tctcatccat gtaaatcaga ggctggcaaa    31200
tattttctgt aaagggccaa gatagtaaat gttttaggct ttgagggcca caagtggtat    31260
ctgttgcatt ttttttttaat tatgacccctt taaaatgcaa aaatcgttgt tagcttgtgc    31320
atagtataaa aataggctgg ccgcatgctg tggctcatgc ctgtaatccc agaaatgagg    31380
tgggaagccg aggtgggcac accacctgag gtcaggagtt cgaggccagc ctggccaacg    31440
tggttgaaac cccgtctcta ctaaaaatac aaaacttagc caggcgtggt ggcgggtgcc    31500
tgttatcctg gctactcaag gggctgaggc agtagaattg cttgaacctg agaggcagag    31560
gctgtagtga gcccagatca agccagtgca caccagcctg gacgaccgag cgagactctg    31620
tctcaaaaaa aaaaaaaaa ggctgtggct gcatttggtc cattggctgt aatatgctga    31680
ttcctaattc tctgggtaac tttagtgttt gattagctac tagaagttag gttaaacttt    31740
tgtattttac aggctaactt taataatctt aaagtaaaac ttaacatagt tcatggaaag    31800
gaaatagaaa ttttacccta gtactctttt ttttttttt tttttttttt gaggcagagt    31860
ctccctctgt cacccaggct ggagtgcagt ggtgggatct tggctgattg caacctcctc    31920
ctcctgggtt caagcaattc ttgtgcctca gcctcccgag cagctgggac tacaggcacg    31980
caccaccaca cctgactgat ttttgtattt ttagtagaga cagggtttcg ccatgttggc    32040
caggctggtc ttgaactcct ggcatcaagt gatcctccca tctgagcctc ccagtgtgct    32100
gggattacag acgtgagtca ctgtgcctgg tctctagtat tttttttttt tttgagacgg    32160
tctcactgtt gccaggctgg agtgcagtgg cgcgatcctg gctcactgca acctccgctt    32220
cccggattca gcgattttc ctgcctcagc tcctgagta gctgggacta tgggtgcaca    32280
ccaccacgcc cagctaattt ttgtattttt agtagagacg gggtttcacc atgttggcca    32340
atatggtctc aatctcttga cctcgtgatc tgcccgtctc ggcctcccaa agtgctggga    32400
ttacaggcgt gagccactgt gcccagctgt acttttaag ataagaattg cagggtatat    32460
attttacca acttaataac ttataatttt aaaaagctaa ttacttggct agaatataat    32520
gcgttacata ttcttacac tcagttcagt ccatatctga aagcaaata gaattatttt    32580
ctgctagtac attgtgtagt ccctatgttc ctagtgtata aggactgtta cctagttcac    32640
atttatctgg gttgttgaca gattttcctg gtcccttttgg acagtgcatg gccatgttgg    32700
caaaagctgt caaaattgaa acattgacac catgagaatt gtgtgttttc cagtctgcta    32760
```

```
aaatcaaaag tgggagggtt cagtaaggtg aataacagaa gcagagtttt cggggtatct    32820
gttactcctc attcggcttt tctgctctct gggggtctca atttaaatat aatgtgaaaa    32880
ttagttttac gaacctaaaa atgttgagtg attcatttcc tggttttgtt gttaatttct    32940
agatatttaa attaattgtt agaagaaccc cgttaaagaa tgctttgcaa aacaacctcc    33000
ttatgtgcta tgtctctgtt aatagtagt tgagtttgtg tacatgagat caatattttg    33060
aactatagct ttttatgagt taaaaattga cggaacagtt actgtgcact tgctgtgcac    33120
catggtagtc tcccaagtag tggttttttct gcatttcaat agtacatgag ataggctgtg    33180
ggtggcaagg tttcttgaga aagtgaggga tgcacagttg ggttttagaa tacatcttgt    33240
tcctccatgc ccttccccac caaaaggctg gtagtcttgc atttgtatat agttagggta    33300
tttgatgtgt tgcttccttg acagagtttt gcaagaattt gcagatttaa caggaacaaa    33360
aacttactta aaacaaaatc tcttagtaaa agcatagtct agcaagattt agaatgatac    33420
tttggctaac agtactttct ctatatggag tgctttgttt ccatagcctc acaagtatgt    33480
tttcagataa tagttgagtt gaaaatgttg tcaatctctt gattttaaaa aatttacata    33540
tttaaagttg tatacttttg ttcctacgta ttttcagttg ttcttaaagt ttaataagtg    33600
acatttgaaa atgagtatat gtgtataaaa acaaaagtag gctaggcacg gtggctcatg    33660
cctataatcc tagcacttg ggaggctgag gcaggcggat cacaaggtca ggagtttgag    33720
accagcctgg gcaatatggt gaaaccccc tctactaaaa atacaaaaat tagctgggtg    33780
tggtggtgca tgcctgtagt cccagctact caggaggctg aggcaggaga atcgcttgaa    33840 cccgaggtg gcggttgcag tgagccgaga ttgcaccact gcagtccagc ctgggcggca    33900
gagcgagact ccatctcaaa aaaaaaaaac aaaaaaagaa aaagttaaaa aaaaacaaaa    33960
aacccccaca aaatgagtat atgtggcaac aagtcctatt ctcaaaaaaa ttattgtgtg    34020
ctagttaaga gcttaatgag tagccagtcg gtattaaata tctgtttcag ctatatttta    34080
tctttaaaaa ttatctacag attttggaat gtgaaaaact agtgttttgt ttcataggta    34140
tatactgtag gcattttaaa aataagagcc agtgccagtg gtttacagtg tacacaagga    34200
taatgttctc atgttctctt gatgtcagta tgacttttaaa gcatattatc aagaaataac    34260
taagtctgaa aaactgtggt aaataactgg tactctaaaa cctaagtttc ttattactaa    34320
aaataagaaa tggtaaaagt caccctgtgc tgttaattat atgagccact gaggtcctga    34380
cactgaattc ttggtggtgg ataataatct cttctttta attattggct tccaattctc    34440
tctgcattgc tggaaacaaa aatcatatat ttcactattg gtggtgggga tgctgtcact    34500
gaaaaagtag acacattcat attgatttta gtagacacat tcatattgat tttagaaaat    34560
aagttaaaat caaatttgc ttctgctaaa ttagtagagg accaatactg tttttctcct    34620
tcatagtatg ttttggtact tctacattga cattataact ttttttttt taaacagaaa    34680 tagaagttta cattcttaga aaatttatga aaatatgagc ttttacctgg tttgtgtgtg    34740
tgcgtatata tatacacata ttttaaatt tcttacattg attttcaaat tgaaagagaa    34800
ccatttgtga agtatctta acagagctca tgctttacat tttacatgct acaaagttat    34860
tttagtgcct taaattattt atgttgctta ttaatgaaaa ttttggatac ataatttttt    34920
caagacaaag gtaaaaataa taaaccctt ccttctgagg attaatgata aatataaact    34980
ttaaaacgat taaaaaatt tttttagaga cagggtcttg ctctgttgcc cagactgaag    35040
tgcagtggtg cagtcatagc tcaatgaagc ctcaaactcc tgggcccagg caaccctcct    35100
gcctcagcct tttgagtagc tgggacttca ggctcatgcc aacatgccta atttatctta    35160
```

```
tttttagtag agatgaggtc tcaaactcct ggcatctctt gccctctcaa agtgctggta   35220
ctacaggcat tagtcaccac acctgacact taaaatcttt tatatacagg tgtaagtggg   35280
tatctaactt aaagtgccaa cgaatgtagt tgaaagtttg tagttggctt agctaactag   35340
ttaactaaat tgattccatt aaaaataaga taagactgct cttagaatat aatgattttt   35400
gttattcgtt aaatataaat atatcactgg atagtatatg ttaatgactt gagatacgca   35460
ttttaacata taatcacgtt acttaaatgc ctgcctttga actgaaactt aacattatga   35520
atttaaatta aagtttgact ttagaggtaa atttctgtac tttactaaag cagttcttaa   35580
tataattctg agatttctaa aaattagtgt gccctaaaga attgaggtgt gttttcttta   35640
actactgtag gcagtagatg tacagatgac ttctgcatgc aaaaattaag ccctagccat   35700
tggtttactt caactaatac ttagttgcca attctctgtg tgtgattgaa tttaaaactg   35760
caaatggtac tggtgataca ttaactttt aggtgctagg tccactttgt tacatttggt    35820
tcagtagaaa cattgatgtt accaatctca gaaagctaaa atatgtatgc caatccccaa   35880
attaggtaat ttattcttaa ttttaagata aaagaataga attcccttaa aattaaatgt   35940
ggagtaaaat ataccagctt taaaaaatat tcacctttct gttagaagaa tgaacataat   36000
attacatctt ttaatttgca ctatatatag attaatattt ctgtgtattt ctctgtgccc   36060
ctactttgat ggtatgcttt tctgaacaaa ctagcagcac agttaactaa gcactttgcc   36120
ccgtttgatg actgcctaat tttctagatt ggaaaatatt aaaaacttt atctccatat    36180 ggccaatata tgattgtacc tgttgtcata gctctcttat gtttaagcaa gaaaaacct    36240 attaagagta tttaaattag aatggaaggc acacagccag tatgattgaa cactgttcta   36300
aaaattattt ttaagacttg tagtaaggcc aggtttggtg gctcatggct gtaatcccag   36360
cccttaggag gccaaggtgg gcggatcact tgtgctcagg agtttgagac cagcccgggc   36420
aacatggcaa aaccctgtct ctacgaaaaa tacaaaaatc agtcaggtgt ggtggtgctt   36480
gcctgtagtc ccagctattt gagaggctga ggcagggga tcacctagcc tgggaggtcg    36540
aggctgcagt catgatcgtg ccattgcact ccatcctggg caacccagtg agaccctgtc   36600
tctaaaacaa aaaaataaaa aaagaacttg tagtaaggat acaaaatgct cctattttgt   36660
gtgtgtcctt taattcatga tgttttata ttatggtaag cagctctcat ttaagatttt    36720
aataatgtaa ttaaacatgt acagaagacc cagtctcagc ttcacttgta taccctggaa   36780
atagactgaa aggtgttaaa atttaagata aaactcaagg ttccagtttc ttgactcacc   36840
tttgagattc ttttatgttt ttgttgtttt ttaacaaagg tttcacgtcc atattttacc   36900
atttttcttc tcattctccc ctggaggagg gtgtgggaat cgatagtata taaatcactt   36960
ttttcctaag tcaagaagt aatttaaagc taacttcagt ttaggcttta attccaggac    37020
tagcaaacta aaatggttgc attaattgac aaacagatgc taatacctgt gtttaggctt   37080
gtcataatct ctcctaattc ctaatttaaa aattttaaaa tttaattcca ttagaaaaca   37140
aaactgactt ttaagaacaa accaggattc tagcccatat tttaaaactg catcctcagt   37200
tttattcaaa cagtctgatg tctgttaaa aaaaaaaaaa tctcaagctc ataatctcaa   37260
acttcttgca catggctttc ccagtaaatt actcttacca atgcaacaga ctttaaagaa   37320
gttgtgtttt acaatgcaga gagtggagga tgctttttat acattggtga gagagatccg   37380
acaatacaga ttgaaaaaaa tcagcaaaga agaaagagact cctggctgtg tgaaaattaa   37440
aaaatgcatt ataatgtaat ctggtaagtt taagttcagc acattaattt tggcagaaag   37500
```

```
cagatgtctt ttaaaggtaa caaggtggca accactttag aactacttag gtgtagtatt   37560
ctaacttgaa gtattaaaag ataagaaact tgtttccata attagtacat ttatttttaa   37620
tctagtggga attaattata attgagacaa ttttgatggc tgtagtagac taatctatat   37680
ttggcataaa gtctaatgat ttaatgagtc ttaagtaaac taaatatttg gaaactgata   37740
tttaccttta ttttaagggg aaaagttttg agataatcag cagcttttt ttttttttt     37800 ttttttttag tagggagaaa aagatatgag ctatagtaga cagcagtaat attgaatggc   37860
ccagaaggtg ggaaaaagcc actcttaaat gtatttttc ttttggatat tttacaagca    37920
aataataact tctgcctaag ttcgccatct cagtggcatc agcagcacag cactttctta   37980
tcccagtgag aaacctggga atttaggat gactcctacc gccctctttt cccctggtt     38040 tggaagtatc cacaaattcc tgtgacgtta cattctgtgt cttttatgtc atcattagtt   38100
caggccccta tcatttcttg ttggactgtt agaacctcct atttggttta ccagttgctg   38160
ccatcattca ttgtgaaacc ggagagatac actttaaaga aatgtcattt ttggccgggc   38220
gcggtggctc acgcctgtaa tcccagcact ttgggaggcc taggcgggtg atcacctgag   38280
gtcaggagtt caagaccagc ctggctaaca tggtgaaacc ctatttctac taaaaataca   38340
aaaaattagc cgggcgtggt ggcacgtgcc tgtaatccca gctacttggg aggctgaggc   38400
aggagaattg cttgaacctg ggaggcagag gttgcagtga gctgagaatg caccattgca   38460
ctccagcttg agcaacaaga gcgaaactct gtctcaaaaa aaaaaaaaa aagtcatttt    38520 agctatagaa taaaatctca tgttccacat gtgttgcaga tagtccttac taccttccca   38580
ccactccagc tcttttttgg tcttatatct aaaaacgtca tcttgcctga atttcttttg   38640
ttcttctata aataaatacc atgttatttc ctaccttccc ttgagtcttg gctcttgttt   38700
ggaatgccag tattttatc cctagtctta ctaattagct aacactctca tgattcccca    38760
gtctcctact ctctaaaaac ctttctttaa acccttagac taggcatgga gcccttcctg   38820
tgtattccca gaatactatt cttaactatt atatgcttcc catgttatgt tgaaataact   38880
aacctcttct gtttcattcc tatattactt gacagcaaaa tcttagccag aattacatat   38940
ttttaatctt tgcacaccca ttgcctagta aggttcctgg gacatagtaa ctacccagta   39000
aatatttatt gcgtggaatt ctcattttcg tttctaaacc cgtattaaac tctgtcttgc   39060
tcagaaaata cttcactagg tatcataaag ttcatggcag agcttaagct ttggatgcat   39120
attgtttgta atatatcatg ttcttaagaa taggcaataa aattacagtt ttcaaaaact   39180
actacattta ttatatttat tacaagttgg tgttctttat tacatgaatt ttaggtattt   39240
cccaaaagta taaatatac atttgaatag tagactcaat cccaaaagat actacgtggt    39300
gtactaatct actaaactca gaaacaaagc atgactggca ttaattttg ttgaaattta    39360 tgaactctga atgttttga atatcattct gtaaagcaat attttgcaat taaagcaatt    39420
ttgcatgtta aattttacca caacctctaa aatattgcaa atttaacaat acagtttgaa   39480
aagttacaca ttttaaataa cagtaccatg accagattta ggtggtggtt ttaatttttt   39540 atttctcct cctattgtct caccattaga tgattttaaa aatagaattg tttagagtaa    39600
aataagtgtt atgctctaat ttatatttaa aatgaaggtt taagcacgta ctattctaaa   39660
atttctaatt tgtgcaaatt atgttttata cagtgactgt aggtgaatgt cacaattgtt   39720
tgatgtgacg aatccttgtt tttcagtaca cgtggaagta attcatataa aagagaagta   39780
tacttggtaa ttaaaaattt aaaattaaat acaatttaaa aaaaaattta tttgacaagc   39840
tggctgtggt gtgtgtgcct gtagtatcag ctgcttggga gcctgaggca ggaggattgc   39900
```

```
ctgacccag gagtttgagg ttgaagggag ctatgatggt gccatggcac tgtagcctag   39960
gcaacagaaa gagactccat ctcttaaaaa aagtaaaaat aaaaaaattt tggcacaggg   40020
acagtggctc acacttataa tgccagaact ttaggagtcc acagcgcgag gactgcttga   40080
ggccaggagt ttaagaccag actgggcaac gtaatgagac cccacccttta ggaaataaat   40140 acataaataa aaatttgaca atgataaaca tatataaatt agcttttctt agtcctgaaa   40200
aagataatgt tatgtgtatg tgtgagaatg attagttctc atatgagaaa aaagaattc    40260 attgctctgt gtaggttgtg acatttcctt cacgattgaa attaattaat ttttttttat   40320
tacttattta ttttttaaaat agagacaggt tcttgctgtg ttgcccaggc tggtctcaaa  40380
ctcctggcct caagcagttc tcctgcctca gcctcccaaa ttgctgtgac tgtaggtgtg   40440
agccactgca ctgggccaaa attacttaat tttaacaaga tgatgtagag aggagagttc   40500
attgcaacat aagcctagaa tctttgtcag aatcttagga agtaatgttt tcaaattctg   40560
tgttttcacc ataaaatgtg tcttctctgt gtccatcaca tggttttca ttgttttctg   40620 ctttaccatt ttagtaccat tggcattttt cttcattgta aaagtagtag aaatggagta   40680
gattacataa ggatgtgatc agagggaatt tattcattca gggtaaggga gttagatcct   40740
cttttaagat tctatcacat tctaagggtt tatgattcta aactgtcaag taaattgtca   40800
agtgctggca agctacagaa taattttttat tgtatcattg gaattttcc cctctatatg   40860 tgttaaagag tttagcctga agggatacat acacatacat atatgtaatc aaaccttgat   40920
ggtattgtat tgctgataaa ttatttctta ccacttttcc tttctcctgt gggagaaaca   40980
aaagcatatg tttgtgtagt atcagtaatg atattagaga gtgggaaaca tcagtgagtg   41040
cagtttgggg actttattgg agactttcac tagtgctcaa ataaaataatg ctggttttta  41100 tcctactgtt tgcttaatgt ggactagcct cttattccca ttctatgttt acctctctta   41160
aaatattggt cacgctttct tgaattatag atctattagg aaaattcatg aactgtagct   41220
aattttcatt gttcatgctc cagatttatt ttgaaatatc gttaatctta gtagtacagt   41280
aaaggagaaa taccacttaa catttttgt ttttttttct ttgagacaga gtcatgctct   41340
gtcacccagt ctggagtgca gtggtgctat ctcggctcac tgcaatgcac ttcgcctctc   41400
cgggttcagc aattctcctg cctcagcctc ctgagtagct gggattacag gcacctgcta   41460
ccacacccag ctaattttg tatttttagt agagacaggg tttcaccatg ttggccaggc   41520
tggtctgaaa ctcctcacct caagtgatcc acccgtcttg gcctcccaaa gtgctgggat   41580
tacaggcttg agccaccgca ccccgcccac ttaacattt aaattaattt caagataata   41640
tcacttgaat attttacac atataattt tttaatacat ttatttacac agtttataat   41700
atcctacaaa gtgattacaa tgagtaaaaa cccagttttc attgttccta aagtggcttg   41760
atttatacaa cttaatgtgt tgggtatttg tttctaagac tccctctgct gtctaggttt   41820
ggaagtattg tgaggttaac agattttctt tttatagtta ctactcagtt gaacaggctt   41880
taaaatacag agagaatcat atttttcct cattttttgc ttttatttat attttctttt   41940
taattggaga catgacaaga attgacttgt gtatggatct tgcataattt aagtactgca   42000
ggtttaaaat ctactctact accagtttga gagtgccatt tttcacactg tagattatta   42060
ggttgaaaag tattatggct taaaatcgct tttagccatt aaatttaaat aaccttgctt   42120
taatcataaa tagatggtgg tcacaatgac taactgttaa actctttgaa gacaggatat   42180
ttggctttat atggcaagct tttgaataca acagaaatta aaactttatg ggatagaaag   42240
```

```
aatctcctcc aaattggtaa actataagac ctttcaaatg atttagctaa tttctccaca    42300
aatctgaggt attagtgttt tttttaaagt ggtattctcc tgtgttgggg tcactttaaa    42360
ccttttcttt aatgataaat atatgaattg aaactaatcc cttaatatat atcatttgaa    42420
aactgaaata atatgtttag atactgttta cttgttgata aattattgga ataggatgtt    42480
cgaatactgt ttacttcttg gtaaattttt aaatccaatg gattttacgt aagtatagaa    42540
ctggagctca atactgttta ctgtgtgtga agatatatga acatagttta cagttgcatg    42600
gcttatatct aaagtccaga aacataagga caattaagtg tacacacaca cacatgcatt    42660
tggattttga tgacttaggt ttgccaatgt ggaaaaaata gtagcaaatt aagttctcct    42720
gtgaaaaagt cgttacctta tttaaaattc tgtgccattg gttatccttg tcttttgtga    42780
aaattagtgt tcctgtttat aatattgaca aaacacctat gcggatgaca tttaagaatt    42840
ctaaaagtcc taatatatgt aatatatatt cagttgcctg aagagaaaca taagaatcc    42900 tttcttaata ttttttccat taatgaaatt tgttacctgt acacatgaag ccatcgtata    42960
tattcacatt ttaatacttt ttatgtattt cagggtgttg atgatgcctt ctatacatta    43020
gttcgagaaa ttcgaaaaca taaagaaaag atgagcaaag atggtaaaaa gaagaaaaag    43080
aagtcaaaga caaagtgtgt aattatgtaa atacaatttg tactttttc ttaaggcata    43140 ctagtacaag tggtaatttt tgtacattac actaaattat tagcatttgt tttagcatta    43200 cctaatttt ttcctgctcc atgcagactg ttagctttta ccttaaatgc ttattttaaa    43260
atgacagtgg aagttttttt ttcctctaag tgccagtatt cccagagttt ggttttga    43320 actagcaatg cctgtgaaaa agaaactgaa tacctaagat ttctgtcttg gggttttgg    43380 tgcatgcagt tgattacttc ttattttct taccaattgt gaatgttggt gtgaaacaaa    43440
ttaatgaagc ttttgaatca tccctattct gtgttttatc tagtcacata aatggattaa    43500
ttactaattt cagttgagac cttctaattg gttttactg aaacattgag ggaacacaaa    43560
tttatgggct tcctgatgat gattcttcta ggcatcatgt cctatagttt gtcatccctg    43620
atgaatgtaa agttacactg ttcacaaagg ttttgtctcc tttccactgc tattagtcat    43680
ggtcactctc cccaaaatat tatattttt ctataaaaag aaaaaaatgg aaaaaaatta    43740
caaggcaatg gaaactatta taaggccatt tccttttcac attagataaa ttactataaa    43800
gactcctaat agcttttcct gttaaggcag acccagtatg aaatggggat tattatagca    43860 accatttgg ggctatattt acatgctact aaattttat aataattgaa aagattttaa    43920
caagtataaa aaattctcat aggaattaaa tgtagtctcc ctgtgtcaga ctgctctttc    43980
atagtataac tttaaatctt ttcttcaact tgagtctttg aagatagttt taattctgct    44040
tgtgacatta aaagattatt tgggccagtt atagcttatt aggtgttgaa gagaccaagg    44100
ttgcaaggcc aggccctgtg tgaacctttg agctttcata gagagtttca cagcatggac    44160
tgtgtcccca cggtcatcca gtgttgtcat gcattggtta gtcaaaatgg ggagggacta    44220
gggcagtttg gatagctcaa caagatacaa tctcactctg tggtggtcct gctgacaaat    44280
caagagcatt gcttttgttt cttaagaaaa caaactcttt tttaaaaatt acttttaaat    44340
attaactcaa aagttgagat tttggggtgg tggtgtgcca agacattaat tttttttta    44400 aacaatgaag tgaaaaagtt ttacaatctc taggtttggc tagttctctt aacactggtt    44460
aaattaacat tgcataaaca cttttcaagt ctgatccata tttaataatg ctttaaaata    44520
aaaataaaaa caatcctttt gataaattta aaatgttact tattttaaaa taaatgaagt    44580
gagatggcat ggtgaggtga aagtatcact ggactaggaa gaaggtgact taggttctag    44640
```

```
ataggtgtct tttaggactc tgattttgag gacatcactt actatccatt tcttcatgtt   44700
aaaagaagtc atctcaaact cttagttttt ttttttttaca actatgtgat ttatattcca   44760
tttacataag gatacactta tttgtcaagc tcagcacaat ctgtaaattt ttaacctatg   44820
ttacaccatc ttcagtgcca gtcttgggca aaattgtgca agaggtgaag tttatatttg   44880
aatatccatt ctcgttttag gactcttctt ccatattagt gtcatcttgc ctccctacct   44940
tccacatgcc ccatgacttg atgcagtttt aatacttgta attcccctaa ccataagatt   45000
tactgctgct gtggatatct ccatgaagtt ttcccactga gtcacatcag aaatgcccta   45060
catcttattt cctcagggct caagagaatc tgacagatac cataaaggga tttgacctaa   45120
tcactaattt tcaggtggtg gctgatgctt tgaacatctc tttgctgccc aatccattag   45180
cgacagtagg attttttcaaa cctggtatga atagacagaa ccctatccag tggaaggaga   45240
atttaataaa gatagtgctg aaagaattcc ttaggtaatc tataactagg actactcctg   45300
gtaacagtaa tacattccat tgttttagta accagaaatc ttcatgcaat gaaaaatact   45360
ttaattcatg aagcttactt ttttttttttg gtgtcagagt ctcgctcttg tcacccaggc   45420
tggaatgcag tggcgccatc tcagctcact gcaacctcca tctcccaggt tcaagcgatt   45480
ctcgtgcctc ggcctcctga gtagctggga ttacaggcgt gtgccactac actcaactaa   45540
tttttgtatt tttaggagag acggggtttc accctgttgg ccaggctggt ctcgaactcc   45600
tgacctcaag tgattcaccc accttggcct cataaacctg ttttgcagaa ctcatttatt   45660
cagcaaatat ttattgagtg cctaccagat gccagtcacc gcacaaggca ctgggtatat   45720
ggtatcccca aacaagagac ataatcccgg tccttaggta gtgctagtgt ggtctgtaat   45780
atcttactaa ggcctttggt atacgaccca gagataacac gatgcgtatt ttagttttgc   45840
aaagaagggg tttggtctct gtgccagctc tataattgtt ttgctacgat tccactgaaa   45900
ctcttcgatc aagctacttt atgtaaatca cttcattgtt ttaaaggaat aaacttgatt   45960
atattgtttt tttatttggc ataactgtga ttcttttagg acaattactg tacacattaa   46020
ggtgtatgtc agatattcat attgacccaa atgtgtaata ttccagtttt ctctgcataa   46080
gtaattaaaa tatacttaaa aattaatagt tttatctggg tacaaataaa caggtgcctg   46140
aactagttca cagacaagga aacttctatg taaaaatcac tatgattttct gaattgctat   46200 gtgaaactac agatctttgg aacactgttt aggtaggggtg ttaagactta cacagtacct   46260
cgtttctaca cagagaaaga aatggccata cttcaggaac tgcagtgctt atgaggggat   46320
atttaggcct cttgaatttt tgatgtagat gggcattttt ttaaggtagt ggttaattac   46380
ctttatgtga actttgaatg gtttaacaaa agatttgttt ttgtagagat tttaaggggg   46440
gagaattcta gaaataaatg ttacctaatt attcagcct taaagacaaa aatccttgtt   46500
gaagtttttt taaaaaagc taaattacat agacttaggc attaacatgt ttgtggaaga   46560
atatagcaga cgtatattgt atcatttgag tgaatgttcc caagtaggca ttctaggctc   46620
tatttaactg agtcacactg cataggaatt tagaacctaa cttttatagg ttatcaaaac   46680
tgttgtcacc attgcacaat tttgtcctaa tatatacata gaaactttgt ggggcatgtt   46740
aagttacagt ttgcacaagt tcatctcatt tgtattccat tgattttttt tttcttctaa   46800 acatttttc ttcaaacagt atataacttt ttttagggga ttttttttta gacagcaaaa   46860
actatctgaa gatttccatt tgtcaaaaag taatgatttc ttgataattg tgtagtaatg   46920
ttttttagaa cccagcagtt accttaaagc tgaatttata tttagtaact tctgtgttaa   46980
```

```
tactggatag catgaattct gcattgagaa actgaatagc tgtcataaaa tgaaactttc   47040
tttctaaaga aagatactca catgagttct tgaagaatag tcataactag attaagatct   47100
gtgttttagt ttaatagttt gaagtgcctg tttgggataa tgataggtaa tttagatgaa   47160
tttaggggaa aaaaagtta tctgcagata tgttgagggc ccatctctcc ccccacaccc    47220
ccacagagct aactgggtta cagtgtttta tccgaaagtt tccaattcca ctgtcttgtg   47280
ttttcatgtt gaaaatactt ttgcatttt cctttgagtg ccaatttctt actagtacta    47340
tttcttaatg taacatgttt acctggaatg tattttaact attttttgtat agtgtaaact  47400 gaaacatgca cattttttgt acattgtgct ttcttttgtg ggacatatgc agtgtgatcc   47460
agttgttttc catcatttgg ttgcgctgac ctaggaatgt tggtcatatc aaacattaaa   47520
aatgaccact cttttaattg aaattaactt ttaaatgttt ataggagtat gtgctgtgaa   47580
gtgatctaaa atttgtaata tttttgtcat gaactgtact actcctaatt attgtaatgt   47640
aataaaaata gttacagtga ctatgagtgt gtatttattc atgaaatttg aactgtttgc   47700
cccgaaatgg atatggaata ctttataagc catagacact atagtatacc agtgaatctt   47760
ttatgcagct tgttagaagt atcctttatt tctaaaaggt gctgtggata ttatgtaaag   47820
gcgtgtttgc ttaaacttaa aaccatattt agaagtagat gcaaaacaaa tctgccttta   47880
tgacaaaaaa ataggata acattattta tttatttcct tttatcaaag aaggtaattg    47940
atacacaaca ggtgacttgg ttttaggccc aaaggtagca gcagcaacat taataatgga   48000
aataattgaa tagttagtta tgtatgttaa tgccagtcac cagcaggcta tttcaaggtc   48060
agaagtaatg actccataca tattatttat ttctataact acatttaaat cattaccagg   48120
aactgtttgt tttgtagtga accttgagta tgtgctgtta atataccaaa ttgggtgaaa   48180
aaataaggga ttccttttcaa aagttaagag aagtaagtgt gtaagaaatt attttgctta  48240
ttaaatgttc ggtaaatggc attctcttgt cagtaaaatg gagaaataag ctaaaaataa  48300
ttggctaagt cctattaagt tagaggatta agtgtattat attttcattc aaaattgggt   48360
gctcattaat ttatgatcgg tagtatagct aaattgctat gtttgtatca aaattgagca   48420
taaagttgct gatactttct ccgtatgaac agaagttgaa acctatttag ttcagtaggg   48480
cagctcaggg atttttttac acaacatgta tatcttccca ttttaagtta gaattatttt   48540
acaacatctg gtatacataa acagctggca ctgatagcta aattaaagta gtaatgatca   48600
attagttttg ttggtatctg aataatagcg ttgtttcata gctctgtatt tcctaaggaa   48660
gtacaaagct tctagctctt tcattacaaa ttcgccctgt gcaataagtt ctttgatctt   48720
ctctggattc ttcacatctt tgtttttaag gaaaatgttc ttcaaacgct ttttaaaata   48780
gtctgctcct tttggatagt ctcgtccaag atacagcagc ttcaaaaaga aagattatat  48840
atttctaaac aatccatgtc atataataac attttttataa aattggcaac ataattactt  48900 acattttttat aaagttttag tacttctcct cttaaagaat tggccatttt catttatcat  48960
gtaaattatc cacttttatg cataacatac ctaaagaaag gaaaattttt ttgcaattag   49020
ctgcattgta gtcttaaaaa aataaaaaaa ggttatacac attgagaaaa tggtaacctt   49080
ttttacattc aataaatatt tcttgataac ttttttcgttc cacgtactgg gatatagtta  49140
taaacacttc cgataaaatt acctgctgtc ataattgacg ttttcctatg ggagacataa   49200
gcaaagacaa ttgtgattgt gagaagtcac atgaaggaaa tgagaaagtg gattgtcatc   49260
acagataggt acgtgtacct cctttttatgc cacagtggaa tgagttaaac tagatttaaa   49320
ttccagttgc ataatgtaca gattaattaa ccttgctgag cctgagtttt ccttatcaac   49380
```

```
aaacaagaga ttatctttac cctgctctca aggcaaggcc agagccactt gaaggacatt    49440
gagcagaagc ctgatcaaat gctgatgggt gcttatccaa agggaggctg aaaactagca    49500
gaaactgggt gagttaagca ggttggaata gtagatgggc agtaagattg gtggtgaaga    49560
ggccaaatga acaacctgta agagggtgtc cctgaggaac aggcaaaatc atgcttcttt    49620
atgtgtaatg tgttaactct actttgtaga ggaggctcca aac                      49663
```

<210> SEQ ID NO 65
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 65
guuggagcug auggcguagt t                                              21

<210> SEQ ID NO 66
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 66
cuacgccauc agcuccaact t                                              21

<210> SEQ ID NO 67
<211> LENGTH: 19
<212> TYPE: RNA
<213> ORGANISM: Artificial Sequence
<220> FEATURE:
<223> OTHER INFORMATION: siRNA antisense strand

<400> SEQUENCE: 67
cuacgccaac agcuccaac                                                 19

<210> SEQ ID NO 68
<211> LENGTH: 19
<212> TYPE: RNA
<213> ORGANISM: Homo sapiens

<400> SEQUENCE: 68
ugccagggac cauguuuug                                                 19

<210> SEQ ID NO 69
<211> LENGTH: 21
<212> TYPE: DNA
<213> ORGANISM: Artificial Sequence
<220> FEATURE:

<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 69
ugccagggac cauguuuugt t                                              21

<210> SEQ ID NO 70
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 70
caaaacaugg ucccuggcat t                                              21

<210> SEQ ID NO 71
<211> LENGTH: 19
<212> TYPE: RNA
<213> ORGANISM: Homo sapiens

<400> SEQUENCE: 71
cggaaauguu augaagcag                                                 19

<210> SEQ ID NO 72
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 72
cggaaauguu augaagcagt t                                              21

<210> SEQ ID NO 73
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

```
<400> SEQUENCE: 73
cugcuucaua acauuccgt t                                               21

<210> SEQ ID NO 74
<211> LENGTH: 19
<212> TYPE: RNA
<213> ORGANISM: Homo sapiens

<400> SEQUENCE: 74
gcugaagaaa cuugguaau                                                 19

<210> SEQ ID NO 75
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 75
gcugaagaaa cuugguaaut t                                              21

<210> SEQ ID NO 76
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 76
auuaccaagu uucuucagct t                                              21

<210> SEQ ID NO 77
<211> LENGTH: 19
<212> TYPE: RNA
<213> ORGANISM: Homo sapiens

<400> SEQUENCE: 77
ugauuuauac uucucuguu                                                 19

<210> SEQ ID NO 78
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
```

<223> OTHER INFORMATION: DNA

<400> SEQUENCE: 78
ugauuuauac uucucuguut t                                               21

<210> SEQ ID NO 79
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 79
aacagagaag uauaaaucat t                                               21

<210> SEQ ID NO 80
<211> LENGTH: 19
<212> TYPE: RNA
<213> ORGANISM: Homo sapiens

<400> SEQUENCE: 80
ugauuuauac uucucuguu                                                  19

<210> SEQ ID NO 81
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 81
ugauuuauac uucucuguut t                                               21

<210> SEQ ID NO 82
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 82
aacagagaag uauaaaucat t                                               21

<210> SEQ ID NO 83
<211> LENGTH: 19

```
<212> TYPE: RNA
<213> ORGANISM: Homo sapiens

<400> SEQUENCE: 83
augaauggaa ccagcaaca                                                    19

<210> SEQ ID NO 84
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 84
augaauggaa ccagcaacat t                                                 21

<210> SEQ ID NO 85
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 85
uguugcuggu uccauucaut t                                                 21

<210> SEQ ID NO 86
<211> LENGTH: 22
<212> TYPE: RNA
<213> ORGANISM: Homo sapiens

<400> SEQUENCE: 86
cugagcaucg gauuugagac ug                                                22

<210> SEQ ID NO 87
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 87
cugagcaucg gauuugagat t                                                 21

<210> SEQ ID NO 88
```

```
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 88
ucucaaaucc gaugcucagt t                                              21

<210> SEQ ID NO 89
<211> LENGTH: 19
<212> TYPE: RNA
<213> ORGANISM: Homo sapiens

<400> SEQUENCE: 89
ggcgcagauc gauuugaau                                                 19

<210> SEQ ID NO 90
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 90
ggcgcagauc gauuugaaut t                                              21

<210> SEQ ID NO 91
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 91
ugagacgcuc ggcccucuut t                                              21

<210> SEQ ID NO 92
<211> LENGTH: 19
<212> TYPE: RNA
<213> ORGANISM: Homo sapiens

<400> SEQUENCE: 92
aagagggccg agcgucuca                                                 19
```

```
<210> SEQ ID NO 93
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 93
aagagggccg agcgucucat t                                             21

<210> SEQ ID NO 94
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 94
auucaaaucg aucugcgcct t                                             21

<210> SEQ ID NO 95
<211> LENGTH: 19
<212> TYPE: RNA
<213> ORGANISM: Homo sapiens

<400> SEQUENCE: 95
gaacguuccg cagagaaaa                                                19

<210> SEQ ID NO 96
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 96
gaacguuccg cagagaaaat t                                             21

<210> SEQ ID NO 97
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
```

```
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 97
uuuucucugc ggaacguuct t                                              21

<210> SEQ ID NO 98
<211> LENGTH: 19
<212> TYPE: RNA
<213> ORGANISM: Homo sapiens

<400> SEQUENCE: 98
gcacuuccuc uacuccuca                                                 19

<210> SEQ ID NO 99
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 99
gcacuuccuc uacuccucat t                                              21

<210> SEQ ID NO 100
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 100
ugaggaguag aggaagugct t                                              21

<210> SEQ ID NO 101
<211> LENGTH: 19
<212> TYPE: RNA
<213> ORGANISM: Homo sapiens

<400> SEQUENCE: 101
caccaagaag uucaucucc                                                 19

<210> SEQ ID NO 102
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
```

```
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 102
caccaagaag uucaucucct t                                              21

<210> SEQ ID NO 103
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 103
ggagaugaac uucuuggugt t                                              21

<210> SEQ ID NO 104
<211> LENGTH: 19
<212> TYPE: RNA
<213> ORGANISM: Homo sapiens

<400> SEQUENCE: 104
caucgccagc aucaucaaa                                                 19

<210> SEQ ID NO 105
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 105
caucgccagc aucaucaaat t                                              21

<210> SEQ ID NO 106
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 106
```
uuugaugaug cuggcgaugt t                                    21

<210> SEQ ID NO 107
<211> LENGTH: 19
<212> TYPE: RNA
<213> ORGANISM: Homo sapiens

<400> SEQUENCE: 107
gacucauauc caccaaaca                                       19

<210> SEQ ID NO 108
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 108
gacucauauc caccaaacat t                                    21

<210> SEQ ID NO 109
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 109
uguuuggugg auaugaguct t                                    21

<210> SEQ ID NO 110
<211> LENGTH: 19
<212> TYPE: RNA
<213> ORGANISM: Homo sapiens

<400> SEQUENCE: 110
cagggagauu cauguggau                                       19

<210> SEQ ID NO 111
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 111
cagggagauu cauguggaut t                                               21

<210> SEQ ID NO 112
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 112
auccacauga aucuccugt t                                                21

<210> SEQ ID NO 113
<211> LENGTH: 19
<212> TYPE: RNA
<213> ORGANISM: Homo sapiens

<400> SEQUENCE: 113
gucuuggucc uucucauua                                                  19

<210> SEQ ID NO 114
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 114
gucuuggucc uucucauuat t                                               21

<210> SEQ ID NO 115
<211> LENGTH: 23
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 115
uaaugagaag gaccaagacd tdt                                             23

<210> SEQ ID NO 116
<211> LENGTH: 19
<212> TYPE: RNA
<213> ORGANISM: Homo sapiens

```
<400> SEQUENCE: 116
gcugaagaaa cuugguaau                                                      19

<210> SEQ ID NO 117
<211> LENGTH: 19
<212> TYPE: RNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (3)..(3)
<223> OTHER INFORMATION: 2'-O-methyl modified residue
<220> FEATURE:
<221> NAME/KEY: misc_feature
<222> LOCATION: (13)..(13)
<223> OTHER INFORMATION: 2'-O-methyl modified residue
<220> FEATURE:
<221> NAME/KEY: misc_feature
<222> LOCATION: (16)..(16)
<223> OTHER INFORMATION: 2'-O-methyl modified residue

<400> SEQUENCE: 117
gcugaagaaa cuugguaau                                                      19

<210> SEQ ID NO 118
<211> LENGTH: 19
<212> TYPE: RNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (3)..(3)
<223> OTHER INFORMATION: 2'-O-methyl modified residue
<220> FEATURE:
<221> NAME/KEY: misc_feature
<222> LOCATION: (6)..(6)
<223> OTHER INFORMATION: 2'-O-methyl modified residue
<220> FEATURE:
<221> NAME/KEY: misc_feature
<222> LOCATION: (16)..(16)
<223> OTHER INFORMATION: 2'-O-methyl modified residue

<400> SEQUENCE: 118
auuaccaagu uucuucagc                                                      19

<210> SEQ ID NO 119
<211> LENGTH: 19
<212> TYPE: RNA
<213> ORGANISM: Homo sapiens

<400> SEQUENCE: 119
gacucauauc caccaaaca                                                      19

<210> SEQ ID NO 120
<211> LENGTH: 19
<212> TYPE: RNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (5)..(5)
<223> OTHER INFORMATION: 2'-O-methyl modified residue
<220> FEATURE:
<221> NAME/KEY: misc_feature
<222> LOCATION: (7)..(7)
<223> OTHER INFORMATION: 2'-O-methyl modified residue
<220> FEATURE:
<221> NAME/KEY: misc_feature
```

```
<222> LOCATION: (11)..(11)
<223> OTHER INFORMATION: 2'-O-methyl modified residue
<220> FEATURE:
<221> NAME/KEY: misc_feature
<222> LOCATION: (14)..(14)
<223> OTHER INFORMATION: 2'-O-methyl modified residue
<220> FEATURE:
<221> NAME/KEY: misc_feature
<222> LOCATION: (18)..(18)
<223> OTHER INFORMATION: 2'-O-methyl modified residue

<400> SEQUENCE: 120
gacucauauc caccaaaca                                                  19

<210> SEQ ID NO 121
<211> LENGTH: 19
<212> TYPE: RNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(1)
<223> OTHER INFORMATION: 2'-O-methyl modified residue
<220> FEATURE:
<221> NAME/KEY: misc_feature
<222> LOCATION: (5)..(5)
<223> OTHER INFORMATION: 2'-O-methyl modified residue
<220> FEATURE:
<221> NAME/KEY: misc_feature
<222> LOCATION: (8)..(8)
<223> OTHER INFORMATION: 2'-O-methyl modified residue
<220> FEATURE:
<221> NAME/KEY: misc_feature
<222> LOCATION: (14)..(14)
<223> OTHER INFORMATION: 2'-O-methyl modified residue

<400> SEQUENCE: 121
uguuuggugg auaugaguc                                                  19

<210> SEQ ID NO 122
<211> LENGTH: 19
<212> TYPE: RNA
<213> ORGANISM: Homo sapiens

<400> SEQUENCE: 122
ggcauaccuu aaacaagcu                                                  19

<210> SEQ ID NO 123
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 123
ggcauaccuu aaacaagcut t                                               21

<210> SEQ ID NO 124
<211> LENGTH: 23
<212> TYPE: DNA
<213> ORGANISM: Artificial Sequence
<220> FEATURE:
```

```
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 124
agcuuguuua agguaugccd tdt                                              23

<210> SEQ ID NO 125
<211> LENGTH: 19
<212> TYPE: RNA
<213> ORGANISM: Homo sapiens

<400> SEQUENCE: 125
gacgacaaua agcucuuca                                                   19

<210> SEQ ID NO 126
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 126
gacgacaaua agcucuucat t                                                21

<210> SEQ ID NO 127
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 127
ugaagagcuu auugucguct t                                                21

<210> SEQ ID NO 128
<211> LENGTH: 19
<212> TYPE: RNA
<213> ORGANISM: Homo sapiens

<400> SEQUENCE: 128
ccuuaugacc acucuagag                                                   19

<210> SEQ ID NO 129
<211> LENGTH: 21
<212> TYPE: DNA
<213> ORGANISM: Artificial Sequence
```

```
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 129
ccuuaugacc acucuagagt t                                              21

<210> SEQ ID NO 130
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 130
cucuagagug gucauaaggt t                                              21

<210> SEQ ID NO 131
<211> LENGTH: 19
<212> TYPE: RNA
<213> ORGANISM: Homo sapiens

<400> SEQUENCE: 131
gaugagacac caauuauug                                                 19

<210> SEQ ID NO 132
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 132
gaugagacac caauuauugt t                                              21

<210> SEQ ID NO 133
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
```

<223> OTHER INFORMATION: DNA

<400> SEQUENCE: 133
caauaauugg ugucucauct t         21

<210> SEQ ID NO 134
<211> LENGTH: 19
<212> TYPE: RNA
<213> ORGANISM: Homo sapiens

<400> SEQUENCE: 134
gccaaaacuu caaauccaa         19

<210> SEQ ID NO 135
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 135
gccaaaacuu caaauccaat t         21

<210> SEQ ID NO 136
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 136
uuggauuuga aguuuuggct t         21

<210> SEQ ID NO 137
<211> LENGTH: 19
<212> TYPE: RNA
<213> ORGANISM: Homo sapiens

<400> SEQUENCE: 137
ccacaagaac agcaagcac         19

<210> SEQ ID NO 138
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature

<222> LOCATION: (20)..(21)
<223> OTHER INFORMATION: DNA

<400> SEQUENCE: 138
ccacaagaac agcaagcact t                                              21

<210> SEQ ID NO 139
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 139
gugcuugcug uucuugtggt t                                              21

<210> SEQ ID NO 140
<211> LENGTH: 19
<212> TYPE: RNA
<213> ORGANISM: Homo sapiens

<400> SEQUENCE: 140
cgacgacaug aauaagauc                                                 19

<210> SEQ ID NO 141
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 141
cgacgacaug aauaagauct t                                              21

<210> SEQ ID NO 142
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 142
gaucuuauuc augucgucgt t                                              21

<210> SEQ ID NO 143

```
<211> LENGTH: 19
<212> TYPE: RNA
<213> ORGANISM: Homo sapiens

<400> SEQUENCE: 143
ccaucagcua cccauauuc                                                    19

<210> SEQ ID NO 144
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 144
ccaucagcua cccauauuct t                                                 21

<210> SEQ ID NO 145
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 145
gaauaugggu agcugauggt t                                                 21

<210> SEQ ID NO 146
<211> LENGTH: 19
<212> TYPE: RNA
<213> ORGANISM: Homo sapiens

<400> SEQUENCE: 146
ggaaggcaac cagcuguua                                                    19

<210> SEQ ID NO 147
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 147
ggaaggcaac cagcuguuat t                                                 21
```

```
<210> SEQ ID NO 148
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 148
uaacagcugg uugccuucct t                                              21

<210> SEQ ID NO 149
<211> LENGTH: 19
<212> TYPE: RNA
<213> ORGANISM: Homo sapiens

<400> SEQUENCE: 149
gcugagaacc aauaccaga                                                 19

<210> SEQ ID NO 150
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 150
gcugagaacc aauaccagat t                                              21

<210> SEQ ID NO 151
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 151
ucugguauug guucucagct t                                              21

<210> SEQ ID NO 152
<211> LENGTH: 19
<212> TYPE: RNA
<213> ORGANISM: Homo sapiens

<400> SEQUENCE: 152
caacucucag gcagugugu                                                 19
```

```
<210> SEQ ID NO 153
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 153
caacucucag gcagugugut t                                              21

<210> SEQ ID NO 154
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 154
acacacugcc ugagaguugt t                                              21

<210> SEQ ID NO 155
<211> LENGTH: 19
<212> TYPE: RNA
<213> ORGANISM: Homo sapiens

<400> SEQUENCE: 155
cacgaaggcu gugcugcuu                                                 19

<210> SEQ ID NO 156
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 156
cacgaaggcu gugcugcuut t                                              21

<210> SEQ ID NO 157
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
```

```
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 157
aagcagcaca gccuucgugt t                                            21

<210> SEQ ID NO 158
<211> LENGTH: 19
<212> TYPE: RNA
<213> ORGANISM: Homo sapiens

<400> SEQUENCE: 158
cgugcuguga caccgacuu                                               19

<210> SEQ ID NO 159
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 159
cgugcuguga caccgacuut t                                            21

<210> SEQ ID NO 160
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 160
aagucggugu cacagcacgt t                                            21

<210> SEQ ID NO 161
<211> LENGTH: 19
<212> TYPE: RNA
<213> ORGANISM: Homo sapiens

<400> SEQUENCE: 161
ccaacgcagc cagcaccaa                                               19

<210> SEQ ID NO 162
<211> LENGTH: 21
<212> TYPE: DNA
<213> ORGANISM: Artificial Sequence
<220> FEATURE:
<223> OTHER INFORMATION: siRNA sense strand
<220> FEATURE:
```

<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 162
ccaacgcagc cagcaccaat t                                              21

<210> SEQ ID NO 163
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 163
uuggugcugg cugcguuggt t                                              21

<210> SEQ ID NO 164
<211> LENGTH: 19
<212> TYPE: RNA
<213> ORGANISM: Homo sapiens

<400> SEQUENCE: 164
cuggaaugcu caggaaugu                                                 19

<210> SEQ ID NO 165
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 165
cuggaaugcu caggaaugut t                                              21

<210> SEQ ID NO 166
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 166
acauuccuga gcauuccagt t                                         21

<210> SEQ ID NO 167
<211> LENGTH: 19
<212> TYPE: RNA
<213> ORGANISM: Homo sapiens

<400> SEQUENCE: 167
ccugaccucu gucuuacuu                                            19

<210> SEQ ID NO 168
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 168
ccugaccucu gucuuacuut t                                         21

<210> SEQ ID NO 169
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 169
aaguaagaca gaggucaggt t                                         21

<210> SEQ ID NO 170
<211> LENGTH: 19
<212> TYPE: RNA
<213> ORGANISM: Homo sapiens

<400> SEQUENCE: 170
cugggaagaa aucugagaa                                            19

<210> SEQ ID NO 171
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 171
cugggaagaa aucugagaat t                                               21

<210> SEQ ID NO 172
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 172
uucucagauu ucuucccagt t                                               21

<210> SEQ ID NO 173
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 173
guuggagcug uuggcguagt t                                               21

<210> SEQ ID NO 174
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (20)..(21)
<223> OTHER INFORMATION: DNA

<400> SEQUENCE: 174
cuacgccaac agcuccaact t                                               21

<210> SEQ ID NO 175
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (3)..(3)
<223> OTHER INFORMATION: 2'-O-methyl modified residue

```
<220> FEATURE:
<221> NAME/KEY: misc_feature
<222> LOCATION: (13)..(13)
<223> OTHER INFORMATION: 2'-O-methyl modified residue
<220> FEATURE:
<221> NAME/KEY: misc_feature
<222> LOCATION: (16)..(16)
<223> OTHER INFORMATION: 2'-O-methyl modified residue
<220> FEATURE:
<221> NAME/KEY: misc_feature
<222> LOCATION: (20)..(21)
<223> OTHER INFORMATION: DNA

<400> SEQUENCE: 175
gcugaagaaa cuugguaaut t                                              21

<210> SEQ ID NO 176
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (3)..(3)
<223> OTHER INFORMATION: 2'-O-methyl modified residue
<220> FEATURE:
<221> NAME/KEY: misc_feature
<222> LOCATION: (6)..(6)
<223> OTHER INFORMATION: 2'-O-methyl modified residue
<220> FEATURE:
<221> NAME/KEY: misc_feature
<222> LOCATION: (16)..(16)
<223> OTHER INFORMATION: 2'-O-methyl modified residue
<220> FEATURE:
<221> NAME/KEY: misc_feature
<222> LOCATION: (20)..(21)
<223> OTHER INFORMATION: DNA

<400> SEQUENCE: 176
auuaccaagu uucuucagct t                                              21

<210> SEQ ID NO 177
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (5)..(5)
<223> OTHER INFORMATION: 2'-O-methyl modified residue
<220> FEATURE:
<221> NAME/KEY: misc_feature
<222> LOCATION: (7)..(7)
<223> OTHER INFORMATION: 2'-O-methyl modified residue
<220> FEATURE:
<221> NAME/KEY: misc_feature
<222> LOCATION: (11)..(11)
<223> OTHER INFORMATION: 2'-O-methyl modified residue
<220> FEATURE:
<221> NAME/KEY: misc_feature
<222> LOCATION: (14)..(14)
<223> OTHER INFORMATION: 2'-O-methyl modified residue
<220> FEATURE:
<221> NAME/KEY: misc_feature
<222> LOCATION: (18)..(18)
```

<223> OTHER INFORMATION: 2'-O-methyl modified residue
<220> FEATURE:
<221> NAME/KEY: misc_feature
<222> LOCATION: (20)..(21)
<223> OTHER INFORMATION: DNA

<400> SEQUENCE: 177
gacucauauc caccaaacat t                                              21

<210> SEQ ID NO 178
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (1)..(1)
<223> OTHER INFORMATION: 2'-O-methyl modified residue
<220> FEATURE:
<221> NAME/KEY: misc_feature
<222> LOCATION: (5)..(5)
<223> OTHER INFORMATION: 2'-O-methyl modified residue
<220> FEATURE:
<221> NAME/KEY: misc_feature
<222> LOCATION: (8)..(8)
<223> OTHER INFORMATION: 2'-O-methyl modified residue
<220> FEATURE:
<221> NAME/KEY: misc_feature
<222> LOCATION: (14)..(14)
<223> OTHER INFORMATION: 2'-O-methyl modified residue
<220> FEATURE:
<221> NAME/KEY: misc_feature
<222> LOCATION: (20)..(21)
<223> OTHER INFORMATION: DNA

<400> SEQUENCE: 178
uguuuggugg auaugaguct t                                              21

<210> SEQ ID NO 179
<211> LENGTH: 11
<212> TYPE: PRT
<213> ORGANISM: Human immunodeficiency virus type 1

<400> SEQUENCE: 179

Tyr Gly Arg Lys Lys Arg Arg Gln Arg Arg Arg
1               5                   10

<210> SEQ ID NO 180
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (32)..(32)
<223> OTHER INFORMATION: amide_modification

<400> SEQUENCE: 180

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 181

<211> LENGTH: 17
<212> TYPE: PRT
<213> ORGANISM: Artificial Sequence
<220> FEATURE:
<223> OTHER INFORMATION: Synthetic Peptide

<400> SEQUENCE: 181

Gly Ala Leu Phe Leu Gly Phe Leu Gly Ala Ala Gly Ser Thr Met Gly
1               5                   10                  15

Ala

<210> SEQ ID NO 182
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 182

Lys Glu Thr Trp Trp Glu Thr Trp Trp Thr Glu Trp
1               5                   10

<210> SEQ ID NO 183
<211> LENGTH: 4
<212> TYPE: PRT
<213> ORGANISM: Artificial Sequence
<220> FEATURE:
<223> OTHER INFORMATION: Synthetic peptide

<400> SEQUENCE: 183

Cys Ala Asp Tyr
1

<210> SEQ ID NO 184
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: residue acylated at N-terminus
<220> FEATURE:
<221> NAME/KEY: MISC_FEATURE
<222> LOCATION: (20)..(20)
<223> OTHER INFORMATION: residue modified by attaching cysteamide at
      C-terminus

<400> SEQUENCE: 184

Gly Leu Trp Arg Ala Leu Trp Arg Leu Leu Arg Ser Leu Trp Arg Leu
1               5                   10                  15

Leu Trp Arg Ala
            20

<210> SEQ ID NO 185
<211> LENGTH: 3677
<212> TYPE: DNA
<213> ORGANISM: Homo sapiens

<400> SEQUENCE: 185
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180
catttttttt taaaactgta ttgtttctcg ttttaattta tttttgcttg ccattcccca     240

```
cttgaatcgg gccgacggct tggggagatt gctctacttc cccaaatcac tgtggatttt    300
ggaaaccagc agaaagagga aagaggtagc aagagctcca gagagaagtc gaggaagaga    360
gagacgggt  cagagagagc gcgcgggcgt gcgagcagcg aaagcgacag gggcaaagtg    420
agtgacctgc ttttgggggt gaccgccgga gcgcggcgtg agccctcccc cttgggatcc    480
cgcagctgac cagtcgcgct gacggacaga cagacagaca ccgcccccag ccccagctac    540
cacctcctcc ccggccggcg gcggacagtg gacgcggcgg cgagccgcgg gcaggggccg    600
gagcccgcgc ccggaggcgg ggtggagggg gtcgggctc gcggcgtcgc actgaaactt     660
ttcgtccaac ttctgggctg ttctcgcttc ggaggagccg tggtccgcgc ggggaagcc    720
gagccgagcg gagccgcgag aagtgctagc tcggccggg  aggagccgca gccggaggag    780
ggggaggagg aagaagagaa ggaagaggag aggggccgc agtggcgact cggcgctcgg     840
aagccgggct catggacggg tgaggcggcg gtgtgcgcag acagtgctcc agccgcgcgc    900
gctcccagg  ccctggcccg ggcctcgggc cgggaggaa gagtagctcg ccgaggcgcc     960
gaggagagcg ggccgcccca gcccgagc cggagaggga gcgcgagccg cgccggcccc     1020
ggtcgggcct ccgaaaccat gaactttctg ctgtcttggg tgcattggag ccttgccttg   1080
ctgctctacc tccaccatgc caagtggtcc caggctgcac ccatggcaga aggaggaggg   1140
cagaatcatc acgaagtggt gaagttcatg gatgtctatc agcgcagcta ctgccatcca   1200
atcgagaccc tggtggacat cttccaggag taccctgatg agatcgagta catcttcaag   1260
ccatcctgtg tgcccctgat gcgatgcggg ggctgctgca atgacgaggg cctggagtgt   1320
gtgcccactg aggagtccaa catcaccatg cagattatgc ggatcaaacc tcaccaaggc   1380
cagcacatag agagatgag  cttcctacag cacaacaaat gtgaatgcag accaaagaaa   1440
gatagagcaa gacaagaaaa aaaatcagtt cgaggaaagg gaaagggca aaaacgaaag    1500
cgcaagaaat cccggtataa gtcctggagc gtgtacgttg gtgccgctg ctgtctaatg    1560
ccctggagcc tccctggccc ccatccctgt gggccttgct cagagcggag aaagcatttg   1620
tttgtacaag atccgcagac gtgtaaatgt tcctgcaaaa acacagactc gcgttgcaag   1680
gcgaggcagc ttgagttaaa cgaacgtact tgcagatgtg acaagccgag gcggtgagcc   1740
gggcaggagg aaggagcctc cctcagggtt tcgggaacca gatctctcac caggaaagac   1800
tgatacagaa cgatcgatac agaaaccacg ctgccgccac cacaccatca ccatcgacag   1860
aacagtcctt aatccagaaa cctgaaatga aggaagagga gactctgcgc agagcacttt   1920
gggtccggag ggcgagactc cggcggaagc attcccgggc gggtgaccca gcacggtccc   1980
tcttggaatt ggattcgcca ttttattttt cttgctgcta aatcaccgag cccggaagat   2040
tagagagttt tatttctggg attcctgtag acacacccac ccacatacat acatttatat   2100
atatatatat tatatatata taaaaataaa tatctctatt ttatatatat aaaatatata   2160
tattctttt  ttaaattaac agtgctaatg ttattggtgt cttcactgga tgtatttgac   2220
tgctgtggac ttgagttggg aggggaatgt tcccactcag atcctgacag ggaagaggag   2280
gagatgagag actctggcat gatcttttt ttgtcccact tggtggggcc agggtcctct    2340
cccctgccca ggaatgtgca aggccagggc atggggcaa atatgaccca gttttgggaa    2400
caccgacaaa cccagccctg gcgctgagcc tctctacccc aggtcagacg gacagaaaga   2460
cagatcacag gtacagggat gaggacaccg gctctgacca ggagtttggg gagcttcagg   2520
acattgctgt gctttgggga ttccctccac atgctgcacg cgcatctcgc ccccagggc    2580
```

| | |
|---|---|
| actgcctgga agattcagga gcctgggcgg ccttcgctta ctctcacctg cttctgagtt | 2640 |
| gcccaggaga ccactggcag atgtcccggc gaagagaaga gacacattgt tggaagaagc | 2700 |
| agcccatgac agctcccctt cctgggactc gccctcatcc tcttcctgct cccctcctg | 2760 |
| gggtgcagcc taaaaggacc tatgtcctca caccattgaa accactagtt ctgtcccccc | 2820 |
| aggagacctg gttgtgtgtg tgtgagtggt tgaccttcct ccatcccctg gtccttccct | 2880 |
| tcccttcccg aggcacagag agacagggca ggatccacgt gcccattgtg gaggcagaga | 2940 |
| aaagagaaag tgttttatat acggtactta tttaatatcc cttttttaatt agaaattaaa | 3000 |
| acagttaatt taattaaaga gtagggtttt ttttcagtat tcttggttaa tatttaattt | 3060 |
| caactattta tgagatgtat cttttgctct ctcttgctct cttatttgta ccggttttttg | 3120 |
| tatataaaat tcatgtttcc aatctctctc tccctgatcg gtgacagtca ctagcttatc | 3180 |
| ttgaacagat atttaatttt gctaacactc agctctgccc tccccgatcc cctggctccc | 3240 |
| cagcacacat tcctttgaaa taaggtttca atatacatct acatactata tatatatttg | 3300 |
| gcaacttgta tttgtgtgta tatatatata tatatgttta tgtatatatg tgattctgat | 3360 |
| aaaatagaca ttgctattct gttttttata tgtaaaaaca aaacaagaaa aaatagagaa | 3420 |
| ttctacatac taaatctctc tcctttttta attttaatat ttgttatcat ttatttattg | 3480 |
| gtgctactgt ttatccgtaa taattgtggg gaaaagatat taacatcacg tctttgtctc | 3540 |
| tagtgcagtt tttcgagata ttccgtagta catatttatt tttaaacaac gacaaagaaa | 3600 |
| tacagatata tcttaaaaaa aaaaaagcat tttgtattaa agaatttaat tctgatctca | 3660 |
| aaaaaaaaaa aaaaaaa | 3677 |

<210> SEQ ID NO 186
<211> LENGTH: 3608
<212> TYPE: DNA
<213> ORGANISM: Homo sapiens

<400> SEQUENCE: 186

| | |
|---|---|
| tcgcggaggc ttggggcagc cgggtagctc ggaggtcgtg gcgctggggg ctagcaccag | 60 |
| cgctctgtcg ggaggcgcag cggttaggtg gaccggtcag cggactcacc ggccagggcg | 120 |
| ctcggtgctg gaatttgata ttcattgatc cgggttttat ccctcttctt ttttcttaaa | 180 |
| cattttttt taaaactgta ttgtttctcg ttttaattta ttttttgcttg ccattccca | 240 |
| cttgaatcgg gccgacggct tggggagatt gctctacttc cccaaatcac tgtggatttt | 300 |
| ggaaaccagc agaaagagga aagaggtagc aagagctcca gagagaagtc gaggaagaga | 360 |
| gagacgggggt cagagagagc gcgcgggcgt gcgagcagcg aaagcgacag gggcaaagtg | 420 |
| agtgacctgc ttttggggt gaccgccgga gcgcggcgtg agccctcccc cttgggatcc | 480 |
| cgcagctgac cagtcgcgct gacggacaga cagacagaca ccgcccccag ccccagctac | 540 |
| cacctcctcc ccggccggcg gcggacagtg gacgcggcgg cgagccgcgg gcaggggccg | 600 |
| gagcccgcgc ccggaggcgg ggtggagggg gtcgggctc gcggcgtcgc actgaaactt | 660 |
| ttcgtccaac ttctgggctg ttctcgcttc ggaggagccg tggtccgcgc gggggaagcc | 720 |
| gagccgagcg gagccgcgag aagtgctagc tcggccgggg aggagccgca gccggaggag | 780 |
| ggggaggagg aagaagagaa ggaagaggag agggggccgc agtggcgact cggcgctcgg | 840 |
| aagccgggct catggacggg tgaggcggcg gtgtgcgcag acagtgctcc agccgcgcgc | 900 |
| gctccccagg ccctggcccg ggcctcgggc cggggaggaa gagtagctcg ccgaggcgcc | 960 |
| gaggagagcg ggccgccca cagcccgagc cggagaggga gcgcgagccg cgccggcccc | 1020 |

```
ggtcgggcct ccgaaaccat gaactttctg ctgtcttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
atcgagaccc tggtggacat cttccaggag taccctgatg agatcgagta catcttcaag    1260
ccatcctgtg tgcccctgat gcgatgcggg ggctgctgca atgacgaggg cctggagtgt    1320
gtgcccactg aggagtccaa catcaccatg cagattatgc ggatcaaacc tcaccaaggc    1380
cagcacatag gagagatgag cttcctacag cacaacaaat gtgaatgcag accaagaaaa    1440
gatagagcaa gacaagaaaa aaaatcagtt cgaggaaagg gaaaggggca aaaacgaaag    1500
cgcaagaaat cccgtccctg tgggccttgc tcagagcgga gaaagcattt gtttgtacaa    1560
gatccgcaga cgtgtaaatg ttcctgcaaa aacacagact cgcgttgcaa ggcgaggcag    1620
cttgagttaa acgaacgtac ttgcagatgt gacaagccga ggcggtgagc cgggcaggag    1680
gaaggagcct ccctcagggt ttcgggaacc agatctctca ccaggaaaga ctgatacaga    1740
acgatcgata cagaaaccac gctgccgcca ccacaccatc accatcgaca gaacagtcct    1800
taatccagaa acctgaaatg aaggaagagg agactctgcg cagagcactt tgggtccgga    1860
gggcgagact ccggcggaag cattcccggg cgggtgaccc agcacggtcc ctcttggaat    1920
tggattcgcc atttatttt tcttgctgct aaatcaccga gcccggaaga ttagagagtt    1980
ttatttctgg gattcctgta gacacaccca cccacataca tacatttata tatatatata   2040
ttatatatat ataaaaataa atatctctat tttatatata taaaatatat atattctttt    2100
tttaaattaa cagtgctaat gttattggtg tcttcactgg atgtatttga ctgctgtgga    2160
cttgagttgg gaggggaatg ttcccactca gatcctgaca gggaagagga ggagatgaga    2220
gactctggca tgatcttttt tttgtcccac ttggtgggc cagggtcctc tcccctgccc      2280
aggaatgtgc aaggccaggg catgggggca aatatgaccc agttttggga acaccgacaa    2340
acccagccct ggcgctgagc ctctctaccc caggtcagac ggacagaaag acagatcaca    2400
ggtacaggga tgaggacacc ggctctgacc aggagtttgg ggagcttcag gacattgctg    2460
tgctttgggg attccctcca catgctgcac gcgcatctcg cccccagggg cactgcctgg    2520
aagattcagg agcctgggcg gccttcgctt actctcacct gcttctgagt tgcccaggag    2580
accactggca gatgtcccgg cgaagagaag agacacattg ttggaagaag cagcccatga    2640
cagctcccct tcctgggact cgccctcatc ctcttcctgc tccccttcct ggggtgcagc    2700
ctaaaaggac ctatgtcctc acaccattga aaccactagt tctgtccccc caggagacct    2760
ggttgtgtgt gtgtgagtgg ttgaccttcc tccatcccct ggtccttccc ttcccttccc    2820
gaggcacaga gagacagggc aggatccacg tgcccattgt ggaggcagag aaaagagaaa    2880
gtgttttata tacggtactt atttaatatc ccttttaat tagaaattaa aacagttaat     2940
ttaattaaag agtagggttt tttttcagta ttccttggtta atatttaatt tcaactattt    3000
atgagatgta tcttttgctc tctcttgctc tcttatttgt accggttttt gtatataaaa    3060
ttcatgtttc caatctctct ctccctgatc ggtgacagtc actagcttat cttgaacaga    3120
tatttaattt tgctaacact cagctctgcc ctccccgatc ccctggctcc ccagcacaca    3180
ttcctttgaa ataaggtttc aatatacatc tacatactat atatatattt ggcaacttgt    3240
atttgtgtgt atatatatat atatatgttt atgtatatat gtgattctga taaaatagac    3300
attgctattc tgttttttat atgtaaaaac aaaacaagaa aaaatagaga attctacata    3360
```

-continued

| | |
|---|---|
| ctaaatctct ctcctttttt aattttaata tttgttatca tttatttatt ggtgctactg | 3420 |
| tttatccgta ataattgtgg ggaaaagata ttaacatcac gtctttgtct ctagtgcagt | 3480 |
| ttttcgagat attccgtagt acatatttat ttttaaacaa cgacaaagaa atacagatat | 3540 |
| atcttaaaaa aaaaaaagca ttttgtatta aagaatttaa ttctgatctc aaaaaaaaaa | 3600 |
| aaaaaaaa | 3608 |

<210> SEQ ID NO 187
<211> LENGTH: 3554
<212> TYPE: DNA
<213> ORGANISM: Homo sapiens

<400> SEQUENCE: 187

| | |
|---|---|
| tcgcggaggc ttgggcagc cgggtagctc ggaggtcgtg gcgctggggg ctagcaccag | 60 |
| cgctctgtcg ggaggcgcag cggttaggtg gaccggtcag cggactcacc ggccagggcg | 120 |
| ctcggtgctg gaatttgata ttcattgatc cgggttttat ccctcttctt ttttcttaaa | 180 |
| cattttttt taaaactgta ttgtttctcg ttttaattta ttttgcttg ccattcccca | 240 |
| cttgaatcgg gccgacggct tgggagatt gctctacttc cccaaatcac tgtggatttt | 300 |
| ggaaaccagc agaaagagga aagagtagc aagagctcca gagagaagtc gaggaagaga | 360 |
| gagacggggt cagagagagc gcgcgggcgt gcgagcagcg aaagcgacag gggcaaagtg | 420 |
| agtgacctgc ttttggggt gaccgccgga gcgcggcgtg agccctcccc cttgggatcc | 480 |
| cgcagctgac cagtcgcgct gacggacaga cagacagaca ccgcccccag ccccagctac | 540 |
| cacctcctcc ccggccggcg gcggacagtg gacgcggcgg cgagccgcgg gcaggggccg | 600 |
| gagcccgcgc ccggaggcgg ggtggagggg gtcgggctc gcggcgtcgc actgaaactt | 660 |
| ttcgtccaac ttctgggctg ttctcgcttc ggaggagccg tggtccgcgc gggggaagcc | 720 |
| gagccgagcg gagccgcgag aagtgctagc tcgggccggg aggagccgca gccggaggag | 780 |
| ggggaggagg aagaagagaa ggaagaggag aggggggccgc agtggcgact cggcgctcgg | 840 |
| aagccgggct catggacggg tgaggcggcg gtgtgcgcag acagtgctcc agccgcgcgc | 900 |
| gctcccagg ccctggcccg ggcctcgggc cggggaggaa gagtagctcg ccgaggcgcc | 960 |
| gaggagagcg ggccgcccca cagcccgagc cggagaggga gcgcgagccg cgccggcccc | 1020 |
| ggtcgggcct ccgaaaccat gaactttctg ctgtcttggg tgcattggag ccttgccttg | 1080 |
| ctgctctacc tccaccatgc caagtggtcc caggctgcac ccatggcaga aggaggaggg | 1140 |
| cagaatcatc acgaagtggt gaagttcatg gatgtctatc agcgcagcta ctgccatcca | 1200 |
| atcgagaccc tggtggacat cttccaggag taccctgatg agatcgagta catcttcaag | 1260 |
| ccatcctgtg tgccctgat gcgatgcggg ggctgctgca atgacgaggg cctggagtgt | 1320 |
| gtgcccactg aggagtccaa catcaccatg cagattatgc ggatcaaacc tcaccaaggc | 1380 |
| cagcacatag agagatgag cttcctacag cacaacaaat gtgaatgcag accaaagaaa | 1440 |
| gatagagcaa gacaagaaaa tccctgtggg ccttgctcag agcggagaaa gcatttgttt | 1500 |
| gtacaagatc cgcagacgtg taaatgttcc tgcaaaaaca cagactcgcg ttgcaaggcg | 1560 |
| aggcagcttg agttaaacga acgtacttgc agatgtgaca agccgaggcg gtgagccggg | 1620 |
| caggaggaag gagcctccct cagggtttcg ggaaccagat ctctcaccag gaaagactga | 1680 |
| tacagaacga tcgatacaga aaccacgctg ccgccaccac accatcacca tcgacagaac | 1740 |
| agtccttaat ccagaaacct gaaatgaagg aagaggagac tctgcgcaga gcactttggg | 1800 |
| tccggagggc gagactccgg cggaagcatt cccgggcggg tgacccagca cggtccctct | 1860 |

| | |
|---|---|
| tggaattgga ttcgccattt tatttttctt gctgctaaat caccgagccc ggaagattag | 1920 |
| agagttttat ttctgggatt cctgtagaca cacccaccca catacataca tttatatata | 1980 |
| tatatattat atatatataa aaataaatat ctctatttta tatatataaa atatatatat | 2040 |
| tctttttta aattaacagt gctaatgtta ttggtgtctt cactggatgt atttgactgc | 2100 |
| tgtggacttg agttgggagg ggaatgttcc cactcagatc ctgacaggga agaggaggag | 2160 |
| atgagagact ctggcatgat cttttttttg tcccacttgg tggggccagg gtcctctccc | 2220 |
| ctgcccagga atgtgcaagg ccagggcatg ggggcaaata tgacccagtt ttgggaacac | 2280 |
| cgacaaaccc agccctggcg ctgagcctct ctaccccagg tcagacggac agaaagacag | 2340 |
| atcacaggta cagggatgag gacaccggct ctgaccagga gtttggggag cttcaggaca | 2400 |
| ttgctgtgct ttggggattc cctccacatg ctgcacgcgc atctcgcccc caggggcact | 2460 |
| gcctggaaga ttcaggagcc tgggcggcct tcgcttactc tcacctgctt ctgagttgcc | 2520 |
| caggagacca ctggcagatg tcccggcgaa gagaagagac acattgttgg aagaagcagc | 2580 |
| ccatgacagc tcccccttcct gggactcgcc ctcatcctct tcctgctccc cttcctgggg | 2640 |
| tgcagcctaa aaggacctat gtcctcacac cattgaaacc actagttctg tcccccagg | 2700 |
| agacctggtt gtgtgtgtgt gagtggttga ccttcctcca tcccctggtc cttcccttcc | 2760 |
| cttcccgagg cacagagaga cagggcagga tccacgtgcc cattgtggag gcagagaaaa | 2820 |
| gagaaagtgt tttatatacg gtacttattt aatatccctt tttaattaga aattaaaaca | 2880 |
| gttaatttaa ttaaagagta gggtttttt tcagtattct tggttaatat ttaatttcaa | 2940 |
| ctatttatga gatgtatctt ttgctctctc ttgctctctt atttgtaccg gttttttgtat | 3000 |
| ataaaattca tgtttccaat ctctctctcc ctgatcggtg acagtcacta gcttatcttg | 3060 |
| aacagatatt taattttgct aacactcagc tctgccctcc ccgatcccct ggctccccag | 3120 |
| cacacattcc tttgaaataa ggtttcaata tacatctaca tactatatat atatttggca | 3180 |
| acttgtatt gtgtgtatat atatatatat atgtttatgt atatatgtga ttctgataaa | 3240 |
| atagacattg ctattctgtt ttttatatgt aaaaacaaaa caagaaaaaa tagagaattc | 3300 |
| tacatactaa atctctctcc ttttttaatt ttaatatttg ttatcattta tttattggtg | 3360 |
| ctactgttta tccgtaataa ttgtggggaa aagatattaa catcacgtct ttgtctctag | 3420 |
| tgcagttttt cgagatattc cgtagtacat atttattttt aaacaacgac aaagaaatac | 3480 |
| agatatatct taaaaaaaaa aaagcatttt gtattaaaga atttaattct gatctcaaaa | 3540 |
| aaaaaaaaaa aaaa | 3554 |

<210> SEQ ID NO 188
<211> LENGTH: 3519
<212> TYPE: DNA
<213> ORGANISM: Homo sapiens

<400> SEQUENCE: 188

| | |
|---|---|
| tcgcggaggc ttggggcagc cgggtagctc ggaggtcgtg gcgctggggg ctagcaccag | 60 |
| cgctctgtcg ggaggcgcag cggttaggtg gaccggtcag cggactcacc ggccagggcg | 120 |
| ctcggtgctg gaatttgata ttcattgatc cgggttttat ccctcttctt ttttcttaaa | 180 |
| cattttttt taaaactgta ttgtttctcg ttttaattta ttttgcttg ccattcccca | 240 |
| cttgaatcgg gccgacggct tggggagatt gctctacttc cccaaatcac tgtggatttt | 300 |
| ggaaaccagc agaaagagga aagaggtagc aagagctcca gagagaagtc gaggaagaga | 360 |

```
gagacggggt cagagagagc gcgcgggcgt gcgagcagcg aaagcgacag gggcaaagtg      420
agtgacctgc ttttggggt gaccgccgga gcgcggcgtg agccctcccc cttgggatcc      480
cgcagctgac cagtcgcgct gacggacaga cagacagaca ccgcccccag ccccagctac      540
cacctcctcc ccggccggcg gcggacagtg gacgcgcgg cgagccgcgg gcaggggccg      600
gagcccgcgc ccggaggcgg ggtggagggg gtcgggctc gcggcgtcgc actgaaactt      660
ttcgtccaac ttctgggctg ttctcgcttc ggaggagccg tggtccgcgc ggggaagcc      720 gagccgagcg gagccgcgag aagtgctagc tcgggccggg aggagccgca gccggaggag      780 ggggaggag aagaagagaa ggaagaggag aggggccgc agtggcgact cggcgctcgg      840
aagccgggct catggacggg tgaggcggcg gtgtgcgcag acagtgctcc agccgcgcgc      900 gctcccagg ccctggccg gcctcgggc cggggaggaa gagtagctcg ccgaggcgcc      960
gaggagagcg ggccgcccca cagcccgagc cggagaggga gcgcgagccg cgccggcccc     1020
ggtcgggcct ccgaaaccat gaactttctg ctgtcttggg tgcattggag ccttgccttg     1080
ctgctctacc tccaccatgc caagtggtcc caggctgcac ccatggcaga aggaggaggg     1140
cagaatcatc acgaagtggt gaagttcatg gatgtctatc agcgcagcta ctgccatcca     1200
atcgagaccc tggtggacat cttccaggag taccctgatg agatcgagta catcttcaag     1260
ccatcctgtg tgccctgat gcgatgcggg ggctgctgca atgacgaggg cctggagtgt     1320
gtgcccactg aggagtccaa catcaccatg cagattatgc ggatcaaacc tcaccaaggc     1380
cagcacatag gagagatgag cttcctacag cacaacaaat gtgaatgcag accaaagaaa     1440
gatagagcaa gacaagaaaa tccctgtggg ccttgctcag agcggagaaa gcatttgttt     1500
gtacaagatc cgcagacgtg taaatgttcc tgcaaaaaca cagactcgcg ttgcaagatg     1560
tgacaagccg aggcggtgag ccgggcagga ggaaggagcc tccctcaggg tttcgggaac     1620
cagatctctc accaggaaag actgatacag aacgatcgat acagaaacca cgctgccgcc     1680
accacaccat caccatcgac agaacagtcc ttaatccaga aacctgaaat gaaggaagag     1740
gagactctgc gcagagcact ttgggtccgg agggcgagac tccggcggaa gcattcccgg     1800
gcgggtgacc cagcacggtc cctcttggaa ttggattcgc cattttattt ttcttgctgc     1860
taaatcaccg agcccggaag attagagagt tttatttctg ggattcctgt agacacaccc     1920
acccacatac atacatttat atatatatat attatatata tataaaaata aatatctcta     1980
ttttatatat ataaaatata tatattcttt ttttaaatta acagtgctaa tgttattggt     2040
gtcttcactg gatgtatttg actgctgtgg acttgagttg ggaggggaat gttcccactc     2100
agatcctgac agggaagagg aggagatgag agactctggc atgatctttt ttttgtccca     2160
cttggtgggg ccagggtcct ctcccctgcc caggaatgtg caaggccagg gcatggggc     2220 aaatatgacc cagttttggg aacaccgaca aacccagccc tggcgctgag cctctctacc     2280
ccaggtcaga cggacagaaa gacagatcac aggtacaggg atgaggacac cggctctgac     2340
caggagtttg gggagcttca ggacattgct gtgctttggg gattccctcc acatgctgca     2400
cgcgcatctc gcccccaggg gcactgcctg gaagattcag gagcctgggc ggccttcgct     2460
tactctcacc tgcttctgag ttgcccagga gaccactggc agatgtcccg gcgaagagaa     2520
gagacacatt gttggaagaa gcagcccatg acagctcccc ttcctgggac tcgccctcat     2580
cctcttcctg ctccccttcc tggggtgcag cctaaaagga cctatgtcct cacaccattg     2640
aaaccactag ttctgtcccc ccaggagacc tggttgtgtg tgtgtgagtg gttgaccttc     2700
ctccatcccc tggtccttcc cttcccttcc cgaggcacag agagacaggg caggatccac     2760
```

| | |
|---|---|
| gtgcccattg tggaggcaga gaaaagagaa agtgttttat atacggtact tatttaatat | 2820 |
| cccttttaa ttagaaatta aaacagttaa tttaattaaa gagtagggtt ttttttcagt | 2880 |
| attcttggtt aatatttaat ttcaactatt tatgagatgt atcttttgct ctctcttgct | 2940 |
| ctcttatttg taccggtttt tgtatataaa attcatgttt ccaatctctc tctccctgat | 3000 |
| cggtgacagt cactagctta tcttgaacag atatttaatt ttgctaacac tcagctctgc | 3060 |
| cctccccgat cccctggctc cccagcacac attcctttga aataaggttt caatatacat | 3120 |
| ctacatacta tatatatatt tggcaacttg tatttgtgtg tatatatata tatatatgtt | 3180 |
| tatgtatata tgtgattctg ataaaataga cattgctatt ctgttttta tatgtaaaaa | 3240 |
| caaaacaaga aaaatagag aattctacat actaaatctc tctcctttt taattttaat | 3300 |
| atttgttatc atttatttat tggtgctact gtttatccgt aataattgtg gggaaaagat | 3360 |
| attaacatca cgtctttgtc tctagtgcag ttttcgaga tattccgtag tacatattta | 3420 |
| ttttaaaca acgacaaaga aatacagata tatcttaaaa aaaaaaaagc attttgtatt | 3480 |
| aaagaattta attctgatct caaaaaaaaa aaaaaaaa | 3519 |

<210> SEQ ID NO 189
<211> LENGTH: 3422
<212> TYPE: DNA
<213> ORGANISM: Homo sapiens

<400> SEQUENCE: 189

| | |
|---|---|
| tcgcggaggc ttgggcagc cgggtagctc ggaggtcgtg gcgctggggg ctagcaccag | 60 |
| cgctctgtcg ggaggcgcag cggttaggtg gaccggtcag cggactcacc ggccagggcg | 120 |
| ctcggtgctg gaatttgata ttcattgatc cgggttttat ccctcttctt ttttcttaaa | 180 |
| catttttttt taaaactgta ttgtttctcg ttttaattta ttttgcttg ccattcccca | 240 |
| cttgaatcgg gccgacggct tggggagatt gctctacttc cccaaatcac tgtggatttt | 300 |
| ggaaaccagc agaaagagga aagaggtagc aagagctcca gagagaagtc gaggaagaga | 360 |
| gagacggggt cagagagagc gcgcggggcgt gcgagcagcg aaagcgacag ggcaaagtg | 420 |
| agtgacctgc ttttgggggt gaccgccgga gcgcggcgtg agccctcccc cttgggatcc | 480 |
| cgcagctgac cagtcgcgct gacggacaga cagacagaca ccgcccccag ccccagctac | 540 |
| cacctcctcc ccggccggcg gcggacagtg gacgcggcgg cgagccgcgg gcaggggccg | 600 |
| gagcccgcgc ccggaggcgg ggtggagggg gtcgggctc gcggcgtcgc actgaaactt | 660 |
| ttcgtccaac ttctgggctg ttctcgcttc ggaggagccg tggtccgcgc ggggaagcc | 720 |
| gagccgagcg gagccgcgag aagtgctagc tcgggccggg aggagccgca gccggaggag | 780 |
| ggggaggagg aagaagagaa ggaagaggag aggggccgc agtggcgact cggcgctcgg | 840 |
| aagccgggct catggacggg tgaggcggcg gtgtgcgcag acagtgctcc agccgcgcgc | 900 |
| gctccccagg ccctggcccg ggcctcgggc cggggaggaa gagtagctcg ccgaggcgcc | 960 |
| gaggagagcg ggccgcccca cagcccgagc cggagaggga gcgcgagccg cgccggcccc | 1020 |
| ggtcgggcct ccgaaaccat gaactttctg ctgtcttggg tgcattggag ccttgccttg | 1080 |
| ctgctctacc tccaccatgc caagtggtcc caggctgcac ccatggcaga aggaggaggg | 1140 |
| cagaatcatc acgaagtggt gaagttcatg gatgtctatc agcgcagcta ctgccatcca | 1200 |
| atcgagaccc tggtggacat cttccaggag taccctgatg agatcgagta catcttcaag | 1260 |
| ccatcctgtg tgcccctgat gcgatgcggg ggctgctgca atgacgaggg cctggagtgt | 1320 |

```
gtgcccactg aggagtccaa catcaccatg cagattatgc ggatcaaacc tcaccaaggc   1380
cagcacatag gagagatgag cttcctacag cacaacaaat gtgaatgcag accaaagaaa   1440
gatagagcaa gacaagaaaa atgtgacaag ccgaggcggt gagccgggca ggaggaagga   1500
gcctccctca gggtttcggg aaccagatct ctcaccagga aagactgata cagaacgatc   1560
gatacagaaa ccacgctgcc gccaccacac catcaccatc gacagaacag tccttaatcc   1620
agaaacctga aatgaaggaa gaggagactc tgcgcagagc actttgggtc cggagggcga   1680
gactccggcg gaagcattcc cgggcgggtg acccagcacg gtccctcttg gaattggatt   1740
cgccatttta ttttcttgc tgctaaatca ccgagcccgg aagattagag agttttattt     1800
ctgggattcc tgtagacaca cccacccaca tacatacatt tatatatata tatattatat   1860
atatataaaa ataaatatct ctattttata tatataaaat atatatattc ttttttttaaa  1920
ttaacagtgc taatgttatt ggtgtcttca ctggatgtat ttgactgctg tggacttgag   1980
ttgggagggg aatgttccca ctcagatcct gacaggaag aggaggagat gagagactct    2040
ggcatgatct ttttttgtc ccacttggtg gggccagggt cctctcccct gcccaggaat    2100
gtgcaaggcc agggcatggg ggcaaatatg acccagtttt gggaacaccg acaaacccag   2160
ccctggcgct gagcctctct accccaggtc agacggacag aaagacagat cacaggtaca   2220
gggatgagga caccggctct gaccaggagt ttggggagct tcaggacatt gctgtgcttt   2280
ggggattccc tccacatgct gcacgcgcat ctcgccccca ggggcactgc ctggaagatt   2340
caggagcctg ggcggccttc gcttactctc acctgcttct gagttgccca ggagaccact   2400
ggcagatgtc ccggcgaaga gaagagacac attgttggaa gaagcagccc atgacagctc   2460
cccttcctgg gactcgccct catcctcttc ctgctcccct tcctggggtg cagcctaaaa   2520
ggacctatgt cctcacacca ttgaaaccac tagttctgtc cccccaggag acctggttgt   2580
gtgtgtgtga gtggttgacc ttcctccatc ccctggtcct tcccttccct tcccgaggca   2640
cagagagaca gggcaggatc cacgtgccca ttgtggaggc agagaaaaga gaaagtgttt   2700
tatatacggt acttatttaa tatccctttt taattagaaa ttaaaacagt taatttaatt   2760
aaagagtagg gttttttttc agtattcttg gttaatattt aatttcaact atttatgaga   2820
tgtatctttt gctctctctt gctctcttat ttgtaccggt ttttgtatat aaaattcatg   2880
tttccaatct ctctctccct gatcggtgac agtcactagc ttatcttgaa cagatattta   2940
attttgctaa cactcagctc tgccctcccc gatccctgg ctccccagca cacattcctt    3000
tgaaataagg tttcaatata catctacata ctatatatat atttggcaac ttgtatttgt   3060
gtgtatatat atatatatat gtttatgtat atatgtgatt ctgataaaat agacattgct   3120
attctgtttt ttatatgtaa aaacaaaaca agaaaaaata gagaattcta catactaaat   3180
ctctctcctt ttttaatttt aatatttgtt atcatttatt tattggtgct actgtttatc   3240
cgtaataatt gtggggaaaa gatattaaca tcacgtctttt gtctctagtg cagttttttcg  3300
agatattccg tagtacatat ttattttttaa acaacgacaa agaaatacag atatatctta  3360
aaaaaaaaaa agcattttgt attaaagaat ttaattctga tctcaaaaaa aaaaaaaaa    3420
aa                                                                   3422
```

<210> SEQ ID NO 190
<211> LENGTH: 3488
<212> TYPE: DNA
<213> ORGANISM: Homo sapiens

<400> SEQUENCE: 190

```
tcgcggaggc ttggggcagc cgggtagctc ggaggtcgtg gcgctggggg ctagcaccag    60
cgctctgtcg ggaggcgcag cggttaggtg gaccggtcag cggactcacc ggccagggcg   120
ctcggtgctg gaatttgata ttcattgatc cgggttttat ccctcttctt ttttcttaaa   180
catttttttt taaaactgta ttgtttctcg ttttaattta tttttgcttg ccattcccca   240
cttgaatcgg gccgacggct tggggagatt gctctacttc cccaaatcac tgtggatttt   300
ggaaaccagc agaagagga aagaggtagc aagagctcca gagagaagtc gaggaagaga   360
gagacggggt cagagagagc gcgcgggcgt gcgagcagcg aaagcgacag ggcaaagtg   420 agtgacctgc ttttgggggt gaccgccgga gcgcggcgtg agccctcccc cttgggatcc   480
cgcagctgac cagtcgcgct gacggacaga cagacagaca ccgcccccag ccccagctac   540
cacctcctcc ccggccggcg gcggacagtg gacgcggcgg cgagccgcgg gcaggggccg   600
gagcccgcgc ccggaggcgg ggtggagggg gtcgggctc gcggcgtcgc actgaaactt   660
ttcgtccaac ttctgggctg ttctcgcttc ggaggagccg tggtccgcgc ggggaagcc   720 gagccgagcg gagccgcgag aagtgctagc tcggccgggg aggagccgca gccggaggag   780
ggggaggagg aagaagagaa ggaagaggag aggggccgc agtggcgact cggcgctcgg   840
aagccgggct catggacggg tgaggcggcg gtgtgcgcag acagtgctcc agccgcgcgc   900 gctcccagg ccctggcccg ggcctcgggc cggggaggaa gagtagctcg ccgaggcgcc   960
gaggagagcg ggccgcccca cagcccgagc cggagaggga gcgcgagccg cgccggcccc  1020
ggtcgggcct ccgaaaccat gaactttctg ctgtcttggg tgcattggag ccttgccttg  1080
ctgctctacc tccaccatgc caagtggtcc caggctgcac ccatggcaga aggaggaggg  1140
cagaatcatc acgaagtggt gaagttcatg gatgtctatc agcgcagcta ctgccatcca  1200
atcgagaccc tggtggacat cttccaggag taccctgatg agatcgagta catcttcaag  1260
ccatcctgtg tgccctgat gcgatgcggg ggctgctgca atgacgaggg cctggagtgt  1320
gtgcccactg aggagtccaa catcaccatg cagattatgc ggatcaaacc tcaccaaggc  1380
cagcacatag agagatgag cttcctacag cacaacaaat gtgaatgcag accaaagaaa  1440
gatagagcaa gacaagaaaa tccctgtggg ccttgctcag agcggagaaa gcatttgttt  1500
gtacaagatc cgcagacgtg taaatgttcc tgcaaaaaca cagactcgcg ttgcaaggcg  1560
aggcagcttg agttaaacga acgtacttgc agatctctca ccaggaaaga ctgatacaga  1620
acgatcgata cagaaaccac gctgccgcca ccacaccatc accatcgaca gaacagtcct  1680
taatccagaa acctgaaatg aaggaagagg agactctgcg cagagcactt tgggtccgga  1740
gggcgagact ccggcggaag cattcccggg cgggtgaccc agcacggtcc ctcttggaat  1800
tggattcgcc attttatttt tcttgctgct aaatcaccga gcccggaaga ttagagagtt  1860
ttatttctgg gattcctgta gacacaccca cccacataca tacatttata tatatatata  1920
ttatatatat ataaaaataa atatctctat tttatatata taaatatat atattctttt  1980 tttaaattaa cagtgctaat gttattggtg tcttcactgg atgtatttga ctgctgtgga  2040
cttgagttgg gagggaatg ttcccactca gatcctgaca gggaagagga ggagatgaga  2100
gactctggca tgatcttttt tttgtcccac ttggtggggc cagggtcctc tcccctgccc  2160
aggaatgtgc aaggccaggg catggggca aatatgaccc agttttggga acaccgacaa  2220 acccagcct ggcgctgagc ctctctaccc caggtcagac ggacagaaag acagatcaca  2280
ggtacaggga tgaggacacc ggctctgacc aggagtttgg ggagcttcag gacattgctg  2340
```

```
tgctttgggg attccctcca catgctgcac gcgcatctcg cccccagggg cactgcctgg    2400
aagattcagg agcctgggcg gccttcgctt actctcacct gcttctgagt tgcccaggag    2460
accactggca gatgtcccgg cgaagagaag agacacattg ttggaagaag cagcccatga    2520
cagctcccct tcctgggact cgccctcatc ctcttcctgc tccccttcct ggggtgcagc    2580
ctaaaaggac ctatgtcctc acaccattga aaccactagt tctgtccccc aggagacct    2640 ggttgtgtgt gtgtgagtgg ttgaccttcc tccatcccct ggtccttccc ttcccttccc    2700
gaggcacaga gagacagggc aggatccacg tgcccattgt ggaggcagag aaaagagaaa    2760
gtgttttata tacggtactt atttaatatc cctttttaat tagaaattaa acagttaat    2820 ttaattaaag agtagggttt ttttcagta ttcttggtta atatttaatt tcaactattt    2880
atgagatgta tctttgctc tctcttgctc tcttatttgt accggttttt gtatataaaa    2940
ttcatgtttc caatctctct ctccctgatc ggtgacagtc actagcttat cttgaacaga    3000
tatttaattt tgctaacact cagctctgcc ctccccgatc ccctggctcc ccagcacaca    3060
ttcctttgaa ataaggttc aatatacatc tacatactat atatatattt ggcaacttgt    3120
atttgtgtgt atatatatat atatgtttt atgtatatat gtgattctga taaaatagac    3180
attgctattc tgtttttat atgtaaaaac aaaacaagaa aaaatagaga attctacata    3240
ctaaatctct ctccttttt aattttaata tttgttatca tttatttatt ggtgctactg    3300
tttatccgta ataattgtgg ggaaaagata ttaacatcac gtctttgtct ctagtgcagt    3360
ttttcgagat attccgtagt acatatttat ttttaaacaa cgacaaagaa atacagatat    3420
atcttaaaaa aaaaaaagca ttttgtatta aagaatttaa ttctgatctc aaaaaaaaa    3480 aaaaaaaa                                                            3488

<210> SEQ ID NO 191
<211> LENGTH: 3392
<212> TYPE: DNA
<213> ORGANISM: Homo sapiens

<400> SEQUENCE: 191
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180 cattttttt taaaactgta ttgtttctcg ttttaattta tttttgcttg ccattcccca     240
cttgaatcgg gccgacggct tggggagatt gctctacttc cccaaatcac tgtggatttt     300
ggaaaccagc agaaagagga aagaggtagc aagagctcca gagagaagtc gaggaagaga     360 gagacgggt cagagagagc gcgcgggcgt gcgagcagcg aaagcgacag gggcaaagtg     420
agtgacctgc ttttgggggt gaccgccgga gcgcggcgtg agccctcccc cttgggatcc     480
cgcagctgac cagtcgcgct gacggacaga cagacagaca ccgcccccag ccccagctac     540
cacctcctcc ccggccggcg gcggacagtg gacgcggcgg cgagccgcgg gcaggggccg     600
gagcccgcgc ccggaggcgg ggtggagggg gtcgggctc gcggcgtcgc actgaaactt     660
ttcgtccaac ttctggctg ttctcgcttc ggaggagccg tggtccgcgc ggggaagcc     720 gagccgagcg gagccgcgag aagtgctagc tcggccgggg aggagccgca gccggaggag     780
ggggaggagg aagaagagaa ggaagaggag agggggccgc agtggcgact cggcgctcgg     840
aagccgggct catggacggg tgaggcggcg gtgtgcgcag acagtgctcc agccgcgcgc     900
gctccccagg ccctggcccg ggcctcgggc cggggaggaa gagtagctcg ccgaggcgcc     960
```

```
gaggagagcg ggccgcccca cagcccgagc cggagaggga gcgcgagccg cgccggcccc    1020
ggtcgggcct ccgaaaccat gaactttctg ctgtcttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
atcgagaccc tggtggacat cttccaggag taccctgatg agatcgagta catcttcaag    1260
ccatcctgtg tgcccctgat gcgatgcggg ggctgctgca atgacgaggg cctggagtgt    1320
gtgcccactg aggagtccaa catcaccatg cagattatgc ggatcaaacc tcaccaaggc    1380
cagcacatag gagagatgag cttcctacag cacaacaaat gtgaatgcag atgtgacaag    1440
ccgaggcggt gagccgggca ggaggaagga gcctccctca gggtttcggg aaccagatct    1500
ctcaccagga aagactgata cagaacgatc gatacagaaa ccacgctgcc gccaccacac    1560
catcaccatc gacagaacag tccttaatcc agaaacctga aatgaaggaa gaggagactc    1620
tgcgcagagc actttgggtc cggagggcga gactccggcg gaagcattcc cgggcgggtg    1680
acccagcacg gtccctcttg gaattggatt cgccatttta ttttcttgc tgctaaatca     1740 ccgagcccgg aagattagag agtttttattt ctgggattcc tgtagacaca cccacccaca   1800
tacatacatt tatatatata tatattatat atatataaaa ataaatatct ctattttata    1860
tatataaaat atatatattc ttttttttaaa ttaacagtgc taatgttatt ggtgtcttca   1920
ctggatgtat ttgactgctg tggacttgag ttgggagggg aatgttccca ctcagatcct    1980
gacagggaag aggaggagat gagagactct ggcatgatct tttttttgtc ccacttggtg    2040
gggccagggt cctctcccct gcccaggaat gtgcaaggcc agggcatggg ggcaaatatg    2100 acccagttttt gggaacaccg acaaacccag ccctggcgct gagcctctct accccaggtc   2160
agacggacag aaagacagat cacaggtaca gggatgagga caccggctct gaccaggagt    2220
ttggggagct tcaggacatt gctgtgcttt ggggattccc tccacatgct gcacgcgcat    2280
ctcgccccca ggggcactgc ctggaagatt caggagcctg ggcggccttc gcttactctc    2340
acctgcttct gagttgccca ggagaccact ggcagatgtc ccggcgaaga aagagacac     2400 attgttggaa gaagcagccc atgacagctc cccttcctgg gactcgccct catcctcttc    2460
ctgctcccct tcctggggtg cagcctaaaa ggacctatgt cctcacacca ttgaaaccac    2520
tagttctgtc cccccaggag acctggttgt gtgtgtgtga gtggttgacc ttcctccatc    2580
ccctggtcct tcccttccct tcccgaggca cagagagaca gggcaggatc cacgtgccca    2640
ttgtggaggc agagaaaaga gaaagtgttt tatatacggt acttatttaa tatccctttt    2700
taattagaaa ttaaaacagt taatttaatt aaagagtagg gtttttttc agtattcttg     2760 gttaatatttt aatttcaact atttatgaga tgtatcttttt gctctctctt gctctcttat  2820
ttgtaccggt ttttgtatat aaaattcatg tttccaatct ctctctccct gatcggtgac    2880
agtcactagc ttatcttgaa cagatattta attttgctaa cactcagctc tgccctcccc    2940
gatcccctgg ctccccagca cacattcctt tgaaataagg tttcaatata catctacata    3000
ctatatatat atttggcaac ttgtatttgt gtgtatatat atatatatat gtttatgtat    3060
atatgtgatt ctgataaaat agacattgct attctgtttt ttatatgtaa aaacaaaaca    3120
agaaaaaata gagaattcta catactaaat ctctctcctt ttttaatttt aatatttgtt    3180
atcatttatt tattggtgct actgtttatc cgtaataatt gtggggaaaa gatattaaca    3240
tcacgtcttt gtctctagtg cagttttttcg agatattccg tagtacatat ttattttttaa  3300
```

```
acaacgacaa agaaatacag atatatctta aaaaaaaaaa agcattttgt attaaagaat    3360
ttaattctga tctcaaaaaa aaaaaaaaaa aa                                  3392

<210> SEQ ID NO 192
<211> LENGTH: 3677
<212> TYPE: DNA
<213> ORGANISM: Homo sapiens

<400> SEQUENCE: 192
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180
catttttttt taaaactgta ttgtttctcg ttttaattta ttttttgcttg ccattcccca    240 cttgaatcgg gccgacggct tggggagatt gctctacttc cccaaatcac tgtggatttt     300
ggaaaccagc agaaagagga aagaggtagc aagagctcca gagagaagtc gaggaagaga     360
gagacggggt cagagagagc gcgcgggcgt gcgagcagcg aaagcgacag ggcaaagtg      420 agtgacctgc ttttgggggt gaccgccgga gcgcggcgtg agccctcccc cttgggatcc     480
cgcagctgac cagtcgcgct gacggacaga cagacagaca ccgcccccag ccccagctac     540
cacctcctcc ccggccggcg gcggacagtg gacgcggcgg cgagccgcgg gcaggggccg     600
gagcccgcgc ccggaggcgg ggtggagggg gtcgggcgctc gcggcgtcgc actgaaactt    660
ttcgtccaac ttctgggctg ttctcgcttc ggaggagccg tggtccgcgc gggggaagcc    720
gagccgagcg gagccgcgag aagtgctagc tcgggccggg aggagccgca gccggaggag    780
ggggaggagg aagaagagaa ggaagaggag aggggccgc agtggcgact cggcgctcgg     840
aagccgggct catggacggg tgaggcggcg gtgtgcgcag acagtgctcc agccgcgcgc    900 gctcccagg ccctggcccg ggcctcgggc cggggaggaa gagtagctcg ccgaggcgcc    960
gaggagagcg ggccgcccca gcccgagc cggagaggga gcgcgagccg cgccggcccc    1020
ggtcgggcct ccgaaaccat gaactttctg ctgtcttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
atcgagaccc tggtggacat cttccaggag taccctgatg agatcgagta catcttcaag    1260
ccatcctgtg tgcccctgat gcgatgcggg ggctgctgca atgacgaggg cctggagtgt    1320
gtgcccactg aggagtccaa catcaccatg cagattatgc ggatcaaacc tcaccaaggc    1380
cagcacatag gagagatgag cttcctacag cacaacaaat gtgaatgcag accaaagaaa    1440
gatagagcaa gacaagaaaa aaaatcagtt cgaggaaagg gaaagggca aaaacgaaag    1500 cgcaagaaat cccggtataa gtcctggagc gtgtacgttg gtgcccgctg ctgtctaatg    1560
ccctggagcc tccctggccc ccatccctgt gggccttgct cagagcggag aaagcatttg    1620
tttgtacaag atccgcagac gtgtaaatgt tcctgcaaaa acacagactc gcgttgcaag    1680
gcgaggcagc ttgagtttaaa cgaacgtact tgcagatgtg acaagccgag gcggtgagcc    1740
gggcaggagg aaggagcctc cctcagggtt tcggaaccca gatctctcac caggaaagac    1800
tgatacagaa cgatcgatac agaaaccacg ctgccgccac cacaccatca ccatcgacag    1860
aacagtcctt aatccagaaa cctgaaatga aggaagagga gactctgcgc agagcacttt    1920
gggtccggag ggcgagactc cggcggaagc attcccgggc gggtgaccca gcacggtccc    1980
tcttggaatt ggattcgcca tttttatttt cttgctgcta aatcaccgag cccggaagat    2040
```

| | |
|---|---|
| tagagagttt tatttctggg attcctgtag acacacccac ccacatacat acatttatat | 2100 |
| atatatatat tatatatata taaaaataaa tatctctatt ttatatatat aaaatatata | 2160 |
| tattcttttt ttaaattaac agtgctaatg ttattggtgt cttcactgga tgtatttgac | 2220 |
| tgctgtggac ttgagttggg aggggaatgt tcccactcag atcctgacag ggaagaggag | 2280 |
| gagatgagag actctggcat gatctttttt ttgtcccact tggtgggggcc agggtcctct | 2340 |
| cccctgccca ggaatgtgca aggccagggc atggggcaa atatgaccca gttttgggaa | 2400 |
| caccgacaaa cccagccctg gcgctgagcc tctctacccc aggtcagacg gacagaaaga | 2460 |
| cagatcacag gtacagggat gaggacaccg gctctgacca ggagtttggg gagcttcagg | 2520 |
| acattgctgt gctttgggga ttccctccac atgctgcacg cgcatctcgc ccccaggggc | 2580 |
| actgcctgga agattcagga gcctggggcgg ccttcgctta ctctcacctg cttctgagtt | 2640 |
| gcccaggaga ccactggcag atgtcccggc gaagagaaga gacacattgt tggaagaagc | 2700 |
| agcccatgac agctcccctt cctgggactc gccctcatcc tcttcctgct ccccttcctg | 2760 |
| gggtgcagcc taaaaggacc tatgtcctca caccattgaa accactagtt ctgtcccccc | 2820 |
| aggagacctg gttgtgtgtg tgtgagtggt tgaccttcct ccatcccctg gtccttccct | 2880 |
| tcccttcccg aggcacagag agacagggca ggatccacgt gcccattgtg gaggcagaga | 2940 |
| aaagagaaag tgttttatat acggtactta tttaatatcc ctttttaatt agaaattaaa | 3000 |
| acagttaatt taattaaaga gtagggtttt ttttcagtat tcttggttaa tatttaatttt | 3060 |
| caactattta tgagatgtat cttttgctct ctcttgctct cttatttgta ccggtttttg | 3120 |
| tatataaaat tcatgtttcc aatctctctc tccctgatcg gtgacagtca ctagcttatc | 3180 |
| ttgaacagat atttaatttt gctaacactc agctctgccc tccccgatcc cctggctccc | 3240 |
| cagcacacat tcctttgaaa taaggtttca atatacatct acatactata tatatatttg | 3300 |
| gcaacttgta tttgtgtgta tatatatata tatgtgttta tgtatatatg tgattctgat | 3360 |
| aaaatagaca ttgctattct gttttttata tgtaaaaaca aaacaagaaa aaatagagaa | 3420 |
| ttctacatac taaatctctc tcctttttta attttaatat ttgttatcat ttatttattg | 3480 |
| gtgctactgt ttatccgtaa taattgtggg gaaaagatat taacatcacg tctttgtctc | 3540 |
| tagtgcagtt tttcgagata ttccgtagta catatttatt tttaaacaac gacaaagaaa | 3600 |
| tacagatata tcttaaaaaa aaaaaagcat tttgtattaa agaatttaat tctgatctca | 3660 |
| aaaaaaaaaa aaaaaaa | 3677 |

<210> SEQ ID NO 193
<211> LENGTH: 3626
<212> TYPE: DNA
<213> ORGANISM: Homo sapiens

<400> SEQUENCE: 193

| | |
|---|---|
| tcgcggaggc ttggggcagc cgggtagctc ggaggtcgtg gcgctggggg ctagcaccag | 60 |
| cgctctgtcg ggaggcgcag cggttaggtg gaccggtcag cggactcacc ggccagggcg | 120 |
| ctcggtgctg gaatttgata ttcattgatc cgggttttat ccctcttctt ttttcttaaa | 180 |
| catttttttt taaaactgta ttgtttctcg ttttaattta tttttgcttg ccattcccca | 240 |
| cttgaatcgg gccgacggct tggggagatt gctctacttc cccaaatcac tgtggatttt | 300 |
| ggaaaccagc agaaagagga aagaggtagc aagagctcca gagagaagtc gaggaagaga | 360 |
| gagacgggt cagagagagc gcgcgggcgt gcgagcagcg aaagcgacag gggcaaagtg | 420 |

-continued

```
agtgacctgc tttttggggt gaccgccgga gcgcggcgtg agccctcccc cttgggatcc      480
cgcagctgac cagtcgcgct gacggacaga cagacagaca ccgcccccag ccccagctac      540
cacctcctcc ccggccggcg gcggacagtg gacgcggcgg cgagccgcgg gcaggggccg      600
gagcccgcgc ccggaggcgg ggtggagggg gtcggggctc gcggcgtcgc actgaaactt      660
ttcgtccaac ttctgggctg ttctcgcttc ggaggagccg tggtccgcgc ggggaagcc      720
gagccgagcg gagccgcgag aagtgctagc tcgggccggg aggagccgca gccggaggag      780
ggggaggagg aagaagagaa ggaagaggag aggggccgc agtggcgact cggcgctcgg      840
aagccgggct catggacggg tgaggcgcg gtgtgcgcag acagtgctcc agccgcgcgc      900
gctccccagg ccctggcccg ggcctcgggc cggggaggaa gagtagctcg ccgaggcgcc      960
gaggagagcg ggccgcccca cagcccgagc cggagaggga gcgcgagccg cgccggcccc     1020
ggtcgggcct ccgaaaccat gaactttctg ctgtcttggg tgcattggag ccttgccttg     1080
ctgctctacc tccaccatgc caagtggtcc caggctgcac ccatggcaga aggaggaggg     1140
cagaatcatc acgaagtggt gaagttcatg gatgtctatc agcgcagcta ctgccatcca     1200
atcgagaccc tggtggacat cttccaggag taccctgatg agatcgagta catcttcaag     1260
ccatcctgtg tgcccctgat gcgatgcggg ggctgctgca atgacgaggg cctggagtgt     1320
gtgcccactg aggagtccaa catcaccatg cagattatgc ggatcaaacc tcaccaaggc     1380
cagcacatag agagatgag cttcctacag cacaacaaat gtgaatgcag accaaagaaa     1440
gatagagcaa gacaagaaaa aaaatcagtt cgaggaaagg gaaaggggca aaaacgaaag     1500
cgcaagaaat cccggtataa gtcctggagc gttccctgtg ggccttgctc agagcggaga     1560
aagcatttgt ttgtacaaga tccgcagacg tgtaaatgtt cctgcaaaaa cacagactcg     1620
cgttgcaagg cgaggcagct tgagttaaac gaacgtactt gcagatgtga caagccgagg     1680
cggtgagccg ggcaggagga aggagcctcc ctcagggttt cgggaaccag atctctcacc     1740
aggaaagact gatacagaac gatcgataca gaaaccacgc tgccgccacc acaccatcac     1800
catcgacaga acagtcctta atccagaaac ctgaaatgaa ggaagaggag actctgcgca     1860
gagcactttg ggtccggagg gcgagactcc ggcggaagca ttcccgggcg ggtgacccag     1920
cacggtccct cttggaattg gattcgccat tttatttttc ttgctgctaa atcaccgagc     1980
ccggaagatt agagagtttt atttctggga ttccctgtaga cacacccacc cacatacata     2040
catttatata tatatatatt atatatatat aaaaataaat atctctattt tatatatata     2100
aaatatatat attcttttt taaattaaca gtgctaatgt tattggtgtc ttcactggat      2160
gtatttgact gctgtggact tgagttggga ggggaatgtt cccactcaga tcctgacagg      2220
gaagaggagg agatgagaga ctctggcatg atctttttt tgtcccactt ggtgggcca      2280
gggtcctctc ccctgcccag gaatgtgcaa ggccagggca tgggggcaaa tatgacccag      2340
ttttgggaac accgacaaac ccagccctgg cgctgagcct ctctacccca ggtcagacgg      2400
acagaaagac agatcacagg tacagggatg aggacaccgg ctctgaccag gagtttgggg      2460
agcttcagga cattgctgtg ctttgggat ccctccaca tgctgcacgc gcatctcgcc       2520
cccagggca ctgcctggaa gattcaggag cctgggcggc cttcgcttac tctcacctgc       2580
ttctgagttg cccaggagac cactggcaga tgtcccggcg aagagaagag acacattgtt      2640
ggaagaagca gcccatgaca gctcccttc ctgggactcg ccctcatcct cttcctgctc       2700
cccttcctgg ggtgcagcct aaaaggacct atgtcctcac accattgaaa ccactagttc      2760
tgtccccca ggagacctgg ttgtgtgtgt gtgagtggtt gaccttcctc catcccctgg       2820
```

```
tccttcccctt cccttcccga ggcacagaga gacagggcag gatccacgtg cccattgtgg    2880
aggcagagaa aagagaaagt gttttatata cggtacttat ttaatatccc ttttttaatta   2940 gaaattaaaa cagttaattt aattaaagag tagggttttt tttcagtatt cttggttaat    3000
atttaatttc aactatttat gagatgtatc ttttgctctc tcttgctctc ttatttgtac    3060 cggttttttgt atataaaatt catgtttcca atctctctct ccctgatcgg tgacagtcac   3120
tagcttatct tgaacagata tttaattttg ctaacactca gctctgccct ccccgatccc    3180
ctggctcccc agcacacatt cctttgaaat aaggtttcaa tatacatcta catactatat    3240
atatatttgg caacttgtat ttgtgtgtat atatatatat atatgtttat gtatatatgt    3300
gattctgata aaatagacat tgctattctg tttttatat gtaaaaacaa aacaagaaaa     3360
aatagagaat tctacatact aaatctctct ccttttttaa ttttaatatt tgttatcatt   3420
tatttattgg tgctactgtt tatccgtaat aattgtgggg aaaagatatt aacatcacgt    3480
ctttgtctct agtgcagttt ttcgagatat tccgtagtac atatttattt ttaaacaacg   3540
acaaagaaat acagatatat cttaaaaaaa aaaaagcatt ttgtattaaa gaatttaatt   3600
ctgatctcaa aaaaaaaaaa aaaaaa                                         3626

<210> SEQ ID NO 194
<211> LENGTH: 3608
<212> TYPE: DNA
<213> ORGANISM: Homo sapiens

<400> SEQUENCE: 194
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg    120
ctcggtgctg gaatttgata ttcattgatc cgggttttat ccctcttctt ttttcttaaa    180 cattttttt taaaactgta ttgtttctcg ttttaattta ttttttgcttg ccattcccca    240 cttgaatcgg gccgacggct tggggagatt gctctacttc cccaaatcac tgtggatttt    300
ggaaaccagc agaaagagga aagaggtagc aagagctcca gagagaagtc gaggaagaga    360
gagacggggt cagagagagc gcgcgggcgt gcgagcagcg aaagcgacag gggcaaagtg    420
agtgacctgc ttttgggggt gaccgccgga gcgcggcgtg agccctcccc cttgggatcc    480
cgcagctgac cagtcgcgct gacggacaga cagacagaca ccgccccccag ccccagctac    540 cacctcctcc ccggccggcg gcggacagtg gacgcggcgg cgagccgcgg gcaggggccg    600
gagcccgcgc ccggaggcgg ggtggagggg gtcgggcctc gcggcgtcgc actgaaactt    660
ttcgtccaac ttctgggctg ttctcgcttc ggaggagccg tggtccgcgc gggggaagcc    720
gagccgagcg gagccgcgag aagtgctagc tcggccgggg aggagccgca gccggaggag    780
ggggaggagg aagaagagaa ggaagaggag agggggccgc agtggcgact cggcgctcgg    840
aagccgggct catggacggg tgaggcgcg gtgtgcgcag acagtgctcc agccgcgcgc     900 gctcccagg ccctggcccg ggcctcgggc cggggaggaa gagtagctcg ccgaggcgcc    960
gaggagagcg ggccgcccca cagcccgagc cggagaggga gcgcgagccg cgccggcccc    1020
ggtcgggcct ccgaaaccat gaactttctg ctgtcttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
atcgagaccc tggtggacat cttccaggag taccctgatg agatcgagta catcttcaag    1260
```

| | |
|---|---|
| ccatcctgtg tgcccctgat gcgatgcggg ggctgctgca atgacgaggg cctggagtgt | 1320 |
| gtgcccactg aggagtccaa catcaccatg cagattatgc ggatcaaacc tcaccaaggc | 1380 |
| cagcacatag gagagatgag cttcctacag cacaacaaat gtgaatgcag accaaagaaa | 1440 |
| gatagagcaa gacaagaaaa aaaatcagtt cgaggaaagg gaaaggggca aaaacgaaag | 1500 |
| cgcaagaaat cccgtccctg tgggccttgc tcagagcgga gaaagcattt gtttgtacaa | 1560 |
| gatccgcaga cgtgtaaatg ttcctgcaaa aacacagact cgcgttgcaa ggcgaggcag | 1620 |
| cttgagttaa acgaacgtac ttgcagatgt gacaagccga ggcggtgagc cgggcaggag | 1680 |
| gaaggagcct ccctcagggt ttcgggaacc agatctctca ccaggaaaga ctgatacaga | 1740 |
| acgatcgata cagaaaccac gctgccgcca ccacaccatc accatcgaca gaacagtcct | 1800 |
| taatccagaa acctgaaatg aaggaagagg agactctgcg cagagcactt tgggtccgga | 1860 |
| gggcgagact ccggcggaag cattcccggg cgggtgaccc agcacggtcc ctcttggaat | 1920 |
| tggattcgcc atttattttt tcttgctgct aaatcaccga gcccggaaga ttagagagtt | 1980 |
| ttatttctgg gattcctgta gacacaccca cccacataca tacatttata tatatatata | 2040 |
| ttatatatat ataaaaataa atatctctat tttatatata taaaatatat atattctttt | 2100 |
| tttaaattaa cagtgctaat gttattggtg tcttcactgg atgtatttga ctgctgtgga | 2160 |
| cttgagttgg gaggggaatg ttcccactca gatcctgaca gggaagagga ggagatgaga | 2220 |
| gactctggca tgatcttttt tttgtcccac ttggtggggc cagggtcctc tcccctgccc | 2280 |
| aggaatgtgc aaggccaggg catggggca aatatgaccc agttttggga acaccgacaa | 2340 |
| acccagccct ggcgctgagc ctctctaccc caggtcagac ggacagaaag acagatcaca | 2400 |
| ggtacaggga tgaggacacc ggctctgacc aggagtttgg ggagcttcag gacattgctg | 2460 |
| tgctttgggg attccctcca catgctgcac gcgcatctcg cccccagggg cactgcctgg | 2520 |
| aagattcagg agcctgggcg gccttcgctt actctcacct gcttctgagt tgcccaggag | 2580 |
| accactggca gatgtcccgg cgaagagaag agacacattg ttggaagaag cagcccatga | 2640 |
| cagctcccct tcctgggact cgccctcatc ctcttcctgc tccccttcct ggggtgcagc | 2700 |
| ctaaaaggac ctatgtcctc acaccattga aaccactagt tctgtccccc caggagacct | 2760 |
| ggttgtgtgt gtgtgagtgg ttgaccttcc tccatcccct ggtccttccc ttcccttccc | 2820 |
| gaggcacaga gagacagggc aggatccacg tgcccattgt ggaggcagag aaaagagaaa | 2880 |
| gtgtttata tacggtactt atttaatatc ccttttttaat tagaaattaa aacagttaat | 2940 |
| ttaattaaag agtagggttt ttttcagta ttccttggtta atatttaatt tcaactattt | 3000 |
| atgagatgta tcttttgctc tctcttgctc tcttatttgt accggttttt gtatataaaa | 3060 |
| ttcatgtttc caatctctct ctccctgatc ggtgacagtc actagcttat cttgaacaga | 3120 |
| tatttaattt tgctaacact cagctctgcc ctccccgatc ccctggctcc ccagcacaca | 3180 |
| ttcctttgaa ataaggtttc aatatacatc tacatactat atatatattt ggcaacttgt | 3240 |
| atttgtgtgt atatatatat atatatgttt atgtatatat gtgattctga taaaatagac | 3300 |
| attgctattc tgtttttttat atgtaaaaac aaaacaagaa aaaatagaga attctacata | 3360 |
| ctaaatctct ctccttttt aattttaata tttgttatca tttatttatt ggtgctactg | 3420 |
| tttatccgta ataattgtgg ggaaaagata ttaacatcac gtctttgtct ctagtgcagt | 3480 |
| ttttcgagat attccgtagt acatatttat ttttaaacaa cgacaaagaa atacagatat | 3540 |
| atcttaaaaa aaaaaaagca ttttgtatta aagaatttaa ttctgatctc aaaaaaaaaa | 3600 |
| aaaaaaaa | 3608 |

<210> SEQ ID NO 195
<211> LENGTH: 3554
<212> TYPE: DNA
<213> ORGANISM: Homo sapiens

<400> SEQUENCE: 195

```
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180
catttttttt taaaactgta ttgtttctcg ttttaattta tttttgcttg ccattcccca     240
cttgaatcgg gccgacggct tggggagatt gctctacttc cccaaatcac tgtggatttt     300
ggaaaccagc agaaagagga aagaggtagc aagagctcca gagagaagtc gaggaagaga     360
gagacggggt cagagagagc gcgcgggcgt gcgagcagcg aaagcgacag gggcaaagtg     420
agtgacctgc ttttgggggt gaccgccgga gcgcggcgtg agccctcccc cttgggatcc     480
cgcagctgac cagtcgcgct gacggacaga cagacagaca ccgcccccag ccccagctac     540
cacctcctcc ccggccggcg gcggacagtg gacgcggcgg cgagccgcgg gcaggggccg     600
gagcccgcgc ccggaggcgg ggtggagggg gtcggggctc gcggcgtcgc actgaaactt     660
ttcgtccaac ttctgggctg ttctcgcttc ggaggagccg tggtccgcgc gggggaagcc     720
gagccgagcg gagccgcgag aagtgctagc tcgggccggg aggagccgca gccggaggag     780
ggggaggagg aagaagagaa ggaagaggag aggggggccgc agtggcgact cggcgctcgg     840
aagccgggct catggacggg tgaggcggcg gtgtgcgcag acagtgctcc agccgcgcgc     900
gctccccagg ccctggcccg ggcctcgggc cggggaggaa gagtagctcg ccgaggcgcc     960
gaggagagcg ggccgcccca cagcccgagc cggagaggga gcgcgagccg cgccggcccc    1020
ggtcgggcct ccgaaaccat gaactttctg ctgtcttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
atcgagaccc tggtggacat cttccaggag taccctgatg agatcgagta catcttcaag    1260
ccatcctgtg tgcccctgat gcgatgcggg ggctgctgca atgacgaggg cctggagtgt    1320
gtgcccactg aggagtccaa catcaccatg cagattatgc ggatcaaacc tcaccaaggc    1380
cagcacatag agagatgagg cttcctacag cacaacaaat gtgaatgcag accaaagaaa    1440
gatagagcaa gacaagaaaa tccctgtggg ccttgctcag agcggagaaa gcatttgttt    1500
gtacaagatc cgcagacgtg taaatgttcc tgcaaaaaca cagactcgcg ttgcaaggcg    1560
aggcagcttg agttaaacga acgtacttgc agatgtgaca agccgaggcg gtgagccggg    1620
caggaggaag gagcctccct cagggtttcg ggaaccagat ctctcaccag gaaagactga    1680
tacagaacga tcgatacaga aaccacgctg ccgccaccac accatcacca tcgacagaac    1740
agtccttaat ccagaaacct gaaatgaagg aagaggagac tctgcgcaga gcactttggg    1800
tccggagggc gagactccgg cggaagcatt cccgggcggg tgacccagca cggtccctct    1860
tggaattgga ttcgccattt tatttttctt gctgctaaat caccgagccc ggaagattag    1920
agagttttat ttctgggatt cctgtagaca cacccaccca catacataca tttatatata    1980
tatatattat atatatataa aaataaatat ctctatttta tatatataaa atatatatat    2040
tctttttta  aattaacagt gctaatgtta ttggtgtctt cactgatgt  atttgactgc    2100
```

| | |
|---|---|
| tgtggacttg agttgggagg ggaatgttcc cactcagatc ctgacaggga agaggaggag | 2160 |
| atgagagact ctggcatgat cttttttttg tcccacttgg tggggccagg gtcctctccc | 2220 |
| ctgcccagga atgtgcaagg ccagggcatg ggggcaaata tgacccagtt ttgggaacac | 2280 |
| cgacaaaccc agccctggcg ctgagcctct taccccagg tcagacggac agaaagacag | 2340 |
| atcacaggta cagggatgag gacaccggct ctgaccagga gtttgggag cttcaggaca | 2400 |
| ttgctgtgct ttggggattc cctccacatg ctgcacgcgc atctcgcccc caggggcact | 2460 |
| gcctggaaga ttcaggagcc tgggcggcct tcgcttactc tcacctgctt ctgagttgcc | 2520 |
| caggagacca ctggcagatg tcccggcgaa gagaagagac acattgttgg aagaagcagc | 2580 |
| ccatgacagc tcccctttcct gggactcgcc ctcatcctct tcctgctccc cttcctgggg | 2640 |
| tgcagcctaa aaggacctat gtcctcacac cattgaaacc actagttctg tcccccagg | 2700 |
| agacctggtt gtgtgtgtgt gagtggttga ccttcctcca tccctggtc cttcccttcc | 2760 |
| cttcccgagg cacagagaga cagggcagga tccacgtgcc cattgtggag gcagagaaaa | 2820 |
| gagaaagtgt tttatatacg gtacttattt aatatccctt tttaattaga aattaaaaca | 2880 |
| gttaatttaa ttaaagagta gggtttttttt tcagtattct tggttaatat ttaatttcaa | 2940 |
| ctatttatga gatgtatctt ttgctctctc ttgctctctt atttgtaccg gttttttgtat | 3000 |
| ataaaattca tgtttccaat ctctctctcc ctgatcggtg acagtcacta gcttatcttg | 3060 |
| aacagatatt taattttgct aacactcagc tctgccctcc ccgatccct ggctccccag | 3120 |
| cacacattcc tttgaaataa ggtttcaata tacatctaca tactatatat atatttggca | 3180 |
| acttgtattt gtgtgtatat atatatatat atgtttatgt atatatgtga ttctgataaa | 3240 |
| atagacattg ctattctgtt tttatatgt aaaacaaaa caagaaaaa tagagaattc | 3300 |
| tacatactaa atctctctcc ttttttaatt taaatatttg ttatcattta tttattggtg | 3360 |
| ctactgttta tccgtaataa ttgtggggaa aagatattaa catcacgtct ttgtctctag | 3420 |
| tgcagttttt cgagatattc cgtagtacat atttatttt aaacaacgac aaagaaatac | 3480 |
| agatatatct taaaaaaaaa aaagcatttt gtattaaaga atttaattct gatctcaaaa | 3540 |
| aaaaaaaaaa aaaa | 3554 |

<210> SEQ ID NO 196
<211> LENGTH: 3519
<212> TYPE: DNA
<213> ORGANISM: Homo sapiens

<400> SEQUENCE: 196

| | |
|---|---|
| tcgcggaggc ttggggcagc cgggtagctc ggaggtcgtg gcgctggggg ctagcaccag | 60 |
| cgctctgtcg ggaggcgcag cggttaggtg gaccggtcag cggactcacc ggccagggcg | 120 |
| ctcggtgctg gaatttgata ttcattgatc cgggttttat ccctcttctt ttttcttaaa | 180 |
| cattttttt taaaactgta ttgtttctcg ttttaattta ttttttgcttg ccattccccca | 240 |
| cttgaatcgg gccgacggct tggggagatt gctctacttc cccaaatcac tgtggatttt | 300 |
| ggaaaccagc agaaagagga aagaggtagc aagagctcca gagagaagtc gaggaagaga | 360 |
| gagacgggt cagagagagc gcgcgggcgt gcgagcagcg aaagcgacag gggcaaagtg | 420 |
| agtgacctgc ttttgggggt gaccgccgga gcgcggcgtg agccctcccc cttgggatcc | 480 |
| cgcagctgac cagtcgcgct gacggacaga cagacagaca ccgcccccag ccccagctac | 540 |
| cacctcctcc ccggccggcg gcggacagtg gacgcggcgg cgagccgcgg gcaggggccg | 600 |
| gagcccgcgc ccggaggcgg ggtggagggg gtcgggctc gcggcgtcgc actgaaactt | 660 |

-continued

```
ttcgtccaac ttctgggctg ttctcgcttc ggaggagccg tggtccgcgc gggggaagcc      720
gagccgagcg gagccgcgag aagtgctagc tcgggccggg aggagccgca gccggaggag      780
ggggaggagg aagaagagaa ggaagaggag aggggccgc agtggcgact cggcgctcgg       840
aagccgggct catggacggg tgaggcggcg gtgtgcgcag acagtgctcc agccgcgcgc      900
gctccccagg ccctggcccg ggcctcgggc cggggaggaa gagtagctcg ccgaggcgcc      960
gaggagagcg ggccgcccca cagcccgagc cggagaggga gcgcgagccg cgccggcccc     1020
ggtcgggcct ccgaaaccat gaactttctg ctgtcttggg tgcattggag ccttgccttg     1080
ctgctctacc tccaccatgc caagtggtcc caggctgcac ccatggcaga aggaggaggg     1140
cagaatcatc acgaagtggt gaagttcatg gatgtctatc agcgcagcta ctgccatcca     1200
atcgagaccc tggtggacat cttccaggag taccctgatg agatcgagta catcttcaag     1260
ccatcctgtg tgcccctgat gcgatgcggg ggctgctgca atgacgaggg cctggagtgt     1320
gtgcccactg aggagtccaa catcaccatg cagattatgc ggatcaaacc tcaccaaggc     1380
cagcacatag agagatgag cttcctacag cacaacaaat gtgaatgcag accaaagaaa     1440
gatagagcaa gacaagaaaa tccctgtggg ccttgctcag agcggagaaa gcatttgttt     1500
gtacaagatc cgcagacgtg taaatgttcc tgcaaaaaca cagactcgcg ttgcaagatg     1560
tgacaagccg aggcggtgag ccgggcagga ggaaggagcc tccctcaggg tttcgggaac     1620
cagatctctc accaggaaag actgatacag aacgatcgat acagaaacca cgctgccgcc     1680
accacaccat caccatcgac agaacagtcc ttaatccaga aacctgaaat gaaggaagag     1740
gagactctgc gcagagcact ttgggtccgg agggcgagac tccggcggaa gcattcccgg     1800
gcgggtgacc cagcacggtc cctcttggaa ttggattcgc cattttattt ttcttgctgc     1860
taaatcaccg agcccggaag attagagagt tttatttctg ggattcctgt agacacaccc     1920
acccacatac atacatttat atatatatat attatatata tataaaaata aatatctcta     1980
ttttatatat ataaaatata tatattcttt ttttaaatta acagtgctaa tgttattggt     2040
gtcttcactg gatgtatttg actgctgtgg acttgagttg ggagggaat gttcccactc      2100 agatcctgac agggaagagg aggagatgag agactctggc atgatctttt ttttgtccca     2160
cttggtgggg ccagggtcct ctcccctgcc caggaatgtg caaggccagg catgggggc      2220 aaaatatgacc cagttttggg aacaccgaca aacccagccc tggcgctgag cctctctacc    2280
ccaggtcaga cggacagaaa gacagatcac aggtacaggg atgaggacac cggctctgac    2340
caggagtttg gggagcttca ggacattgct gtgctttggg gattccctcc acatgctgca    2400
cgcgcatctc gccccagggg cactgcctg gaagattcag gagcctgggc ggccttcgct    2460
tactctcacc tgcttctgag ttgcccagga gaccactggc agatgtcccg gcgaagagaa    2520
gagacacatt gttggaagaa gcagcccatg acagctcccc ttcctgggac tcgccctcat    2580
cctcttcctg ctcccttcc tggggtgcag cctaaaagga cctatgtcct cacaccattg      2640
aaaccactag ttctgtcccc ccaggagacc tggttgtgtg tgtgtgagtg gttgaccttc    2700
ctccatcccc tggtccttcc cttcccttcc cgaggcacag agagacaggg caggatccac    2760
gtgcccattg tggaggcaga gaaaagagaa agtgttttat atacggtact tatttaatat    2820 cccttttaa ttagaaatta aaacagttaa tttaattaaa gagtagggtt ttttttcagt      2880
attcttggtt aatatttaat ttcaactatt tatgagatgt atcttttgct ctctcttgct    2940
ctcttatttg taccggtttt tgtatataaa attcatgttc ccaatctctc tctccctgat    3000
```

```
cggtgacagt cactagctta tcttgaacag atatttaatt ttgctaacac tcagctctgc    3060
cctccccgat cccctggctc cccagcacac attcctttga aataaggttt caatatacat    3120
ctacatacta tatatatatt tggcaacttg tatttgtgtg tatatatata tatatatgtt    3180
tatgtatata tgtgattctg ataaaataga cattgctatt ctgtttttta tatgtaaaaa    3240
caaaacaaga aaaatagag aattctacat actaaatctc tctccttttt taattttaat     3300
atttgttatc atttatttat tggtgctact gtttatccgt aataattgtg gggaaaagat    3360
attaacatca cgtctttgtc tctagtgcag ttttttcgaga tattccgtag tacatattta   3420
tttttaaaca acgacaaaga aatacagata tatcttaaaa aaaaaaaagc attttgtatt    3480
aaagaattta attctgatct caaaaaaaaa aaaaaaaa                            3519

<210> SEQ ID NO 197
<211> LENGTH: 3422
<212> TYPE: DNA
<213> ORGANISM: Homo sapiens

<400> SEQUENCE: 197
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg    120
ctcggtgctg gaatttgata ttcattgatc cgggttttat ccctcttctt tttttcttaaa  180 cattttttt taaaactgta ttgtttctcg ttttaattta ttttttgcttg ccattcccca    240 cttgaatcgg gccgacggct tggggagatt gctctacttc cccaaatcac tgtggatttt    300
ggaaaccagc agaagagga aagaggtagc aagagctcca gagagaagtc gaggaagaga     360
gagacggggt cagagagagc gcgcgggcgt gcgagcagcg aaagcgacag gggcaaagtg    420
agtgacctgc ttttgggggt gaccgccgga gcgcggcgtg agccctcccc cttgggatcc    480
cgcagctgac cagtcgcgct gacggacaga cagacagaca ccgcccccag ccccagctac    540
cacctcctcc ccggccggcg gcggacagtg gacgcggcgg cgagccgcgg gcaggggccg    600
gagcccgcgc ccggaggcgg ggtggagggg gtcgggctc gcggcgtcgc actgaaactt     660
ttcgtccaac ttctgggctg ttctcgcttc ggaggagccg tggtccgcgc gggggaagcc    720
gagccgagcg gagccgcgag aagtgctagc tcgggccggg aggagccgca gccggaggag    780
ggggaggagg aagaagagaa ggaagaggag agggggccgc agtggcgact cggcgctcgg    840
aagccgggct catggacggg tgaggcggcg gtgtgcgcag acagtgctcc agccgcgcgc    900 gctcccagg ccctggcccg ggcctcgggc cggggaggaa gagtagctcg ccgaggcgcc     960
gaggagagcg ggccgcccca cagcccgagc cggagaggga gcgcgagccg cgccggcccc   1020
ggtcgggcct ccgaaaccat gaactttctg ctgtcttggg tgcattggag ccttgccttg    1080
ctgctctacc tccaccatgc caagtggtcc caggctgcac ccatggcaga aggaggaggg   1140
cagaatcatc acgaagtggt gaagttcatg gatgtctatc agcgcagcta ctgccatcca   1200
atcgagaccc tggtggacat cttccaggag taccctgatg agatcgagta catcttcaag    1260
ccatcctgtg tgcccctgat gcgatgcggg ggctgctgca atgacgaggg cctggagtgt   1320
gtgcccactg aggagtccaa catcaccatg cagattatgc ggatcaaacc tcaccaaggc    1380
cagcacatag gagagatgag cttcctacag cacaacaaat gtgaatgcag accaaagaaa   1440
gatagagcaa gacaagaaaa atgtgacaag ccgaggcggt gagccgggca ggaggaagga   1500
gcctccctca gggtttcggg aaccagatct ctcaccagga aagactgata cagaacgatc   1560
gatacagaaa ccacgctgcc gccaccacac catcaccatc gacagaacag tccttaatcc   1620
```

```
agaaacctga aatgaaggaa gaggagactc tgcgcagagc actttgggtc cggagggcga    1680
gactccggcg gaagcattcc cgggcgggtg acccagcacg gtccctcttg gaattggatt    1740
cgccatttta ttttcttgc tgctaaatca ccgagcccgg aagattagag agttttattt     1800
ctgggattcc tgtagacaca cccacccaca tacatacatt tatatatata tatattatat    1860
atatataaaa ataaatatct ctatttata tatataaaat atatatattc ttttttaaa      1920
ttaacagtgc taatgttatt ggtgtcttca ctggatgtat ttgactgctg tggacttgag    1980
ttgggagggg aatgttccca ctcagatcct gacagggaag aggaggagat gagagactct    2040
ggcatgatct tttttttgtc ccacttggtg gggccaggt cctctcccct gcccaggaat     2100
gtgcaaggcc agggcatggg ggcaaatatg acccagtttt gggaacaccg acaaacccag    2160
ccctggcgct gagcctctct accccaggtc agacggacag aaagacagat cacaggtaca    2220
gggatgagga caccggctct gaccaggagt ttggggagct tcaggacatt gctgtgcttt    2280
ggggattccc tccacatgct gcacgcgcat ctcgcccca gggcactgc ctggaagatt      2340
caggagcctg gcggccttc gcttactctc acctgcttct gagttgccca ggagaccact     2400
ggcagatgtc ccggcgaaga gaagagacac attgttggaa gaagcagccc atgacagctc    2460
cccttcctgg gactcgccct catcctcttc ctgctcccct tcctggggtg cagcctaaaa    2520
ggacctatgt cctcacacca ttgaaaccac tagttctgtc cccccaggag acctggttgt    2580
gtgtgtgtga gtggttgacc ttcctccatc ccctggtcct tcccttccct tcccgaggca    2640
cagagagaca gggcaggatc cacgtgccca ttgtggaggc agagaaaga gaaagtgttt     2700
tatatacggt acttatttaa tatccctttt taattagaaa ttaaaacagt taatttaatt    2760
aaagagtagg gtttttttc agtattcttg gttaatattt aatttcaact atttatgaga    2820
tgtatctttt gctctctctt gctctcttat ttgtaccggt ttttgtatat aaaattcatg    2880
tttccaatct ctctctccct gatcggtgac agtcactagc ttatcttgaa cagatattta    2940
attttgctaa cactcagctc tgccctcccc gatcccctgg ctccccagca cacattcctt    3000
tgaaataagg tttcaatata catctacata ctatatatat atttggcaac ttgtatttgt    3060
gtgtatatat atatatatat gtttatgtat atatgtgatt ctgataaaat agacattgct    3120
attctgttt ttatatgtaa aaacaaaaca agaaaaaata gagaattcta catactaaat    3180
ctctctcctt ttttaatttt aatatttgtt atcatttatt tattggtgct actgtttatc    3240
cgtaataatt gtggggaaaa gatattaaca tcacgtcttt gtctctagtg cagttttcg     3300
agatattccg tagtacatat ttatttttaa acaacgacaa agaaatacag atatatctta    3360
aaaaaaaaaa agcattttgt attaaagaat ttaattctga tctcaaaaaa aaaaaaaaa     3420
aa                                                                   3422
```

<210> SEQ ID NO 198
<211> LENGTH: 3488
<212> TYPE: DNA
<213> ORGANISM: Homo sapiens

<400> SEQUENCE: 198

```
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa    180
catttttttt taaaactgta ttgtttctcg ttttaattta ttttgcttg ccattcccca     240
```

```
cttgaatcgg gccgacggct tggggagatt gctctacttc cccaaatcac tgtggatttt      300
ggaaaccagc agaaagagga aagaggtagc aagagctcca gagagaagtc gaggaagaga      360
gagacggggt cagagagagc gcgcgggcgt gcgagcagcg aaagcgacag gggcaaagtg      420
agtgacctgc ttttggggt gaccgccgga gcgcggcgtg agccctcccc cttgggatcc       480
cgcagctgac cagtcgcgct gacggacaga cagacagaca ccgccccag ccccagctac       540 cacctcctcc ccggccggcg gcggacagtg gacgcggcgg cgagccgcgg gcaggggccg      600
gagcccgcgc ccggaggcgg ggtggagggg gtcgggctc gcggcgtcgc actgaaactt       660
ttcgtccaac ttctgggctg ttctcgcttc ggaggagccg tggtccgcgc ggggaagcc      720 gagccgagcg gagccgcgag aagtgctagc tcggccggg aggagccgca gccggaggag      780
ggggaggagg aagaagagaa ggaagaggag aggggccgc agtggcgact cggcgctcgg      840
aagccgggct catggacggg tgaggcggcg gtgtgcgcag acagtgctcc agccgcgcgc      900 gctcccagg ccctggcccg ggcctcgggc cggggaggaa gagtagctcg ccgaggcgcc      960
gaggagagcg ggccgcccca cagcccgagc cggagaggga gcgcgagccg cgccggcccc     1020
ggtcgggcct ccgaaaccat gaactttctg ctgtcttggg tgcattggag ccttgccttg     1080
ctgctctacc tccaccatgc caagtggtcc caggctgcac ccatggcaga aggaggaggg     1140
cagaatcatc acgaagtggt gaagttcatg gatgtctatc agcgcagcta ctgccatcca     1200
atcgagaccc tggtggacat cttccaggag taccctgatg agatcgagta catcttcaag     1260
ccatcctgtg tgcccctgat gcgatgcggg ggctgctgca atgacgaggg cctggagtgt     1320
gtgcccactg aggagtccaa catcaccatg cagattatgc ggatcaaacc tcaccaaggc     1380
cagcacatag agagatgag cttcctacag cacaacaaat gtgaatgcag accaaagaaa     1440
gatagagcaa gacaagaaaa tccctgtggg ccttgctcag agcggagaaa gcatttgttt     1500
gtacaagatc cgcagacgtg taaatgttcc tgcaaaaaca cagactcgcg ttgcaaggcg     1560
aggcagcttg agttaaacga acgtacttgc agatctctca ccaggaaaga ctgatacaga     1620
acgatcgata cagaaaccac gctgccgcca ccacaccatc accatcgaca gaacagtcct     1680
taatccagaa acctgaaatg aaggaagagg agactctgcg cagagcactt tgggtccgga     1740
gggcgagact ccggcggaag cattcccggg cgggtgaccc agcacggtcc ctcttggaat     1800
tggattcgcc attttatttt tcttgctgct aaatcaccga gcccggaaga ttagagagtt     1860
ttatttctgg gattcctgta gacacaccca cccacataca tacatttata tatatatata     1920
ttatatatat ataaaaataa atatctctat tttatatata taaatatat atattctttt      1980 tttaaattaa cagtgctaat gttattggtg tcttcactgg atgtatttga ctgctgtgga     2040
cttgagttgg gagggaatg ttcccactca gatcctgaca gggaagagga ggagatgaga      2100
gactctggca tgatcttttt tttgtcccac ttggtggggc cagggtcctc tcccctgccc     2160
aggaatgtgc aaggccaggg catggggca aatatgaccc agttttggga acaccgacaa      2220
acccagccct ggcgctgagc ctctctaccc caggtcagac ggacagaaag acagatcaca     2280
ggtacaggga tgaggacacc ggctctgacc aggagtttgg ggagcttcag gacattgctg     2340
tgctttgggg attccctcca catgctgcac gcgcatctcg cccccagggg cactgcctgg     2400
aagattcagg agcctgggcg ccttcgctt actctcacct gcttctgagt tgcccaggag      2460
accactggca gatgtcccgg cgaagagaag agacacattg ttggaagaag cagcccatga     2520
cagctcccct tcctgggact cgccctcatc ctcttcctgc tccccttcct ggggtgcagc     2580
ctaaaaggac ctatgtcctc acaccattga aaccactagt tctgtccccc caggagacct     2640
```

```
ggttgtgtgt gtgtgagtgg ttgaccttcc tccatcccct ggtccttccc ttcccttccc    2700
gaggcacaga gagacagggc aggatccacg tgcccattgt ggaggcagag aaaagagaaa    2760
gtgttttata tacggtactt atttaatatc ccttttaat tagaaattaa aacagttaat    2820
ttaattaaag agtagggttt tttttcagta ttcttggtta atatttaatt tcaactattt    2880
atgagatgta tcttttgctc tctcttgctc tcttatttgt accggttttt gtatataaaa    2940
ttcatgtttc caatctctct ctccctgatc ggtgacagtc actagcttat cttgaacaga    3000
tatttaattt tgctaacact cagctctgcc ctccccgatc ccctggctcc ccagcacaca    3060
ttcctttgaa ataaggtttc aatatacatc tacatactat atatatattt ggcaacttgt    3120
atttgtgtgt atatatatat atatatgttt atgtatatat gtgattctga taaaatagac    3180
attgctattc tgttttttat atgtaaaaac aaaacaagaa aaaatagaga attctacata    3240
ctaaatctct ctccttttt aattttaata tttgttatca tttatttatt ggtgctactg    3300
tttatccgta ataattgtgg ggaaaagata ttaacatcac gtctttgtct ctagtgcagt    3360
ttttcgagat attccgtagt acatattat tttaaacaa cgacaaagaa atacagatat    3420
atcttaaaaa aaaaaaagca ttttgtatta aagaatttaa ttctgatctc aaaaaaaaaa    3480
aaaaaaaa                                                              3488

<210> SEQ ID NO 199
<211> LENGTH: 3392
<212> TYPE: DNA
<213> ORGANISM: Homo sapiens

<400> SEQUENCE: 199
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180
catttttttt taaaactgta ttgtttctcg ttttaattta ttttgcttg ccattcccca      240 cttgaatcgg gccgacggct tgggagatt gctctacttc cccaaatcac tgtggatttt     300
ggaaaccagc agaaagagga aagaggtagc aagagctcca gagagaagtc gaggaagaga     360 gagacgggt cagagagagc gcgcgggcgt gcgagcagcg aaagcgacag gggcaaagtg     420
agtgacctgc ttttggggt gaccgccgga gcgcggcgtg agccctcccc cttgggatcc     480
cgcagctgac cagtcgcgct gacggacaga cagacagaca ccgcccccag ccccagctac    540
cacctcctcc ccggccggcg gcggacagtg gacgcggcgg cgagccgcgg gcaggggccg    600
gagcccgcgc ccggaggcgg ggtggagggg gtcgggctc gcggcgtcgc actgaaactt    660
ttcgtccaac ttctgggctg ttctcgcttc ggaggagccg tggtccgcgc ggggaagcc    720 gagccgagcg gagccgcgag aagtgctagc tcggccgggg aggagccgca gccggaggag    780
ggggaggagg aagaagagaa ggaagaggag agggggccgc agtggcgact cggcgctcgg    840
aagccgggct catggacggg tgaggcggcg gtgtgcgcag acagtgctcc agccgcgcgc    900
gctccccagg ccctggcccg ggcctcgggc cggggaggaa gagtagctcg ccgaggcgcc    960
gaggagagcg ggccgcccca cagcccgagc cggagaggga gcgcgagccg cgccggcccc   1020
ggtcgggcct ccgaaaccat gaactttctg ctgtcttggg tgcattggag ccttgccttg   1080
ctgctctacc tccaccatgc caagtggtcc caggctgcac ccatggcaga aggaggaggg   1140
cagaatcatc acgaagtggt gaagttcatg gatgtctatc agcgcagcta ctgccatcca   1200
```

```
atcgagaccc tggtggacat cttccaggag taccctgatg agatcgagta catcttcaag    1260
ccatcctgtg tgcccctgat gcgatgcggg ggctgctgca atgacgaggg cctggagtgt    1320
gtgcccactg aggagtccaa catcaccatg cagattatgc ggatcaaacc tcaccaaggc    1380
cagcacatag agagatgag cttcctacag cacaacaaat gtgaatgcag atgtgacaag    1440
ccgaggcggt gagccgggca ggaggaagga gcctccctca gggtttcggg aaccagatct    1500
ctcaccagga aagactgata cagaacgatc gatacagaaa ccacgctgcc gccaccacac    1560
catcaccatc gacagaacag tccttaatcc agaaacctga atgaaggaa gaggagactc    1620 tgcgcagagc actttgggtc cggagggcga gactccggcg gaagcattcc cgggcgggtg    1680
acccagcacg gtccctcttg gaattggatt cgccatttta ttttcttgc tgctaaatca    1740 ccgagcccgg aagattagag agttttattt ctgggattcc tgtagacaca cccacccaca    1800
tacatacatt tatatatata tatattatat atatataaaa ataaatatct ctattttata    1860
tatataaaat atatatattc ttttttttaaa ttaacagtgc taatgttatt ggtgtcttca    1920
ctggatgtat ttgactgctg tggacttgag ttgggagggg aatgttccca ctcagatcct    1980 gacaggaag aggaggagat gagagactct ggcatgatct ttttttttgtc ccacttggtg    2040 gggccagggt cctctcccct gcccaggaat gtgcaaggcc agggcatggg ggcaaatatg    2100
acccagtttt gggaacaccg acaaacccag ccctggcgct gagcctctct accccaggtc    2160
agacggacag aaagacagat cacaggtaca gggatgagga caccggctct gaccaggagt    2220
ttggggagct tcaggacatt gctgtgcttt ggggattccc tccacatgct gcacgcgcat    2280
ctcgccccca gggcactgc ctggaagatt caggagcctg gcggccttc gcttactctc    2340 acctgcttct gagttgccca ggagaccact ggcagatgtc ccggcgaaga aagagacac    2400 attgttggaa gaagcagccc atgacagctc cccttcctgg gactcgccct catcctcttc    2460
ctgctcccct tcctggggtg cagcctaaaa ggacctatgt cctcacacca ttgaaaccac    2520
tagttctgtc ccccccaggag acctggttgt gtgtgtgtga gtggttgacc ttcctccatc    2580
ccctggtcct tcccttccct tcccgaggca cagagagaca gggcaggatc cacgtgccca    2640
ttgtggaggc agagaaaaga gaaagtgttt tatatacggt acttatttaa tatccctttt    2700
taattagaaa ttaaaacagt taattaatt aaagagtagg gttttttttc agtattcttg    2760
gttaatattt aatttcaact atttatgaga tgtatctttt gctctctctt gctctcttat    2820
ttgtaccggt ttttgtatat aaaattcatg tttccaatct ctctctccct gatcggtgac    2880
agtcactagc ttatcttgaa cagatattta attttgctaa cactcagctc tgccctcccc    2940
gatcccctgg ctccccagca cacattcctt tgaaataagg tttcaatata catctacata    3000
ctatatatat atttggcaac ttgtatttgt gtgtatatat atatatatat gtttatgtat    3060
atatgtgatt ctgataaaat agacattgct attctgtttt ttatatgtaa aaacaaaaca    3120
agaaaaaata gagaattcta catactaaat ctctctcctt ttttaatttt aatatttgtt    3180
atcatttatt tattggtgct actgtttatc cgtaataatt gtggggaaaa gatattaaca    3240
tcacgtcttt gtctctagtg cagttttttcg agatattccg tagtacatat ttattttaa    3300 acaacgacaa agaaatacag atatatctta aaaaaaaaaa agcattttgt attaaagaat    3360
ttaattctga tctcaaaaaa aaaaaaaaaa aa                                  3392
```

<210> SEQ ID NO 200
<211> LENGTH: 3494
<212> TYPE: DNA
<213> ORGANISM: Homo sapiens

<400> SEQUENCE: 200

```
tcgcggaggc ttggggcagc cgggtagctc ggaggtcgtg gcgctggggg ctagcaccag    60
cgctctgtcg ggaggcgcag cggttaggtg gaccggtcag cggactcacc ggccagggcg   120
ctcggtgctg gaatttgata ttcattgatc cgggttttat ccctcttctt ttttcttaaa   180
catttttttt taaaactgta ttgtttctcg ttttaattta ttttgcttg ccattcccca    240
cttgaatcgg gccgacggct tggggagatt gctctacttc cccaaatcac tgtggatttt   300
ggaaaccagc agaaagagga aagaggtagc aagagctcca gagagaagtc gaggaagaga   360
gagacggggt cagagagagc gcgcgggcgt gcgagcagcg aaagcgacag ggcaaagtg    420
agtgacctgc ttttgggggt gaccgccgga gcgcggcgtg agccctcccc cttgggatcc   480
cgcagctgac cagtcgcgct gacggacaga cagacagaca ccgcccccag ccccagctac   540
cacctcctcc ccggccggcg gcggacagtg gacgcggcgg cgagccgcgg gcaggggccg   600
gagcccgcgc ccggaggcgg ggtggagggg gtcgggctc gcggcgtcgc actgaaactt    660
ttcgtccaac ttctgggctg ttctcgcttc ggaggagccg tggtccgcgc ggggggaagcc  720
gagccgagcg gagccgcgag aagtgctagc tcgggccggg aggagccgca gccggaggag   780
ggggaggagg aagaagagaa ggaagaggag agggggccgc agtggcgact cggcgctcgg   840
aagccgggct catggacggg tgaggcgcg gtgtgcgcag acagtgctcc agccgcgcgc    900
gctccccagg ccctggcccg ggcctcgggc cggggaggaa gagtagctcg ccgaggcgcc   960
gaggagagcg ggccgcccca cagcccgagc cggagaggga gcgcgagccg cgccggcccc  1020
ggtcgggcct ccgaaaccat gaactttctg ctgtcttggg tgcattggag ccttgccttg  1080
ctgctctacc tccaccatgc caagtggtcc caggctgcac ccatggcaga aggaggaggg  1140
cagaatcatc acgaagtggt gaagttcatg gatgtctatc agcgcagcta ctgccatcca  1200
atcgagaccc tggtggacat cttccaggag taccctgatg agatcgagta catcttcaag  1260
ccatcctgtg tgcccctgat gcgatgcggg ggctgctgca atgacgaggg cctggagtgt  1320
gtgcccactg aggagtccaa catcaccatg cagattatgc ggatcaaacc tcaccaaggc  1380
cagcacatag gagagatgag cttcctacag cacaacaaat gtgaatgcag accaaagaaa  1440
gatagagcaa gacaagaaaa aaaatcagtt cgaggaaagg gaaaggggca aaaacgaaag  1500
cgcaagaaat cccggtataa gtcctggagc gtatgtgaca gccgaggcg gtgagccggg   1560
caggaggaag gagcctccct cagggtttcg ggaaccagat ctctcaccag gaaagactga  1620
tacagaacga tcgatacaga aaccacgctg ccgccaccac accatcacca tcgacagaac  1680
agtccttaat ccagaaacct gaaatgaagg aagaggagac tctgcgcaga gcactttggg  1740
tccggagggc gagactccgg cggaagcatt cccgggcggg tgacccagca cggtccctct  1800
tggaattgga ttcgccattt tatttttctt gctgctaaat caccgagccc ggaagattag  1860
agagttttat ttctgggatt cctgtagaca cacccaccca catacataca tttatatata  1920
tatatattat atatatataa aaataaatat ctctatttta tatatataaa atatatatat  1980
tctttttta aattaacagt gctaatgtta ttggtgtctt cactggatgt atttgactgc   2040
tgtggacttg agttgggagg ggaatgttcc cactcagatc ctgacaggga agaggaggag  2100
atgagagact ctggcatgat cttttttttg tcccacttgg tggggccagg gtcctctccc  2160
ctgcccagga atgtgcaagg ccagggcatg ggggcaaata tgcccagtt ttgggaacac   2220
cgacaaaccc agccctggcg ctgagcctct ctaccccagg tcagacggac agaaagacag  2280
```

| | |
|---|---|
| atcacaggta cagggatgag gacaccggct ctgaccagga gtttgggggag cttcaggaca | 2340 |
| ttgctgtgct ttggggattc cctccacatg ctgcacgcgc atctcgcccc caggggcact | 2400 |
| gcctggaaga ttcaggagcc tgggcggcct tcgcttactc tcacctgctt ctgagttgcc | 2460 |
| caggagacca ctggcagatg tcccggcgaa gagaagagac acattgttgg aagaagcagc | 2520 |
| ccatgacagc tcccccttcct gggactcgcc ctcatcctct tcctgctccc cttcctgggg | 2580 |
| tgcagcctaa aaggacctat gtcctcacac cattgaaacc actagttctg tcccccagg | 2640 |
| agacctggtt gtgtgtgtgt gagtggttga ccttcctcca tcccctggtc cttcccttcc | 2700 |
| cttcccgagg cacagagaga cagggcagga tccacgtgcc cattgtggag gcagagaaaa | 2760 |
| gagaaagtgt tttatatacg gtacttattt aatatcccctt tttaattaga aattaaaaca | 2820 |
| gttaatttaa ttaaagagta gggttttttt tcagtattct tggttaatat ttaatttcaa | 2880 |
| ctatttatga gatgtatctt ttgctctctc ttgctctctt atttgtaccg ttttttgtat | 2940 |
| ataaaattca tgtttccaat ctctctctcc ctgatcggtg acagtcacta gcttatcttg | 3000 |
| aacagatatt taattttgct aacactcagc tctgccctcc ccgatcccct ggctccccag | 3060 |
| cacacattcc tttgaaataa ggtttcaata tacatctaca tactatatat atatttggca | 3120 |
| acttgtattt gtgtgtatat atatatatat atgtttatgt atatatgtga ttctgataaa | 3180 |
| atagacattg ctattctgtt ttttatatgt aaaaacaaaa caagaaaaaa tagagaattc | 3240 |
| tacatactaa atctctctcc ttttttaatt ttaatatttg ttatcattta tttattggtg | 3300 |
| ctactgttta tccgtaataa ttgtggggaa aagatattaa catcacgtct ttgtctctag | 3360 |
| tgcagttttt cgagatattc cgtagtacat atttatttt aaacaacgac aaagaaatac | 3420 |
| agatatatct taaaaaaaaa aaagcatttt gtattaaaga atttaattct gatctcaaaa | 3480 |
| aaaaaaaaaa aaaa | 3494 |

<210> SEQ ID NO 201
<211> LENGTH: 3494
<212> TYPE: DNA
<213> ORGANISM: Homo sapiens

<400> SEQUENCE: 201

| | |
|---|---|
| tcgcggaggc ttggggcagc cgggtagctc ggaggtcgtg gcgctggggg ctagcaccag | 60 |
| cgctctgtcg ggaggcgcag cggttaggtg gaccggtcag cggactcacc ggccagggcg | 120 |
| ctcggtgctg gaatttgata ttcattgatc cgggttttat ccctcttctt ttttcttaaa | 180 |
| cattttttt taaaactgta ttgtttctcg ttttaattta ttttttgcttg ccattccccca | 240 |
| cttgaatcgg gccgacggct tggggagatt gctctacttc cccaaatcac tgtggatttt | 300 |
| ggaaaccagc agaaagagga aagaggtagc aagagctcca gagagaagtc gaggaagaga | 360 |
| gagacggggt cagagagagc gcgcgggcgt gcgagcagcg aaagcgacag gggcaaagtg | 420 |
| agtgacctgc ttttgggggt gaccgccgga gcgcggcgtg agccctcccc cttgggatcc | 480 |
| cgcagctgac cagtcgcgct gacggacaga cagacagaca ccgcccccag ccccagctac | 540 |
| cacctcctcc ccggccggcg gcggacagtg gacgcggcgg cgagccgcgg gcaggggccg | 600 |
| gagcccgcgc ccggaggcgg ggtggagggg gtcgggggctc gcggcgtcgc actgaaactt | 660 |
| ttcgtccaac ttctgggctg ttctcgcttc ggaggagccg tggtccgcgc gggggaagcc | 720 |
| gagccgagcg gagccgcgag aagtgctagc tcgggccggg aggagccgca gccgaggag | 780 |
| ggggaggagg aagaagagaa ggaagaggag aggggggccgc agtggcgact cggcgctcgg | 840 |
| aagccgggct catggacggg tgaggcggcg gtgtgcgcag acagtgctcc agccgcgcgc | 900 |

-continued

```
gctccccagg ccctggcccg ggcctcgggc cggggaggaa gagtagctcg ccgaggcgcc    960
gaggagagcg ggccgcccca cagcccgagc cggagaggga gcgcgagccg cgccggcccc   1020
ggtcgggcct ccgaaaccat gaactttctg ctgtcttggg tgcattggag ccttgccttg   1080
ctgctctacc tccaccatgc caagtggtcc caggctgcac ccatggcaga aggaggaggg   1140
cagaatcatc acgaagtggt gaagttcatg gatgtctatc agcgcagcta ctgccatcca   1200
atcgagaccc tggtggacat cttccaggag taccctgatg agatcgagta catcttcaag   1260
ccatcctgtg tgccctgat gcgatgcggg ggctgctgca atgacgaggg cctggagtgt   1320
gtgcccactg aggagtccaa catcaccatg cagattatgc ggatcaaacc tcaccaaggc   1380
cagcacatag gagagatgag cttcctacag cacaacaaat gtgaatgcag accaaagaaa   1440
gatagagcaa gacaagaaaa aaaatcagtt cgaggaaagg gaaaggggca aaaacgaaag   1500
cgcaagaaat cccggtataa gtcctggagc gtatgtgaca agccgaggcg gtgagccggg   1560
caggaggaag gagcctccct cagggtttcg ggaaccagat ctctcaccag gaaagactga   1620
tacagaacga tcgatacaga aaccacgctg ccgccaccac accatcacca tcgacagaac   1680
agtccttaat ccagaaaacct gaaatgaagg aagaggagag tctgcgcaga gcactttggg   1740
tccggagggc gagactccgg cggaagcatt cccgggcggg tgacccagca cggtccctct   1800
tggaattgga ttcgccattt tatttttctt gctgctaaat caccgagccc ggaagattag   1860
agagtttat ttctgggatt cctgtagaca caccaccca catacataca tttatatata   1920
tatatattat atatatataa aaataaatat ctctatttta tatatataaa atatatatat   1980
tcttttttta aattaacagt gctaatgtta ttggtgtctt cactggatgt atttgactgc   2040
tgtggacttg agttgggagg ggaatgttcc cactcagatc ctgacaggga agaggaggag   2100
atgagagact ctggcatgat cttttttttg tcccacttgg tggggccagg gtcctctccc   2160
ctgcccagga atgtgcaagg ccagggcatg ggggcaaata tgacccagtt ttgggaacac   2220
cgacaaaccc agccctggcg ctgagcctct ctaccccagg tcagacggac agaaagacag   2280
atcacaggta cagggatgag gacaccggct ctgaccagga gtttggggag cttcaggaca   2340
ttgctgtgct ttggggattc cctccacatg ctgcacgcgc atctcgcccc caggggcact   2400
gcctggaaga ttcaggagcc tgggcggcct tcgcttactc tcacctgctt ctgagttgcc   2460
caggagacca ctggcagatg tcccggcgaa gagaagagac acattgttgg aagaagcagc   2520
ccatgacagc tccccttcct gggactcgcc ctcatcctct tcctgctccc cttcctgggg   2580
tgcagcctaa aaggacctat gtcctcacac cattgaaacc actagttctg tcccccagg    2640
agacctggtt gtgtgtgtgt gagtggttga ccttcctcca tccctggtc cttcccttcc   2700
cttcccgagg cacagagaga cagggcagga tccacgtgcc cattgtggag gcagagaaaa   2760
gagaaagtgt tttatatacg gtacttattt aatatccctt tttaattaga aattaaaaca   2820
gttaatttaa ttaaagagta gggttttttt tcagtattct tggttaatat ttaatttcaa   2880
ctatttatga gatgtatctt ttgctctctc ttgctctctt atttgtaccg gttttttgtat  2940
ataaaattca tgtttccaat ctctctctcc ctgatcggtg acagtcacta gcttatcttg   3000
aacagatatt taatttttgct aacactcagc tctgccctcc ccgatcccct ggctccccag  3060
cacacattcc tttgaaataa ggtttcaata tacatctaca tactatatat atatttggca   3120
acttgtattt gtgtgtatat atatatatat atgtttatgt atatatgtga ttctgataaa   3180
atagacattg ctattctgtt ttttatatgt aaaaacaaaa caagaaaaaa tagagaattc   3240
```

```
tacatactaa atctctctcc ttttttaatt ttaatatttg ttatcattta tttattggtg    3300
ctactgttta tccgtaataa ttgtggggaa aagatattaa catcacgtct ttgtctctag    3360
tgcagttttt cgagatattc cgtagtacat atttatttttt aaacaacgac aaagaaatac    3420
agatatatct taaaaaaaaa aaagcatttt gtattaaaga atttaattct gatctcaaaa    3480
aaaaaaaaaa aaaa                                                      3494

<210> SEQ ID NO 202
<211> LENGTH: 3626
<212> TYPE: DNA
<213> ORGANISM: Homo sapiens

<400> SEQUENCE: 202
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180
catttttttt taaaactgta ttgtttctcg ttttaattta ttttttgcttg ccattcccca    240 cttgaatcgg gccgacggct tgggagatt gctctacttc cccaaatcac tgtggatttt     300
ggaaaccagc agaaagagga aagagtagc aagagctcca gagagaagtc gaggaagaga     360
gagacggggt cagagagagc gcgcgggcgt gcgagcagcg aaagcgacag gggcaaagtg     420
agtgacctgc ttttgggggt gaccgccgga gcgcggcgtg agccctcccc cttgggatcc     480
cgcagctgac cagtcgcgct gacggacaga cagacagaca ccgcccccag ccccagctac     540
cacctcctcc ccgccggcg gcggacagtg gacgcggcgg cgagccgcgg gcaggggccg     600
gagcccgcgc ccggaggcgg ggtggagggg gtcggggctc gcggcgtcgc actgaaactt     660
ttcgtccaac ttctgggctg ttctcgcttc ggaggagccg tggtccgcgc gggggaagcc     720
gagccgagcg gagccgcgag aagtgctagc tcgggccggg aggagccgca gccggaggag     780
ggggaggagg aagaagagaa ggaagaggag aggggggccgc agtggcgact cggcgctcgg     840
aagccgggct catggacggg tgaggcggcg gtgtgcgcag acagtgctcc agccgcgcgc     900 gctcccagg ccctggcccg ggcctcgggc cggggaggaa gagtagctcg ccgaggcgcc     960
gaggagagcg ggccgcccca cagcccgagc cggagaggga gcgcgagccg cgccggcccc    1020
ggtcgggcct ccgaaaccat gaactttctg ctgtcttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
atcgagaccc tggtggacat cttccaggag taccctgatg agatcgagta catcttcaag    1260
ccatcctgtg tgccctgat gcgatgcggg ggctgctgca atgacgaggg cctggagtgt    1320
gtgcccactg aggagtccaa catcaccatg cagattatgc ggatcaaacc tcaccaaggc    1380
cagcacatag agagatgag cttcctacag cacaacaaat gtgaatgcag accaaagaaa    1440
gatagagcaa gacaagaaaa aaaatcagtt cgaggaaagg gaaaggggca aaaacgaaag    1500
cgcaagaaat cccggtataa gtcctggagc gttccctgtg ggccttgctc agagcggaga    1560
aagcatttgt ttgtacaaga tccgcagacg tgtaaatgtt cctgcaaaaa cacagactcg    1620
cgttgcaagg cgaggcagct tgagttaaac gaacgtactt gcagatgtga caagccgagg    1680
cggtgagccg ggcaggagga aggagcctcc ctcagggttt cgggaaccag atctctcacc    1740
aggaaagact gatacagaac gatcgataca gaaaccacgc tgccgccacc acaccatcac    1800
catcgacaga acagtcctta atccagaaac ctgaaatgaa ggaagaggag actctgcgca    1860
```

-continued

| | |
|---|---|
| gagcactttg ggtccggagg gcgagactcc ggcggaagca ttcccgggcg ggtgacccag | 1920 |
| cacggtccct cttggaattg gattcgccat tttatttttc ttgctgctaa atcaccgagc | 1980 |
| ccggaagatt agagagtttt atttctggga ttcctgtaga cacacccacc cacatacata | 2040 |
| catttatata tatatatatt atatatatat aaaaataaat atctctattt tatatatata | 2100 |
| aaatatatat attcttttt taaattaaca gtgctaatgt tattggtgtc ttcactggat | 2160 |
| gtatttgact gctgtggact tgagttggga ggggaatgtt cccactcaga tcctgacagg | 2220 |
| gaagaggagg agatgagaga ctctggcatg atcttttttt tgtcccactt ggtggggcca | 2280 |
| gggtcctctc ccctgcccag gaatgtgcaa ggccagggca tggggcaaa tatgacccag | 2340 |
| ttttgggaac accgacaaac ccagccctgg cgctgagcct ctctacccca ggtcagacgg | 2400 |
| acagaaagac agatcacagg tacgggatg aggacaccgg ctctgaccag gagtttgggg | 2460 |
| agcttcagga cattgctgtg ctttggggat tccctccaca tgctgcacgc gcatctcgcc | 2520 |
| cccaggggca ctgcctggaa gattcaggag cctgggcggc cttcgcttac tctcacctgc | 2580 |
| ttctgagttg cccaggagac cactggcaga tgtcccggcg aagagaagag acacattgtt | 2640 |
| ggaagaagca gcccatgaca gctcccttc ctgggactcg ccctcatcct cttcctgctc | 2700 |
| cccttcctgg ggtgcagcct aaaaggacct atgtcctcac accattgaaa ccactagttc | 2760 |
| tgtcccccca ggagacctgg ttgtgtgtgt gtgagtggtt gaccttcctc catcccctgg | 2820 |
| tccttccctt cccttcccga ggcacagaga gacagggcag gatccacgtg cccattgtgg | 2880 |
| aggcagagaa aagagaaagt gttttatata cggtacttat ttaatatccc ttttttaatta | 2940 |
| gaaattaaaa cagttaattt aattaaagag tagggttttt tttcagtatt cttggttaat | 3000 |
| atttaatttc aactatttat gagatgtatc ttttgctctc tcttgctctc ttatttgtac | 3060 |
| cggttttgt atataaaatt catgtttcca atctctctct ccctgatcgg tgacagtcac | 3120 |
| tagcttatct tgaacagata tttaatttg ctaacactca gctctgccct ccccgatccc | 3180 |
| ctggctcccc agcacacatt cctttgaaat aaggtttcaa tatacatcta catactatat | 3240 |
| atatatttgg caacttgtat ttgtgtgtat atatatatat atatgtttat gtatatatgt | 3300 |
| gattctgata aaatagacat tgctattctg tttttatat gtaaaaacaa aacaagaaaa | 3360 |
| aatagagaat tctacatact aaatctctct cctttttaa ttttaatatt tgttatcatt | 3420 |
| tatttattgg tgctactgtt tatccgtaat aattgtgggg aaaagatatt aacatcacgt | 3480 |
| ctttgtctct agtgcagttt ttcgagatat tccgtagtac atatttattt ttaaacaacg | 3540 |
| acaaagaaat acagatatat cttaaaaaaa aaaagcatt ttgtattaaa gaatttaatt | 3600 |
| ctgatctcaa aaaaaaaaa aaaaaa | 3626 |

<210> SEQ ID NO 203
<211> LENGTH: 1224
<212> TYPE: DNA
<213> ORGANISM: Homo sapiens

<400> SEQUENCE: 203

| | |
|---|---|
| cggggcggga gatttgaaaa gtccttggcc agggcgcggc gtggcagatt cagttgtttg | 60 |
| cgggcggccg ggagagtagc agtgccttgg accccaggct ccatctggcc tgagcaccct | 120 |
| gccccagcga gtcctccgga aagagcctgt caccccatct gcacttgtcc tcatgagccg | 180 |
| ctccaatgtc cagcccacag ctgccctgg ccagaaggtg atggagaata gcagtgggac | 240 |
| acccgacatc ttaacgcggc acttcacaat tgatgacttt gagattgggc gtcctctggg | 300 |

```
caaaggcaag tttggaaacg tgtacttggc tcgggagaag aaaagccatt tcatcgtggc    360
gctcaaggtc ctcttcaagt cccagataga aaggagggc gtggagcatc agctgcgcag    420
agagatcgaa atccaggccc acctgcacca tcccaacatc ctgcgtctct acaactattt   480
ttatgaccgg aggaggatct acttgattct agagtatgcc ccccgcgggg agctctacaa   540
ggagctgcag aagagctgca catttgacga gcagcgaaca gccacgatca tggaggagtt   600
ggcagatgct ctaatgtact gccatgggaa gaaggtgatt cacagagaca taaagccaga   660
aaatctgctc ttagggctca agggagagct gaagattgct gacttcggct ggtctgtgca   720
tgcgccctcc ctgaggagga agacaatgtg tggcaccctg gactacctgc ccccagagat   780
gattgagggg cgcatgcaca atgagaaggt ggatctgtgg tgcattggag tgctttgcta   840
tgagctgctg gtggggaacc cacccttgga gagtgcatca cacaacgaga cctatcgccg   900
catcgtcaag gtggacctaa agttccccgc ttccgtgccc atgggagccc aggacctcat   960
ctccaaactg ctcaggcata cccctcggga acggctgccc ctggcccagg tctcagccca  1020
cccttgggtc cgggccaact ctcggagggt gctgcctccc tctgcccttc aatctgtcgc  1080
ctgatggtcc ctgtcattca ctcgggtgcg tgtgtttgta tgtctgtgta tgtataggg   1140
aaagaaggga tccctaactg ttcccttatc tgttttctac ctcctccttt gtttaataaa  1200
ggctgaagct ttttgtactc atga                                         1224
```

<210> SEQ ID NO 204
<211> LENGTH: 1317
<212> TYPE: DNA
<213> ORGANISM: Homo sapiens

<400> SEQUENCE: 204

```
cggggcggga gatttgaaaa gtccttggcc agggcgcggc gtggcagatt cagttgtttg     60
cgggcggccg ggagagtagc agtgccttgg accccagctc tcctcccct ttctctctaa    120
ggatggccca gaaggagaac tcctacccct ggccctacgg ccgacagacg gctccatctg   180
gcctgagcac cctgccccag cgagtcctcc ggaaagagcc tgtcacccca tctgcacttg   240
tcctcatgag ccgctccaat gtccagccca cagctgcccc tggccagaag gtgatggaga   300
atagcagtgg gacacccgac atcttaacca ggcggcactt cacaattgat gactttgaga   360
ttgggcgtcc tctgggcaaa ggcaagtttg gaaacgtgta cttggctcgg gagaagaaaa   420
gccatttcat cgtggcgctc aaggtcctct tcaagtccca gatagagaag gagggcgtgg   480
agcatcagct gcgcagagag atcgaaatcc aggcccacct gcaccatccc aacatcctgc   540
gtctctacaa ctatttttat gaccggagga ggatctactt gattctagag tatgccccc    600
gcggggagct ctacaaggag ctgcagaaga gctgcacatt tgacgagcag cgaacagcca   660
cgatcatgga ggagttggca gatgctctaa tgtactgcca tgggaagaag gtgattcaca   720
gagacataaa gccagaaaat ctgctcttag ggctcaaggg agagctgaag attgctgact   780
tcggctggtc tgtgcatgcg ccctccctga ggaggaagac aatgtgtggc accctggact   840
acctgccccc agagatgatt gagggcgca tgcacaatga aggtggat ctgtggtgca     900
ttggagtgct tgctatgag ctgctggtgg ggaacccacc ctttgagagt gcatcacaca    960
acgagaccta tcgccgcatc gtcaaggtgg acctaaagtt ccccgcttcc gtgcccatgg  1020
gagcccagga cctcatctcc aaactgctca ggcataaccc ctcggaacgg ctgcccctgg  1080
cccaggtctc agcccaccct tgggtccggg ccaactctcg gagggtgctg cctccctctg  1140
cccttcaatc tgtcgcctga tggtccctgt cattcactcg ggtgcgtgtg tttgtatgtc  1200
```

```
tgtgtatgta tagggggaaag aagggatccc taactgttcc cttatctgtt ttctacctcc    1260
tcctttgttt aataaaggct gaagcttttt gtactcatga aaaaaaaaaa aaaaaaa        1317
```

<210> SEQ ID NO 205
<211> LENGTH: 1314
<212> TYPE: DNA
<213> ORGANISM: Homo sapiens

<400> SEQUENCE: 205

```
cggggcggga gatttgaaaa gtccttggcc agggcgcggc gtggcagatt cagttgtttg      60
cgggcggccg ggagagtagc agtgccttgg accccagctc tcctccccct ttctctctaa     120
ggatggccca gaaggagaac tcctacccct ggccctacgg ccgacagacg gctccatctg     180
gcctgagcac cctgccccag cgagtcctcc ggaaagagcc tgtcacccca tctgcacttg     240
tcctcatgag ccgctccaat gtccagccca cagctgcccc tggccagaag gtgatggaga     300
atagcagtgg gacacccgac atcttaacgc ggcacttcac aattgatgac tttgagattg     360
ggcgtcctct gggcaaaggc aagtttggaa acgtgtactt ggctcgggag aagaaaagcc     420
atttcatcgt ggcgctcaag gtcctcttca gtcccagat agagaaggag ggcgtggagc      480
atcagctgcg cagagagatc gaaatccagg cccacctgca ccatcccaac atcctgcgtc     540
tctacaacta tttttatgac cggaggagga tctacttgat tctagagtat gccccccgcg     600
gggagctcta caaggagctg cagaagagct gcacatttga cgagcagcga acagccacga     660
tcatggagga gttggcagat gctctaatgt actgccatgg gaagaaggtg attcacagag     720
acataaagcc agaaaatctg ctcttagggc tcaagggaga gctgaagatt gctgacttcg     780
gctggtctgt gcatgcgccc tccctgagga ggaagacaat gtgtggcacc ctggactacc     840
tgcccccaga gatgattgag gggcgcatgc acaatgagaa ggtggatctg tggtgcattg     900
gagtgctttg ctatgagctg ctggtgggga acccaccctt tgagagtgca tcacacaacg     960
agacctatcg ccgcatcgtc aaggtggacc taaagttccc cgcttccgtg cccatgggag    1020
cccaggacct catctccaaa ctgctcaggc ataacccctc ggaacggctg ccctggccc     1080 aggtctcagc ccaccctgg gtccgggcca actctcggag ggtgctgcct ccctctgccc     1140
ttcaatctgt cgcctgatgg tccctgtcat tcactcgggt gcgtgtgttt gtatgtctgt    1200
gtatgtatag ggggaaagaag ggatcccctaa ctgttccctt atctgttttc tacctcctcc   1260
tttgtttaat aaaggctgaa gcttttgta ctcatgaaaa aaaaaaaaa aaaa            1314
```

<210> SEQ ID NO 206
<211> LENGTH: 5616
<212> TYPE: DNA
<213> ORGANISM: Homo sapiens

<400> SEQUENCE: 206

```
ccccggcgca gcgcggccgc agcagcctcc gcccccgca cggtgtgagc gcccgacgcg       60
gccgaggcgg ccggagtccc gagctagccc cggcggccgc cgccgcccag accggacgac    120
aggccacctc gtcggcgtcc gcccgagtcc ccgcctcgcc gccaacgcca caaccaccgc    180
gcacggcccc ctgactccgt ccagtattga tcggagagc cggagcgagc tcttcgggga    240
gcagcgatgc gaccctccgg gacggccggg gcagcgctcc tggcgctgct ggctgcgctc    300
tgcccggcga gtcgggctct ggaggaaaag aaagtttgcc aaggcacgag taacaagctc    360
acgcagttgg gcacttttga agatcatttt ctcagcctcc agaggatgtt caataactgt    420
```

```
gaggtggtcc ttgggaattt ggaaattacc tatgtgcaga ggaattatga tctttccttc    480
ttaaagacca tccaggaggt ggctggttat gtcctcattg ccctcaacac agtggagcga    540
attcctttgg aaaacctgca gatcatcaga ggaaatatgt actacgaaaa ttcctatgcc    600
ttagcagtct tatctaacta tgatgcaaat aaaaccggac tgaaggagct gcccatgaga    660
aatttacagg aaatcctgca tggcgccgtg cggttcagca caaccctgc cctgtgcaac     720
gtggagagca tccagtggcg ggacatagtc agcagtgact ttctcagcaa catgtcgatg    780
gacttccaga accacctggg cagctgccaa aagtgtgatc aagctgtcc caatggggagc    840
tgctggggtg caggagagga gaactgccag aaactgacca aaatcatctg tgcccagcag    900
tgctccgggc gctgccgtgg caagtccccc agtgactgct gccacaacca gtgtgctgca    960
ggctgcacag gccccggga gagcgactgc ctggtctgcc gcaaattccg agacgaagcc   1020
acgtgcaagg acacctgccc cccactcatg ctctacaacc ccaccacgta ccagatggat   1080
gtgaaccccg agggcaaata cagctttggt gccacctgcg tgaagaagtg tcccgtaat    1140
tatgtggtga cagatcacgg ctcgtgcgtc cgagcctgtg gggccgacag ctatgagatg   1200
gaggaagacg gcgtccgcaa gtgtaagaag tgcgaagggc cttgccgcaa agtgtgtaac   1260
ggaataggta ttggtgaatt taaagactca ctctccataa atgctacgaa tattaaacac   1320
ttcaaaaact gcacctccat cagtggcgat ctccacatcc tgccggtggc atttagggt    1380
gactccttca cacatactcc tcctctggat ccacaggaac tggatattct gaaaaccgta   1440
aaggaaatca cagggttttt gctgattcag gcttggcctg aaaacaggac ggacctccat   1500
gcctttgaga acctagaaat catacgcggc aggaccaagc aacatggtca gttttctctt   1560
gcagtcgtca gcctgaacat aacatccttg ggattacgct ccctcaagga gataagtgat   1620
ggagatgtga aatttcagg aaacaaaaat ttgtgctatg caaatacaat aaaactggaaa   1680
aaactgtttg ggacctccgg tcagaaaacc aaaattataa gcaacagagg tgaaaacagc   1740
tgcaaggcca caggccaggt ctgccatgcc ttgtgctccc ccgagggctg ctggggcccg   1800
gagcccaggg actgcgtctc ttgccggaat gtcagccgag cagggaatg cgtggacaag   1860
tgcaaccttc tggagggtga gccaagggag tttgtggaga actctgagtg catacagtgc   1920
cacccagagt gcctgcctca ggccatgaac atcacctgca caggacgggg accagacaac   1980
tgtatccagt gtgcccacta cattgacggc ccccactgcg tcaagacctg cccggcagga   2040
gtcatgggag aaaacaacac cctggtctgg aagtacgcag acgccggcca tgtgtgccac   2100
ctgtgccatc caaactgcac ctacggatgc actgggccag tcttgaagg ctgtccaacg    2160
aatgggccta agatcccgtc catcgccact gggatggtgg gggcctcct cttgctgctg    2220
gtggtggccc tggggatcgg cctcttcatg cgaaggcgcc acatcgttcg gaagcgcacg   2280
ctgcggaggc tgctgcagga gagggagctt gtggagcctc ttacacccag tggagaagct   2340
cccaaccaag ctctcttgag gatcttgaag gaaactgaat tcaaaaagat caaagtgctg   2400
ggctccggtg cgttcggcac ggtgtataag ggactctgga tcccagaagg tgagaaagtt   2460
aaaattcccg tcgctatcaa ggaattaaga gaagcaacat ctccgaaagc caacaaggaa   2520
atcctcgatg aagcctacgt gatggccagc gtggacaacc cccacgtgtg ccgcctgctg   2580
ggcatctgcc tcacctccac cgtgcagctc atcacgcagc tcatgccctt cggctgcctc   2640
ctggactatg tccgggaaca caaagacaat attggctccc agtacctgct caactggtgt   2700
gtgcagatcg caaagggcat gaactacttg gaggaccgtc gcttggtgca ccgcgacctg   2760
gcagccagga acgtactggt gaaaacaccg cagcatgtca agatcacaga ttttgggctg   2820
```

```
gccaaactgc tgggtgcgga agagaaagaa taccatgcag aaggaggcaa agtgcctatc   2880
aagtggatgg cattggaatc aattttacac agaatctata cccaccagag tgatgtctgg   2940
agctacgggg tgaccgtttg ggagttgatg acctttggat ccaagccata tgacggaatc   3000
cctgccagcg agatctcctc catcctggag aaaggagaac gcctccctca gccacccata   3060
tgtaccatcg atgtctacat gatcatggtc aagtgctgga tgatagacgc agatagtcgc   3120
ccaaagttcc gtgagttgat catcgaattc tccaaaatgg cccgagaccc ccagcgctac   3180
cttgtcattc aggggatga aagaatgcat ttgccaagtc ctacagactc caacttctac   3240
cgtgccctga tggatgaaga agacatggac gacgtggtgg atgccgacga gtacctcatc   3300
ccacagcagg gcttcttcag cagcccctcc acgtcacgga ctcccctcct gagctctctg   3360
agtgcaacca gcaacaattc caccgtggct tgcattgata gaaatgggct gcaaagctgt   3420
cccatcaagg aagacagctt cttgcagcga tacagctcag accccacagg cgccttgact   3480
gaggacagca tagacgacac cttcctccca gtgcctgaat acataaacca gtccgttccc   3540
aaaaggcccg ctggctctgt gcagaatcct gtctatcaca atcagcctct gaaccccgcg   3600
cccagcagag acccacacta ccaggacccc cacagcactg cagtgggcaa ccccgagtat   3660
ctcaacactg tccagcccac ctgtgtcaac agcacattcg acagccctgc ccactgggcc   3720
cagaaaggca gccaccaaat tagcctggac aaccctgact accagcagga cttctttccc   3780
aaggaagcca agccaaatgg catctttaag gctccacag ctgaaaatgc agaataccta   3840
agggtcgcgc cacaaagcag tgaatttatt ggagcatgac cacggaggat agtatgagcc   3900
ctaaaaatcc agactctttc gatacccagg accaagccac agcaggtcct ccatcccaac   3960
agccatgccc gcattagctc ttagacccac agactggttt tgcaacgttt acaccgacta   4020
gccaggaagt acttccacct cgggcacatt ttgggaagtt gcattccttt gtcttcaaac   4080
tgtgaagcat ttacagaaac gcatccagca agaatattgt cccttgagc agaaatttat   4140 ctttcaaaga ggtatatttg aaaaaaaaaa aagtatatg tgaggatttt tattgattgg   4200
ggatcttgga gtttttcatt gtcgctattg attttactt caatgggctc ttccaacaag   4260
gaagaagctt gctggtagca cttgctaccc tgagttcatc caggcccaac tgtgagcaag   4320
gagcacaagc cacaagtctt ccagaggatg cttgattcca gtggttctgc ttcaaggctt   4380
ccactgcaaa acactaaaga tccaagaagg ccttcatggc cccagcaggc cggatcggta   4440
ctgtatcaag tcatggcagg tacagtagga taagccactc tgtcccttcc tgggcaaaga   4500
agaaacggag gggatggaat tcttccttag acttactttt gtaaaaatgt ccccacggta   4560
cttactcccc actgatggac cagtggtttc cagtcatgag cgttagactg acttgtttgt   4620
cttccattcc attgttttga aactcagtat gctgcccctg tcttgctgtc atgaaatcag   4680
caagagagga tgacacatca ataataact cggattccag cccacattgg attcatcagc   4740
atttggacca atagcccaca gctgagaatg tggaatacct aaggatagca ccgcttttgt   4800
tctcgcaaaa acgtatctcc taatttgagg ctcagatgaa atgcatcagg tcctttgggg   4860
catagatcag aagactacaa aaatgaagct gctctgaaat ctcctttagc catcacccca   4920 acccccaaa attagtttgt gttacttatg aagatagtt ttctcctttt acttcacttc   4980
aaaagctttt tactcaaaga gtatatgttc cctccaggtc agctgccccc aaaccccctc   5040
cttacgcttt gtcacacaaa aagtgtctct gccttgagtc atctattcaa gcacttacag   5100
ctctggccac aacagggcat tttacaggtg cgaatgacag tagcattatg agtagtgtgg   5160
```

```
aattcaggta gtaaatatga aactagggtt tgaaattgat aatgctttca caacatttgc      5220
agatgtttta gaaggaaaaa agttccttcc taaaataatt tctctacaat tggaagattg      5280
gaagattcag ctagttagga gcccaccttt tttcctaatc tgtgtgtgcc ctgtaacctg      5340
actggttaac agcagtcctt tgtaaacagt gttttaaact ctcctagtca atatccaccc      5400
catccaattt atcaaggaag aaatggttca gaaatatttt tcagcctaca gttatgttca      5460
gtcacacaca catacaaaat gttccttttg cttttaaagt aattttttgac tcccagatca     5520 gtcagagccc ctacagcatt gttaagaaag tatttgattt ttgtctcaat gaaaataaaa      5580
ctatattcat ttccactcta aaaaaaaaaa aaaaaa                                5616

<210> SEQ ID NO 207
<211> LENGTH: 2239
<212> TYPE: DNA
<213> ORGANISM: Homo sapiens

<400> SEQUENCE: 207
ccccggcgca gcgcggccgc agcagcctcc gcccccgca cggtgtgagc gcccgacgcg         60
gccgaggcgg ccggagtccc gagctagccc cggcggccgc cgccgcccag accggacgac       120
aggccacctc gtcggcgtcc gcccgagtcc ccgcctcgcc gccaacgcca caaccaccgc       180
gcacggcccc ctgactccgt ccagtattga tcgggagagc cggagcgagc tcttcgggga       240
gcagcgatgc gaccctccgg gacggccggg gcagcgctcc tggcgctgct ggctgcgctc       300
tgcccggcga gtcgggctct ggaggaaaag aaagtttgcc aaggcacgag taacaagctc       360
acgcagttgg gcacttttga agatcatttt ctcagcctcc agaggatgtt caataactgt       420
gaggtggtcc ttgggaattt ggaaattacc tatgtgcaga ggaattatga tctttccttc       480
ttaaagacca tccaggaggt ggctggttat gtcctcattg ccctcaacac agtggagcga       540
attcctttgg aaaacctgca gatcatcaga ggaaatatgt actacgaaaa ttcctatgcc       600
ttagcagtct tatctaacta tgatgcaaat aaaaccggac tgaaggagct gcccatgaga       660
aatttacagg aaatcctgca tggcgccgtg cggttcagca caaccctgc cctgtgcaac       720 gtggagagca tccagtggcg ggacatagtc agcagtgact ttctcagcaa catgtcgatg       780
gacttccaga accacctggg cagctgccaa aagtgtgatc caagctgtcc caatgggagc       840
tgctggggtg caggagagga gaactgccag aaactgacca aaatcatctg tgcccagcag      900
tgctccgggc gctgccgtgg caagtccccc agtgactgct gccacaacca gtgtgctgca       960
ggctgcacag gccccggga gcgactgc ctggtctgcc gcaaattccg agacgaagcc         1020
acgtgcaagg acacctgccc cccactcatg ctctacaacc ccaccacgta ccagatggat      1080
gtgaaccccg agggcaaata cagctttggt gccacctgcg tgaagaagtg tccccgtaat      1140
tatgtggtga cagatcacgg ctcgtgcgtc cgagcctgtg gggccgacag ctatgagatg      1200
gaggaagacg gcgtccgcaa gtgtaagaag tgcgaaggc cttgccgcaa agtgtgtaac      1260
ggaataggta ttggtgaatt taaagactca ctctccataa atgctacgaa attaaacac      1320 ttcaaaaact gcacctccat cagtggcgat ctccacatcc tgccggtggc atttagggt      1380 gactccttca cacatactcc tcctctggat ccacaggaac tggatattct gaaaaccgta     1440
aaggaaatca cagggttttt gctgattcag gcttggcctg aaaacaggac ggacctccat      1500
gcctttgaga acctagaaat catacgcggc aggaccaagc aacatggtca gttttctctt      1560
gcagtcgtca gcctgaacat aacatccttg ggattacgct ccctcaagga gataagtgat      1620
ggagatgtga aatttcagg aaacaaaaat ttgtgctatg caaatacaat aaactggaaa      1680
```

-continued

| | |
|---|---|
| aaactgtttg ggacctccgg tcagaaaacc aaaattataa gcaacagagg tgaaaacagc | 1740 |
| tgcaaggcca caggccaggt ctgccatgcc ttgtgctccc ccgagggctg ctggggcccg | 1800 |
| gagcccaggg actgcgtctc ttgccggaat gtcagccgag gcaggaatg cgtggacaag | 1860 |
| tgcaaccttc tggagggtga gccaaggag tttgtggaga actctgagtg catacagtgc | 1920 |
| cacccagagt gcctgcctca ggccatgaac atcacctgca caggacgggg accagacaac | 1980 |
| tgtatccagt gtgccacta cattgacggc cccactgcg tcaagacctg cccggcagga | 2040 |
| gtcatgggag aaacaacac cctggtctgg aagtacgcag acgccggcca tgtgtgccac | 2100 |
| ctgtgccatc caaactgcac ctacgggtcc taataaatct tcactgtctg actttagtct | 2160 |
| cccactaaaa ctgcatttcc tttctacaat ttcaatttct ccctttgctt caaataaagt | 2220 |
| cctgacacta ttcatttga | 2239 |

<210> SEQ ID NO 208
<211> LENGTH: 1595
<212> TYPE: DNA
<213> ORGANISM: Homo sapiens

<400> SEQUENCE: 208

| | |
|---|---|
| ccccggcgca gcgcggccgc agcagcctcc gccccccgca cggtgtgagc gcccgacgcg | 60 |
| gccgaggcgg ccggagtccc gagctagccc cggcggccgc cgccgcccag accgacgac | 120 |
| aggccacctc gtcggcgtcc gcccgagtcc ccgcctcgcc gccaacgcca caaccaccgc | 180 |
| gcacggcccc ctgactccgt ccagtattga tcgggagagc cggagcgagc tcttcgggga | 240 |
| gcagcgatgc gaccctccgg gacggccggg gcagcgctcc tggcgctgct ggctgcgctc | 300 |
| tgcccggcga gtcgggctct ggaggaaaag aaagtttgcc aaggcacgag taacaagctc | 360 |
| acgcagttgg gcacttttga agatcatttt ctcagcctcc agaggatgtt caataactgt | 420 |
| gaggtggtcc ttgggaattt ggaaattacc tatgtgcaga ggaattatga tctttccttc | 480 |
| ttaaagacca tccaggaggt ggctggttat gtcctcattg ccctcaacac agtggagcga | 540 |
| attcctttgg aaaacctgca gatcatcaga ggaaatatgt actacgaaaa ttcctatgcc | 600 |
| ttagcagtct tatctaacta tgatgcaaat aaaaccggac tgaaggagct gcccatgaga | 660 |
| aatttacagg aaatcctgca tggcgccgtg cggttcagca caacccctgc cctgtgcaac | 720 |
| gtggagagca tccagtggcg ggacatagtc agcagtgact ttctcagcaa catgtcgatg | 780 |
| gacttccaga accacctggg cagctgccaa aagtgtgatc caagctgtcc caatgggagc | 840 |
| tgctggggtg caggagagga gaactgccag aaactgacca aaatcatctg tgcccagcag | 900 |
| tgctccgggc gctgccgtgg caagtccccc agtgactgct gccacaacca gtgtgctgca | 960 |
| ggctgcacag gccccggga gcgactgc ctggtctgcc gcaaattccg agacgaagcc | 1020 |
| acgtgcaagg acacctgccc cccactcatg ctctacaacc ccaccacgta ccagatggat | 1080 |
| gtgaaccccg agggcaaata cagctttggt gccacctgcg tgaagaagtg tccccgtaat | 1140 |
| tatgtggtga cagatcacgg ctcgtgcgtc cgagcctgtg gggccgacag ctatgagatg | 1200 |
| gaggaagacg gcgtccgcaa gtgtaagaag tgcgaagggc cttgccgcaa agtgtgtaac | 1260 |
| ggaataggta ttggtgaatt taaagactca ctctccataa atgctacgaa tattaaacac | 1320 |
| ttcaaaaact gcacctccat cagtggcgat ctccacatcc tgccggtggc atttagggt | 1380 |
| gactccttca cacatactcc tcctctggat ccacaggaac tggatattct gaaaaccgta | 1440 |
| aaggaaatca caggtttgag ctgaattatc acatgaatat aaatgggaaa tcagtgtttt | 1500 |

| agagagagaa | cttttcgaca | tatttcctgt | tcccttggaa | taaaaacatt | tcttctgaaa | 1560 |
| ttttaccgtt | aaaaaaaaaa | aaaaaaaaaa | aaaaa | | | 1595 |

<210> SEQ ID NO 209
<211> LENGTH: 2865
<212> TYPE: DNA
<213> ORGANISM: Homo sapiens

<400> SEQUENCE: 209

| ccccggcgca | gcgcggccgc | agcagcctcc | gcccccgca | cggtgtgagc | gcccgacgcg | 60 |
| gccgaggcgg | ccggagtccc | gagctagccc | cggcggccgc | cgccgcccag | accgacgac | 120 |
| aggccacctc | gtcggcgtcc | gcccgagtcc | ccgcctcgcc | gccaacgcca | caaccaccgc | 180 |
| gcacggcccc | ctgactccgt | ccagtattga | tcgggagagc | cggagcgagc | tcttcgggga | 240 |
| gcagcgatgc | gaccctccgg | gacggccggg | gcagcgctcc | tggcgctgct | ggctgcgctc | 300 |
| tgcccggcga | gtcgggctct | ggaggaaaag | aaagtttgcc | aaggcacgag | taacaagctc | 360 |
| acgcagttgg | gcacttttga | agatcatttt | ctcagcctcc | agaggatgtt | caataactgt | 420 |
| gaggtggtcc | ttgggaattt | ggaaattacc | tatgtgcaga | ggaattatga | tctttccttc | 480 |
| ttaaagacca | tccaggaggt | ggctggttat | gtcctcattg | ccctcaacac | agtggagcga | 540 |
| attcctttgg | aaaacctgca | gatcatcaga | ggaaatatgt | actacgaaaa | ttcctatgcc | 600 |
| ttagcagtct | tatctaacta | tgatgcaaat | aaaaccggac | tgaaggagct | gcccatgaga | 660 |
| aatttacagg | aaatcctgca | tggcgccgtg | cggttcagca | caaccctgc | cctgtgcaac | 720 |
| gtggagagca | tccagtggcg | ggacatagtc | agcagtgact | ttctcagcaa | catgtcgatg | 780 |
| gacttccaga | accacctggg | cagctgccaa | aagtgtgatc | caagctgtcc | caatggagc | 840 |
| tgctggggtg | caggagagga | gaactgccag | aaactgacca | aaatcatctg | tgcccagcag | 900 |
| tgctccgggc | gctgccgtgg | caagtccccc | agtgactgct | gccacaacca | gtgtgctgca | 960 |
| ggctgcacag | gccccggga | gagcgactgc | ctggtctgcc | gcaaattccg | agacgaagcc | 1020 |
| acgtgcaagg | acacctgccc | cccactcatg | ctctacaacc | ccaccacgta | ccagatggat | 1080 |
| gtgaaccccg | agggcaaata | cagctttggt | gccacctgcg | tgaagaagtg | tccccgtaat | 1140 |
| tatgtggtga | cagatcacgg | ctcgtgcgtc | cgagcctgtg | gggccgacag | ctatgagatg | 1200 |
| gaggaagacg | gcgtccgcaa | gtgtaagaag | tgcgaaggc | cttgccgcaa | agtgtgtaac | 1260 |
| ggaataggta | ttggtgaatt | taaagactca | ctctccataa | atgctacgaa | tattaaacac | 1320 |
| ttcaaaaact | gcacctccat | cagtggcgat | ctccacatcc | tgccggtggc | atttaggggt | 1380 |
| gactccttca | cacatactcc | tcctctggat | ccacaggaac | tggatattct | gaaaaccgta | 1440 |
| aaggaaatca | cagggttttt | gctgattcag | gcttggcctg | aaaacaggac | ggacctccat | 1500 |
| gcctttgaga | acctagaaat | catacgcggc | aggaccaagc | aacatggtca | gttttctctt | 1560 |
| gcagtcgtca | gcctgaacat | aacatccttg | ggattacgct | ccctcaagga | gataagtgat | 1620 |
| ggagatgtga | taatttcagg | aaacaaaaat | ttgtgctatg | caaatacaat | aaactggaaa | 1680 |
| aaactgtttg | ggacctccgg | tcagaaaacc | aaaattataa | gcaacagagg | tgaaaacagc | 1740 |
| tgcaaggcca | caggccaggt | ctgccatgcc | ttgtgctccc | ccgagggctg | ctggggcccg | 1800 |
| gagcccaggg | actgcgtctc | ttgccggaat | gtcagccgag | cagggaatg | cgtggacaag | 1860 |
| tgcaaccttc | tggagggtga | gccaagggag | tttgtggaga | actctgagtg | catacagtgc | 1920 |
| cacccagagt | gcctgcctca | ggccatgaac | atcacctgca | caggacgggg | accagacaac | 1980 |
| tgtatccagt | gtgcccacta | cattgacggc | ccccactgcg | tcaagacctg | cccggcagga | 2040 |

```
gtcatgggag aaaacaacac cctggtctgg aagtacgcag acgccggcca tgtgtgccac    2100
ctgtgccatc caaactgcac ctacgggcca ggaaatgaga gtctcaaagc catgttattc    2160
tgccttttta aactatcatc ctgtaatcaa agtaatgatg gcagcgtgtc ccaccagagc    2220
gggagcccag ctgctcagga gtcatgctta ggatggatcc cttctcttct gccgtcagag    2280
tttcagctgg gttggggtgg atgcagccac ctccatgcct ggccttctgc atctgtgatc    2340
atcacggcct cctcctgcca ctgagcctca tgccttcacg tgtctgttcc ccccgctttt    2400
cctttctgcc accctgcac gtgggccgcc aggttcccaa gagtatccta cccatttcct     2460
tccttccact cccttgcca gtgcctctca ccccaactag tagctaacca tcacccccag     2520
gactgacctc ttcctcctcg ctgccagatg attgttcaaa gcacagaatt tgtcagaaac    2580
ctgcagggac tccatgctgc cagccttctc cgtaattagc atggcccag tccatgcttc     2640 tagccttggt tccttctgcc cctctgtttg aaattctaga gccagctgtg ggacaattat    2700
ctgtgtcaaa agccagatgt gaaaacatct caataacaaa ctggctgctt tgttcaatgc    2760
tagaacaacg cctgtcacag agtagaaact caaaaatatt tgctgagtga atgaacaaat    2820
gaataaatgc ataataaata attaaccacc aatccaacat ccaga                    2865
```